United States Patent
Katz et al.

(10) Patent No.: US 8,455,477 B2
(45) Date of Patent: Jun. 4, 2013

(54) THERAPEUTIC COMPOUNDS

(75) Inventors: Jason Katz, Newton Highlands, MA (US); James Jewell, Somerville, MA (US); Joon Jung, Newton, MA (US); Solomon Kattar, Arlington, MA (US); Yongquan Hou, Cambridge, MA (US); Rachel MacCoss, Brookline, MA (US); Satoru Ito, Tsukuba (JP)

(73) Assignees: Merck Sharp & Dohme Corp., Rahway, NJ (US); MSD K.K., Tokyo (JP)

( * ) Notice: Subject to any disclaimer, the term of this patent is extended or adjusted under 35 U.S.C. 154(b) by 0 days.

(21) Appl. No.: 13/057,325

(22) PCT Filed: Jul. 27, 2009

(86) PCT No.: PCT/US2009/051786
§ 371 (c)(1),
(2), (4) Date: Feb. 3, 2011

(87) PCT Pub. No.: WO2010/017047
PCT Pub. Date: Feb. 11, 2010

(65) Prior Publication Data
US 2011/0207711 A1    Aug. 25, 2011

Related U.S. Application Data

(60) Provisional application No. 61/137,979, filed on Aug. 5, 2008.

(51) Int. Cl.
| | | |
|---|---|---|
| *A61K 31/437* | (2006.01) |
| *A61K 31/438* | (2006.01) |
| *A61K 31/4439* | (2006.01) |
| *A61K 31/444* | (2006.01) |
| *A61K 31/5377* | (2006.01) |
| *A61K 31/397* | (2006.01) |
| *A61K 31/505* | (2006.01) |
| *A61K 31/495* | (2006.01) |
| *A61K 31/496* | (2006.01) |
| *A61K 31/50* | (2006.01) |
| *C07F 7/02* | (2006.01) |
| *C07D 487/02* | (2006.01) |
| *C07D 413/14* | (2006.01) |
| *C07D 401/02* | (2006.01) |
| *C07D 401/14* | (2006.01) |
| *C07D 221/20* | (2006.01) |

(52) U.S. Cl.
USPC .......... 514/210.18; 514/233.2; 514/235.5; 514/252.01; 514/252.13; 514/255.05; 514/256; 514/278; 514/300; 544/124; 544/127; 544/238; 544/333; 544/360; 544/362; 544/405; 546/14; 546/15; 546/16; 546/121

(58) Field of Classification Search
USPC ........... 514/210.18, 233.2, 235.5, 252.01, 514/252.13, 255.05, 256, 278, 300; 544/124, 544/127, 238, 333, 360, 362, 405; 546/14, 546/15, 16, 121
See application file for complete search history.

(56) References Cited

U.S. PATENT DOCUMENTS

| | | |
|---|---|---|
| 5,200,415 A | 4/1993 | Higashino et al. |
| 5,420,138 A | 5/1995 | Corbier et al. |
| 7,125,888 B2 | 10/2006 | Bilodeau et al. |
| 7,763,617 B2 | 7/2010 | Kohno et al. |
| 7,795,273 B2 | 9/2010 | Imbach et al. |
| 2007/0043068 A1 | 2/2007 | Arnold et al. |
| 2007/0129364 A1 | 6/2007 | Dong et al. |

FOREIGN PATENT DOCUMENTS

| | | |
|---|---|---|
| JP | 2001139575 A | 5/2001 |
| JP | 2006117647 A | 5/2006 |
| JP | 2006169138 A | 6/2006 |

OTHER PUBLICATIONS

Biondi, RM et al., The EMBO Journal, vol. 21, No. 16, (2002), pp. 4219-4228, "High resolution crystal structure of the human PDK1 catalytic domain defines the regulatory phosphopeptide docking site".

*Primary Examiner* — Samantha Shterengarts
(74) *Attorney, Agent, or Firm* — Peter Haeberli; David A. Muthard

(57) ABSTRACT

The present invention relates to pyrazolopyridines and imidazopyridines which are inhibitors of the kinase PDK1 and are thus useful for the treatment of myeloproliferative disorders or cancer. The compounds are also useful as inhibitors of other kinases such as FGFR3, NTRK3, RP-S6K and WEE1. Furthermore, the present compounds also selectively inhibit microtubule affinity regulating kinase (MARK) and are therefore useful for the treatment or prevention of Alzheimer's disease.

7 Claims, No Drawings

SEQUENCE LISTING

<160> NUMBER OF SEQ ID NOS: 5

<210> SEQ ID NO 1
<211> LENGTH: 7
<212> TYPE: PRT
<213> ORGANISM: Artificial Sequence
<220> FEATURE:
<223> OTHER INFORMATION: Completely synthetic amino acid

<400> SEQUENCE: 1

Met Glu Tyr Met Pro Met Glu
 1               5

<210> SEQ ID NO 2
<211> LENGTH: 6
<212> TYPE: PRT
<213> ORGANISM: Artificial Sequence
<220> FEATURE:
<223> OTHER INFORMATION: Completely synthetic amino acid

<400> SEQUENCE: 2

Glu Tyr Met Pro Met Glu
 1               5

<210> SEQ ID NO 3
<211> LENGTH: 28
<212> TYPE: PRT
<213> ORGANISM: Artificial Sequence
<220> FEATURE:
<223> OTHER INFORMATION: Completely synthetic amino acid

<400> SEQUENCE: 3

Gly Gly Asp Gly Ala Thr Met Lys Thr Phe Cys Gly Gly Thr Pro Ser
 1               5                  10                  15

Asp Gly Asp Pro Asp Gly Gly Glu Phe Thr Glu Phe
            20                  25

<210> SEQ ID NO 4
<211> LENGTH: 17
<212> TYPE: PRT
<213> ORGANISM: Artificial Sequence
<220> FEATURE:
<223> OTHER INFORMATION: Completely synthetic amino acid

<400> SEQUENCE: 4

Glu Gln Glu Asp Glu Pro Glu Gly Asp Tyr Phe Glu Trp Leu Glu Pro
 1               5                  10                  15

Glu

<210> SEQ ID NO 5
<211> LENGTH: 16
<212> TYPE: PRT
<213> ORGANISM: Artificial Sequence
<220> FEATURE:
<223> OTHER INFORMATION: Completely synthetic amino acid

<400> SEQUENCE: 5

Gly Glu Glu Glu Leu Ser Asn Tyr Ile Cys Met Gly Gly Arg Arg Arg
 1               5                  10                  15

THERAPEUTIC COMPOUNDS

REFERENCE TO SEQUENCE LISTING SUBMITTED ELECTRONICALLY

The sequence listing of the present application is being submitted electronically via EFS-Web as an ASCII formatted sequence listing with a file name "MRLONC22531USPCT-SEQTXT-03FEB2011.txt", creation date of Jan. 25, 2011 and a size of 1,657 bytes. This sequence listing submitted via EFS-Web is part of the specification and is herein incorporated by reference in its entirety.

BACKGROUND OF THE INVENTION

The present invention relates to pyrazolopyridines and imidazopyridines which are inhibitors of the kinase PDK1 and are thus useful for the treatment of myeloproliferative disorders or cancer. The compounds are also useful as inhibitors of other kinases such as FGFR3, NTRK3, RP-S6K and WEE1. Furthermore, the present compounds also selectively inhibit microtubule affinity regulating kinase (MARK) and are therefore useful for the treatment or prevention of Alzheimer's disease.

PDK1

PDK1 is a Ser/Thr protein kinase possessing a kinase domain at its N-terminus (residues 70-359) and a Pleckstrin homology (PH) domain at its C-terminus (residues 459-550). The kinase can phosphorylate and activate a number of kinases in the AGC kinase superfamily, including Akt/protein kinase B, protein kinase C(PKC), PKC-related kinases (PRK1 and PRK2), p70 ribobsomal S6-kinase (S6K1) and serum and glucocorticoid-regulated kinase (SGK). Akt comprises a family of Ser/Thr protein kinases containing three highly homologous members (AKT1, AKT2 and AKT3) and its activation in cells by PDK1 requires stimulation of phosphoinositide 3-kinase (PI 3-kinase) (Feldman, Richard I., et al., *The Journal of Biological Chemistry*, Vol. 280, No. 20, Issue of May 20, pp. 19867-19874, 2005). The activation of Akt in tumor cells has been shown to have multiple upstream effects that promote disease progression, including suppression of apoptosis and stimulation of tumor cell proliferation, metabolism and angiogenesis. Thus the PI 3-kinase/PDK1/Akt signaling pathway plays a key role in regulating cancer cell growth, invasion, apoptosis and tumor angiogenesis. Furthermore, this pathway has been found to be highly activated in common cancers, including melanoma and haematological, breast, colon, pancreatic, prostate and ovarian cancers (Feldman, Richard I., et al, supra). The PI 3-kinase/PDK1/Akt signaling pathway is therefore a useful target for the developments of anticancer agents.

FGFR3

The Tec family kinase, Bmx, a non-receptor protein-tyrosine kinase, controls the proliferation of mammary epithelial cancer cells. Fibroblast growth factor receptor 3 (FGFR3) has been shown to exert a negative regulatory effect on bone growth and on inhibition of chondrocyte proliferation. Thanatophoric dysplasia is caused by different mutations in fibroblast growth factor receptor 3, and one mutation, TDII FGFR3, has a constitutive tyrosine kinase activity which activates the transcription factor Stat1, leading to expression of a cell-cycle inhibitor, growth arrest and abnormal bone development (Su et al., Nature, 1997, 386, 288-292). FGFR3 is also often expressed in multiple myeloma-type cancers. Inhibitors of FGFR3 activity are useful in the treatment of T-cell mediated inflammatory or autoimmune diseases including but not limited to rheumatoid arthritis (RA), collagen II arthritis, multiple sclerosis (MS), systemic lupus erythematosus (SLE), psoriasis, juvenile onset diabetes, Sjogren's disease, thyroid disease, sarcoidosis, autoimmune uveitis, inflammatory bowel disease (Crohn's and ulcerative colitis), celiac disease and myasthenia gravis.

NTRK3

NTRK3 (TRKC) is a member of the trk family of neurotrophin receptors and is able to control tumor cell growth and survival as well as differentiation, migration and metastasis. NTRK3 and its closely related family members NTRK1 (TRKA) and NTRK2 (TRKB) are implicated in the development and progression of cancer, possibly by upregulation of either the receptor, their ligand (Nerve Growth Factor, Brain Derived Neurotrophic Factor, Neurotrophins) or both. High expression of NTRK2 and/or its ligand BDNF has been shown in pancreatic and prostate carcinomas, Wilm's tumors and neuroblastomas. In addition, high expression of NTRK3 is a hallmark of Melanoma, especially in cases with brain metastasis. In many cases high Trk expression is associated with aggressive tumor behaviour, poor prognosis and metastasis.

Genetic abnormalities, i.e. point mutations and chromosomal rearrangements involving both NTRK2 and NTRK3 have been found in a variety of cancer types. In a kinome-wide approach to identify point mutants in tyrosine kinases both NTRK2 and NTRK3 mutations were found in cell lines and primary samples from patients with colorectal cancer (Manning et al., 2002, Bardelli et al., 2003). In addition, chromosomal translocations involving both NTRK1 and NTRK3 have been found in several different types of tumors. Moreover, secretary breast cancer, infant fibrosarcoma and congenital mesoblastic nephroma have been shown to be associated with a chromosomal rearrangement t(12; 15) generating a ETV6-NTRK3 fusion gene that was shown to have constitutive kinase activity and transforming potential in several different cell lines including fibroblasts, hematopoietic cells and breast epithelial cells.

RP-S6K

The ribosomal protein S6 kinase (RP-S6K/p70S6K1) is a serine/threonine kinase implicated in the development and progression of cancer. Thus, compounds which inhibit the action of this kinase are useful as anti-cancer agents.

WEE1

Cells have a checkpoint mechanism of such that, when the DNA therein is damaged, then the cells temporarily stop the cell cycle and repair the damaged DNA (Cell Proliferation, Vol. 33, pp. 261-274). In about a half of human cancers, a cancer-suppressor gene, p53 is mutated or depleted and the cells thereby have lost the G1 checkpoint function thereof. However, such cancer cells still keep the G2 checkpoint function remaining therein, which is considered to be one factor of lowering the sensitivity of the cells to DNA-active anticancer agents and to radiations.

A Wee1 kinase is a tyrosine kinase that participates in the G2 checkpoint of a cell cycle. Wee1 phosphorylates Cdc2 (Cdk1) tyrosine 15 that participates in the progress to the M stage from the G2 stage in a cell cycle, thereby inactivating Cdc2 and temporarily stopping the cell cycle at the G2 stage (Tfie EMBO Journal, Vol. 12, pp. 75-85). Accordingly, in cancer cells having lost the p53 function therein, it is considered that the G2 checkpoint function by Wee1 is important for repairing the damaged DNA so as to evade the cell death. Heretofore, it has been reported that the Wee1 expression reduction by RNA interference or the Wee1 inhibition by compounds may increase the sensitivity of cancer cells to adriamycin, X ray and gamma ray (Cancer Biology & Therapy, Vol. 3, pp. 305-313; Cancer Research, Vol. 61, pp.

8211-8217). From the above, it is considered that a Wee1 inhibitor may inhibit the G2 checkpoint function of p53-depleted cancer cells, thereby enhancing the sensitivity of the cells to DNA-active anticancer agents and to radiations. Wee1 inhibitors are therefore suitable for the treatment of tumor diseases, such as gliomas, sarcomas, prostate tumors, and tumors of the colon, breast, and ovary.

MARK

The classic clinical and neuropathological features of AD consist of senile or neuritic plaques and tangled bundles of fibers (neurofibrillary tangles) [Verdile, G., et al, Pharm. Res. 50:397-409 (2004)]. In addition, there is a severe loss of neurons in the hippocampus and the cerebral cortex. Neuritic plaques are extracellular lesions, consisting mainly of deposits of β-amyloid peptide (Aβ), surrounded by dystrophic (swollen, damaged and degenerating) neurites and glial cells activated by inflammatory processes. In contrast, neurofibrillary tangles (NFTs) are intracellular clusters composed of a hyperphosphorylated form of the protein tau, which are found extensively in the brain (e.g. mainly in cortex and hippocampus in AD). Tau is a soluble cytoplasmic protein which has a role in microtubule stabilisation. Excessive phosphorylation of this protein renders it insoluble and leads to its aggregation into paired helical filaments, which in turn form NFTs.

The microtubule affinity-regulating kinase (MARK) is part of the AMP-dependent protein kinase (AMPK) family and exists in four isoforms. MARK is thought to phosphorylate tau to result in an unbound, hyperphosphorylated tau which is delocalised to the somatodendritic compartment and then cleaved by caspases to form fragments prone to aggregation [Drewes, G. (2004). Trends Biochem. Sci 29:548-555; Gamblin, T. C., et al, (2003) Proc. Natl. Acad. Sci. U.S.A. 100: 10032-10037]. These aggregates can grow into filaments, which are potentially toxic, eventually forming the NFTs found in AD.

Thus, MARK inhibitors are useful for preventing or ameliorating neurodegeneration in AD and other tauopathies.

The instant invention provides compounds which inhibit the activity of the PDK1 kinase and/or other kinases such as FGFR3, NTRK3, RP-S6K and/or WEE1. The compounds also inhibit the activity of the microtubule affinity regulating kinase (MARK). The present invention provides compounds of formula I:

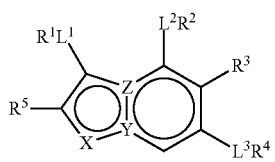

(I)

wherein:
either X and Y are both N and Z is C, or X and Z are both N and Y is C;

$L^1$ is a direct bond, $-(C\equiv C)_a(C=O)_b(NR^c)_c(CR^aR^b)_d(NR^c)_c(C=O)_b-$ or $-(CR^aR^b)_d(C=O)_b(NR^c)_c(CR^aR^b)_d-$;

a is 1 or 2;
b is 0 or 1;
c is 0 or 1;
d is 0, 1, 2, 3, 4, 5 or 6;
$L^2$ is $-O(CR^aR^b)_d-$ or $-(NR^c)(C=O)_b-$;
$L^3$ is a direct bond, $-C\equiv C-$ or $-(HC=CH)_e(CR^aR^b)_d(NR^c)_c-$;
e is 0 or 1;

$R^1$ is hydrogen, hydroxy, cyano, halogen, $C_{1-6}$alkyl, $C_{2-10}$alkenyl, halo$C_{1-6}$alkyl, hydroxy$C_{1-6}$alkyl, $C_{1-6}$alkylcarbonyl, $C_{1-6}$alkoxy, halo$C_{1-6}$alkoxy, $C_{1-6}$alkoxycarbonyl, carboxy, nitro, $N(R^x)_2$, $SO_2R^x$, $Si(R^x)_3$ or a ring which is: $C_{6-10}$aryl, $C_{3-10}$cycloalkyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O, and S, not more than one heteroatom of which is O or S, a 6 membered heteroaromatic ring containing 1, 2 or 3 N atoms or a 7-15 membered unsaturated, partially saturated or saturated heterocyclic ring containing 1, 2, 3 or 4 heteroatoms independently selected from N, O and S; optionally substituted by one, two or three groups independently selected from $L^4$-$R^d$;

$R^2$ is selected from hydroxy, cyano, halogen, $C_{1-6}$alkyl, $C_{2-10}$alkenyl, halo$C_{1-6}$alkyl, hydroxy$C_{1-6}$alkyl, $C_{1-6}$alkylcarbonyl, $C_{1-6}$alkoxy, halo$C_1$alkoxy, $C_{1-6}$alkoxycarbonyl, carboxy, nitro, $N(R^x)_2$ or a ring which is: $C_{6-10}$aryl, $C_{3-10}$cycloalkyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 nitrogen atoms or a 7-15 membered unsaturated, partially saturated or saturated heterocyclic ring containing 1, 2, 3 or 4 heteroatoms independently selected from N, O and S; any of which rings being optionally substituted by one, two or three groups independently selected from $R^e$;

$R^3$ is selected from hydrogen, hydroxy, cyano, halogen, $C_{1-6}$alkyl, $C_{2-10}$alkenyl, halo$C_{1-6}$alkyl, hydroxy$C_{1-6}$alkyl, $C_{1-6}$alkylcarbonyl, $C_{1-6}$alkoxy, halo$C_1$alkoxy, $C_{1-6}$alkoxycarbonyl, carboxy, nitro, $N(R^x)_2$ or a ring which is: $C_{6-10}$aryl, $C_{6-10}$aryl$C_{1-6}$alkyl, $C_{3-10}$cycloalkyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 nitrogen atoms or a 7-15 membered unsaturated, partially saturated or saturated heterocyclic ring containing 1, 2, 3 or 4 heteroatoms independently selected from N, O and S; any of which rings being optionally substituted by one, two or three groups independently selected hydroxy, cyano, halogen, $C_{1-6}$alkyl, $C_{2-10}$alkenyl, halo$C_{1-6}$alkyl and hydroxy$C_{1-6}$alkyl;

$R^4$ is selected from hydrogen, hydroxy, cyano, halogen, $C_{1-6}$alkyl, $C_{2-10}$alkenyl, halo$C_{1-6}$alkyl, hydroxy$C_{1-6}$alkyl, $C_{1-6}$alkylcarbonyl, $C_{1-6}$alkoxy, halo$C_1$alkoxy, $C_{1-6}$alkoxycarbonyl, carboxy, nitro, $N(R^x)_2$ or a ring which is: $C_{6-10}$aryl, $C_{6-10}$aryl$C_{1-6}$alkyl, $C_{3-10}$cycloalkyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 nitrogen atoms or a 7-15 membered unsaturated, partially saturated or saturated heterocyclic ring containing 1, 2, 3 or 4 heteroatoms independently selected from N, O and S; any of which rings being optionally substituted by one, two or three groups independently selected from $L^5$-$R^f$;

$R^5$ is hydrogen, hydroxy, cyano, halogen, $C_{1-6}$alkyl, $C_{2-10}$alkenyl, halo$C_{1-6}$alkyl, hydroxy$C_{1-6}$alkyl, $C_{1-6}$alkylcarbonyl, $C_{1-6}$alkoxy, halo$C_1$alkoxy, $C_{1-6}$alkoxycarbonyl, carboxy, nitro or $N(R^x)_2$;

$L^4$ is a direct bond, —$(CR^aR^b)_d(C=O)_b(NR^c)_c(C=O)_b(O)_g(CR^aR^b)_d(NR^c)_c$— or —$(NR^c)_c(SO_2)_f(NR^c)_c(CR^aR^b)_d$;

$L^5$ is a direct bond or —$(C=O)_b(NR^c)_c(C=O)_b(CR^aR^b)_d$—;

f is 0 or 1;

g is 0 or 1;

each of $R^a$ and $R^b$ is independently hydrogen, hydroxy, halogen, $C_{1-6}$alkyl, $C_{2-10}$alkenyl, halo$C_{1-6}$alkyl, hydroxy$C_{1-6}$alkyl, $C_{1-6}$alkoxy or halo$C_{1-6}$alkoxy;

$R^c$ is hydrogen or $C_{1-6}$alkyl;

$R^d$ is hydroxy, oxo, cyano, halogen, $C_{1-6}$alkyl, $C_{2-10}$alkenyl, halo$C_{1-6}$alkyl, hydroxy$C_{1-6}$alkyl, $C_{1-6}$alkylcarbonyl, $C_{1-6}$alkoxy, halo$C_{1-6}$alkoxy, amino, $(C_{1-6}$alkyl)amino, di$(C_{1-6}$alkyl)amino or a ring which is: $C_{6-10}$aryl, $C_{3-10}$cycloalkyl, azetidinyl, a 5, 6 or 7 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O, and S, not more than one heteroatom of which is O or S or a 6 membered heteroaromatic ring containing 1, 2 or 3 N atoms; any of which rings being optionally substituted by one, two or three groups independently selected from hydroxy, oxo, cyano, halogen, $C_{1-6}$alkyl, $C_{2-10}$alkenyl, hydroxy$C_{1-6}$alkyl, $C_{1-6}$alkylcarbonyl, $C_{1-6}$alkoxy, halo$C_{1-6}$alkoxy, $C_{1-6}$alkoxycarbonyl, carboxy, nitro, amino, $(C_{1-6}$alkyl)amino and di$(C_{1-6}$alkyl)amino;

$R^e$ is hydroxy, cyano, halogen, $C_{1-6}$alkyl, $C_{2-10}$alkenyl, hydroxy$C_{1-6}$alkyl, $C_{1-6}$alkylcarbonyl, $C_{1-6}$alkoxy, halo$C_{1-6}$alkoxy, $C_{1-6}$alkoxycarbonyl, carboxy, or $SO_2R^x$;

$R^f$ is hydroxy, oxo, cyano, halogen, $C_{1-6}$alkyl, $C_{2-40}$alkenyl, hydroxy$C_{1-6}$alkyl, $C_{1-6}$alkylcarbonyl, $C_{1-6}$alkoxy, halo$C_{1-6}$alkoxy or a ring which is: $C_{6-10}$aryl, $C_{3-10}$cycloalkyl, azetidinyl, a 5, 6 or 7 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O, and S, not more than one heteroatom of which is O or S or a 6 membered heteroaromatic ring containing 1, 2 or 3 N atoms; any of which rings being optionally substituted by one, two or three groups independently selected from hydroxy, oxo, cyano, halogen, $C_{1-6}$alkyl, $C_{2-10}$alkenyl, halo$C_{1-6}$alkyl, hydroxy$C_{1-6}$alkyl, $C_{1-6}$alkylcarbonyl, $C_{1-6}$alkoxy, halo$C_{1-6}$alkoxy, $C_{1-6}$alkoxycarbonyl, carboxy, nitro, amino, $(C_{1-6}$alkyl)amino and di$(C_{1-6}$alkyl)amino;

each of $R^x$ and $R^y$ is independently hydrogen or $C_{1-6}$alkyl;

or a pharmaceutically acceptable salt, stereoisomer or tautomer thereof.

In an embodiment a is 1.

In an embodiment b is 0. In another embodiment b is 1.

In an embodiment c is 0. In another embodiment c is 1.

In an embodiment d is 0, 1, 2 or 3.

In an embodiment $L^1$ is a direct bond.

In another embodiment $L^1$ is —$(C≡C)_a(C=O)_b(NR^c)_c(CR^aR^b)_d(NR^c)_c(C=O)_b$—.

In an embodiment $L^1$ is —$(C≡C)$—.

In an embodiment a is 1.

In another embodiment $L^1$ is —$(CR^aR^b)_d(C=O)_b(NR^c)_c(CR^aR^b)_d$—.

Particular $L^1$ groups are a direct bond, —$(C=O)$—, —$(C≡C)$—, —$(C≡C)(CR^aR^b)$—, —$(C≡C)(C=O)NR^c$—, —$(C≡C)(CR^aR^b)_2NR^c$—, —$(C≡C)_2$—, —$(CR^aR^b)$—, —$(CR^aR^b)NR^c$—, —$(CR^aR^b)NR^c(CR^aR^b)_2$—, —$(CR^aR^b)NR^c(CR^aR^b)$—, —$NR^c(CR^aR^b)_2$—, —$NR^c$—, —$NR^c(CR^aR^b)_3$—, —$(C=O)NR^c$—, —$(C=O)NH(CR^aR^b)_2$—, —$(C=O)NR^c(CR^aR^b)$—, —$(C=O)NR^c(CR^aR^b)_3$—, —$(CR^aR^b)_2$—, —$(C=O)(CR^aR^b)$—, —$(C≡C)(CR^aR^b)NR^c$—, —$(C≡C)(CR^aR^b)$— and —$(C≡C)(CR^aR^b)NR^c(C=O)$—.

Specific $L^1$ groups are a direct bond, —$(C=O)$—, —$(C≡C)$—, —$(C≡C)(CH_2)$—, —$(C≡C)(C=O)NH$—, —$(C≡C)(CH_2)_2NH$—, —$(C≡C)_2$—, —$(CH_2)$—, —$CH_2NH$—, —$CH_2NH(CH_2)_2$—, —$CH_2NHCH_2$—, —$NH(CH_2)$—, —$NH(CH_2)_2$—, —$NH$—, —$NH(CH_2)_3$—, —$(C=O)NH$—, —$(C=O)NH(CH_2)_2$—, —$(C=O)NH(CH_2)$—, —$(C=O)NH(CH_2)_3$—, —$(CH_2)_2$—, —$(C=O)(CH_2)$—, —$(C≡C)(CH_2)NH$—, —$(C≡C)(CHOH)$— and —$(C≡C)(CH_2)NH(C=O)$—.

In an embodiment $R^1$ is hydrogen, hydroxy, cyano, halogen, $C_{1-6}$alkyl, halo$C_{1-6}$alkyl, hydroxy$C_{1-6}$alkyl, $C_{1-6}$alkoxy, halo$C_{1-6}$alkoxy, $N(R^x)_2$, $SO_2R^x$ or $Si(R^x)_3$ or a ring which is: $C_{6-10}$aryl, $C_{3-10}$cycloalkyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O, and S, not more than one heteroatom of which is O or S, a 6 membered heteroaromatic ring containing 1, 2 or 3 N atoms or a 7-10 membered unsaturated, partially saturated or saturated heterocyclic ring containing 1, 2, 3 or 4 heteroatoms independently selected from N, O and S; any of which rings being optionally substituted by one, two or three groups independently selected from $L^4$-$R^d$;

In an embodiment $R^1$ is hydrogen, cyano, methoxy, iodine, chlorine, bromine, trimethylsilyl, hydroxy, methylsulfonyl, dimethylamino, methyl, ethyl, amino or a ring selected from: pyridinyl, cyclopropyl, pyrazolyl, phenyl, imidazolyl, pyrrolidinyl, azetidinyl, piperidinyl, isoxazolyl, thiazolyl, pyrrolyl, imidazopyridinyl, pyrazolopyridinyl, imidazopyrazinyl, thiadiazolyl, tetrahydroimidazopyridinyl, dihydrotriazolopyrazinyl, diazaspiro[3.5]nonyl, diazaspiro[3.3]heptyl, pyrazinyl, pyridazinyl, indazolyl, benzimidazolyl, dihydrobenzimidazolyl, indolyl, pyrimidinyl, morpholinyl, benzothienyl, cyclopentyl, quinolinyl, thienyl, isothiazolyl, naphthyridinyl, quinazolinyl and triazolyl; any of which rings being optionally substituted by one, two or three groups independently selected from $L^4$-$R^d$.

In an embodiment $L^4$ is a direct bond.

In another embodiment $L^4$ is —$(CR^aR^b)_d(C=O)_b(NR^c)_c(C=O)_b(O)_g(CR^aR^b)_d(NR^c)_c$—.

In another embodiment $L^4$ is —$(NR^c)_c(SO_2)_f(NR^c)_c$.

In an embodiment $L^4$ is a direct bond, —$N(R^c)(C=O)$—, —$(C=O)$—, —$SO_2N(R^c)$—, —$CR^aR^b$—, —$SO_2$—, —$N(R^c)(SO_2)$—, —$(CR^aR^b)(C=O)$, —$(C=O)N(R^c)(CR^aR^b)$—, —$(C=O)N(R^c)$—, —$(C=O)N(R^c)(CR^aR^b)_2$—, —$(C=O)N(R^c)(CR^aR^b)_3$—, —$N(R^c)(C=O)N(R^c)$—, —$(C=O)(O)(CR^aR^b)$—, —$(CR^aR^b)_2$—, —$(CR^aR^b)N(R^c)$— or —$SO_2N(R^c)(CR^aR^b)$—.

Specific $L^4$ groups are a direct bond, —$NH(C=O)$—, —$(C=O)$—, —$SO_2N(CH_3)$—, —$CH_2$—, —$SO_2$—, —$C(OH)H$—, —$NH(SO_2)$—, —$CH_2(C=O)$—, —$(C=O)NH(CH_2)$—, —$(C=O)NH$—, —$(C=O)NH(CH_2)_2$—, —$(C=O)NH(CH_2)_3$—, —$NH(C=O)NH$—, —$(C=O)(O)(CH_2)$—, —$(CH_2)_2$—, —$(CH_2)NH$— and —$SO_2NH(CH_2)$—.

In an embodiment $R^d$ is hydroxy, oxo, cyano, halogen, $C_{1-6}$alkyl, halo$C_{1-6}$alkyl, hydroxy$C_{1-6}$alkyl, $C_{1-6}$alkylcarbonyl, $C_{1-6}$alkoxy, halo$C_{1-6}$alkoxy, amino, $(C_{1-6}$alkyl)amino, di$(C_{1-6}$alkyl)amino or a ring which is: $C_{6-10}$aryl, $C_{3-10}$cycloalkyl, azetidinyl, a 5, 6 or 7 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O, and S, not more than one heteroatom of which is O or S or a 6 membered heteroaromatic ring containing 1, 2 or 3 N atoms; any of which rings being optionally substituted by one, two or three groups independently selected from hydroxy, oxo, cyano, halogen, $C_{1-6}$alkyl, $C_{2-10}$alkenyl, halo$C_{1-6}$alkyl, hydroxy$C_{1-6}$alkyl, $C_{1-6}$alkylcarbonyl, $C_{1-6}$alkoxy, halo$C_1$alkoxy, $C_{1-6}$alkoxycarbonyl, carboxy, nitro, amino, $(C_{1-6}$alkyl)amino and di$(C_{1-6}$alkyl)amino.

In an embodiment when $R^d$ is a ring it is optionally substituted by one or two independently selected groups. In another embodiment the $R^d$ ring is unsubstituted or monosubstituted.

In an embodiment the optional substituents on the $R^d$ ring are selected from halogen, oxo, $C_{1-6}$alkyl, $C_{1-6}$alkoxy, amino, $C_{1-6}$alkylamino and di$C_{1-6}$alkylamino.

Particular optional substituents on the $R^d$ ring are methyl, fluorine, chlorine, tertbutyl, methoxy, amino and oxo.

In an embodiment $R^d$ is methyl, methoxy, tertbutoxy, amino, hydroxy, chlorine, fluorine, tertbutyl, ethyl, trifluoromethyl, bromine, cyano, oxo, isopropyl, fluoromethyl, acetyl, ethylamino or a ring selected from: cyclopropyl, phenyl, pyridinyl, pyrrolidinyl, pyrazolyl, cyclohexyl, piperazinyl, thienyl, thiazolyl, cyclobutyl, tetrahydrofuranyl, furyl, cyclopentyl, isoxazolyl, thiazolyl and morpholinyl; the ring being optionally substituted as defined above.

Particular $R^d$ groups are methyl, phenyl, pyridinyl, methoxy, tertbutoxy, amino, pyrrolidinyl, hydroxy, chlorine, fluorine, methylpyrazolyl, tertbutyl, cyclopropyl, ethyl, fluorophenyl, chlorophenyl, tertbutylphenyl, methylphenyl, methoxyphenyl, trifluoromethyl, bromine, cyano, oxo, aminocyclohexyl, piperazinyl, oxopyrrolidinyl, thienyl, dimethylthiazolyl, dimethylphenyl, isopropyl, cyclobutyl, tetrahydrofuranyl, furyl, cyclopentyl, fluoromethyl, methylisoxazolyl, methylthiazolyl, dimethylpyrazolyl, morpholinyl, dimethylisoxazolyl, fluoropyridinyl, acetyl and ethylamino.

Specific $R^d$ groups are methyl, phenyl, pyridin-2-yl, methoxy, tertbutoxy, amino, pyrrolidin-1-yl, hydroxy, chlorine, fluorine, 1-methyl-1H-pyrazol-4-yl, tertbutyl, cyclopropyl, ethyl, 2-fluorophenyl, 4-chlorophenyl, 4-tertbutylphenyl, 4-fluorophenyl, 2-chlorophenyl, 3-methylphenyl, 3-methoxyphenyl, pyridin-3-yl, trifluoromethyl, bromine, cyano, oxo, (1S,2R)-2-aminocyclohexyl, (1S,2S)-2-aminocyclohexyl, piperazin-1-yl, 2-oxopyrrolidin-1-yl, 2-thienyl, 3-chlorophenyl, 3-fluorophenyl, 2-methoxyphenyl, 4,5-dimethyl-1,3-thiazol-2-yl, 2,6-dimethylphenyl, isopropyl, cyclobutyl, 3-thienyl, tetrahydrofuran-3-yl, 3-furyl, cyclopentyl, fluoromethyl, 5-methylisoxazol-3-yl, 2-furyl, 4-methyl-1,3-thiazol-2-yl, 2-methyl-1,3-thiazol-4-yl, 2-methylphenyl, 3,5-dimethyl-1H-pyrazol-4-yl, morpholin-4-yl, 3,5-dimethylisoxazol-4-yl, 2-fluoropyridin-3-yl, pyridin-4-yl, acetyl and ethylamino.

Particular $R^1$ groups are hydrogen, cyano, methoxy, iodine, chlorine, bromine, pyridinyl, cyclopropyl, (methyl)(phenyl)pyrazolyl, (methyl)(pyridinyl)pyrazolyl, trimethylsilyl, methoxyphenyl, hydroxy, methylimidazolyl, (acetylamino)phenyl, methylsulfonyl, (tertbutoxycarbonyl)pyrrolidinyl, aminopyridinyl, (tertbutoxycarbonyl)azetidinyl, (tertbutoxycarbonyl)piperidinyl, pyrrolidinylpyridinyl, acetylphenyl, hydroxyphenyl, dimethylpyrazolyl, dimethylisoxazolyl, [(dimethylamino)sulfonyl]imidazolyl, methylpyrazolyl, (aminocarbonyl)pyridinyl, methoxypyridinyl, hydroxypyridinyl, chloropyridinyl, fluoropyridinyl, aminothiazolyl, (acetylamino)pyridinyl, thiazolyl, methylisoxazolyl, imidazolyl, trimethylpyrazolyl, (tertbutoxycarbonyl)pyrazolyl, pyrazolyl, benzylpyrazolyl, azetidinyl, pyrrolidinyl, (methoxycarbonyl)pyrrolyl, imidazopyridinyl, (methoxy)(methylpyrazolyl)pyrazolopyridinyl, (amino)(methyl)pyrazolyl, imidazopyrazinyl, (tertbutyl)thiadiazolyl, (methyl)thiadiazolyl, cyclopropylthiadiazolyl, tetrahydroimidazopyridinyl, ethylthiadiazolyl, (tertbutoxycarbonyl)dihydrotriazolopyrazinyl, (acetylamino)thiazolyl, methylimidazopyridinyl, (methyl)(phenyl)imidazolyl, (fluorophenyl)(methyl)pyrazolyl, (chlorophenyl)(methyl)pyrazolyl, (tertbutylphenyl)(methyl)pyrazolyl, (fluorophenyl)(methyl)pyrazolyl, (chlorophenyl)(methyl)pyrazolyl, dimethylimidazolyl, phenylpyrazolyl, dimethylpyrazolyl, (methyl)(methylphenyl)pyrazolyl, (methoxyphenyl)(methyl)pyrazolyl, (methyl)(pyridinyl)pyrazolyl, diazaspiro[3.5]nonyl, diazaspiro[3.3]heptyl, (carboxy)(methyl)phenyl, (trifluoromethyl)pyridinyl, bromopyridinyl, cyanopyridinyl, (acetylamino)phenyl, pyrazinyl, pyridazinyl, hydroxypyridinyl, aminophenyl, indazolyl, benzimidazolyl, oxodihydrobenzimidazolyl, indolyl, methylpyridinyl, pyrimidinyl, thiadiazolyl, phenyl, morpholinyl, dimethylamino, bromobenzothienyl, dimethylpyridinyl, (acetylamino)phenyl, methyl, benzylpyrrolidinyl, (hydroxymethyl)cyclopentyl, (ethylsulfonyl)(hydroxy)phenyl, methoxyquinolinyl, (cylopropyl)(methyl)pyrazolyl, (aminocarbonyl)(ethyl)pyrazolyl, (trifluoroacetyl)azetidinyl, ethyl, cyclopentyl, (trifluoromethyl)phenyl, chlorophenyl, thienyl, cyanophenyl, fluorophenyl, methylphenyl, difluorophenyl, amino, [(methylsulfonyl)amino]phenyl, {[(aminocyclohexyl)amino]carbonyl}thienyl, (methoxycarbonyl)phenyl, (aminocarbonyl)phenyl, [(aminocarbonyl)methyl]pyrazolyl, (methoxycarbonyl)thienyl, carboxythienyl, [(aminocyclohexyl)amino]carbonylthienyl, (aminocarbonyl)thienyl, pyrrolyl, {[(trifluoroethyl)amino]carbonyl}thienyl, {[(aminoethyl)amino]carbonyl}thienyl, (piperazinylcarbonyl)thienyl, ({[(oxopyrrolidinyl)propyl]amino}carbonyl)thienyl, isothiazolyl, aminocarbonylpyrrolyl, (dimethyl)(phenyl)pyrazolyl, (ethyl)(phenyl)pyrazolyl, (cyclopropyl)(phenyl)pyrazolyl, (methyl)(thienyl)pyrazolyl, [(methoxyphenyl)sulfonylamino]pyridinyl, {[(phenylamino)carbonyl]amino}pyridinyl, [(pyridinylmethyl)methoxycarbonyl]azetidinyl, (dimethylthiazolyl)(methyl)pyrazolyl, (dimethylphenyl)(methyl)pyrazolyl, (tertbutyl)(phenyl)pyrazolyl, (isopropyl)(phenyl)pyrazolyl, (cyclobutyl)(phenyl)pyrazolyl, (methyl)(methylpyrazolyl)pyrazolyl, pyrrolidinyl, pyridinylthiadiazolyl, (methyl)(thienyl)imidazolyl, (methoxyethyl)(methyl)imidazolyl, (isopropyl)(methyl)imidazolyl, (cyclobutyl)(methyl)imidazolyl, (methyl)(tetrahydrofuranyl)imidazolyl, (furyl)(methyl)imidazolyl, (cyclopentyl)(methyl)imidazolyl, (fluoromethyl)(methyl)imidazolyl, (methyl)(methylisoxazolyl)imidazolyl, (methyl)(pyridinyl)imidazolyl, (methyl)(methylthiazolyl)imidazolyl, naphthyridinyl, quinazolinyl, {[(methylphenyl)sulfonyl]amino}pyridinyl, [(phenylsulfonyl)amino]pyridinyl, [(dimethylpyrazolyl)ethyl]triazolyl, (morpholinylethyl)triazolyl, [(dimethylisoxazolyl)ethyl]triazolyl, (fluoropyridinyl)triazolyl, pyridinylphenyl, indazolyl, [(acetylamino)methyl]phenyl, [(benzylamino)carbonyl]phenyl, (aminocarbonyl)phenyl, [(furylmethyl)amino]carbonylphenyl, {[(ethylamino)carbonyl]amino}(methoxy)phenyl, (fluoro)[(phenylamino)carbonyl]phenyl, (methoxy)[(benzylamino)sulfonyl]phenyl and (pyridinylmethyl)pyrazolyl.

Specific $R^1$ groups are hydrogen, cyano, methoxy, iodine, chlorine, bromine, pyridin-3-yl, cyclopropyl, 5-methyl-1-phenyl-1H-pyrazol-4-yl, 5 methyl-1-pyridin-2-yl-1H-pyrazol-4-yl, trimethylsilyl, 4-methoxyphenyl, hydroxy, 1-methyl-1H-imidazol-5-yl, 3-(acetylamino)phenyl, methylsulfonyl, 1-(tert-butoxycarbonyl)pyrrolidin-3-yl, 1-(tert-butoxycarbonyl)pyrrolidin-2-yl, pyridin-4-yl, 6-aminopyridin-3-yl, 2-aminopyridin-4-yl, 1-(tert-butoxycarbonyl)azetidin-3-yl, 1-(tert-butoxycarbonyl)piperidin-4-yl, 6-pyrrolidin-1-ylpyridin-3-yl, 3-acetylphenyl, 3-hydroxyphenyl, 3,5-dimethyl-1H-pyrazol-4-yl, 3,5-dimethylisoxazol-4-yl, 1-[(dimethylamino)sulfonyl]-1H-imidazol-4-yl, 1-methyl-1H-pyrazol-4-yl, 2-(aminocarbonyl)pyridin-4-yl, 6-methoxypyridin-3-yl, 6-hydroxyypyridin-3-yl, 2-chloropyridin-4-yl, 1-methyl-1H-imidazol-4-yl, 6-fluoropyridin-6-yl, 2-amino-1,3-thiazol-5-yl, 2-(acetylamino)pyridin-4-yl, 1,3-thiazol-2-yl, 5-methylisoxazol-4-yl, 1H-imidazol-4-yl, 1,3,5-trimethyl-1H-pyrazol-4-yl, 1-(tert-butoxycarbonyl)-1H-pyrazol-4-yl, 1H-pyrazol-4-yl, 1-benzyl-1H-pyrazol-4-yl, azetidin-3-yl, 2-methyl-1H-imidazol-4-yl, pyrrolidin-3-yl, 5-(methoxycarbonyl)-1H-pyrrol-3-yl, imidazo[1,2-a]pyridin-3-yl, 4-methoxy-6-(1-methyl-1H-pyrazol-4-yl)pyrazolo[1,5-a]pyridin-3-yl, 3-amino-1-methyl-1H-pyrazol-4-yl, imidazo[1,2-a]pyrazin-3-yl, 5-tertbutyl-1,3,4-thiadiazol-2-yl, 5-methyl-1,3,4-thiadiazol-2-yl, 5-cyclopropyl-1,3,4-thiadiazol-2-yl, 5,6,7,8-tetrahydroimidazo[1,2-a]pyridin-3-yl, 5-ethyl-1,3,4-thiadiazol-2-yl, 7-(tertbutoxycarbonyl)-5,6-dihydro[1,2,4]triazolo[4,3-a]pyrazin-3(8H)-yl, 2-(acetylamino)-1,3-thiazol-5-yl, 6-methylimidazo[1,2-a]pyridin-3-yl, 1-methyl-2-phenyl-1H-imidazol-5-yl, 1-(2-fluorophenyl)-5-methyl-1H-pyrazol-4-yl, 1-(4-chlorophenyl)-5-methyl-1H-pyrazol-4-yl, 7-methylimidazo[1,2-a]pyridin-3-yl, 1-(4-tertbutylphenyl)-5-methyl-1H-pyrazol-4-yl, 1-(4-fluorophenyl)-5-methyl-1H-pyrazol-4-yl, 1-(2-chlorophenyl)-5-methyl-1H-pyrazol-4-yl, 8-methylimidazo[1,2-a]pyridin-3-yl, 1,2-dimethyl-1H-imidazol-5-yl, 1-phenyl-1H-pyrazol-4-yl, 1,5-dimethyl-1H-pyrazol-4-yl, 5-methyl-1-(3-methylphenyl)-1H-pyrazol-4-yl, 1-(3-methoxyphenyl)-5-methyl-1H-pyrazol-4-yl, 5-methyl-1-pyridin-3-yl-1H-pyrazol-4-yl, 2,7-diazaspiro[3.5]non-2-yl, 2,6-diazaspiro[3.3]hept-2-yl, pyrrolidin-1-yl, 2-carboxy-3-methylphenyl, 3-(trifluoromethyl)pyridin-4-yl, 3-bromopyridin-4-yl, 6-cyanopyridin-4-yl, imidazo[1,2-a]pyridin-3-yl, 3-(acetylamino)phenyl, pyrazin-2-yl, pyridazin-3-yl, 2-hydroxypyridin-3-yl, 4-aminophenyl, 1H-indazol-5-yl, 1H-benzimidazol-5-yl, 1,3-dihydro-2-oxo-2H-benzimidazol-5-yl, 1H-indol-6-yl, 4-methylpyridin-3-yl, 2-methylpyridin-3-yl, pyrimidin-5-yl, 6-methylpyridin-3-yl, 1,2,3-thiadiazol-5-yl, phenyl, morpholin-4-yl, 2,6-diazaspiro[3.5]non-2-yl, pyridin-2-yl, dimethylamino, 5-bromo-1-benzothien-2-yl, 2,3-dimethylpyridin-4-yl, 4-(acetylamino)phenyl, methyl, 1-benzylpyrrolidin-3-yl, 1-(hydroxymethyl)cyclopentyl, 5-(ethylsulfonyl)-2-hydroxyphenyl, 4-aminopyridin-2-yl, 6-methoxyquinolin-4-yl, 3-cyclopropyl-1-methyl-1H-pyrazol-5-yl, 5-(aminocarbonyl)-1-ethyl-1H-pyrazol-4-yl, 1-(trifluoroacetyl)azetidin-3-yl, ethyl, cyclopentyl, 4-(trifluoromethyl)phenyl, 4-chlorophenyl, thien-3-yl, 4-cyanophenyl, 4-fluorophenyl, 2-methylphenyl, 2-chlorophenyl, 2-fluorophenyl, 3-chlorophenyl, 3-fluorophenyl, 3-methylphenyl, 1-methyl-1H-imidazol-5-yl, thien-2-yl, 2-methoxyphenyl, 2,4-difluorophenyl, amino, 3-aminophenyl, 3-[(methylsulfonyl)amino]phenyl, 5-({[(1S,2R)-2-aminocyclohexyl]amino}carbonyl)thien-3-yl, 4-(methoxycarbonyl)phenyl, 4-(aminocarbonyl)phenyl, 1-[(aminocarbonyl)methyl]-1H-pyrazol-4-yl, 5-(methoxycarbonyl)thien-3-yl, 5-carboxythien-3-yl, 5-{[(1S,2R)-2-aminocyclohexyl]amino}carbonylthien-3-yl, 5-(aminocarbonyl)thien-3-yl, 1H-pyrrol-3-yl, 5-[(2,2,2-trifluoroethyl)amino]carbonylthien-3-yl, 5-{[(1S,2S)-2-aminocyclohexyl]amino}carbonylthien-3-yl, 5-[(2-aminoethyl)amino]carbonylthien-3-yl, 5-(piperazin-1-ylcarbonyl)thien-3-yl, 5-({[3-(2-oxopyrrolidin-1-yl)propyl]amino}carbonyl)thien-3-yl, 3-isothiazol-4-yl, 5-(aminocarbonyl)-1H-pyrrol-3-yl, 3,5-dimethyl-1-phenyl-1H-pyrazol-4-yl, 5-ethyl-1-phenyl-1H-pyrazol-4-yl, 5-cyclopropyl-1-phenyl-1H-pyrazol-4-yl, 5-methyl-1-(2-thienyl)-1H-pyrazol-4-yl, 1-methyl-2-(2-thienyl)-1H-imidazol-5-yl, 2-[(3-methoxyphenyl)sulfonylamino]pyridin-4-yl, 1-{[(phenylamino)carbonyl]amino}pyridin-4-yl, 1-[(pyridin-3-ylmethyl)methoxycarbonyl]azetidin-3-yl, 1-(3-chlorophenyl)-5-methyl-1H-pyrazol-4-yl, 1-(3-fluorophenyl)-5-methyl-1H-pyrazol-4-yl, 1-(2-methoxyphenyl)-5-methyl-1H-pyrazol-4-yl, 1-(4,5-dimethyl-1,3-thiazol-2-yl)-5-methyl-1H-pyrazol-4-yl, 1-(2,6-dimethylphenyl)-5-methyl-1H-pyrazol-4-yl, 1-(2-fluorophenyl)-3-methyl-1H-pyrazol-4-yl, 1-(4-fluorophenyl)-3-methyl-1H-pyrazol-4-yl, 3-methyl-1-phenyl-1H-pyrazol-4-yl, 5-tert-butyl-1-phenyl-1H-pyrazol-4-yl, 5-isopropyl-1-phenyl-1H-pyrazol-4-yl, 5-cyclobutyl-1-phenyl-1H-pyrazol-4-yl, 5-methyl-1-(3-thienyl)-1H-pyrazol-4-yl, 5-methyl-1-(1-methyl-1H-pyrazol-4-yl)-1H-pyrazol-4-yl, pyrrolidin-3-yl, 5-pyridin-3-yl-1,3,4-thiadiazol-2-yl, 1-methyl-2-(3-thienyl)-1H-imidazol-5-yl, 2-(2-methoxyethyl)-1-methyl-1H-imidazol-5-yl, 2-isopropyl-1-methyl-1H-imidazol-5-yl, 2-cyclobutyl-1-methyl-1H-imidazol-5-yl, 1-methyl-2-(tetrahydrofuran-3-yl)-1H-imidazol-5-yl, 2-(3-furyl)-1-methyl-1H-imidazol-5-yl, 2-cyclopentyl-1-methyl-1H-imidazol-5-yl, 2-(fluoromethyl)-1-methyl-1H-imidazol-5-yl, 1-methyl-2-(5-methylisoxazol-3-yl)-1H-imidazol-5-yl, 2-(2-furyl)-1-methyl-1H-imidazol-5-yl, 1-methyl-2-pyridin-2-yl-1H-imidazol-5-yl, 1-methyl-2-(4-methyl-1,3-thiazol-2-yl)-1H-imidazol-5-yl, 1-methyl-2-(2-methyl-1,3-thiazol-4-yl)-1H-imidazol-5-yl, 1,5-naphthyridin-4-yl, 1,8-naphthyridin-4-yl, quinazolin-4-yl, 2-{[(2-methylphenyl)sulfonyl]amino}pyridin-4-yl, 2-[(phenylsulfonyl)amino]pyridin-4-yl, 1-[2-(3,5-dimethyl-1H-pyrazol-4-yl)ethyl]-1H-1,2,3-triazol-4-yl, 1-(2-morpholin-4-ylethyl)-1H-1,2,3-triazol-4-yl, 1-[2-(3,5-dimethylisoxazol-4-yl)ethyl]-1H-1,2,3-triazol-4-yl, 1-(2-fluoropyridin-3-yl)-1H-1,2,3-triazol-4-yl, 4-pyridin-4-ylphenyl, 1H-indazol-5-yl, 4-[(acetylamino)methyl]phenyl, 4-[(benzylamino)carbonyl]phenyl, 4-(aminocarbonyl)phenyl, 4-pyridin-2-ylphenyl, 4-[(2-furylmethyl)amino]carbonylphenyl, 4-{[(ethylamino)carbonyl]amino}-3-methoxyphenyl, 3-fluoro-4-[(phenylamino)carbonyl]phenyl, 4-methoxy-3-[(benzylamino)sulfonyl]phenyl, 1-(pyridin-2-ylmethyl)-1H-pyrazol-4-yl and 4-pyridin-3-ylphenyl.

In an embodiment $L^2$ is —O(CR$^a$R$^b$)$_d$— or —NR$^c$(C=O)—.

In an embodiment $L^2$ is —O(CR$^a$R$^b$)$_d$—. In another embodiment $L^2$ is —NR$^c$(C=O)$_b$—.

Particular $L^2$ groups are —O—, —OCH$_2$— and NH(C=O)—.

In an embodiment $L^2$ is —O—.

In an embodiment $R^2$ is $C_{1-6}$alkyl, halo$C_{1-6}$alkyl, $C_{1-6}$alkoxy, halo$C_{1-6}$alkoxy or a ring which is: $C_{6-10}$aryl, $C_{3-10}$cycloalkyl, azetidinyl, a 5, 6 or 7 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, or a 6 membered heteroaromatic ring containing 1, 2 or 3 nitrogen atoms; any of which rings being optionally substituted by one, two or three groups independently selected from R$^e$.

In an embodiment $R^2$ is methyl, tertbutoxy or a ring selected from: phenyl, piperidinyl, pyridinyl and pyrrolidinyl; any of which rings being optionally substituted by one, two or three groups independently selected from R$^e$.

In an embodiment when $R^2$ is a ring it is optionally substituted by one or two independently selected R$^e$ groups. In another embodiment the $R^1$ ring is unsubstituted or monosubstituted.

In an embodiment R$^e$ is $C_{1-6}$alkoxycarbonyl or $C_{1-6}$alkylsulfonyl.

Specific $R^e$ groups are tertbutoxycarbonyl and methylsulfonyl.

Particular $R^2$ groups are methyl, phenyl, piperidinyl, pyridinyl, (tertbutoxycarbonyl)piperidinyl, (methylsulfonyl)pyrrolidinyl and tertbutoxy.

Specific $R^2$ groups are methyl, phenyl, piperidin-3-yl, pyridin-3-yl, pyridin-2-yl, 1-(tertbutoxycarbonyl)piperidin-3-yl, pyridin-4-yl, 1-(methylsulfonyl)pyrrolidin-3-yl and tertbutoxy.

In an embodiment $L^2R^2$ is methoxy.

In an embodiment when $R^3$ is a ring it is optionally substituted by one or two independently selected groups. In another embodiment the $R^3$ ring is unsubstituted or monosubstituted.

A specific $R^3$ group is hydrogen.

In an embodiment $L^3$ is a direct bond. In another embodiment $L^3$ is —C≡C—.

In another embodiment $L^3$ is —(HC═CH)$_e$(CR$^a$R$^b$)$_d$(NR$^c$)$_c$—.

In another embodiment $L^3$ is —(HC═CH)$_e$(CH$_2$)$_d$(NH)$_c$—.

Specific $L^3$ groups are a direct bond, —NH—, —(HC═CH)(CH$_2$)NH—, —(HC═CH)—, —(HC═CH)(CH$_2$)—, —(CH$_2$)—, —(CH$_2$)$_2$ and —(C≡C)—.

In an embodiment $R^4$ is hydrogen, halogen, C$_{1-6}$alkyl, haloC$_{1-6}$alkyl, C$_{1-6}$alkoxy, haloC$_{1-6}$alkoxy, C$_{1-6}$alkoxycarbonyl or a ring which is: C$_{6-10}$aryl, C$_{6-10}$arylC$_{1-6}$alkyl, C$_{3-10}$cycloalkyl, azetidinyl, a 5, 6 or 7 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S or a 6 membered heteroaromatic ring containing 1, 2 or 3 nitrogen atoms; any of which rings being optionally substituted by one, two or three groups independently selected from $L^5$-$R^f$.

In an embodiment $R^4$ is bromine, methoxy, hydrogen, butoxycarbonyl, ethyl or a ring selected from: pyrazolyl, thienyl, pyridinyl, phenyl, furyl, morpholinyl, cyclopropyl, pyrimidinyl and dioxanyl; any of which rings being optionally substituted by one, two or three groups independently selected from $L^5$-$R^f$.

In an embodiment when $R^4$ is a ring it is optionally substituted by one or two independently selected groups. In another embodiment the $R^4$ ring is unsubstituted or monosubstituted.

In an embodiment $L^5$ is a direct bond.

In an embodiment $L^5$ is —(C═O)$_b$(NR$^c$)$_c$(C═O)$_b$(CR$^a$R$^b$)$_d$—.

In an embodiment $L^5$ is a direct bond, —(C═O)N(R$^c$)(CR$^a$R$^b$)—, —(C═O)—, —N(R$^c$)(C═O)—, —(C═O)N(R$^c$)—, —(C═O)N(R$^c$)(CR$^a$R$^d$)$_2$— or —(CR$^a$R$^b$)$_3$—.

Specific $L^5$ groups are a direct bond, —(C═O)NH(CH$_2$)—, —(C═O)—, —NH(C═O)—, —(C═O)NH—, —(C═O)NH(CH$_2$)$_2$— and —CH$_2$CHFCH$_2$—.

In an embodiment $R^f$ is hydroxy, halogen, C$_{1-6}$alkyl, haloC$_{1-6}$alkyl, C$_{1-6}$alkoxy, haloC$_{1-6}$alkoxy, amino, (C$_{1-6}$alkyl)amino, di(C$_{1-6}$alkyl)amino or a ring which is: C$_{6-10}$aryl, C$_{3-10}$cycloalkyl, azetidinyl, a 5, 6 or 7 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O, and S, not more than one heteroatom of which is O or S or a 6 membered heteroaromatic ring containing 1, 2 or 3 N atoms; any of which rings being optionally substituted by one, two or three groups independently selected from hydroxy, oxo, cyano, halogen, C$_{1-6}$alkyl, C$_{2-10}$alkenyl, haloC$_{1-6}$alkyl, hydroxy C$_{1-6}$alkyl, C$_{1-6}$alkylcarbonyl, C$_{1-6}$alkoxy, haloC$_{1-6}$alkoxy, C$_{1-6}$alkoxycarbonyl, carboxy, nitro, amino, (C$_{1-6}$alkyl)amino and di(C$_{1-6}$alkyl)amino.

In an embodiment $R^f$ is methyl, methoxy, hydroxyl, amino, dimethylamino, or a ring selected from: furyl, morpholinyl, piperazinyl, oxaazabicyclo[2.2.1]heptyl, piperidinyl, pyridinyl and phenyl, any of which rings may be optionally substituted by one, two or three groups independently selected from hydroxy, oxo, cyano, halogen, C$_{1-6}$alkyl, C$_{2-10}$alkenyl, haloC$_{1-6}$alkyl, hydroxyC$_{1-6}$alkyl, C$_{1-6}$alkylcarbonyl, C$_{1-6}$alkoxy, haloC$_{1-6}$alkoxy, C$_{1-6}$alkoxycarbonyl, carboxy, nitro, amino, (C$_{1-6}$alkyl)amino and di(C$_{1-6}$alkyl)amino.

In an embodiment when $R^f$ is a ring it is optionally substituted by one or two independently selected groups. In another embodiment the $R^f$ ring is unsubstituted or monosubstituted.

In an embodiment the optional substituents on the $R^f$ ring are selected from C$_{1-6}$alkyl and C$_{1-6}$alkoxy.

Particular optional substituents on the $R^f$ ring are methyl and methoxy.

Particular $R^f$ groups are methyl, furyl, morpholinyl, methylpiperazinyl, dimethylamino, oxaazabicyclo[2.2.1]heptyl, methoxypiperidinyl, pyridinyl, phenyl, methoxy, amino and hydroxy.

Specific $R^f$ groups are methyl, 2-furyl, morpholin-4-yl, 4-methylpiperazin-1-yl, dimethylamino, 2-oxa-5-azabicyclo[2.2.1]hept-5-yl, 4-methoxypiperidin-1-yl, pyridin-4-yl, phenyl, methoxy, amino and hydroxy.

Particular $R^4$ groups are bromine, methoxy, hydrogen, methylpyrazolyl, methylthienyl, pyridinyl, phenyl, {[(furylmethyl)amino]carbonyl}phenyl, (morpholinylcarbonyl)phenyl, morpholinylpyridinyl, (methylpiperazinyl)pyridinyl, (dimethylamino)pyridinyl, furyl, [(morpholinylcarbonyl)amino]phenyl, (oxaazabicyclo[2.2.1]heptylcarbonyl)phenyl, [(methoxypiperidinyl)carbonyl]phenyl, pyridinylphenyl, [(phenylamino)carbonyl]phenyl, {[(methoxyethyl)amino]carbonyl}phenyl, aminopyridinyl, hydroxypyridinyl, morpholinyl, (fluoropropanol)pyrazolyl, cyclopropyl, pyrazolyl, pyrimidinyl, tert-butoxycarbonyl, ethyl, fluorophenyl, hydroxydimethyldioxanyl and aminopyrimidinyl.

Specific $R^4$ groups are bromine, methoxy, hydrogen, 1-methyl-1H-pyrazol-4-yl, 4-methylthien-3-yl, pyridin-4-yl, phenyl, 4-{[(2-furylmethyl)amino]carbonyl}phenyl, 4-(morpholin-4-ylcarbonyl)phenyl, 6-morpholin-4-ylpyridin-3-yl, 2-(4-methylpiperazin-1-yl)pyridin-4-yl, 6-(dimethylamino)pyridin-3-yl, 3-furyl, 4-[(morpholin-4-ylcarbonyl)amino]phenyl, 4-(2-oxa-5-azabicyclo[2.2.1]hept-5-ylcarbony)phenyl, 4-[(4-methoxypiperidin-1-yl)carbonyl]phenyl, 4-pyridin-4-ylphenyl, 4-[(phenylamino)carbonyl]phenyl, 4-{[(2-methoxyethyl)amino]carbonyl}phenyl, 6-aminopyridin-3-yl, 6-hydroxypyridin-3-yl, morpholin-4-yl, 1-(2-fluoropropan-3-ol)-1H-pyrazol-4-yl, cyclopropyl, 1H-pyrazol-5-yl, pyridin-3-yl, pyrimidin-5-yl, tert-butoxycarbonyl, ethyl, 4-fluorophenyl, 5-hydroxy-2,2-dimethyl-1,3-dioxan-5-yl and 2-aminopyrimidin-5-yl.

In an embodiment $L^3R^4$ is a 5 membered heteroaromatic ring containing 1, 2, 3 or 4 heteroatoms independently selected from N, O and S, not more than one heteroatom of which is O or S or a 6 membered heteroaromatic ring containing 1, 2 or 3 nitrogen atoms; any of which rings being optionally substituted by one, two or three groups independently selected from $L^5$-$R^f$.

In an embodiment $L^3R^4$ is 1-methyl-1H-pyrazol-4-yl.

In an embodiment $R^5$ is hydrogen, C$_{1-6}$alkyl or amino.

Particular $R^5$ groups are amino, hydrogen and methyl.

In an embodiment each of $R^3$ and $R^5$ is hydrogen.

In an embodiment each of $R^3$ and $R^5$ is hydrogen and $L^2R^2$ is methoxy.

In an embodiment:

$R^1$ is hydrogen, cyano, methoxy, iodine, chlorine, bromine, trimethylsilyl, hydroxy, methylsulfonyl, dimethylamino, methyl, ethyl, amino or a ring selected from: pyridinyl, cyclopropyl, pyrazolyl, phenyl, imidazolyl, pyrrolidinyl, azetidinyl, piperidinyl, isoxazolyl, thiazolyl, pyrrolyl, imidazopyridinyl, pyrazolopyridinyl, imidazopyrazinyl, thiadiazolyl, tetrahydroimidazopyridinyl, dihydrotriazolopyrazinyl, diazaspiro[3.5]nonyl, diazaspiro[3.3]heptyl, pyrazinyl, pyridazinyl, indazolyl, benzimidazolyl, dihydrobenzimidazolyl, indolyl, pyrimidinyl, morpholinyl, benzothienyl, cyclopentyl, quinolinyl, thienyl, isothiazolyl, naphthyridinyl, quinazolinyl and triazolyl; any of which rings being optionally substituted by one, two or three groups independently selected from $L^4$-$R^d$;

$R^2$ is methyl, tertbutoxy or a ring selected from: phenyl, piperidinyl, pyridinyl and pyrrolidinyl; any of which rings being optionally substituted by one, two or three groups independently selected from $R^e$;

$R^3$ is hydrogen;

$R^4$ is bromine, methoxy, hydrogen, butoxycarbonyl, ethyl or a ring selected from: pyrazolyl, thienyl, pyridinyl, phenyl, furyl, morpholinyl, cyclopropyl, pyrimidinyl and dioxanyl; any of which rings being optionally substituted by one, two or three groups independently selected from $L^5$-$R^f$; and $R^5$ is hydrogen, $C_{1-6}$alkyl or amino.

In another embodiment:

$R^1$ is hydrogen, cyano, methoxy, iodine, chlorine, bromine, trimethylsilyl, hydroxy, methylsulfonyl, dimethylamino, methyl, ethyl, amino or a ring selected from: pyridinyl, cyclopropyl, pyrazolyl, phenyl, imidazolyl, pyrrolidinyl, azetidinyl, piperidinyl, isoxazolyl, thiazolyl, pyrrolyl, imidazopyridinyl, pyrazolopyridinyl, imidazopyrazinyl, thiadiazolyl, tetrahydroimidazopyridinyl, dihydrotriazolopyrazinyl, diazaspiro[3.5]nonyl, diazaspiro[3.3]heptyl, pyrazinyl, pyridazinyl, indazolyl, benzimidazolyl, dihydrobenzimidazolyl, indolyl, pyrimidinyl, morpholinyl, benzothienyl, cyclopentyl, quinolinyl, thienyl, isothiazolyl, naphthyridinyl, quinazolinyl and triazolyl; any of which rings being optionally substituted by one, two or three groups independently selected from $L^4$-$R^d$; and $R^4$ is bromine, methoxy, hydrogen, butoxycarbonyl, ethyl or a ring selected from: pyrazolyl, thienyl, pyridinyl, phenyl, furyl, morpholinyl, cyclopropyl, pyrimidinyl and dioxanyl; any of which rings being optionally substituted by one, two or three groups independently selected from $L^5$-$R^f$.

In an embodiment each one of $R^a$ and $R^b$ is independently selected from hydrogen, halogen, hydroxy and $C_{1-6}$alkyl.

In another embodiment each one of $R^a$ and $R^b$ is independently selected from hydrogen, methyl, fluorine and hydroxy. In another embodiment each one of $R^a$ and $R^b$ is hydrogen.

In an embodiment each $R^c$ is independently selected from hydrogen and methyl.

In an embodiment each $R^x$ is independently selected from hydrogen and methyl.

The present invention also provides compounds of formula II:

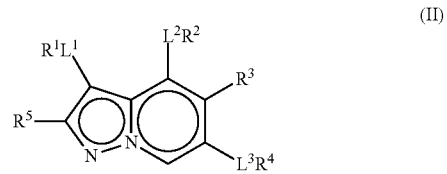

(II)

wherein:
$L^1$, $L^2$, $L^3$, $R^1$, $R^2$, $R^3$, $R^4$ and $R^5$ are as defined above;
or a pharmaceutically acceptable salt, stereoisomer or tautomer thereof.

The present invention also provides compounds of formula III:

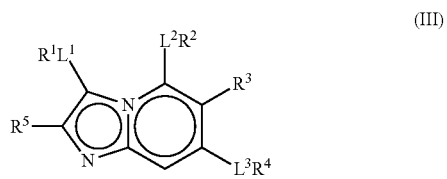

(III)

wherein:
$L^1$, $L^2$, $L^3$, $R^1$, $R^2$, $R^3$, $R^4$ and $R^5$ are as defined above;
or a pharmaceutically acceptable salt, stereoisomer or tautomer thereof.

The present invention also provides compounds of formula IV:

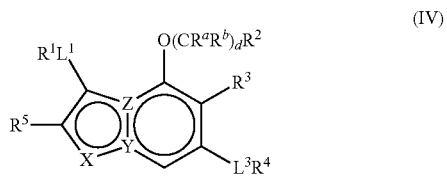

(IV)

wherein:
d, $L^1$, $L^3$, $R^1$, $R^2$, $R^3$, $R^4$, $R^5$, $R^a$, $R^b$, X, Y and Z are as defined above;
or a pharmaceutically acceptable salt, stereoisomer or tautomer thereof.

The present invention also provides compounds of formula V:

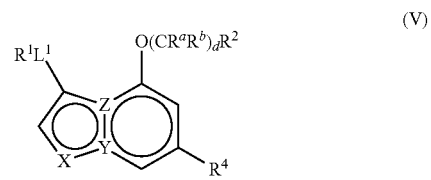

(V)

wherein:
$R^4$ is a 5 membered heteroaromatic ring containing 1, 2, 3 or 4 heteroatoms independently selected from N, O and S, not more than one heteroatom of which is O or S or a 6 membered heteroaromatic ring containing 1, 2 or 3 nitrogen atoms; any of which rings being optionally substituted by one, two or three groups independently selected from $L^5$-$R^f$;
d, $L^1$, $L^5$, $R^1$, $R^2$, $R^a$, $R^b$, $R^f$, X, Y and Z are as defined above;

or a pharmaceutically acceptable stereoisomer or tautomer thereof.

The present invention also provides compounds of formula VI:

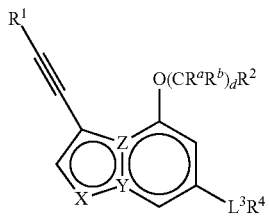
(VI)

wherein:

$d, L^3, R^1, R^2, R^4, R^a, R^b, X, Y$ and $Z$ are as defined above;

or a pharmaceutically acceptable salt, stereoisomer or tautomer thereof.

The present invention also provides compounds of formula VII:

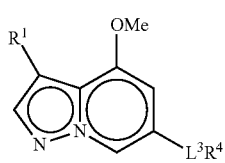
(VII)

wherein:

$L^3, R^1$ and $R^4$ are as defined above;

or a pharmaceutically acceptable salt, stereoisomer or tautomer thereof.

The present invention also provides compounds of formula VIII:

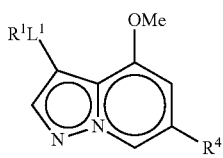
(VIII)

wherein:

$L^1$ is $-(C\equiv C)_a(C=O)_b(NR^c)_c(CR^aR^b)_d(NR^c)_c(C=O)_b$;

$R^4$ is a 5 membered heteroaromatic ring containing 1, 2, 3 or 4 heteroatoms independently selected from N, O and S, not more than one heteroatom of which is O or S or a 6 membered heteroaromatic ring containing 1, 2 or 3 nitrogen atoms; any of which rings being optionally substituted by one, two or three groups independently selected from $L^5$-$R^f$;

$a, b, c, d, L^5, R^1, R^a, R^b, R^e$ and $R^f$ are as defined above;

or a pharmaceutically acceptable salt, stereoisomer or tautomer thereof.

The present invention also provides compounds of formula IX:

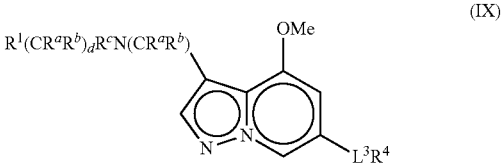
(IX)

wherein:

$d, L^3, R^1, R^4, R^a, R^b$ and $R^c$ are as defined above;

or a pharmaceutically acceptable salt, stereoisomer or tautomer thereof.

The present invention also provides compounds of formula X:

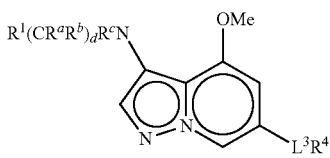
(X)

wherein:

$d, L^3, R^1, R^4, R^a, R^b$ and $R^c$ are as defined above;

or a pharmaceutically acceptable salt, stereoisomer or tautomer thereof.

The present invention also provides compounds of formula XI:

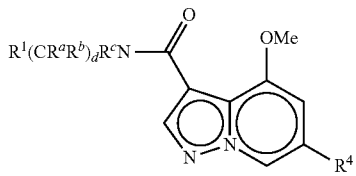
(XI)

wherein:

$d, R^1, R^4, R^a, R^b$ and $R^c$ are as defined above;

or a pharmaceutically acceptable salt, stereoisomer or tautomer thereof.

The present invention also provides compounds of formula XII:

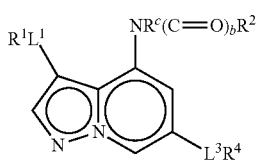
(XII)

wherein:

$b, L^1, L^3, R^1, R^2, R^4$ and $R^c$ are as defined above;

or a pharmaceutically acceptable salt, stereoisomer or tautomer thereof.

The present invention also provides compounds of formula XIII:

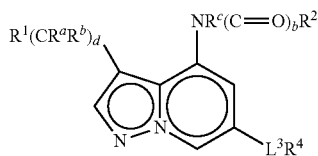

(XIII)

wherein:

b, d, $L^3$, $R^1$, $R^2$, $R^4$, $R^a$, $R^b$ and $R^c$ are as defined above;

or a pharmaceutically acceptable salt, stereoisomer or tautomer thereof.

The present invention also provides compounds of formula XIV:

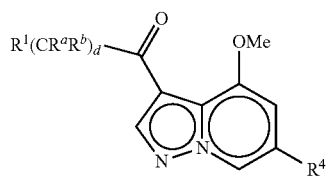

(XIV)

wherein:

d, $R^1$, $R^4$, $R^a$ and $R^b$ are as defined above;

or a pharmaceutically acceptable salt, stereoisomer or tautomer thereof.

The present invention also provides compounds of formula XV:

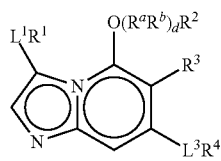

(XV)

wherein:

d, $L^1$, $L^3$, $R^1$, $R^2$, $R^3$, $R^4$, $R^a$ and $R^b$ are as defined above;

or a pharmaceutically acceptable salt, stereoisomer or tautomer thereof.

The present invention also provides compounds of formula XVI:

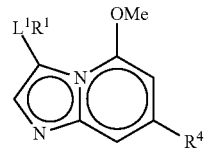

(XVI)

wherein:

$L^1$, $R^1$ and $R^4$ are as defined above;

or a pharmaceutically acceptable salt, stereoisomer or tautomer thereof.

The preferred identities with reference to formulae II, III, IV, V, VI, VII, VIII, IX, X, XI, XII, XIII, XIV, XV and XVI are as defined previously for formula I mutatis mutandis.

The present invention also includes within its scope N-oxides of the compounds of formula I above. In general, such N-oxides may be formed on any available nitrogen atom. The N-oxides may be formed by conventional means, such as reating the compound of formula I with oxone in the presence of wet alumina.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula I and salts thereof, for example, hydrates.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted. If the ring system is bicyclic, it is intended that the bond be attached to any of the suitable atoms on either ring of the bicyclic moiety.

The compounds may exist in different isomeric forms, all of which are encompassed by the present invention.

The compounds may exist in a number of different polymorphic forms.

When any variable (e.g. $R^2$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

In an embodiment one or more hydrogen atoms in the compounds of the present invention may be replaced by Deuterium.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" should be taken to be equivalent to the phrase "unsubstituted or substituted with one or more substituents" and in such cases the preferred embodiment will have from zero to three substituents. More particularly, there are zero to two substituents. A substituent on a saturated, partially saturated or unsaturated heterocycle can be attached at any substitutable position.

As used herein, "alkyl" is intended to include both branched, straight-chain and cyclic saturated aliphatic hydrocarbon groups having the specified number of carbon atoms. For example, "$C_{1-6}$alkyl" is defined to include groups having 1, 2, 3, 4, 5 or 6 carbons in a linear, branched or cyclic arrangement. For example, "$C_{1-6}$alkyl" specifically includes methyl, ethyl, n-propyl, i-propyl, n-butyl, t-butyl, i-butyl, pentyl, hexyl, cyclopropyl, cyclobutyl, cyclopentyl and cyclohexyl, cyclopropylmethyl, cyclobutylmethyl and so on. Preferred alkyl groups are methyl ethyl and cycloalkylmethyl, especially methyl and ethyl. The term "cycloalkyl" means a monocyclic, bicyclic or polycyclic saturated aliphatic hydrocarbon group having the specified number of carbon atoms. For example, "$C_{3-10}$cycloalkyl" is defined to include groups having 3, 4, 5, 6, 7, 8, 9 or 10 carbons and includes cyclopropyl, cyclopropylmethyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl, 7,7-dimethylbicyclo[2.2.1]heptyl and so on. Preferred cycloalkyl groups are cyclopropyl, cyclopropylmethyl, cyclobutyl, cyclopentyl and cyclohexyl.

As used herein, the term "$C_{2-6}$alkenyl" refers to a non-aromatic hydrocarbon radical, straight or branched, containing from 2 to 6 carbon atoms and at least one carbon to carbon double bond. Preferably one carbon to carbon double bond is present, and up to four non-aromatic carbon-carbon double bonds may be present. Alkenyl groups include ethenyl, propenyl, butenyl and 2-methylbutenyl. Preferred alkenyl groups include ethenyl and propenyl.

As used herein, the term "$C_{2-6}$alkynyl" refers to a hydrocarbon radical straight or branched, containing from 2 to 6 carbon atoms and at least one carbon to carbon triple bond. Up to three carbon-carbon triple bonds may be present. Alkynyl groups include ethynyl, propynyl, butynyl, 3-methylbutynyl and so on. Preferred alkynyl groups include ethynyl and propynyl "Alkoxy" represents an alkyl group of indicated number of carbon atoms attached through an oxygen bridge. "Alkoxy" therefore encompasses the definitions of alkyl above. Examples of suitable alkoxy groups include methoxy, ethoxy, n-propoxy, i-propoxy, n-butoxy, s-butoxy and t-butoxy. The preferred alkoxy groups are methoxy and ethoxy. The term '$C_{6-10}$aryloxy' can be construed analogously, and an example of this group is phenoxy.

The terms "halo$C_{1-6}$alkyl" and "halo$C_{1-6}$alkoxy" mean a $C_{1-6}$alkyl or $C_{1-6}$alkoxy group in which one or more (in particular, 1 to 3) hydrogen atoms have been replaced by halogen atoms, especially fluorine or chlorine atoms. Preferred are fluoro$C_{1-6}$alkyl and fluoro$C_{1-6}$alkoxy groups, in particular fluoro$C_{1-3}$alkyl and fluoro$C_{1-3}$alkoxy groups, for example, $CF_3$, $CHF_2$, $CH_2F$, $CH_2CH_2F$, $CH_2CHF_2$, $CH_2CF_3$, $OCF_3$, $OCHF_2$, $OCH_2F$, $OCH_2CH_2F$, $OCH_2CHF_2$ or $OCH_2CF_3$, and most especially $CF_3$, $OCF_3$ and $OCHF_2$.

As used herein, the term "hydroxy$C_{1-6}$alkyl" means a $C_{1-6}$alkyl group in which one or more (in particular, 1 to 3) hydrogen atoms have been replaced by hydroxy groups. Preferred are $CH_2OH$, $CH_2CHOH$ and $CHOHCH_3$.

The term "$C_{1-6}$alkylcarbonyl" or "$C_{1-6}$alkoxycarbonyl" denotes a $C_{1-6}$alkyl or $C_{1-6}$alkoxy radical, respectively, attached via a carbonyl (C=O) radical. Suitable examples of $C_{1-6}$alkylcarbonyl groups include methylcarbonyl, ethylcarbonyl, propylcarbonyl, isopropylcarbonyl and tert-butylcarbonyl. Examples of $C_{1-6}$alkoxycarbonyl include methoxycarbonyl, ethoxycarbonyl, propoxycarbonyl, isopropoxycarbonyl and tert-butoxycarbonyl. The term '$C_{6-10}$arylcarbonyl' can be construed analogously, and an example of this group is benzoyl.

The rings present in the compounds of this invention may be monocyclic or multicyclic, particularly bicyclic. The multicyclic rings may be fused or spiro linked.

As used herein, "$C_{6-10}$aryl" is intended to mean any stable monocyclic or bicyclic carbon ring of 6 to 10 atoms, wherein at least one ring is aromatic. Examples of such aryl elements include phenyl, naphthyl, tetrahydronaphthyl, indanyl and tetrahydrobenzo[7]annulene. The preferred aryl group is phenyl or naphthyl, especially phenyl.

7-15 membered heterocycles include 7, 8, 9, 10, 11, 12, 13, 14 and 15 membered heterocycles.

Examples of particular heterocycles of this invention are benzimidazolyl, benzofurandionyl, benzofuranyl, benzofurazanyl, benzopyrazolyl, benzotriazolyl, benzothienyl, benzoxazolyl, benzoxazolonyl, benzothiazolyl, benzothiadiazolyl, benzodioxolyl, benzoxadiazolyl, benzoisoxazolyl, benzoisothiazolyl, chromenyl, chromanyl, isochromanyl, carbazolyl, carbolinyl, cinnolinyl, epoxidyl, furyl, furazanyl, imidazolyl, indolinyl, indolyl, indolizinyl, indolinyl, isoindolinyl, indazolyl, isobenzofuranyl, isoindolyl, isoquinolyl, isothiazolyl, isoxazolyl, naphthpyridinyl, oxadiazolyl, oxazolyl, oxazolinyl, isoxazolinyl, oxetanyl, purinyl, pyranyl, pyrazinyl, pyrazolyl, pyridazinyl, pyridopyridinyl, pyridazinyl, pyridinyl, pyrimidinyl, triazinyl, tetrazinyl, pyrrolyl, quinazolinyl, quinolinyl, quinoxalinyl, quinolizinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidyl, pyridin-2-onyl, pyrrolidinyl, imidazolinyl, imidazolidinyl, pyrazolinyl, pyrrolinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydroisoquinolinyl, dihydrotetrazolyl, dihydrothiadiazolyl, dihydrothiazolyl, dihydrothienyl, dihydrotriazolyl, dihydroazetidinyl, dihydroisochromenyl, dihydrochromenyl, dihydroimidazolonyl, dihydrotriazolonyl, dihydrobenzodioxinyl, dihydrothiazolopyrimidinyl, dihydroimidazopyrazinyl, methylenedioxybenzoyl, tetrahydrofuranyl, tetrahydrothienyl, tetrahydroquinolinyl, thiazolidinonyl, imidazolonyl, isoindolinonyl, octahydroquinolizinyl, octahydroisoindolyl, imidazopyridinyl, azabicycloheptanyl, chromenonyl, triazolopyrimidinyl, dihydrobenzoxazinyl, thiazolotriazolyl, azoniabicycloheptanyl, azoniabicyclooctanyl, phthalazinyl, naphthyridinyl, quinazolinyl, pteridinyl, dihydroquinazolinyl, dihydrophthalazinyl, benzisoxazolyl, tetrahydronaphthyridinyl, dibenzo[b,d]furanyl, dihydrobenzothiazolyl, imidazothiazolyl, tetrahydroindazolyl, tetrahydrobenzothienyl, hexahydronaphthyridinyl, tetrahydroimidazopyridinyl, tetrahydroimidazopyrazinyl, pyrrolopyridinyl, azoniaspiro[5.5]undecanyl, azepanyl, octahydroindolizinyl, 1'2'-dihydrospirocyclohexane-1,3'-indolyl, azoniabicyclo[3.1.0]hexanyl, diazoniaspiro[4.4]nonanyl, hexahydropyrrolo[3,4-b]pyrrolyl, oxaazoniabicyclo[2.2.1]heptanyl, diazoniaspiro[5.5]undecanyl, diazoniaspiro[3.3]heptanyl, diazoniaspiro[3.5]nonanyl, diazoniaspiro[4.5]decanyl, octahydropyrrolo[3,4-c]pyrrolyl, octahydropyrrolo[3,4-b]pyrrolyl, octahydrocyclopenta[c]pyrrolyl, dihydroindolyl, azoniaspiro[4.5]decanyl, diazoniabicyclo[2.2.2]octanyl, diazoniabicyclo[2.2.1]heptanyl, diazoniabicyclo[3.2.1]octanyl, diazoniabicyclo[2.2.1]heptanyl, azoniabicyclo[3.1.0]hexanyl, tetrahydrothiophenyl, oxaazoniaspiro[4.5]decanyl, oxazepanyl and N-oxides thereof. Attachment of a heterocyclyl substituent can occur via a carbon atom or via a heteroatom.

Preferred 5 or 6 membered saturated or partially saturated hetereocycles are pyrrolidinyl, piperidinyl, piperazinyl, morpholinyl, tetrahydrofuran, thiomorpholinyl, dihydroimidazolyl and tetrahydropyranyl.

A preferred 7 membered saturated heterocycle is diazepanyl, azepanyl and oxazepanyl.

Preferred 5 membered heteroaromatic rings are thienyl, thiazolyl, pyrazolyl, isoxazolyl, isothiazolyl, imidazolyl, thiadiazolyl, oxazolyl, oxadiazolyl, triazolyl, tetrazolyl, furyl and pyrrolyl.

Preferred 6 membered heteroaromatic rings are pyridinyl, pyrimidinyl, pyridazinyl and pyrazinyl.

Preferred 7-15 membered partially saturated or unsaturated heterocyclic rings are tetrahydroquinolinyl, quinolinyl, indolyl, imidazopyridinyl, benzothiazolyl, quinoxalinyl, benzothiadiazolyl, benzoxazolyl, dihydrobenzodioxinyl, benzotriazolyl, benzodioxolyl, dihydroisoindolyl, dihydroindolyl, tetrahydroisoquinolinyl, isoquinolinyl, benzoisothiazolyl, dihydroimidazopyrazinyl, benzothienyl, benzoxadiazolyl, thiazolotriazolyl, dihydrothiazolopyrimidinyl, dihydrobenzoxazinyl, dihydrobenzofuranyl, benzimidazolyl, benzofuranyl, dihydrobenzoxazolyl, dihydroquinazolinyl, dihydrophthalazinyl, indazolyl, benzisoxazolyl, tetrahydronaphthyridinyl, triazolopyrimidinyl, dibenzo[b,d]furanyl, naphthyridinyl, dihydroquinolinyl, dihydroisochromenyl, dihydrochromenyl, dihydrobenzothiazolyl, imidazothiazolyl, tetrahydroindazolyl, tetrahydrobenzothienyl, hexahydronaphthyridinyl, tetrahydroimidazopyridinyl, tetrahydroimidazopyrazinyl, pyrrolopyridinyl, quinazolinyl, indolizinyl, azoniaspiro[5.5]undecanyl, azepanyl, octahydroindolizinyl, 1'2'-dihydrospirocyclohexane-1,3'-indolyl, octahydroisoindolyl, azoniabicyclo[3.1.0]hexanyl, diazoniaspiro[4.4]nonanyl, hexahydropyrrolo[3,4-b]pyrrolyl, oxaazoniabicyclo[2.2.1]heptanyl, diazoniaspiro[5.5]undecanyl, diazoniaspiro[3.3]heptanyl, diazoniaspiro[3.5]nonanyl, diazoniaspiro[4.5]decanyl, octahydropyrrolo[3,4-c]pyrrolyl, octahydropyrrolo[3,4-b]pyrrolyl, octahydrocyclopenta[c]pyrrolyl, dihydroindolyl, azoniaspiro[4.5]decanyl, diazoniabicyclo[2.2.2]octanyl, diazoniabicyclo[2.2.1]heptanyl, diazoniabicyclo[3.2.1]octanyl, diazoniabicyclo[2.2.1]heptanyl, azoniabicyclo[3.1.0]hexanyl, tetrahydrothiophenyl, oxaazoniaspiro[4.5]decanyl and oxazepanyl.

As used herein, the term "halogen" refers to fluorine, chlorine, bromine and iodine, of which fluorine and chlorine are preferred.

Particular compounds within the scope of the present invention are:

Compound 1-1

6-bromo-4-methoxypyrazolo[1,5-a]pyridine

Compound 1-3

2-amino-6-bromo-4-methoxypyrazolo[1,5-a]pyridine-3-carbonitrile

Compound 1-4 methyl 6-bromo-4-methoxy-2-methylpyrazolo[1,5-a]pyridine-3-carboxylate

Compound 2-1

3-iodo-4-methoxy-6-(1-methyl-1H-pyrazol-4-yl)pyrazolo[1,5-a]pyridine

Compound 2-2

3-Chloro-4-methoxy-6-(4-methyl-3-thienyl)pyrazolo[1,5-a]pyridine

Compound 2-3

3-Chloro-4-methoxy-N-4-pyridinylpyrazolo[1,5-a]pyridin-6-amine

Compound 2-4

4-methoxy-6-(1-methyl-1H-pyrazol-4-yl)pyrazolo[1,5-a]pyridine-3-carbonitrile

Compound 2-5

4-methoxy-6-phenylpyrazolo[1,5-a]pyridine-3-carbonitrile

Compound 2-6

6-bromo-3-iodo-4-methoxypyrazolo[1,5-a]pyridine

Compound 2-7 tert-Butyl ((2E)-3-(3-chloro-4-methoxypyrazolo[1,5-a]pyridine-6-yl)-2-propen-1-yl) carbamate Compound 2-8

(2E)-3-(3-Chloro-4-methoxypyrazolo[1,5-a]pyridine-6-yl)-2-propen-1-amine

Compound 2-9

3-Chloro-6-ethyl-4-methoxypyrazolo[1,5-a]pyridine

Compound 2-10

4-methoxy-6-(1-methyl-1H-pyrazol-4-yl)pyrazolo[1,5-a]pyridine

Compound 2-11

6-bromo-4-methoxypyrazolo[1,5-a]pyridine-3-carbonitrile

Compound 2-12

3-bromo-4-methoxy-6-(1-methyl-1H-pyrazol-4-yl)pyrazolo[1,5-a]pyridine

Compound 2-13

3-chloro-4-methoxy-6-(1-methyl-1H-pyrazol-4-yl)pyrazolo[1,5-a]pyridine

Compound 2-14

4-(3-chloro-4-methoxypyrazolo[1,5-a]pyridin-6-yl)-N-(2-furylmethyl)benzamide

Compound 2-15

3-chloro-4-methoxy-6-[4-(morpholin-4-ylcarbonyl)phenyl]pyrazolo[1,5-a]pyridine

Compound 2-16

3-chloro-4-methoxy-6-(6-morpholin-4-ylpyridin-3-yl)pyrazolo[1,5-a]pyridine

Compound 2-17

3-chloro-4-methoxy-6-[2-(4-methylpiperazin-1-yl)pyridin-4-yl]pyrazolo[1,5-a]pyridine Compound 2-18

5-(3-chloro-4-methoxypyrazolo[1,5-a]pyridin-6-yl)-N,N-dimethylpyridin-2-amine

Compound 2-19

3-chloro-6-(3-furyl)-4-methoxypyrazolo[1,5-a]pyridine

Compound 2-20

N-[4-(3-chloro-4-methoxypyrazolo[1,5-a]pyridin-6-yl)phenyl]morpholine-4-carboxamide Compound 2-21

3-chloro-4-methoxy-6-[4-(2-oxa-5-azabicyclo[2.2.1]hept-5-ylcarbonyl)phenyl]pyrazolo[1,5-a]pyridine Compound 2-22

3-chloro-4-methoxy-6-{4-[(4-methoxypiperidin-1-yl)carbonyl]phenyl}pyrazolo[1,5-a]pyridine Compound 2-23

3-chloro-4-methoxy-6-(4-pyridin-4-ylphenyl)pyrazolo[1,5-a]pyridine

Compound 2-24

4-(3-chloro-4-methoxypyrazolo[1,5-a]pyridin-6-yl)-N-phenylbenzamide

Compound 2-25

4-(3-chloro-4-methoxypyrazolo[1,5-a]pyridin-6-yl)-N-(2-methoxyethyl)benzamide

Compound 2-26

5-(3-chloro-4-methoxypyrazolo[1,5-a]pyridin-6-yl)pyridin-2-amine

Compound 2-27

5-(3-chloro-4-methoxypyrazolo[1,5-a]pyridin-6-yl)pyridin-2-ol

Compound 2-28

3-iodo-4-methoxy-2-methyl-6-(1-methyl-1H-pyrazol-4-yl)pyrazolo[1,5-a]pyridine

Compound 2-29

3-chloro-4-methoxy-1-phenylpyrazolo[1,5-a]pyridin-6-amine

Compound 2-30

3-chloro-4-methoxy-6-(4-morpholinyl)pyrazolo[1,5-a]pyridine

Compound 2-31

3-chloro-6((E)-2-cyclopropylvinyl)-4-methoxypyrazolo[1,5-a]pyridine

Compound 2-32

3-chloro-4-methoxy-6((1E)-3-methoxyvinyl)-4-methoxypyrazolo[1,5-a]pyridine

Compound 2-33

3-chloro-6-(4-fluorobenzyl)-4-methoxypyrazolo[1,5-a]pyridine

Compound 2-34

5-(2-(3-chloro-4-methoxypyrazolo[1,5-a]pyridin-6-yl)ethyl)-2,2-dimethyl-1,3-dioxan-5-ol Compound 2-35

5-(3-chloro-4-methoxypyrazolo[1,5-a]pyridin-6-yl)pyrimidin-2-amine

Compound 2-36

3-chloro-4-methoxy-6-(4-methyl-3-thienyl)pyrazolo[1,5-a]pyridine

Compound 3-1

4-methoxy-6-(1-methyl-1H-pyrazol-4-yl)-3-(pyridin-3-ylethynyl)pyrazolo[1,5-a]pyridine Compound 3-2

3-(cyclopropylethynyl)-4-methoxy-6-(1-methyl-1H-pyrazol-4-yl)pyrazolo[1,5-a]pyridine Compound 3-3

3-{4-[3-(cyclopropylethynyl)-4-methoxypyrazolo[1,5-a]pyridin-6-yl]-1H-pyrazol-1-yl}-2-fluoropropan-1-ol Compound 3-4

4-methoxy-3-[(5-methyl-1-phenyl-1H-pyrazol-4-yl)ethynyl]-6-(1-methyl-1H-pyrazol-4-yl)pyrazolo[1,5-a]pyridine Compound 3-5

4-methoxy-6-(1-methyl-1H-pyrazol-4-yl)-3-[(5-methyl-1-pyridin-2-yl-1H-pyrazol-4-yl)ethynyl]pyrazolo[1,5-a]pyridine Compound 3-6

4-methoxy-6-(1-methyl-1H-pyrazol-4-yl)-3-[(3-methyl-1-pyridin-2-yl-1H-pyrazol-4-yl)ethynyl]pyrazolo[1,5-a]pyridine Compound 3-7

3-[(3,5-dimethyl-1-phenyl-1H-pyrazol-4-yl)ethynyl]-4-methoxy-6-(1-methyl-1H-pyrazol-4-yl)pyrazolo[1,5-a]pyridine Compound 3-8

3-[(5-ethyl-1-phenyl-1H-pyrazol-4-yl)ethynyl]-4-methoxy-6-(1-methyl-1H-pyrazol-4-yl)pyrazolo[1,5-a]pyridine Compound 3-9

3-[(5-cyclopropyl-1-phenyl-1H-pyrazol-4-yl)ethynyl]-4-methoxy-6-(1-methyl-1H-pyrazol-4-yl)pyrazolo[1,5-a]pyridine Compound 3-10

4-methoxy-6-(1-methyl-1H-pyrazol-4-yl)-3-{[5-methyl-1-(2-thienyl)-1H-pyrazol-4-yl]ethynyl}pyrazolo[1,5-a]pyridine Compound 3-11

4-methoxy-6-(1-methyl-1H-pyrazol-4-yl)-3-{[1-methyl-2-(2-thienyl)-1H-imidazol-5-yl]ethynyl}pyrazolo[1,5-a]pyridine Compound 3-12

3-methoxy-N-(4-{[4-methoxy-6-(1-methyl-1H-pyrazol-4-yl)pyrazolo[1,5-a]pyridin-3-yl]ethynyl}pyridin-2-yl)benzenesulfonamide Compound 3-13

N-(4-{[4-methoxy-6-(1-methyl-1H-pyrazol-4-yl)pyrazolo[1,5-a]pyridin-3-yl]ethynyl}pyridin-2-yl)-N'-phenylurea Compound 3-14 pyridin-3-ylmethyl 3-{[4-methoxy-6-(1-methyl-1H-pyrazol-4-yl)pyrazolo[1,5-a]pyridin-3-yl]ethynyl}azetidine-1-carboxylate Compound 3-23

6-bromo-3-(cyclopropylethynyl)-4-methoxypyrazolo[1,5-a]pyridine

Compound 3-24

4-methoxy-6-(1-methyl-1H-pyrazol-4-yl)-3-[(trimethylsilyl)ethynyl]pyrazolo[1,5-a]pyridine Compound 3-25

3-ethynyl-4-methoxy-6-(1-methyl-1H-pyrazol-4-yl)pyrazolo[1,5-a]pyridine

Compound 3-26

4-methoxy-3-[(4-methoxyphenyl)ethynyl]-6-(1-methyl-1H-pyrazol-4-yl)pyrazolo[1,5-a]pyridine Compound 3-27

3,6-bis(cyclopropylethynyl)-4-methoxypyrazolo[1,5-a]pyridine

Compound 3-28

3-(cyclopropylethynyl)-4-methoxy-6-phenylpyrazolo[1,5-a]pyridine

Compound 3-29

3-(cyclopropylethynyl)-4-methoxy-6-(1H-pyrazol-5-yl)pyrazolo[1,5-a]pyridine

Compound 3-30

3-(4-methoxy-6-phenylpyrazolo[1,5-a]pyridine-3-yl)prop-2-yn-1-ol

Compound 3-31

3-(4-methoxy-6-phenylpyrazolo[1,5-a]pyridine-3-yl)prop-2-ynamide

Compound 3-32

4-methoxy-3-[(4-methoxyphenyl)ethynyl]-6-phenylpyrazolo[1,5-a]pyridine

Compound 3-33

4-methoxy-6-phenyl-3-(pyridine-3-ylethynyl)pyrazolo[1,5-a]pyridine

Compound 3-34

3-(cyclopropylethynyl)-4-methoxy-6-pyridin-4-ylpyrazolo[1,5-a]pyridine

Compound 3-35

4-methoxy-3-[(1-methyl-1H-imidazol-5-yl)ethynyl]-6-(1-methyl-1H-pyrazol-4-yl)pyrazolo[1,5-a]pyridine Compound 3-36

N-(3-{[4-methoxy-6-(1-methyl-1H-pyrazol-4-yl)pyrazolo[1,5-a]pyridine-3-yl]ethynyl}phenyl)acetamide Compound 3-37

3-(cyclopropylethynyl)-4-methoxy-6-pyridin-3-ylpyrazolo[1,5-a]pyridine

Compound 3-38

3-(cyclopropylethynyl)-4-methoxy-6-pyrimidin-5-ylpyrazolo[1,5-a]pyridine

Compound 3-39

N-{4-[4-methoxy-6-(1-methyl-1H-pyrazol-4-yl)pyrazolo[1,5-a]pyridine-3-yl]but-3-yn-1-yl}methanesulfonamide Compound 3-40 tert-butyl 3-{3-[4-methoxy-6-(1-methyl-1H-pyrazol-4-yl)pyrazolo[1,5-a]pyridine-3-yl]prop-2-yn-1-yl}pyrrolidine-1-carboxylate Compound 3-41 tert-butyl 2-{3-[4-methoxy-6-(1-methyl-1H-pyrazol-4-yl)pyrazolo[1,5-a]pyridine-3-yl]prop-2-yn-1-yl}pyrrolidine-1-carboxylate Compound 3-42

4-methoxy-6-(1-methyl-1H-pyrazol-4-yl)-3-(pyridine-4-ylethynyl)pyrazolo[1,5-a]pyridine Compound 3-43

5-{[4-methoxy-6-(1-methyl-1H-pyrazol-4-yl)pyrazolo[1,5-a]pyridine-3-yl]ethynyl}pyridine-2-amine Compound 3-44

4-{[4-methoxy-6-(1-methyl-1H-pyrazol-4-yl)pyrazolo[1,5-a]pyridine-3-yl]ethynyl}pyridine-2-amine Compound 3-45 tert-butyl 3-{[4-methoxy-6-(1-methyl-1H-pyrazol-4-yl)pyrazolo[1,5-a]pyridine-3-yl]ethynyl}azetidine-1-carboxylate Compound 3-46 tert-butyl 3-{[4-methoxy-6-(1-methyl-1H-pyrazol-4-yl)pyrazolo[1,5-a]pyridine-3-yl]ethynyl}pyrrolidine-1-carboxylate Compound 3-47 tert-butyl 4-{[4-methoxy-6-(1-methyl-1H-pyrazol-4-yl)pyrazolo[1,5-a]pyridine-3-yl]ethynyl}piperidine-1-carboxylate Compound 3-48

4-methoxy-6-(1-methyl-1H-pyrazol-4-yl)-3-[(6-pyrrolidin-1-ylpyridin-3-yl)ethynyl]pyrazolo[1,5-a]pyridine Compound 3-49

1-(3-{[4-methoxy-6-(1-methyl-1H-pyrazol-4-yl)pyrazolo[1,5-a]pyridine-3-yl]ethynyl}phenyl)ethanone Compound 3-50

3-{[4-methoxy-6-(1-methyl-1H-pyrazol-4-yl)pyrazolo[1,5-a]pyridine-3-yl]ethynyl}phenol Compound 3-51

3-[(3,5-dimethyl-1H-pyrazol-4-yl)ethynyl]-4-methoxy-6-(1-methyl-1H-pyrazol-4-yl)pyrazolo[1,5-a]pyridine Compound 3-52

3-[(3,5-dimethylisoxazol-4-yl)ethynyl]-4-methoxy-6-(1-methyl-1H-pyrazol-4-yl)pyrazolo[1,5-a]pyridine Compound 3-53

4-{[4-methoxy-6-(1-methyl-1H-pyrazol-4-yl)pyrazolo[1,5-a]pyridine-3-yl]ethynyl}-N,N-dimethyl-1H-imidazole-1-sulfonamide Compound 3-54

4-methoxy-6-(1-methyl-1H-pyrazol-4-yl)-3-[(1-methyl-1H-pyrazol-4-yl)ethynyl]pyrazolo[1,5-a]pyridine Compound 3-55

4-{[4-methoxy-6-(1-methyl-1H-pyrazol-4-yl)pyrazolo[1,5-a]pyridine-3-yl]ethynyl}pyridine-2-carboxamide Compound 3-56

4-methoxy-3-[(6-methoxypyridin-3-yl)ethynyl]-6-(1-methyl-1H-pyrazol-4-yl)pyrazolo[1,5-a]pyridine Compound 3-57

5-{[4-methoxy-6-(1-methyl-1H-pyrazol-4-yl)pyrazolo[1,5-a]pyridine-3-yl]ethynyl}pyridine-2-ol Compound 3-58

3-[(2-chloropyridin-4-yl)ethynyl]-4-methoxy-6-(1-methyl-1H-pyrazol-4-yl)pyrazolo[1,5-a]pyridine Compound 3-59

4-methoxy-3-[(1-methyl-1H-imidazol-4-yl)ethynyl]-6-(1-methyl-1H-pyrazol-4-yl)pyrazolo[1,5-a]pyridine Compound 3-60

3-[(6-fluoropyridin-3-yl)ethynyl]-4-methoxy-6-(1-methyl-1H-pyrazol-4-yl)pyrazolo[1,5-a]pyridine Compound 3-61

5-{[4-methoxy-6-(1-methyl-1H-pyrazol-4-yl)pyrazolo[1,5-a]pyridine-3-yl]ethynyl}-1,3-thiazol-2-amine Compound 3-62

N-(4-{[4-methoxy-6-(1-methyl-1H-pyrazol-4-yl)pyrazolo[1,5-a]pyridin-3-yl]ethynyl}pyridin-2-yl)acetamide Compound 3-63

4-methoxy-6-(1-methyl-1H-pyrazol-4-yl)-3-(1,3-thiazol-2-ylethynyl)pyrazolo[1,5-a]pyridine Compound 3-64

4-methoxy-3-[(5-methylisoxazol-4-yl)ethynyl]-6-(1-methyl-1H-pyrazol-4-yl)pyrazolo[1,5-a]pyridine Compound 3-65

3-(1H-imidazol-4-ylethynyl)-4-methoxy-6-(1-methyl-1H-pyrazol-4-yl)pyrazolo[1,5-a]pyridine Compound 3-66

4-methoxy-6-(1-methyl-1H-pyrazol-4-yl)-3-[(1,3,5-trimethyl-1H-pyrazol-4-yl)ethynyl]pyrazolo[1,5-a]pyridine Compound 3-67 tert-butyl 4-{[4-methoxy-6-(1-methyl-1H-pyrazol-4-yl)pyrazolo[1,5-a]pyridin-3-yl]ethynyl}-1H-pyrazole-1-carboxylate Compound 3-68

4-methoxy-6-(1-methyl-1H-pyrazol-4-yl)-3-(1H-pyrazol-4-ylethynyl)pyrazolo[1,5-a]pyridine Compound 3-69

3-[(1-benzyl-1H-pyrazol-4-yl)ethynyl]-4-methoxy-6-(1-methyl-1H-pyrazol-4-yl)pyrazolo[1,5-a]pyridine Compound 3-70

3-(azetidin-3-ylethynyl)-4-methoxy-6-(1-methyl-1H-pyrazol-4-yl)pyrazolo[1,5-a]pyridine Compound 3-71

4-methoxy-3-[(2-methyl-1H-imidazol-4-yl)ethynyl]-6-(1-methyl-1H-pyrazol-4-yl)pyrazolo[1,5-a]pyridine Compound 3-72

4-methoxy-6-(1-methyl-1H-pyrazol-4-yl)-3-(pyrrolidin-3-ylethynyl)pyrazolo[1,5-a]pyridine Compound 3-73 methyl 4-{[4-methoxy-6-(1-methyl-1H-pyrazol-4-yl)pyrazolo[1,5-a]pyridin-3-yl]ethynyl}-1H-pyrrole-2-carboxylate Compound 3-74

3-{[4-methoxy-6-(1-methyl-1H-pyrazol-4-yl)pyrazolo[1,5-a]pyridin-3-yl]ethynyl}imidazo[1,2-a]pyridine Compound 3-75

3,3'-buta-1,3-diyne-1,4-diylbis[4-methoxy-6-(1-methyl-1H-pyrazol-4-yl)pyrazolo[1,5-a]pyridine]

Compound 3-76

4-{[4-methoxy-6-(1-methyl-1H-pyrazol-4-yl)pyrazolo[1,5-a]pyridin-3-yl]ethynyl}-1-methyl-1H-pyrazol-3-amine Compound 3-77

3-{[4-methoxy-6-(1-methyl-1H-pyrazol-4-yl)pyrazolo[1,5-a]pyridin-3-yl]ethynyl}imidazo[1,2-a]pyrazine Compound 3-78

3-[(5-tert-butyl-1,3,4-thiadiazol-2-yl)ethynyl]-4-methoxy-6-(1-methyl-1H-pyrazol-4-yl)pyrazolo[1,5-a]pyridine Compound 3-79

4-methoxy-6-(1-methyl-1H-pyrazol-4-yl)-3-[(5-methyl-1,3,4-thiadiazol-2-yl)ethynyl]pyrazolo[1,5-a]pyridine Compound 3-80

3-[(5-cyclopropyl-1,3,4-thiadiazol-2-yl)ethynyl]-4-methoxy-6-(1-methyl-1H-pyrazol-4-yl)pyrazolo[1,5-a]pyridine Compound 3-81

3-{[4-methoxy-6-(1-methyl-1H-pyrazol-4-yl)pyrazolo[1,5-a]pyridin-3-yl]ethynyl}-5,6,7,8-tetrahydroimidazo[1,2-a]pyridine Compound 3-82

3-[(5-ethyl-1,3,4-thiadiazol-2-yl)ethynyl]-4-methoxy-6-(1-methyl-1H-pyrazol-4-yl)pyrazolo[1,5-a]pyridine Compound 3-83 tert-butyl 3-{[4-methoxy-6-(1-methyl-1H-pyrazol-4-yl)pyrazolo[1,5-a]pyridin-3-yl]ethynyl}-5,6-dihydro[1,2,4]triazolo[4,3-a]pyrazine-7(8H)-carboxylate Compound 3-84

N-(5-{[4-methoxy-6-(1-methyl-1H-pyrazol-4-yl)pyrazolo[1,5-a]pyridin-3-yl]ethynyl}-1,3-thiazol-2-yl)acetamide Compound 3-85

3-{[4-methoxy-6-(1-methyl-1H-pyrazol-4-yl)pyrazolo[1,5-a]pyridin-3-yl]ethynyl}-6-methylimidazo[1,2-a]pyridine Compound 3-86

4-methoxy-3-[(1-methyl-2-phenyl-1H-imidazol-5-yl)ethynyl]-6-(1-methyl-1H-pyrazol-4-yl)pyrazolo[1,5-a]pyridine Compound 3-87

3-{[1-(2-fluorophenyl)-5-methyl-1H-pyrazol-4-yl]ethynyl}-4-methoxy-6-(1-methyl-1H-pyrazol-4-yl)pyrazolo[1,5-a]pyridine Compound 3-88

3-{[1-(4-chlorophenyl)-5-methyl-1H-pyrazol-4-yl]ethynyl}-4-methoxy-6-(1-methyl-1H-pyrazol-4-yl)pyrazolo[1,5-a]pyridine Compound 3-89

3-{[4-methoxy-6-(1-methyl-1H-pyrazol-4-yl)pyrazolo[1,5-a]pyridin-3-yl]ethynyl}-7-methylimidazo[1,2-a]pyridine Compound 3-90

3-{[1-(4-tert-butylphenyl)-5-methyl-1H-pyrazol-4-yl]ethynyl}-4-methoxy-6-(1-methyl-1H-pyrazol-4-yl)pyrazolo[1,5-a]pyridine Compound 3-91

3-{[1-(4-fluorophenyl)-5-methyl-1H-pyrazol-4-yl]ethynyl}-4-methoxy-6-(1-methyl-1H-pyrazol-4-yl)pyrazolo[1,5-a]pyridine Compound 3-92

3-{[1-(2-chlorophenyl)-5-methyl-1H-pyrazol-4-yl]ethynyl}-4-methoxy-6-(1-methyl-1H-pyrazol-4-yl)pyrazolo[1,5-a]pyridine Compound 3-93

3-{[4-methoxy-6-(1-methyl-1H-pyrazol-4-yl)pyrazolo[1,5-a]pyridin-3-yl]ethynyl}-8-methylimidazo[1,2-a]pyridine Compound 3-94

3-[(1,2-dimethyl-1H-imidazol-5-yl)ethynyl]-4-methoxy-6-(1-methyl-1H-pyrazol-4-yl)pyrazolo[1,5-a]pyridine Compound 3-95

4-methoxy-6-(1-methyl-1H-pyrazol-4-yl)-3-[(1-phenyl-1H-pyrazol-4-yl)ethynyl]pyrazolo[1,5-a]pyridine Compound 3-96

3-[(1,5-dimethyl-1H-pyrazol-4-yl)ethynyl]-4-methoxy-6-(1-methyl-1H-pyrazol-4-yl)pyrazolo[1,5-a]pyridine Compound 3-97

4-methoxy-3-{[5-methyl-1-(3-methylphenyl)-1H-pyrazol-4-yl]ethynyl}-6-(1-methyl-1H-pyrazol-4-yl)pyrazolo[1,5-a]pyridine Compound 3-98

4-methoxy-3-{[1-(3-methoxyphenyl)-5-methyl-1H-pyrazol-4-yl]ethynyl}-6-(1-methyl-1H-pyrazol-4-yl)pyrazolo[1,5-a]pyridine Compound 3-99

4-methoxy-6-(1-methyl-1H-pyrazol-4-yl)-3-[(5-methyl-1-pyridin-3-yl-1H-pyrazol-4-yl)ethynyl]pyrazolo[1,5-a]pyridine Compound 3-100

3-{[1-(3-chlorophenyl)-5-methyl-1H-pyrazol-4-yl]ethynyl}-4-methoxy-6-(1-methyl-1H-pyrazol-4-yl)pyrazolo[1,5-a]pyridine Compound 3-101

3-{[1-(3-fluorophenyl)-5-methyl-1H-pyrazol-4-yl]ethynyl}-4-methoxy-6-(1-methyl-1H-pyrazol-4-yl)pyrazolo[1,5-a]pyridine Compound 3-102

4-methoxy-3-{[1-(2-methoxyphenyl)-5-methyl-1H-pyrazol-4-yl]ethynyl}-6-(1-methyl-1H-pyrazol-4-yl)pyrazolo[1,5-a]pyridine Compound 3-103

3-{[1-(4,5-dimethyl-1,3-thiazol-2-yl)-5-methyl-1H-pyrazol-4-yl]ethynyl}-4-methoxy-6-(1-methyl-1H-pyrazol-4-yl)pyrazolo[1,5-a]pyridine Compound 3-104

3-{[1-(2,6-dimethylphenyl)-5-methyl-1H-pyrazol-4-yl]ethynyl}-4-methoxy-6-(1-methyl-1H-pyrazol-4-yl)pyrazolo[1,5-a]pyridine Compound 3-105

3-{[1-(2-fluorophenyl)-3-methyl-1H-pyrazol-4-yl]ethynyl}-4-methoxy-6-(1-methyl-1H-pyrazol-4-yl)pyrazolo[1,5-a]pyridine Compound 3-106

3-{[1-(4-fluorophenyl)-3-methyl-1H-pyrazol-4-yl]ethynyl}-4-methoxy-6-(1-methyl-1H-pyrazol-4-yl)pyrazolo[1,5-a]pyridine Compound 3-107

4-methoxy-3-[(3-methyl-1-phenyl-1H-pyrazol-4-yl)ethynyl]-6-(1-methyl-1H-pyrazol-4-yl)pyrazolo[1,5-a]pyridine Compound 3-108

3-[(5-tert-butyl-1-phenyl-1H-pyrazol-4-yl)ethynyl]-4-methoxy-6-(1-methyl-1H-pyrazol-4-yl)pyrazolo[1,5-a]pyridine Compound 3-109

3-[(5-isopropyl-1-phenyl-1H-pyrazol-4-yl)ethynyl]-4-methoxy-6-(1-methyl-1H-pyrazol-4-yl)pyrazolo[1,5-a]pyridine Compound 3-110

3-[(5-cyclobutyl-1-phenyl-1H-pyrazol-4-yl)ethynyl]-4-methoxy-6-(1-methyl-1H-pyrazol-4-yl)pyrazolo[1,5-a]pyridine Compound 3-111

4-methoxy-6-(1-methyl-1H-pyrazol-4-yl)-3-{[5-methyl-1-(3-thienyl)-1H-pyrazol-4-yl]ethynyl}pyrazolo[1,5-a]pyridine Compound 3-112

4-{[4-methoxy-6-(1-methyl-1H-pyrazol-4-yl)pyrazolo[1,5-a]pyridin-3-yl]ethynyl}-1',5-dimethyl-1'H-1,4'-bipyrazole Compound 3-113

4-methoxy-6-(1-methyl-1H-pyrazol-4-yl)-3-(3-pyrrolidin-3-ylprop-1-yn-1-yl)pyrazolo[1,5-a]pyridine Compound 3-114

4-methoxy-6-(1-methyl-1H-pyrazol-4-yl)-3-[(5-pyridin-3-yl-1,3,4-thiadiazol-2-yl)ethynyl]pyrazolo[1,5-a]pyridine Compound 3-115

4-methoxy-6-(1-methyl-1H-pyrazol-4-yl)-3-{[1-methyl-2-(3-thienyl)-1H-imidazol-5-yl]ethynyl}pyrazolo[1,5-a]pyridine Compound 3-116

4-methoxy-3-{[2-(2-methoxyethyl)-1-methyl-1H-imidazol-5-yl]ethynyl}-6-(1-methyl-1H-pyrazol-4-yl)pyrazolo[1,5-a]pyridine Compound 3-117

3-[(2-isopropyl-1-methyl-1H-imidazol-5-yl)ethynyl]-4-methoxy-6-(1-methyl-1H-pyrazol-4-yl)pyrazolo[1,5-a]pyridine Compound 3-118

3-[(2-cyclobutyl-1-methyl-1H-imidazol-5-yl)ethynyl]-4-methoxy-6-(1-methyl-1H-pyrazol-4-yl)pyrazolo[1,5-a]pyridine Compound 3-119

4-methoxy-6-(1-methyl-1H-pyrazol-4-yl)-3-{[1-methyl-2-(tetrahydrofuran-3-yl)-1H-imidazol-5-yl]ethynyl}pyrazolo[1,5-a]pyridine Compound 3-120

3-{[2-(3-furyl)-1-methyl-1H-imidazol-5-yl]ethynyl}-4-methoxy-6-(1-methyl-1H-pyrazol-4-yl)pyrazolo[1,5-a]pyridine Compound 3-121

3-[(2-cyclopentyl-1-methyl-1H-imidazol-5-yl)ethynyl]-4-methoxy-6-(1-methyl-1H-pyrazol-4-yl)pyrazolo[1,5-a]pyridine Compound 3-122

3-{[2-(fluoromethyl)-1-methyl-1H-imidazol-5-yl]ethynyl}-4-methoxy-6-(1-methyl-1H-pyrazol-4-yl)pyrazolo[1,5-a]pyridine Compound 3-123

4-methoxy-3-{[1-methyl-2-(5-methylisoxazol-3-yl)-1H-imidazol-5-yl]ethynyl}-6-(1-methyl-1H-pyrazol-4-yl)pyrazolo[1,5-a]pyridine Compound 3-124

3-{[2-(2-furyl)-1-methyl-1H-imidazol-5-yl]ethynyl}-4-methoxy-6-(1-methyl-1H-pyrazol-4-yl)pyrazolo[1,5-a]pyridine Compound 3-125

4-methoxy-6-(1-methyl-1H-pyrazol-4-yl)-3-[(1-methyl-2-pyridin-2-yl-1H-imidazol-5-yl)ethynyl]pyrazolo[1,5-a]pyridine Compound 3-126

4-methoxy-3-{[1-methyl-2-(4-methyl-1,3-thiazol-2-yl)-1H-imidazol-5-yl]ethynyl}-6-(1-methyl-1H-pyrazol-4-yl)pyrazolo[1,5-a]pyridine Compound 3-127

4-methoxy-3-{[1-methyl-2-(2-methyl-1,3-thiazol-4-yl)-1H-imidazol-5-yl]ethynyl}-6-(1-methyl-1H-pyrazol-4-yl)pyrazolo[1,5-a]pyridine Compound 3-128 methyl 3-{[4-methoxy-6-(1-methyl-1H-pyrazol-4-yl)pyrazolo[1,5-a]pyridin-3-yl]ethynyl}azetidine-1-carboxylate Compound 3-129 benzyl 3-{[4-methoxy-6-(1-methyl-1H-pyrazol-4-yl)pyrazolo[1,5-a]pyridin-3-yl]ethynyl}azetidine-1-carboxylate Compound 3-130 pyridin-2-ylmethyl 3-{[4-methoxy-6-(1-methyl-1H-pyrazol-4-yl)pyrazolo[1,5-a]pyridin-3-yl]ethynyl}azetidine-1-carboxylate Compound 3-131

4-{[4-methoxy-6-(1-methyl-1H-pyrazol-4-yl)pyrazolo[1,5-a]pyridin-3-yl]ethynyl}-1,5-naphthyridine Compound 3-132

4-{[4-methoxy-6-(1-methyl-1H-pyrazol-4-yl)pyrazolo[1,5-a]pyridin-3-yl]ethynyl}-1,8-naphthyridine Compound 3-133

4-{[4-methoxy-6-(1-methyl-1H-pyrazol-4-yl)pyrazolo[1,5-a]pyridin-3-yl]ethynyl}quinazoline Compound 3-134

N-(4-{[4-methoxy-6-(1-methyl-1H-pyrazol-4-yl)pyrazolo[1,5-a]pyridin-3-yl]ethynyl}pyridin-2-yl)-2-methylbenzenesulfonamide Compound 3-135

N-(4-{[4-methoxy-6-(1-methyl-1H-pyrazol-4-yl)pyrazolo[1,5-a]pyridin-3-yl]ethynyl}pyridin-2-yl)benzenesulfonamide Compound 4-1

3-(2,7-diazaspiro[3.5]non-2-ylmethyl)-4-methoxy-6-(1-methyl-1H-pyrazol-4-yl)pyrazolo[1,5-a]pyridine Compound 4-2

N-{[4-methoxy-6-(1-methyl-1H-pyrazol-4-yl)pyrazolo[1,5-a]pyridin-3-yl]methyl}pyridin-3-amine Compound 4-4

3-(2,6-diazaspiro[3.3]hept-2-ylmethyl)-4-methoxy-6-(1-methyl-1H-pyrazol-4-yl)pyrazolo[1,5-a]pyridine Compound 4-5

N-{[4-methoxy-6-(1-methyl-1H-pyrazol-4-yl)pyrazolo[1,5-a]pyridin-3-yl]methyl}-2-pyrrolidin-1-ylethanamine Compound 4-6

2-(1H-imidazol-4-yl)-N-{[4-methoxy-6-(1-methyl-1H-pyrazol-4-yl)pyrazolo[1,5-a]pyridin-3-yl]methyl}ethanamine Compound 4-7

1-cyclopropyl-N-{[4-methoxy-6-(1-methyl-1H-pyrazol-4-yl)pyrazolo[1,5-a]pyridin-3-yl]methyl}methanamine Compound 4-8

N-{[4-methoxy-6-(1-methyl-1H-pyrazol-4-yl)pyrazolo[1,5-a]pyridin-3-yl]methyl}-2-(1,3-thiazol-2-yl)ethanamine Compound 4-9

2-({[4-methoxy-6-(1-methyl-1H-pyrazol-4-yl)pyrazolo[1,5-a]pyridin-3-yl]methyl}amino)-6-methylbenzoic acid Compound 4-10

N-{[4-methoxy-6-(1-methyl-1H-pyrazol-4-yl)pyrazolo[1,5-a]pyridin-3-yl]methyl}-3-(trifluoromethyl)pyridin-4-amine Compound 4-11

3-bromo-N-{[4-methoxy-6-(1-methyl-1H-pyrazol-4-yl)pyrazolo[1,5-a]pyridin-3-yl]methyl}pyridin-4-amine Compound 4.12

5-({[4-methoxy-6-(1-methyl-1H-pyrazol-4-yl)pyrazolo[1,5-a]pyridin-3-yl]methyl}amino)pyridine-2-carbonitrile Compound 4-13

N-{[4-methoxy-6-(1-methyl-1H-pyrazol-4-yl)pyrazolo[1,5-a]pyridin-3-yl]methyl}-1,3,5-trimethyl-1H-pyrazol-4-amine Compound 4-14

2-chloro-N-{[4-methoxy-6-(1-methyl-1H-pyrazol-4-yl)pyrazolo[1,5-a]pyridin-3-yl]methyl}pyridin-4-amine Compound 4-15

N-{[4-methoxy-6-(1-methyl-1H-pyrazol-4-yl)pyrazolo[1,5-a]pyridin-3-yl]methyl}imidazo[1,2-a]pyridin-3-amine Compound 4-16

N-[3-({[4-methoxy-6-(1-methyl-1H-pyrazol-4-yl)pyrazolo[1,5-a]pyridin-3-yl]methyl}amino)phenyl]acetamide Compound 4-17

5-({[4-methoxy-6-(1-methyl-1H-pyrazol-4-yl)pyrazolo[1,5-a]pyridin-3-yl]methyl}amino)pyridin-2-ol Compound 4-18

6-methoxy-N-{[4-methoxy-6-(1-methyl-1H-pyrazol-4-yl)pyrazolo yl]methyl}pyridin-3-amine Compound 4-19

N-{[4-methoxy-6-(1-methyl-1H-pyrazol-4-yl)pyrazolo[1,5-a]pyridin-3-yl]methyl}pyrazin-2-amine Compound 4-20

N-{[4-methoxy-6-(1-methyl-1H-pyrazol-4-yl)pyrazolo[1,5-a]pyridin-3-yl]methyl}pyridazin-3-amine Compound 4-21

3-({[4-methoxy-6-(1-methyl-1H-pyrazol-4-yl)pyrazolo[1,5-a]pyridin-3-yl]methyl}amino)pyridin-2-ol Compound 4-22

N-{[4-methoxy-6-(1-methyl-1H-pyrazol-4-yl)pyrazolo[1,5-a]pyridin-3-yl]methyl}benzene-1,4-diamine Compound 4-23

N-{[4-methoxy-6-(1-methyl-1H-pyrazol-4-yl)pyrazolo[1,5-a]pyridin-3-yl]methyl}-1H-indazol-5-amine Compound 4-24

N-{[4-methoxy-6-(1-methyl-1H-pyrazol-4-yl)pyrazolo[1,5-a]pyridin-3-yl]methyl}-1H-benzimidazol-5-amine Compound 4-25

5-({[4-methoxy-6-(1-methyl-1H-pyrazol-4-yl)pyrazolo[1,5-a]pyridin-3-yl]methyl}amino)-1,3-dihydro-2H-benzimidazol-2-one Compound 4-26

N-{[4-methoxy-6-(1-methyl-1H-pyrazol-4-yl)pyrazolo[1,5-a]pyridin-3-yl]methyl}-1H-indol-6-amine Compound 4-27

N-{[4-methoxy-6-(1-methyl-1H-pyrazol-4-yl)pyrazolo[1,5-a]pyridin-3-yl]methyl}-4-methylpyridin-3-amine Compound 4-28

N-{[4-methoxy-6-(1-methyl-1H-pyrazol-4-yl)pyrazolo[1,5-a]pyridin-3-yl]methyl}-2-methylpyridin-3-amine Compound 4-29

N-{[4-methoxy-6-(1-methyl-1H-pyrazol-4-yl)pyrazolo[1,5-a]pyridin-3-yl]methyl}pyrimidin-5-amine Compound 4-30

N-{[4-methoxy-6-(1-methyl-1H-pyrazol-4-yl)pyrazolo[1,5-a]pyridin-3-yl]methyl}-6-methylpyridin-3-amine Compound 4-31

N-{[4-methoxy-6-(1-methyl-1H-pyrazol-4-yl)pyrazolo[1,5-a]pyridin-3-yl]methyl}-1,2,3-thiadiazol-5-amine Compound 5-1

N-benzyl-4-methoxy-6-(1-methyl-1H-pyrazol-4-yl)pyrazolo[1,5-a]pyridin-3-amine

Compound 5-2

4-methoxy-6-(1-methyl-1H-pyrazol-4-yl)-3-morpholin-4-ylpyrazolo[1,5-a]pyridine

Compound 5-3

3-(2,7-diazaspiro[3.5]non-2-yl)-4-methoxy-6-(1-methyl-1H-pyrazol-4-yl)pyrazolo[1,5-a]pyridine Compound 5-4

3-(2,6-diazaspiro[3.5]non-2-yl)-4-methoxy-6-(1-methyl-1H-pyrazol-4-yl)pyrazolo[1,5-a]pyridine Compound 5-5

4-methoxy-6-(1-methyl-1H-pyrazol-4-yl)-N-(2-pyridin-2-ylethyl)pyrazolo[1,5-a]pyridin-3-amine Compound 5-6

4-methoxy-6-(1-methyl-1H-pyrazol-4-yl)-N-(2-pyridin-3-ylethyl)pyrazolo[1,5-a]pyridin-3-amine Compound 5-7

4-methoxy-6-(1-methyl-1H-pyrazol-4-yl)-N-(2-pyridin-4-ylethyl)pyrazolo[1,5-a]pyridin-3-amine Compound 5-8

4-methoxy-6-(1-methyl-1H-pyrazol-4-yl)-N-(pyridin-3-ylmethyl)pyrazolo[1,5-a]pyridin-3-amine Compound 5-9

4-methoxy-6-(1-methyl-1H-pyrazol-4-yl)-N-(pyridin-4-ylmethyl)pyrazolo[1,5-a]pyridin-3-amine Compound 5-10

4-methoxy-6-(1-methyl-1H-pyrazol-4-yl)-N-(pyridin-2-ylmethyl)pyrazolo[1,5-a]pyridin-3-amine Compound 5-11

4-methoxy-6-(1-methyl-1H-pyrazol-4-yl)-N-pyridin-3-ylpyrazolo[1,5-a]pyridin-3-amine Compound 5-12

4-methoxy-6-(1-methyl-1H-pyrazol-4-yl)-N-[(1-methyl-1H-pyrazol-4-yl)methyl]pyrazolo[1,5-a]pyridin-3-amine Compound 5-13

4-methoxy-6-(1-methyl-1H-pyrazol-4-yl)-N-pyridin-4-ylpyrazolo[1,5-a]pyridin-3-amine Compound 5-14

N'-[4-methoxy-6-(1-methyl-1H-pyrazol-4-yl)pyrazolo[1,5-a]pyridin-3-yl]-N,N-dimethylpropane-1,3-diamine Compound 6-1

3-(5-bromo-1-benzothien-2-yl)-4-methoxy-6-(1-methyl-1H-pyrazol-4-yl)pyrazolo[1,5-a]pyridine Compound 6-2

3-{1-[2-(3,5-dimethyl-1H-pyrazol-4-yl)ethyl]-1H-1,2,3-triazol-4-yl}-4-methoxy-6-(1-methyl-1H-pyrazol-4-yl)pyrazolo[1,5-a]pyridine Compound 6-3

4-Methoxy-6-(1-methyl-1H-pyrazol-4-yl)-3-(1H-pyrazol-4-yl)-pyrazolo[1,5-a]pyridine Compound 6-4

4-Methoxy-6-(1-methyl-1H-pyrazol-4-yl)-3-(1-pyridin-2-ylmethyl-1H-pyrazol-4-yl)-pyrazolo[1,5-a]pyridine Compound 6-5

4-methoxy-6-(1-methyl-1H-pyrazol-4-yl)-3-[1-(2-morpholin-4-ylethyl)-1H-1,2,3-triazol-4-yl]pyrazolo[1,5-a]pyridine Compound 6-6

3-{1-[2-(3,5-dimethylisoxazol-4-yl)ethyl]-1H-1,2,3-triazol-4-yl}-4-methoxy-6-(1-methyl-1H-pyrazol-4-yl)pyrazolo[1,5-a]pyridine Compound 6-7

3-[1-(2-fluoropyridin-3-yl)-1H-1,2,3-triazol-4-yl]-4-methoxy-6-(1-methyl-1H-pyrazol-4-yl)pyrazolo[1,5-a]pyridine Compound 6-8

4-[4-methoxy-6-(1-methyl-1H-pyrazol-4-yl)pyrazolo[1,5-a]pyridin-3-yl]benzonitrile Compound 6-9

4-methoxy-6-(1-methyl-1H-pyrazol-4-yl)-3-(4-pyridin-4-ylphenyl)pyrazolo[1,5-a]pyridine Compound 6-10

5-[4-methoxy-6-(1-methyl-1H-pyrazol-4-yl)pyrazolo[1,5-a]pyridin-3-yl]-1H-indazole Compound 6-11

N-{4-[4-methoxy-6-(1-methyl-1H-pyrazol-4-yl)pyrazolo[1,5-a]pyridin-3-yl]benzyl}acetamide Compound 6-12

N-benzyl-4-[4-methoxy-6-(1-methyl-1H-pyrazol-4-yl)pyrazolo[1,5-a]pyridin-3-yl]benzamide Compound 6-13

4-[4-methoxy-6-(1-methyl-1H-pyrazol-4-yl)pyrazolo[1,5-a]pyridin-3-yl]benzamide

Compound 6-14

4-methoxy-6-(1-methyl-1H-pyrazol-4-yl)-3-(4-pyridin-2-ylphenyl)pyrazolo[1,5-a]pyridine Compound 6-15

N-(2-furylmethyl)-4-[4-methoxy-6-(1-methyl-1H-pyrazol-4-yl)pyrazolo[1,5-a]pyridin-3-yl]benzamide Compound 6-16

1-ethyl-3-{2-methoxy-4-[4-methoxy-6-(1-methyl-1H-pyrazol-4-yl)pyrazolo[1,5-a]pyridin-3-yl]phenyl}urea Compound 6-17

2-fluoro-4-[4-methoxy-6-(1-methyl-1H-pyrazol-4-yl)pyrazolo[1,5-a]pyridin-3-yl]-N-phenylbenzamide Compound 6-18

N-benzyl-2-methoxy-5-[4-methoxy-6-(1-methyl-1H-pyrazol-4-yl)pyrazolo[1,5-a]pyridin-3-yl]benzenesulfonamide Compound 6-19

4-methoxy-6-(1-methyl-1H-pyrazol-4-yl)-3-(4-pyridin-3-ylphenyl)pyrazolo[1,5-a]pyridine Compound 7-1

4-methoxy-6-(1-methyl-1H-pyrazol-4-yl)-N-pyridin-4-yl)pyrazolo[1,5-a]pyridine-3-carboxamide Compound 7-2

N-(2,3-dimethylpyridin-4-yl)-4-methoxy-6-(1-methyl-1H-pyrazol-4-yl)pyrazolo[1,5-a]pyridine-3-carboxamide Compound 7-3

N-[4-(acetylamino)phenyl]-4-methoxy-6-(1-methyl-1H-pyrazol-4-yl)pyrazolo[1,5-a]pyridine-3-carboxamide Compound 7-4

4-methoxy-6-(1-methyl-1H-pyrazol-4-yl)pyrazolo[1,5-a]pyridine-3-carboxamide

Compound 7-5

4-methoxy-6-(1-methyl-1H-pyrazol-4-yl)pyrazolo[1,5-a]pyridine-3-carboxylic acid

Compound 7-6

4-methoxy-6-(1-methyl-1H-pyrazol-4-yl)-N-[2-(1,3-thiazol-2-yl)ethyl]pyrazolo[1,5-a]pyridine-3-carboxamide Compound 7-7

4-methoxy-N-methyl-6-(1-methyl-1H-pyrazol-4-yl)pyrazolo[1,5-a]pyridine-3-carboxamide Compound 7-8

N-(cyclopropylmethyl)-4-methoxy-6-(1-methyl-1H-pyrazol-4-yl)pyrazolo[1,5-a]pyridine-3-carboxamide Compound 7-9

N-[3-(dimethylamino)propyl]-4-methoxy-6-(1-methyl-1H-pyrazol-4-yl)pyrazolo[1,5-a]pyridine-3-carboxamide Compound 7-10

4-methoxy-6-(1-methyl-1H-pyrazol-4-yl)-N-(pyridin-2-ylmethyl)pyrazolo[1,5-a]pyridine-3-carboxamide Compound 7-11

4-methoxy-6-(1-methyl-1H-pyrazol-4-yl)-N-(pyridin-3-ylmethyl)pyrazolo[1,5-a]pyridine-3-carboxamide Compound 7-12

4-methoxy-6-(1-methyl-1H-pyrazol-4-yl)-N-(pyridin-4-ylmethyl)pyrazolo[1,5-a]pyridine-3-carboxamide Compound 7-13

4-methoxy-6-(1-methyl-1H-pyrazol-4-yl)-N-(2-pyridin-2-ylethyl)pyrazolo[1,5-a]pyridine-3-carboxamide Compound 7-14

4-methoxy-6-(1-methyl-1H-pyrazol-4-yl)-N-(2-pyridin-4-ylethyl)pyrazolo[1,5-a]pyridine-3-carboxamide Compound 7-15

4-methoxy-6-(1-methyl-1H-pyrazol-4-yl)-N-pyridin-3-ylpyrazolo[1,5-a]pyridine-3-carboxamide Compound 7-16

4-methoxy-6-(1-methyl-1H-pyrazol-4-yl)-N-[3-(trifluoromethyl)pyridin-4-yl]pyrazolo[1,5-a]pyridine-3-carboxamide Compound 7-17

N-(1-benzylpyrrolidin-3-yl)-4-methoxy-6-(1-methyl-1H-pyrazol-4-yl)pyrazolo[1,5-a]pyridine-3-carboxamide Compound 7-18

N-[1-(hydroxymethyl)cyclopentyl]-4-methoxy-6-(1-methyl-1H-pyrazol-4-yl)pyrazolo[1,5-a]pyridine-3-carboxamide Compound 7-19

N-[5-(ethylsulfonyl)-2-hydroxyphenyl]-4-methoxy-6-(1-methyl-1H-pyrazol-4-yl)pyrazolo[1,5-a]pyridine-3-carboxamide Compound 7-20

N-(4-aminopyridin-2-yl)-4-methoxy-6-(1-methyl-1H-pyrazol-4-yl)pyrazolo[1,5-a]pyridine-3-carboxamide Compound 7-21

4-methoxy-N-(6-methoxyquinolin-4-yl)-6-(1-methyl-1H-pyrazol-4-yl)pyrazolo[1,5-a]pyridine-3-carboxamide Compound 7-22

4-methoxy-N,6-bis(1-methyl-1H-pyrazol-4-yl)pyrazolo[1,5-a]pyridine-3-carboxamide Compound 7-23

N-(3-cyclopropyl-1-methyl-1H-pyrazol-5-yl)-4-methoxy-6-(1-methyl-1H-pyrazol-4-yl)pyrazolo[1,5-a]pyridine-3-carboxamide Compound 7-24

N-imidazo[1,2-a]pyridin-3-yl-4-methoxy-6-(1-methyl-1H-pyrazol-4-yl)pyrazolo[1,5-a]pyridine-3-carboxamide Compound 7-25

N-[5-(aminocarbonyl)-1-ethyl-1H-pyrazol-4-yl]-4-methoxy-6-(1-methyl-1H-pyrazol-4-yl)pyrazolo[1,5-a]pyridine-3-carboxamide Compound 8-1

4-(benzyloxy)-3-bromo-6-(1-methyl-1H-pyrazol-4-yl)pyrazolo[1,5-a]pyridine

Compound 8-2

3-bromo-6-(1-methyl-1H-pyrazol-4-yl)-4-(piperidin-3-ylmethoxy)pyrazolo[1,5-a]pyridine Compound 8-3

3-(cyclopropylethynyl)-6-(1-methyl-1H-pyrazol-4-yl)-4-(pyridin-3-ylmethoxy)pyrazolo[1,5-a]pyridine Compound 8-4

3-(cyclopropylethynyl)-6-(1-methyl-1H-pyrazol-4-yl)-4-(pyridin-2-ylmethoxy)pyrazolo[1,5-a]pyridine Compound 8-5 tert-butyl 3-({[3-bromo-6-(1-methyl-1H-pyrazol-4-yl)pyrazolo[1,5-a]pyridin-4-yl]oxy}methyl)piperidine-1-carboxylate Compound 8-6

6-(1-methyl-1H-pyrazol-4-yl)-4-(pyridin-2-ylmethoxy)pyrazolo[1,5-a]pyridine

Compound 8-7

4-(benzyloxy)-3-(cyclopropylethynyl)-6-(1-methyl-1H-pyrazol-4-yl)pyrazolo[1,5-a]pyridine Compound 8-8

6-(1-methyl-1H-pyrazol-4-yl)-4-(pyridin-4-ylmethoxy)pyrazolo[1,5-a]pyridine

Compound 8-9

3-(cyclopropylethynyl)-6-(1-methyl-1H-pyrazol-4-yl)-4-(pyridin-4-ylmethoxy)pyrazolo[1,5-a]pyridine Compound 8-10 tert-butyl 3-({[6-(1-methyl-1H-pyrazol-4-yl)pyrazolo[1,5-a]pyridin-4-yl]oxy}methyl)piperidine-1-carboxylate Compound 8-11

3-bromo-6-(1-methyl-1H-pyrazol-4-yl)-4-{[1-(methylsulfonyl)piperidin-3-yl]methoxy}pyrazolo[1,5-a]pyridine Compound 8-12

3-[(1-methyl-1H-imidazol-5-yl)ethynyl]-6-(1-methyl-1H-pyrazol-4-yl)-4-(pyridin-3-ylmethoxy)pyrazolo[1,5-a]pyridine Compound 9-1 tert-butyl [6-(1-methyl-1H-pyrazol-4-yl)pyrazolo[1,5-a]pyridin-4-yl]carbamate

Compound 10-1

4-{2-[4-methoxy-6-(1-methyl-1H-pyrazol-4-yl)pyrazolo[1,5-a]pyridin-3-yl]ethyl}pyridin-2-amine Compound 10-2

1-[4-methoxy-6-(1-methyl-1H-pyrazol-4-yl)pyrazolo[1,5-a]pyridin-3-yl]-2-[1-(trifluoroacetyl)azetidin-3-yl]ethanone Compound 10-3

3-ethyl-4-methoxy-6-(1-methyl-1H-pyrazol-4-yl)pyrazolo[1,5-a]pyridine

Compound 11-1

5-(benzyloxy)-7-phenylimidazo[1,2-a]pyridine

Compound 11-2

5-(benzyloxy)-3-iodo-7-phenylimidazo[1,2-a]pyridine

Compound 11-3

3-iodo-5-methoxy-7-phenylimidazo[1,2-a]pyridine

Compound 12-1

5-methoxy-7-phenyl-3-(pyridin-3-ylethynyl)imidazo[1,2-a]pyridine

Compound 12-2

3-(5-methoxy-7-phenylimidazo[1,2-a]pyridin-3-yl)prop-2-ynamide

Compound 12-3

3-(cyclopropylethynyl)-5-methoxy-7-phenylimidazo[1,2-a]pyridine

Compound 12-4

3-(5-methoxy-7-phenylimidazo[1,2-a]pyridin-3-yl)prop-2-yn-1-amine

Compound 12-5

3-(5-methoxy-7-phenylimidazo[1,2-a]pyridin-3-yl)prop-2-yn-1-ol

Compound 12-6

5-(benzyloxy)-3-(cyclopropylethynyl)-7-phenylimidazo[1,2-a]pyridine

Compound 12-7

3-(cyclopropylethynyl)-5-methoxy-7-(1-methyl-1H-pyrazol-4-yl)imidazo[1,2-a]pyridine Compound 12-8

3-(3-cyclopentylprop-1-yn-1-yl)-5-methoxy-7-phenylimidazo[1,2-a]pyridine

Compound 12-9

(2S)-4-(5-methoxy-7-phenylimidazo[1,2-a]pyridin-3-yl)but-3-yn-2-ol

Compound 12-10

(2R)-4-(5-methoxy-7-phenylimidazo[1,2-a]pyridin-3-yl)but-3-yn-2-ol

Compound 12-11

5-methoxy-3-[(4-methoxyphenyl)ethynyl]-7-phenylimidazo[1,2-a]pyridine

Compound 12-12

5-methoxy-7-phenyl-3-{[4-(trifluoromethyl)phenyl]ethynyl}imidazo[1,2-a]pyridine

Compound 12-13

3-[(4-chlorophenyl)ethynyl]-5-methoxy-7-phenylimidazo[1,2-a]pyridine

Compound 12-14

5-methoxy-7-phenyl-3-(3-thienylethynyl)imidazo[1,2-a]pyridine

Compound 12-15

4-[(5-methoxy-7-phenylimidazo[1,2-a]pyridin-3-yl)ethynyl]benzonitrile

Compound 12-16

3-[(4-fluorophenyl)ethynyl]-5-methoxy-7-phenylimidazo[1,2-a]pyridine

Compound 12-17

5-methoxy-7-phenyl-3-(phenylethynyl)imidazo[1,2-a]pyridine

Compound 12-18

5-methoxy-3-[(2-methylphenyl)ethynyl]-7-phenylimidazo[1,2-a]pyridine

Compound 12-19

3-[(2-chlorophenyl)ethynyl]-5-methoxy-7-phenylimidazo[1,2-a]pyridine

Compound 12-20

3-[(2-fluorophenyl)ethynyl]-5-methoxy-7-phenylimidazo[1,2-a]pyridine

Compound 12-21

3-[(3-chlorophenyl)ethynyl]-5-methoxy-7-phenylimidazo[1,2-a]pyridine

Compound 12-22

3-[(3-fluorophenyl)ethynyl]-5-methoxy-7-phenylimidazo[1,2-a]pyridine

Compound 12-23

5-methoxy-3-[(3-methylphenyl)ethynyl]-7-phenylimidazo[1,2-a]pyridine

Compound 12-24

5-methoxy-7-phenyl-3-(pyridin-2-ylethynyl)imidazo[1,2-a]pyridine

Compound 12-25

5-methoxy-3-[(1-methyl-1H-imidazol-5-yl)ethynyl]-7-phenylimidazo[1,2-a]pyridine

Compound 12-26

(1R)-3-(5-methoxy-7-phenylimidazo[1,2-a]pyridin-3-yl)-1-phenylprop-2-yn-1-ol

Compound 12-27

(1S)-3-(5-methoxy-7-phenylimidazo[1,2-a]pyridin-3-yl)-1-phenylprop-2-yn-1-ol

Compound 12-28

5-methoxy-7-phenyl-3-(2-thienylethynyl)imidazo[1,2-a]pyridine

Compound 12-29

5-methoxy-3-[(2-methoxyphenyl)ethynyl]-7-phenylimidazo[1,2-a]pyridine

Compound 12-30

5-methoxy-7-phenyl-3-(pyridin-4-ylethynyl)imidazo[1,2-a]pyridine

Compound 12-31

3-[(2,4-difluorophenyl)ethynyl]-5-methoxy-7-phenylimidazo[1,2-a]pyridine

Compound 12-32

1-[3-(5-methoxy-7-phenylimidazo[1,2-a]pyridin-3-yl)prop-2-yn-1-yl]urea

Compound 12-33

3-[(5-methoxy-7-phenylimidazo[1,2-a]pyridin-3-yl)ethynyl]aniline

Compound 12-34

N-{3-[(5-methoxy-7-phenylimidazo[1,2-a]pyridin-3-yl)ethynyl]phenyl}methanesulfonamide Compound 13-1

N-[(1S,2R)-2-aminocyclohexyl]-4-(5-methoxy-7-phenylimidazo[1,2-a]pyridin-3-yl)thiophene-2-carboxamide Compound 13-2 methyl 4-[5-(benzyloxy)-7-phenylimidazo[1,2-a]pyridin-3-yl]benzoate

Compound 13-3 methyl 4-(5-methoxy-7-phenylimidazo[1,2-a]pyridin-3-yl)benzoate

Compound 13-4

5-methoxy-7-phenyl-3-(1H-pyrazol-4-yl)imidazo[1,2-a]pyridine

Compound 13-5

5-methoxy-3-(1-methyl-1H-pyrazol-4-yl)-7-phenylimidazo[1,2-a]pyridine

Compound 13-6

4-(5-methoxy-7-phenylimidazo[1,2-a]pyridin-3-yl)benzamide

Compound 13-7

5-methoxy-7-phenyl-3-(3-thienyl)imidazo[1,2-a]pyridine

Compound 13-8

5-methoxy-7-phenyl-3-(2-thienyl)imidazo[1,2-a]pyridine

Compound 13-9

2-[4-(5-methoxy-7-phenylimidazo[1,2-a]pyridin-3-yl)-1H-pyrazol-1-yl]acetamide

Compound 13-10 methyl 4-(5-methoxy-7-phenylimidazo[1,2-a]pyridin-3-yl)thiophene-2-carboxylate

Compound 13-11

4-(5-methoxy-7-phenylimidazo[1,2-a]pyridin-3-yl)thiophene-2-carboxylic acid

Compound 13-12

N-[(1S,2R)-2-aminocyclohexyl]-4-(5-methoxy-7-phenylimidazo[1,2-a]pyridin-3-yl)thiophene-2-carboxamide Compound 13-13

4-(5-methoxy-7-phenylimidazo[1,2-a]pyridin-3-yl)thiophene-2-carboxamide

Compound 13-14

5-methoxy-7-phenyl-3-(1H-pyrrol-3-yl)imidazo[1,2-a]pyridine

Compound 13-15

4-(5-methoxy-7-phenylimidazo[1,2-a]pyridin-3-yl)-N-(2,2,2-trifluoroethyl)thiophene-2-carboxamide Compound 13-16

N-[(1S,2S)-2-aminocyclohexyl]-4-(5-methoxy-7-phenylimidazo[1,2-a]pyridin-3-yl)thiophene-2-carboxamide Compound 13-17

N-(2-aminoethyl)-4-(5-methoxy-7-phenylimidazo[1,2-a]pyridin-3-yl)thiophene-2-carboxamide Compound 13-18

5-methoxy-7-phenyl-3-[5-(piperazin-1-ylcarbonyl)-3-thienyl]imidazo[1,2-a]pyridine Compound 13-19

4-(5-methoxy-7-phenylimidazo[1,2-a]pyridin-3-yl)-N-[3-(2-oxopyrrolidin-1-yl)propyl]thiophene-2-carboxamide Compound 13-20

3-isothiazol-4-yl-5-methoxy-7-phenylimidazo[1,2-a]pyridine

Compound 13-21

4-(5-methoxy-7-phenylimidazo[1,2-a]pyridin-3-yl)-1H-pyrrole-2-carboxamide and pharmaceutically acceptable salts, stereoisomers and tautomers thereof.

Included in the instant invention is the free form of compounds of the instant invention, as well as the pharmaceutically acceptable salts and stereoisomers thereof. Some of the isolated specific compounds exemplified herein are the protonated salts of amine compounds. The term "free form" refers to the amine compounds in non-salt form. The encompassed pharmaceutically acceptable salts not only include the isolated salts exemplified for the specific compounds described herein, but also all the typical pharmaceutically acceptable salts of the free form of compounds of the instant invention. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The compounds of the invention can be used in a method of treatment of the human or animal body by therapy.

The compounds of the invention are for use in the treatment or prevention of one or more conditions ameliorated by inhibition of one or more of the kinases selected from PDK1, FGFR3, NTRK3, RP-S6K, WEE1 and MARK, for example those described herein.

The present invention also provides a compound of formula I for use in the manufacture of a medicament for the treatment or prevention of conditions which can be ameliorated by the inhibition of PDK1.

The present invention also provides a method for the treatment or prevention of conditions which can be ameliorated by the inhibition of PDK1, which method comprises administration to a patient in need thereof of an effective amount of a compound of formula I or a composition comprising a compound of formula I.

The present invention also provides a compound of formula I for use in the manufacture of a medicament for the treatment or prevention of conditions which can be ameliorated by the inhibition of FGFR3.

The present invention also provides a method for the treatment or prevention of conditions which can be ameliorated by the inhibition of FGFR3, which method comprises administration to a patient in need thereof of an effective amount of a compound of formula I or a composition comprising a compound of formula I.

The present invention also provides a compound of formula I for use in the manufacture of a medicament for the treatment or prevention of conditions which can be ameliorated by the inhibition of NTRK3.

The present invention also provides a method for the treatment or prevention of conditions which can be ameliorated by the inhibition of NTRK3, which method comprises administration to a patient in need thereof of an effective amount of a compound of formula I or a composition comprising a compound of formula I.

The present invention also provides a compound of formula I for use in the manufacture of a medicament for the treatment or prevention of conditions which can be ameliorated by the inhibition of RP-S6K.

The present invention also provides a method for the treatment or prevention of conditions which can be ameliorated by the inhibition of RP-S6K, which method comprises administration to a patient in need thereof of an effective amount of a compound of formula I or a composition comprising a compound of formula I.

The present invention also provides a compound of formula I for use in the manufacture of a medicament for the treatment or prevention of conditions which can be ameliorated by the inhibition of WEE1.

The present invention also provides a method for the treatment or prevention of conditions which can be ameliorated by the inhibition of WEE1, which method comprises administration to a patient in need thereof of an effective amount of a compound of formula I or a composition comprising a compound of formula I.

The present invention also provides a compound of formula I for use in the manufacture of a medicament for the treatment or prevention of conditions which can be ameliorated by the inhibition of MARK.

The present invention also provides a method for the treatment or prevention of conditions which can be ameliorated by the inhibition of MARK, which method comprises administration to a patient in need thereof of an effective amount of a compound of formula I or a composition comprising a compound of formula I.

An embodiment of the invention provides a method for inhibiting PDK1, comprising administering to the mammal a therapeutically effective amount of any of the compounds or any of the pharmaceutical compositions described herein.

An embodiment of the invention provides a method for inhibiting FGFR3, comprising administering to the mammal a therapeutically effective amount of any of the compounds or any of the pharmaceutical compositions described herein.

An embodiment of the invention provides a method for inhibiting NTRK3, comprising administering to the mammal a therapeutically effective amount of any of the compounds or any of the pharmaceutical compositions described herein.

An embodiment of the invention provides a method for inhibiting RP-S6K, comprising administering to the mammal a therapeutically effective amount of any of the compounds or any of the pharmaceutical compositions described herein.

An embodiment of the invention provides a method for inhibiting WEE1, comprising administering to the mammal a therapeutically effective amount of any of the compounds or any of the pharmaceutical compositions described herein.

An embodiment of the invention provides a method for inhibiting MARK, comprising administering to the mammal a therapeutically effective amount of any of the compounds or any of the pharmaceutical compositions described herein.

The compounds of the present invention are useful for treating or preventing myeloproliferative disorders or cancer in mammals, preferably humans.

The compounds, compositions and methods provided herein are particularly deemed useful for the treatment of myeloproliferative disorder(s). Myeloproliferative disorders that may be treated include polycythemia vera (PV), essential thrombocythemia (ET), myeloid metaplasia with myelofibrosis (MMM), chronic myelogenous leukemia (CML), myelomonocytic leukemia (CMML), hypereosinophilic syndrome (HES), juvenile myelomonocytic leukemia (JMML), and systemic mast cell disease (SMCD).

The compounds, compositions and methods provided herein are also deemed useful for the treatment of cancer. Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, and Adrenal glands: neuroblastoma. Thus, the term "cancerous cell" as provided herein, includes a cell afflicted by any one of the above-identified conditions.

Thus, the present invention provides a compound of formula I for use in the manufacture of a medicament for the treatment or prevention of cancer.

The present invention also provides a method for the treatment or prevention of cancer, which method comprises administration to a patient in need thereof of an effective amount of a compound of formula I or a composition comprising a compound of formula I.

The compounds, compositions and methods of the invention may also be useful in treating the following disease states: keloids and psoriasis.

Cancers that may be treated by the compounds, compositions and methods of the invention include, but are not limited to: breast, ovarian, prostate, colon, colorectal, lung, brain, testicular, stomach, pancrease, skin, small intestine, large intestine, throat, head and neck, oral, bone, liver, bladder, kidney, thyroid and blood.

Cancers that may be treated by the compounds, compositions and methods of the invention include: breast, prostate, colon, ovarian, colorectal and lung (non-small cell lung).

Cancers that may be treated by the compounds, compositions and methods of the invention include: breast, colon, colorectal and lung.

Cancers that may be treated by the compounds, compositions and methods of the invention include: lymphoma and leukemia.

Cancers that may be treated by the compounds, composition and methods of the invention include: ovarian, pancreatic, breast and prostate cancer.

The compounds of the instant invention are useful in the treatment of cancers associated with deregulated activity of the PTEN/PI3K pathway including, but not limited to PTEN loss of function mutations and receptor tyrosine kinase gain of function mutations. Such cancers include, but are not limited to, ovarian, pancreatic, breast and prostate cancer, as well as cancers (including glioblastoma) where the tumor suppressor PTEN is mutated. See, Feldman, Richard I., et al., "Novel Small Molecule Inhibitors of 3-Phosphoinositide-dependent Kinase-1," *The Journal of Biological Chemistry*, Vol. 280, No. 20, Issue of May 20, pp. 19867-19874, 2005.

PDK1 signaling regulates multiple critical steps in angiogenesis. See, Mora, Alfonso et al., "PDK1, the master regulator of AGC kinase signal transduction," *Seminars in Cell & Developmental Biology* 15 (2004) 161-170. The utility of angiogenesis inhibitors in the treatment of cancer is known in the literature, see J. Rak et al. *Cancer Research*, 55:4575-4580, 1995 and Dredge et al., *Expert Opin. Biol. Ther*. (2002) 2(8):953-966, for example. The role of angiogenesis in cancer has been shown in numerous types of cancer and tissues: breast carcinoma (G. Gasparini and A. L. Harris, *J. Clin. Oncol.*, 1995, 13:765-782; M. Toi et al., *Japan. J. Cancer Res.*, 1994, 85:1045-1049); bladder carcinomas (A. J. Dickinson et al., *Br. J. Urol.*, 1994, 74:762-766); colon carcinomas (L. M. Ellis et al., *Surgery*, 1996, 120(5):871-878); and oral cavity tumors (J. K. Williams et al., *Am. J. Surg.*, 1994, 168:373-380). Other cancers include, advanced tumors, hairy cell leukemia, melanoma, advanced head and neck, metastatic renal cell, non-Hodgkin's lymphoma, metastatic breast, breast adenocarcinoma, advanced melanoma, pancreatic, gastric, glioblastoma, lung, ovarian, non-small cell lung, prostate, small cell lung, renal cell carcinoma, various solid tumors, multiple myeloma, metastatic prostate, malignant glioma, renal cancer, lymphoma, refractory metastatic disease, refractory multiple myeloma, cervical cancer, Kaposi's sarcoma, recurrent anaplastic glioma, and metastatic colon cancer (Dredge et al., *Expert Opin. Biol. Ther*. (2002) 2(8): 953-966). Thus, the PDK1 inhibitors disclosed in the instant application are also useful in the treatment of these angiogenesis related cancers.

Tumors which have undergone neovascularization show an increased potential for metastasis. In fact, angiogenesis is essential for tumor growth and metastasis (S. P. Cunningham, et al., *Can. Research*, 61: 3206-3211 (2001)). The PDK1 inhibitors disclosed in the present application are therefore also useful to prevent or decrease tumor cell metastasis.

Further included within the scope of the invention is a method of treating or preventing a disease in which angiogenesis is implicated, which is comprised of administering to a mammal in need of such treatment a therapeutically effective amount of a compound of the present invention. Ocular neovascular diseases are an example of conditions where much of the resulting tissue damage can be attributed to aberrant infiltration of blood vessels in the eye (see WO 00/30651, published 2 Jun. 2000). The undesirable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration. Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Further included within the scope of the invention is a method of treating or preventing a non-malignant disease in which angiogenesis is implicated, including but not limited to: ocular diseases (such as, retinal vascularization, diabetic retinopathy and age-related macular degeneration), atherosclerosis, arthritis, psoriasis, obesity and Alzheimer's disease (Dredge et al., *Expert Opin. Biol. Ther*. (2002) 2(8):953-966). In another embodiment, a method of treating or preventing a disease in which angiogenesis is implicated includes: ocular diseases (such as, retinal vascularization, diabetic retinopathy and age-related macular degeneration), atherosclerosis, arthritis and psoriasis.

In an embodiment, the compounds of the present invention are for use in the treatment or prevention of T-cell mediated inflammatory or autoimmune diseases including but not limited to rheumatoid arthritis (RA), collagen II arthritis, multiple sclerosis (MS), systemic lupus erythematosus (SLE), psoriasis, juvenile onset diabetes, Sjogren's disease, thyroid disease, sarcoidosis, autoimmune uveitis, inflammatory bowel disease (Crohn's and ulcerative colitis), celiac disease and myasthenia gravis.

In an embodiment, the compounds of the present invention are for use in the treatment or prevention of secretary breast cancer, infant fibrosarcoma and congenital mesoblastic nephroma.

In an embodiment, the compounds of the present invention are for use in the treatment or prevention of tumor diseases, such as gliomas, sarcomas, prostate tumors, and tumors of the colon, breast, and ovary.

In an embodiment, the compounds of the present invention are for use in the treatment or prevention of cancers such as colorectal, ovarian, pancreatic, breast, renal, cervical, neuroblastoma, melanoma, lymphoma, prostate and bladder.

Further included within the scope of the invention is a method of treating hyperproliferative disorders such as restenosis, inflammation, autoimmune diseases and allergy/asthma.

Further included within the scope of the instant invention is the use of the instant compounds to coat stents and therefore the use of the instant compounds on coated stents for the treatment and/or prevention of restenosis (WO03/032809).

Further included within the scope of the instant invention is the use of the instant compounds for the treatment and/or prevention of osteoarthritis (WO03/035048).

Further included within the scope of the invention is a method of treating hypoinsulinism.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to cathepsin functioning. Still further exemplifying the invention is the use of any of the compounds described above in the preparation of a medicament for the treatment and/or prevention of hypertension.

In one embodiment of the invention, the compound of formula I is administered to a patient suffering from AD, FTDP-17, Pick's disease or frontotemporal dementia, in particular AD.

Thus, the present invention provides a compound of formula I for use in the manufacture of a medicament for the treatment or prevention of Alzheimer's disease.

The present invention also provides a method for the treatment or prevention of Alzheimer's disease, which method comprises administration to a patient in need thereof of an effective amount of a compound of formula I or a composition comprising a compound of formula I.

In an alternative embodiment of the invention, the compound of formula I is administered to a patient suffering from mild cognitive impairment or age-related cognitive decline. A favourable outcome of such treatment is prevention or delay of the onset of AD. Age-related cognitive decline and mild cognitive impairment (MCI) are conditions in which a memory deficit is present, but other diagnostic criteria for dementia are absent (Santacruz and Swagerty, *American Family Physician*, 63 (2001), 703-13). (See also "The ICD-10 Classification of Mental and Behavioural Disorders", Geneva: World Health Organisation, 1992, 64-5). As used herein, "age-related cognitive decline" implies a decline of at least six months' duration in at least one of: memory and learning; attention and concentration; thinking; language; and visuospatial functioning and a score of more than one standard deviation below the norm on standardized neuropsychologic testing such as the MMSE. In particular, there may be a progressive decline in memory. In the more severe condition MCI, the degree of memory impairment is outside the range considered normal for the age of the patient but AD is not present. The differential diagnosis of MCI and mild AD is described by Petersen et al., *Arch. Neurol.*, 56 (1999), 303-8. Further information on the differential diagnosis of MCI is provided by Knopman et al, *Mayo Clinic Proceedings*, 78 (2003), 1290-1308. In a study of elderly subjects, Tuokko et al (*Arch, Neurol.*, 60 (2003) 577-82) found that those exhibiting MCI at the outset had a three-fold increased risk of developing dementia within 5 years.

Grundman et al (*J. Mol. Neurosci.*, 19 (2002), 23-28) report that lower baseline hippocampal volume in MCI patients is a prognostic indicator for subsequent AD. Similarly, Andreasen et al (*Acta Neurol. Scand*, 107 (2003) 47-51) report that high CSF levels of total tau, high CSF levels of phospho-tau and lowered CSF levels of $A\beta42$ are all associated with increased risk of progression from MCI to AD.

Within this embodiment, the compound of formula I is advantageously administered to patients who suffer impaired memory function but do not exhibit symptoms of dementia. Such impairment of memory function typically is not attributable to systemic or cerebral disease, such as stroke or metabolic disorders caused by pituitary dysfunction. Such patients may be in particular people aged 55 or over, especially people aged 60 or over, and preferably people aged 65 or over. Such patients may have normal patterns and levels of growth hormone secretion for their age. However, such patients may possess one or more additional risk factors for developing Alzheimer's disease. Such factors include a family history of the disease; a genetic predisposition to the disease; elevated serum cholesterol; and adult-onset diabetes mellitus.

In a particular embodiment of the invention, the compound of formula I is administered to a patient suffering from age-related cognitive decline or MCI who additionally possesses one or more risk factors for developing AD selected from: a family history of the disease; a genetic predisposition to the disease; elevated serum cholesterol; adult-onset diabetes mellitus; elevated baseline hippocampal volume; elevated CSF levels of total tau; elevated CSF levels of phospho-tau; and lowered CSF levels of $A\beta(1-42)$.

A genetic predisposition (especially towards early onset AD) can arise from point mutations in one or more of a number of genes, including the APP, presenilin-1 and presenilin-2 genes. Also, subjects who are homozygous for the $\epsilon4$ isoform of the apolipoprotein E gene are at greater risk of developing AD.

The patient's degree of cognitive decline or impairment is advantageously assessed at regular intervals before, during and/or after a course of treatment in accordance with the invention, so that changes therein may be detected, e.g. the slowing or halting of cognitive decline. A variety of neuropsychological tests are known in the art for this purpose, such as the Mini-Mental State Examination (MMSE) with norms adjusted for age and education (Folstein et al., *J. Psych. Res.*, 12 (1975), 196-198, Anthony et al., *Psychological Med.*, 12 (1982), 397-408; Cockrell et al., *Psychopharmacology*, 24 (1988), 689-692; Crum et al., *J. Am. Med. Assoc'n.* 18 (1993), 2386-2391). The MMSE is a brief, quantitative measure of cognitive status in adults. It can be used to screen for cognitive decline or impairment, to estimate the severity of cognitive decline or impairment at a given point in time, to follow the course of cognitive changes in an individual over time, and to document an individual's response to treatment. Another suitable test is the Alzheimer Disease Assessment Scale (ADAS), in particular the cognitive element thereof (ADAS-cog) (See Rosen et al., *Am. J. Psychiatry*, 141 (1984), 1356-64).

The instant compounds are also useful in combination with anti-cancer agents or chemotherapeutic agents.

The compounds of this invention may be useful as chemo- and radiosensitizers for cancer treatment. They are useful for the treatment of mammals who have previously undergone or are presently undergoing treatment for cancer. Such previous treatments include prior chemotherapy, radiation therapy, surgery or immunotherapy, such as cancer vaccines.

Thus, the present invention provides a combination of a compound of formula I and an anti-cancer agent for simultaneous, separate or sequential administration.

The present invention also provides a compound of formula I for use in the manufacture of a medicament for use as an adjunct in cancer therapy or for potentiating tumor cells for treatment with ionizing radiation or chemotherapeutic agents.

The present invention also provides a method of chemotherapy or radiotherapy, which method comprises administration to a patient in need thereof of an effective amount of a compound of formula I or a composition comprising a compound of formula I in combination with ionizing radiation or chemotherapeutic agents.

In combination therapy, the compounds of this invention can be administered prior to (e.g., 5 minutes, 15 minutes, 30 minutes, 45 minutes, 1 hour, 2 hours, 4 hours, 6 hours, 12 hours, 24 hours, 48, hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the other anticancer agent to a subject in need thereof. In various embodiments the instant compounds and another anticancer agent are administered 1 minute apart, 10 minutes apart, 30 minutes apart, less than 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart, or no more than 48 hours apart.

The compounds of this invention and the other anticancer agent can act additively or synergistically. A synergistic combination of the present compounds and another anticancer agent might allow the use of lower dosages of one or both of these agents and/or less frequent dosages of one or both of the instant compounds and other anticancer agents and/or to administer the agents less frequently can reduce any toxicity associated with the administration of the agents to a subject without reducing the efficacy of the agents in the treatment of cancer. In addition, a synergistic effect might result in the improved efficacy of these agents in the treatment of cancer and/or the reduction of any adverse or unwanted side effects associated with the use of either agent alone.

Examples of cancer agents or chemotherapeutic agents for use in combination with the compounds of the present invention can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: HDAC inhibitors, estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

Examples of "HDAC inhibitors" include suberoylanilide hydroxamic acid (SAHA), LAQ824, LBH589, PXD101, MS275, FK228, valproic acid, butyric acid and CI-994.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779 and Ariad's AP23573).

An example of a hypoxia activatable compound is tirapazamine.

Examples of proteosome inhibitors include but are not limited to lactacystin, bortezomib, epoxomicin and peptide aldehydes such as MG 132, MG 115, PSI and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, dimesna, non-camptothecin topoisomerase-1 inhibitors such as indolocarbazoles; and dual topoisomerase-1 and II inhibitors such as benzophenazines, XR 20 115761MLN 576 and benzopyridoindoles.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, Nature, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example BAY-43-9006), inhibitors of MEK (for example CI-1040 and PD-098059), inhibitors of mTOR (for example Wyeth CCI-779 and Ariad's AP23573), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 μM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134,142, 5,380,738, 5,393,790, 5,466,823, 5,633,272 and 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862,5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_{v\beta3}$ integrin, to compounds which selectively antagonize, inhibit or counteract binding of a physiological ligand to the $\alpha v\beta5$ integrin, to compounds which antagonize, inhibit or counteract binding of a physiological ligand to both the $\alpha_{v\beta3}$ integrin and the $\alpha_{v\beta5}$ integrin, and to compounds which antagonize, inhibit or counteract the activity of the particular integrin(s) expressed on capillary endothelial cells. The term also refers to antagonists of the $\alpha_{v\beta6}$, $\alpha_{v\beta8}$, $\alpha_{1\beta1}$, $\alpha_{2\beta1}$, $\alpha_{5\beta1}$, $\alpha_{6\beta1}$ and $\alpha_{6\beta4}$ integrins. The term also refers to antagonists of any combination of $\alpha_{v\beta3}$, $\alpha_{v\beta5}$, $\alpha_{v\beta6}$, $\alpha_{v\beta8}$, $\alpha_{1\beta1}$, $\alpha_{2\beta1}$, $\alpha_{5\beta1}$, $\alpha_{6\beta1}$ and $\alpha_{6\beta4}$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods, for simultaneous, separate or sequential administration. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with inhibitors of Akt. Such inhibitors include compounds described in, but not limited to, the following publications: WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469.

A compound of the instant invention may also be useful for treating or preventing cancer in combination with mTor inhibitors.

A compound of the instant invention may also be useful for treating or preventing cancer in combination with cMet inhibitors.

A compound of the instant invention may also be useful for treating or preventing cancer in combination with PARP inhibitors.

A compound of the instant invention may also be useful for treating cancer in combination with the following therapeutic agents: abarelix (Plenaxis Depot®); (Actiq®); aldesleukin (Prokine®); Aldesleukin (Proleukin®); Alemtuzumab (Campath®); alfuzosin HCl (UroXatral®); alitretinoin (Panretin®); allopurinol (Zyloprim®); altretamine (Hexylen®); amifostine (Ethyol®); anastrozole (Arimidex®); (Anzemet®); (Anexsia®); aprepitant (Emend®); arsenic trioxide (Trisenox®); asparaginase (Elspar®); azacitidine (Vidaza®); bendamustine hydrochloride (Treanda®); bevacuzimab (Avastin®); bexarotene capsules (Targretin®); bexarotene gel (Targretin®); bleomycin (Blenoxane®); bortezomib (Velcade®); (Brofenac®); busulfan intravenous (Busulflex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cinacalcet (Sensipar®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); decitabine (Dacogen®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); DROMOSTANOLONE PROPIONATE (DROMOSTANOLONE®); DROMOSTANOLONE PROPIONATE (MASTERONE INJECTION®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); fentanyl citrate (Fentora®); Filgrastim (Neupogen®); floxuridine (intraarterial) (FUDR®); fludarabine (Fludara®); fluorouracil, 5-FU (Adrucil®); flutamide (Eulexin®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); granisetron (Kytril Solution®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); (Kadian®); ixabepilone (Ixempra®); lapatinib (Tykerb®); lenalidomide (Revlimid®); letrozole (Femara®); leucovorin (Wellcovorin®, Leucovorin®); Leuprolide Acetate (Eligard®); (Lupron Depot®); (Viadur®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitomycin C (Mitozytrex®); mitotane (Lysodren®); mitoxantrone (Novantrone®); nandrolone phenpropionate (Durabolin-50®); nelarabine (Arranon®); nilotinib hydrochloride monohydrate (Tasigna®); Nofetumomab (Verluma®); Oprelvekin (Neumega®); (Neupogen®); oxaliplatin (Eloxatin®); paclitaxel (Paxene®); paclitaxel (Taxol®); paclitaxel protein-bound particles (Abraxane®); palifermin (Kepivance®); palonosetron (Aloxi®); pamidronate (Aredia®); panitumumab (Vectibix®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); (Quadramet®); quadrivalent human papillomavirus (types 6, 11, 16, 18) recombinant vaccine (Gardasil®); quinacrine (Atabrine®); raloxifene hydrochloride (Evista®); Rasburicase (Elitek®); Rituximab (Rituxan®); sargramostim (Leukine®); Sargramostim (Prokine®); secretin (SecreFlo®); sorafenib (Nexavar®); streptozocin (Zanosar®); sunitinib maleate (Sutent®); talc (Sclerosol®); tamoxifen (Nolvadex®); temozolomide (Temodar®); temsirolimus (Torisel®); teniposide, VM-26 (Vumon®); (Temodar®); testolactone (Teslac®); thalidomide (Thalomid®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); (Trelstar LA®); tretinoin, ATRA (Vesanoid®); triptorelin pamoate (Trelstar Depot®); (UltraJect®); Uracil Mustard (Uracil Mustard Capsules®); valrubicin (Valstar®); vinblastine (Velban®); vincristine (Oncovin®); vinorelbine (Navelbine®); vorinostat (Zolinza®); (Zofran ODT®); and zoledronate (Zometa®).

Thus, the scope of the instant invention encompasses the use of the instantly claimed compounds in combination with a second compound selected from: HDAC inhibitor, an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The compound of formula I may also be administered in combination with one or more additional compounds known to be useful in the treatment or prevention of AD or the symptoms thereof. Such additional compounds thus include cognition-enhancing drugs such as acetylcholinesterase inhibitors (e.g. donepezil and galanthamine), NMDA antagonists (e.g. memantine) or PDE4 inhibitors (e.g. Ariflo™ and the classes of compounds disclosed in WO 03/018579, WO 01/46151, WO 02/074726 and WO 02/098878). Such additional compounds also include cholesterol-lowering drugs such as the statins, e.g. simvastatin. Such additional compounds similarly include compounds known to modify the production or processing of Aβ in the brain ("amyloid modifiers"), such as compounds which modulate the secretion of Aβ (including γ-secretase inhibitors, γ-secretase modulators and β-secretase inhibitors), compounds which inhibit the aggregation of Aβ, and antibodies which selectively bind to Aβ. Such additional compounds further include growth hormone secretagogues, e.g. as described in WO 2004/080459.

In this embodiment of the invention, the amyloid modifier may be a compound which inhibits the secretion of Aβ, for example an inhibitor of γ-secretase (such as those disclosed in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, WO 2004/089911, WO 02/081435, WO 02/081433, WO 03/018543, WO 2004/031137, WO 2004/031139, WO 2004/031138, WO 2004/101538, WO 2004/101539 and WO 02/47671), or a β-secretase inhibitor (such as those disclosed in WO 03/037325, WO 03/030886, WO 03/006013, WO 03/006021, WO 03/006423, WO 03/006453, WO 02/002122, WO 01/70672, WO 02/02505, WO 02/02506, WO 02/02512, WO 02/02520, WO 02/098849 and WO 02/100820), or any other compound which inhibits the formation or release of Aβ including those disclosed in WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391, WO 02/057252, US 2002/0025955 and US2002/0022621, and also including GSK-3 inhibitors, particularly GSK-3α inhibitors, such as lithium, as disclosed in Phiel et al, *Nature,* 423 (2003), 435-9.

Alternatively, the amyloid modifier may be a compound which modulates the action of γ-secretase so as to selectively attenuate the production of Aβ(1-42). Compounds reported to show this effect include certain non-steroidal antiinflammatory drugs (NSAIDs) and their analogues (see WO 01/78721 and US 2002/0128319 and Weggen et al *Nature,* 414 (2001) 212-16; Morihara et al, *J. Neurochem.,* 83 (2002), 1009-12; and Takahashi et al, *J. Biol. Chem.,* 278 (2003), 18644-70), and compounds which modulate the activity of PPARα and/or PPARδ (WO 02/100836). Further examples of γ-secretase modulators are disclosed in WO 2005/054193, WO 2005/013985, WO 2005/108362, WO 2006/008558 and WO 2006/043064.

Alternatively, the amyloid modifier may be a compound which inhibits the aggregation of Aβ or otherwise attenuates is neurotoxicicity. Suitable examples include chelating agents such as clioquinol (Gouras and Beal, *Neuron,* 30 (2001), 641-2) and the compounds disclosed in WO 99/16741, in particular that known as DP-109 (Kalendarev et al, *J. Pharm. Biomed. Anal.,* 24 (2001), 967-75). Other inhibitors of Aβ aggregation suitable for use in the invention include the compounds disclosed in WO 96/28471, WO 98/08868 and WO 00/052048, including the compound known as Apan™ (Praecis); WO 00/064420, WO 03/017994, WO 99/59571 (in particular 3-aminopropane-1-sulfonic acid, also known as tramiprosate or Alzhemed™); WO 00/149281 and the compositions known as PTI-777 and PTI-00703 (ProteoTech); WO 96/39834, WO 01/83425, WO 01/55093, WO 00/76988, WO 00/76987, WO 00/76969, WO 00/76489, WO 97/26919, WO 97/16194, and WO 97/16191. Further examples include phytic acid derivatives as disclosed in U.S. Pat. No. 4,847,082 and inositol derivatives as taught in US 2004/0204387.

Alternatively, the amyloid modifier may be an antibody which binds selectively to Aβ Said antibody may be polyclonal or monoclonal, but is preferably monoclonal, and is preferably human or humanized. Preferably, the antibody is capable of sequestering soluble Aβ from biological fluids, as described in WO 03/016466, WO 03/016467, WO 03/015691 and WO 01/62801. Suitable antibodies include humanized antibody 266 (described in WO 01/62801) and the modified version thereof described in WO 03/016466. Suitable antibodies also include those specific to Aβ-derived diffusible ligands (ADDLS), as disclosed in WO 2004/031400.

The compounds of this invention may be administered to mammals, preferably humans, either alone or in combination with pharmaceutically acceptable carriers, excipients, diluents, adjuvants, fillers, buffers, stabilisers, preservatives, lubricants, in a pharmaceutical composition, according to standard pharmaceutical practice.

The compounds of this invention may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, (e.g. by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal); and by implant of a depot (e.g. subcutaneously or intramuscularly).

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutang, gibbon), or a human.

The invention also provides pharmaceutical compositions comprising one or more compounds of this invention and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the instant invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compounds of the instant invention are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

When a compound according to this invention is administered into a subject, the selected dosage level will depend on a variety of factors including, but not limited to, the activity of the particular compound, the severity of the individuals symptoms, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

For treating or preventing Alzheimer's disease, a suitable dosage level is about 0.01 to 250 mg/kg per day, preferably about 0.01 to 100 mg/kg per day, and more preferably about 0.05 to 50 mg/kg of body weight per day, of the active compound. The compounds may be administered on a regimen of 1 to 4 times per day. In some cases, however, a dosage outside these limits may be used.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

Also included in the scope of the claims is a method of treating cancer that comprises administering a therapeutically effective amount of a compound of the instant invention in combination with radiation therapy and/or in combination with a second compound selected from: HDAC inhibitor, an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The instant invention also includes a pharmaceutical composition useful for treating or preventing cancer that comprises a therapeutically effective amount of a compound of the instant invention and a second compound selected from: HDAC inhibitor, an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

All patents, publications and pending patent applications identified are hereby incorporated by reference.

The compounds of the present invention can be prepared according to the following procedures.

Abbreviations:

$BOC_2O$ (di-tert-butyl dicarbonate); CDI (1,1'-carbonyldiimidazole; DCM (Dichloromethane); DIAD (Diisopropyl azodicarboxylate); DMAP (4-Dimethylaminopyridine); DMF (Dimethylformamide); DMSO (Dimethyl sulfoxide); EDC (N-ethyl-$N^2$-(3-dimethylaminopropyl)carbodiimide); $Et_3N$ (Triethylamine); EtOAc (Ethyl acetate); EtOH (Ethanol); HOBt (1-hydroxybenzotriazole); HPLC (High pressure liquid chromatography); LRMS (Low resolution mass spectrometry); MeOH (Methanol); Mes (2,4,6-trimethylphenyl); NaHMDS (Sodium bis(trimethylsilyl)amide); nPrOH (nPropanol); $PCy_3$ (Tricyclohexylphosphine); $PdCl_2(dppf)$-$CH_2Cl_2$ adduct (1,1'-Bis(dipheylphosphino) ferrocene palladium(II) chloride); $Pd(PPh_3)_4$ (Tetrakis(triphenylphosphine) palladium(0)); $Pd_2(dba)_3$ (Tris(dibenzylideneacetone) dipalladium(0)); TFA (trifluoroacetic acid); Tf (trifluoromethanesulfonyl); THF (Tetrahydrofuran); TLC (Thin layer chromatography) and TMSCl (Trimethylchlorosilane).

Where the synthesis of intermediates and starting materials is not described, these compounds are commercially available or can be made from commercially available compounds by standard methods or by extension of the synthesis above, schemes and Examples herein.

Compounds of formula I may be converted to other compounds of formula I by known methods or by methods described in the synthesis above, schemes and Examples herein.

During any of the synthetic sequences described herein it may be necessary and/or desirable to protect sensitive or reactive groups on any of the molecules concerned. This may be achieved by means of conventional protecting groups, such as those described in *Protecting Groups in Organic Synthesis*, 3rd Edition, Greene, T. W. and Wuts, P. G. M.; Wiley Interscience, 1999 and Kocienski, P. J. *Protecting Groups*, Thieme, 1994. The protecting groups may be removed at a convenient subsequent stage using methods known from the art. For example, when the Boc (tert-butoxycarbonyl) or benzylcarbonyl protecting group is present, it may be removed by the addition of solvents such as TFA, DCM and/or MeCN at about room temperature. When a CBz (benzyloxycarbonyl) protecting group is present, the compound may be hydrogenated using standard methods, such as treating with a catalyst such as Pd/C, in a solvent such as methanol under a hydrogen atmosphere. EtOAc in the presence of HCl and 1,4-dioxane may also be added to remove the Boc protecting group, at about room temperature.

When the compounds of the present invention have chiral centres, the enantiomers may be separated from the racemic mixtures by standard separating methods such as using SFC.

Compounds of this invention were tested in the following biological assays and were found to have $IC_{50}$ values of less than 30 μM in at least one of the Kinase assays.

BIOLOGICAL ASSAYS

In vitro PDK1 Kinase Assay

Activated recombinant full-length mT(Glu-Glu-Phe) tagged human PDK1 was used to determine whether the compounds of the instant invention modulate the enzymatic activity of this kinase.

The cDNA, encoding full-length PDK1, was subcloned into a baculovirus expression vector pBlueBac4.5 (Invitrogen), containing an in frame middle T tag (MEYMPME) (SEQ. ID.: 1) at its N-terminus Soluble activated recombinant full-length mT(Glu-Glu-Phe) tagged human PDK1 was expressed in a baculovirus-infected Sf9 insect cells (Kemp Biotechnologies), according to the protocol recommended by the manufacturer. Immunoaffinity purification of the PDK1 kinase from the insect cell lysate was performed using a middle Tag antibody bound to Protein G-EE column. Upon elution using 50 mM Tris pH 7.4, 1 mM EDTA, 1 mM EGTA, 0.5 mM $Na_3VO_4$, 1 mM DTT, 50 mM NaF, Na Pyrophospate, Na-β-glycerophosphate, 10% glycerol, Complete, 1 μM microcystein, and 50 μg/ml EYMPME (SEQ. ID.: 2) peptide, fractions containing PDK1 protein were pooled together, based on SDS-PAGE and western blot analyses, and then analyzed for protein concentration using BCA Protein Assay (Pierce) with BSA as standard. The final product was aliqouted and flash frozen in liquid nitrogen before being stored at −80° C. Resulting PDK1 protein had MW of 64 kDa, was phosphorylated 'by default' and purified as an activated kinase from insect cells.

The procedure for determining the potency of a compound to inhibit PDK1 kinase comprises the following steps:

1. Prepare 3-fold serial diluted compound solutions in 100% dimethyl sulfoxide (DMSO) at 20× of the desired final concentrations in a 384-well plate.
2. Prepare a master reaction mix containing 62.5 mM HEPES (pH 7.5), 12.5 mM $MgCl_2$, 0.013% Brij-35, 1.25 mM EGTA, 2.5 mM dithiothreitol, 1.25 nM recombinant PDK1 and 375 nM biotinylated synthetic peptide substrate (Biotin-GGDGATMKTFCGGTPSDGDPDGGEFTEF-COOH) (SEQ. ID.: 3).
3. In a black assay plate, add 2.5 μl of compound solution (or DMSO) and 22.5 μl of master reaction mix per well. Preincubate for 10 min Initiate the kinase reaction by adding 6 μl of 0.25 mM MgATP per well. Allow the reactions to proceed for 25 min at room temperature. The final conditions for the reaction are 1 nM PDK1, 300 nM peptide substrate, 5 μM MgATP, 10 mM $MgCl_2$, 2 mM DTT, 50 mM HEPES (pH 7.5), 0.01% Brij-35, 1 mM EGTA and 5% DMSO.
4. Stop the kinase reaction with 30 μl of Stop/Detection buffer containing 10 mM EDTA, 1× Lance Detection Buffer (cat. # CR97-100, PerkinElmer), 1% SuperBlocking in TBS (cat. # 37535, Pierce), 5 nM phospho-Akt(T308) monoclonal antibody (cat. # 4056, Cell Signaling Technologies), 5 nM Lance labeled Eu-Anti-rabbit IgG (cat. # AD0083, PerkinElmer), and 100 nM Streptavidin-allophycocyanin conjugate (cat. # PJ25S, Prozyme).
5. Read HTRF signals on an Envision reader (PerkinElmer) in HTRF mode after 60 min.
6. IC50 is determined by fitting the observed relationship between compound concentration and HTRF signal with a 4-parameter logistic equation.

FGFR3 Inhibitory Activity (1) Measurement of activity of FGFR3

The purified recombinant human FGFR3 protein, cytoplasmic domain [436-806(end) amino acids of accession number NP_000133.1] which was expressed as N-terminal GST-fusion protein (68 kDa) using baculovirus expression system, was purchased from Carna Biosciences, Inc.

For measurement of the activity of FGFR3, the substrate used was a synthetic peptide (biotin-6-aminocaproic acid-Glu-Gln-Glu-Asp-Glu-Pro-Glu-Gly-Asp-Tyr-Phe-Glu-Trp-Leu-Glu-Pro-Glu, (SEQ. ID.: 4) which was custom-made by Toray Research Center, Inc.

The phosphorylation reaction was conducted using 384 well plate, and the reaction volume was 10.5 μL/well. The reaction buffer is comprised of 15 mM Tris-chloride buffer (pH 7.5), 0.01% Tween-20, 2 mM dithiothreitol, and 5 mM magnesium chloride. Thereto, FGFR3, 250 nM of the peptide substrate, and 50 μM of adenosine 5'-triphosphate were added, and then the reaction was carried out at 25° C. for 60 minutes.

Thereafter, in order to terminate and detect the reaction, 5 μL of 120 mM of ethylenediamine-N,N,N',N'-tetraacetic acid (EDTA) and 5 μL of detection regent [15 mM Tris-chloride buffer (pH 7.5), 0.1% Tween-20, 125 nM of SureLight Allophycocyanin-streptavidin (APC-SA), 4 nM of Eu(europium)-W1024 labeled anti-phosphotyrosine antibody (PT66) (PerkinElmer, Inc.)] were added to each well. The solution stood still for 90 minutes in the dark and the fluorescence was measured at 620 nm and 665 nm using a high-end microplate reader (excitation wavelength: 485 nm; emission wavelength: 620 nm, 665 nm). A ratio is calculated [(665 nm/620 nm)×$10^4$] for each well.

The compound to be tested was added to the reaction system such that a dilution series of the compound in dimethylsulfoxide (DMSO) was prepared, and then 0.5 μL of this solution was added for the testing to each well. Each control well was provided by adding 0.5 μL of DMSO to the well in place of the DMSO solution containing the compound to be tested.

TRKC/NTRK3 Inhibitory Activity (1) Purification of TrkC Enzyme cDNA of N-terminal His-tagged human TrkC catalytic domain [455-825(end) amino acids of accession number NP_001012338] was integrated into an expression vector, which was then highly expressed in sf9 cells. The sf9 was harvested and lysed, and then the His-tagged human ROCK2 protein was applied onto HisTrap HP (GE Healthcare) and eluted from the column with imidazole. The active fractions were desalted with a desalting column (PD-10, GE Healthcare) to give a purified enzyme.

The pure TrkC enzyme was autophosphorylated by incubation with 1 mM of ATP for 120 minutes at 30° C. and the active enzyme was purified with a desalting column (PD-10).

(2) Measurement of Activity of TrkC

For measurement of the activity of TrkC, the peptide (biotin-Gly-Glu-Glu-Glu-Leu-Ser-Asn-Tyr-Ile-Cys-Met-Gly-Gly-Arg-Arg-Arg-$NH_2$) (SEQ. ID.: 5) was synthesized as a substrate in our laboratory.

The phosphorylation reaction was conducted using 384 well plate, and the reaction volume was 10.5 μL/well. The reaction buffer is comprised of 8 mM 3-Morpholinopropanesulfonic acid buffer (pH 7.0), 5 mM magnesium chloride, and 0.2 mM ethylenediamine-N,N,N',N'-tetraacetic acid (EDTA). Thereto, TrkC, 500 nM of the peptide substrate, and 50 μM of adenosine 5'-triphosphate were added, and then the reaction was carried out at 25° C. for 150 minutes.

Thereafter, in order to terminate and detect the reaction, 5 μL of 120 mM of EDTA and 5 μL of detection regent [15 mM Tris-chloride buffer (pH 7.5), 0.1% Tween 20, 250 nM of SureLight Allophycocyanin-streptavidin (APC-SA), 4 nM of Eu(europium)-W1024 labeled anti-phosphotyrosine antibody (PT66)] were added to each well. The solution stood still for 90 minutes in the dark and the fluorescence was measured at 620 nm and 665 nm using a high-end microplate reader (excitation wavelength: 485 nm; emission wavelength: 620 nm, 665 nm). A ratio is calculated [(665 nm/620 nm)×$10^4$] for each well.

The compound to be tested was added to the reaction system such that a dilution series of the compound in dimethylsulfoxide (DMSO) was prepared, and then 0.5 μL of this solution was added for the testing to each well. Each control well was provided by adding 0.5 μL of DMSO to the well in place of the DMSO solution containing the compound to be tested.

RPS6 KB1/p70S6K1 Inhibitory Activity

The purified recombinant human p70S6K1 protein, catalytic domain [1-421 amino acids and T412E of accession number NP_003152.1] which was expressed as N-terminal GST-fusion protein (75 kDa) using baculovirus expression system, was included in the Assay Kit [QS S Assist p70S6K (RPS6 KB1)_FP Kit] which was purchased from Carna Biosciences Inc.

For measurement of the activity of p70S6K1, the method by Carna Biosciences, Inc. [QS S Assist p70S6K_FP Kit] was referred to, and phosphorylation of the substrate was detected using IMAP® technology (Molecular Devices, Co. Ltd.)

(Gaudet E W. et. al, J. Biomol. Screen, 8, 164-175 (2003)). Concretely, the phosphorylation reaction and the detection were carried out as follows:

The phosphorylation reaction was conducted using 384 well plate, and the reaction volume was 10.5 μL/well. The reaction buffer is comprised of 20 mM HEPES (pH 7.4), 5 mM magnesium chloride, 0.01% Tween 20, and 2 mM dithiothreitol. Thereto, the purified p70S6K1 protein, 100 nM of the peptide substrate, and 25 μM of adenosine 5'-triphosphate were added, and then the reaction was carried out at 25° C. for 90 minutes.

Thereafter, in order to terminate and detect the reaction, 10 μM of the IMAP (registered trademark) binding reagent (IMAP Progressive Binding Reagent) that had been diluted (1:400) in the 1×IMAP binding buffer A (IMAP Progressive Binding Buffer A, 5× stock) was added to each well. The solution stood still for 120 minutes in the dark, and then fluorescence polarization was measured using a high-end microplate reader (excitation wavelength: 485 nm; emission wavelength: 520 nm).

The compound to be tested was added to the reaction system such that a dilution series of the compound in dimethylsulfoxide (DMSO) was prepared, and then 0.5 μL of this solution was added for the testing to each well. Each control well was provided by adding 0.5 μL of DMSO to the well in place of the DMSO solution containing the compound to be tested.

Wee1 Inhibitory Activity (1) Measurement of activity of Wee1

The purified recombinant human Wee1 protein, catalytic domain [215-646 (end) amino acids of accession number NP_003381.1] with N-terminal glutathione-S-transferase (GST) tag, was purchased from Carna Biosciences, Inc. to use as a kinase enzyme. For measurement of the activity of Wee1, Poly(Lys, Tyr) hydrobromide [Lys:Tyr (4:1), mol wt 20,000-50,000], (Poly(Lys, Tyr)) (SIGMA) was used as a substrate.

The phosphorylation reaction was conducted using 384 well plate, and the reaction volume was 10.5 μL/well. The reaction buffer is comprised of 50 mM Tris-chloride buffer (pH 7.4), 10 mM magnesium chloride, and 1 mM dithiothreitol. Thereto, the purified GST-Wee1 protein, 1 μg of Poly(Lys, Tyr), 10 μM adenosine 5'-triphosphate (ATP) and 0.25 μCi [γ-33P] ATP solution were added, and then the reaction was carried out at 25° C. for 100 minutes. The [γ-33P]-labeled ATP was purchased from PerkinElmer Inc.

After the termination of the reaction by adding 20 μL, of 350 mM phosphoric acid (H3PO4), the substrate peptide was adsorbed on a filter plate (Millipore Multiscreen, MZPHN0W50). The substrate-bound filter plate was washed with 130 mM phosphoric acid for several times and then 8 μL of Microscinti-O (PerkinElmer Inc.) was added to the each well. The radiation activity of the peptide was measured with TopCount NXT Microscintillation Counter (PerkinElmer Inc.).

MARK 3 Assays

MARK3 activity was assayed in vitro using a Cdc25C biotinylated peptide substrate (Cell Signalling Technologies). The phosphopeptide product was quantitated using a Homogenous Time-Resolved Fluorescence (HTRF) assay system (Park et al., 1999, *Anal. Biochem.* 269:94-104). The reaction mixture contained 50 mM HEPES/Tris-HCl, pH 7.4; 10 mM NaCl, 5 mM $MgCl_2$, 0.2 mM $NaVO_4$, 5 mM β-glycerol phosphate, 0.1% Tween-20, 2 mM dithiothreitol, 0.1% BSA, 10 μM ATP, 1 μM peptide substrate, and 10 nM recombinant MARK3 enzyme (University of Dundee) in a final volume of 12 μl. The buffer additionally contained protease inhibitor cocktail (Roche EDTA-free, 1 tab per 50 ml). The kinase reaction was incubated for 2 hours at 25° C., and then terminated with 3 μl Stop/Detection Buffer (50 mM HEPES, pH 7.0, 16.6 mM EDTA, 0.5M KF, 0.1% Tween-20, 0.1% BSA, 2 μg/ml $SLX^{ent}$ 665 (CISBIO), and 2 μg/ml $Eu^{3+}$ cryptate label antibody (CISBIO)). The reaction was allowed to equilibrate overnight at 0° C., and relative fluorescent units were read on an HTRF enabled plate reader (e.g. TECAN GENios Pro).

Inhibitor compounds were assayed in the reaction described above to determine compound IC50s. Aliquots of compound dissolved in DMSO were added to the reaction wells in a third-log dilution series covering a range of 1 μM to 30 μM. Relative phospho substrate formation, read as HTRF fluorescence units, was measured over the range of compound concentrations and a titration curve generated.

The compounds active at the MARK kinsase were found to have $IC_{50}$ values of 1 μM or less, typically 500 nM or less, and in preferred cases 50 nM less, in the above assay. PSA (polar molecular surface) of these compounds are typically less than 100 $Å^2$ and in preferred cases range between 60-80 $Å^2$. PSA is an important molecular property that can be a predictor of drug absorption in humans (Luthman et al, *Pharm. Res,* 14 (1997), 568-571).

pTau(S262) Cell Biochemical and Functional Assay

The cell biochemical potency of the below described MARK inhibitors was evaluated by measuring their ability to block the phosphorylation of Tau at S262 in primary cell culture of rat cortical neurons induced by the action of Okadaic acid.

Reagents:
  Neurobasal (Invitrogen, cat. 21103-049)
  B27 (Invitrogen, cat. 17504-044)
  L-Glutamine (Invitrogen, cat. 25030-081)
  Penicillin-Streptomycin (Invitrogen, cat. 15140)
  Papain, sterile lyophilized (Worthington, cat. NC9212788)
    10 mL 1M Hepes added for 10× solution
  Tissue Culture plates:
    384 well: BD FALCON BD BIOCOAT Poly-D-Lysine Black/Clear Microtest, Tissue-Culture Treated Polystyrene (cat. 354663)
  E18 Primary Rat Cortical Cells: BrainBits, cat. cx2
  Stock Media (NB): Neurobasal+B-27 (1:50)+0.5 mM L-Glutamine+1% Pen/Strep Preparation of Isolated Neurons
  1. Store tissue at 4° C. (1-2 days) until ready to use.
  2. When ready to plate, make up 2 mL of enzymatic solution in Hibernate-Ca containing 1× papain. Filter sterile solution with 0.2 μm filter.
  3. Transfer 2 mL of medium from tissue tube into 15 mL falcon tube while not disturbing tissue. Save media.
  4. Add 2 mL enzymatic media (2) to tissue. Incubate for 30' at 37° C.
  5. Remove enzymatic solution while not disturbing tissue. Add back 1 mL of media from (3).
  6. Using pipettor with sterile plastic tip, triturate ~10 times until most of the cells are dispersed.
  7. Let undispersed pieces settle by gravity 1 minute.
  8. Transfer dispersed cells (supernatant) into 15 mL falcon tube containing 1 mL media from (3). Gently mix cells by swirling.
  9. Spin cells at 1,100 rpm for 1 minute. Remove supernatant.
  10. Flick tube to loosen cell pellet. Resuspend cells in 5 mL of NB.

11. Transfer to new 50 mL falcon tube using 40 μm cell strainer. Rinse 15 mL falcon tube with 5 mL media, add to strainer.
12. Count cells using hemacytometer.
13. Dilute cells to 7,000 cells/100 μL/well in NB.
14. Incubate cells at 37° C. with 5% $CO_2$.
    a. 4 DIV: Replace ½ volume (50 μL) NB per well.
    b. 6 DIV: Neurite Assay.

Tissue Culture/Compound Treatment
    Primary rat cortical neurons plated @ 6Kcells/well in 384-well black/clear bottom Poly D-Lysine coated BD Falcon Biocoat plates.
    Media: Neurobasal+1×B27+2 mM L-Glutamine (+10% FBS) at time of plating
    Cells maintained at 37° C. and 5% $CO_2$ for *6 days in culture, w/½ media change every 3-4 days.
    Compound treatment:
    Prepare first plate: 200× compound in 100% DMSO with subsequent 3 fold serial dilution
    Prepare intermediate plate: 1:40 dilution of 200× compound in media (2.5% DMSO)
    Add 5× compound to cell in media at 1:5 dilution (0.5% final DMSO)
    Incubate for 30 min. at 37° C.
    Okadaic Acid (OA) Treatment:
Dilute OA stock (240 uM in 100% DMSO) to 6× final concentration in media (0.5% DMSO)
    Add 6×OA to cells at 1:6 dilution (200 nM final).
Incubate for 1.5 hrs. at 37° C.
Fix and Immunostaining
    Fix: 1% PFA, diluted in PBS
    Wash 1× with PBS, residual 30 ul/well.
Add 30 μl/well warmed 2% PFA and incubate 30 min. at RT (1% PFA final)
    Wash 3× with PBS, 30 μl/well residual
    Permeabilize & Block.
Add 30 μl/well PBS+0.2% Triton X-100+10% normal goat serum (0.1% Triton & 5% NGS final).
Incubate 1 hr at RT or O/N at 4° C.
    Wash 3× with PBS, 30 μl/well residual
    Primary antibody: add 30 μl/well 2× final concentration antibody diluted in PBS
    Mouse anti-tau-3R
    Rabbit anti-tau-pS[262]
    Incubate O/N at 4° C.
    Wash 4× with PBS, 30 μl/well residual
    Secondary antibody & nuclear staining: add 30 μl/well 2× final concentration stain diluted in PBS
        AlexaFluor goat anti mouse 488
        AlexaFluor goat anti rabbit 594
        Hoechst
    Incubate in dark 1 hr. at RT
    Wash 4× with PBS 30 μl/well residual, protect from light
    Acquire images in INCell Analyzer 1000 & Opera.
The compounds active at the MARK kinsase were found to have $IC_{50}$ values of 10 μM or less, typically 1000 nM or less, and in preferred cases 250 nM less, in the above assay measuring inhibition of phosphorylation of Tau at S262.

Scheme 1

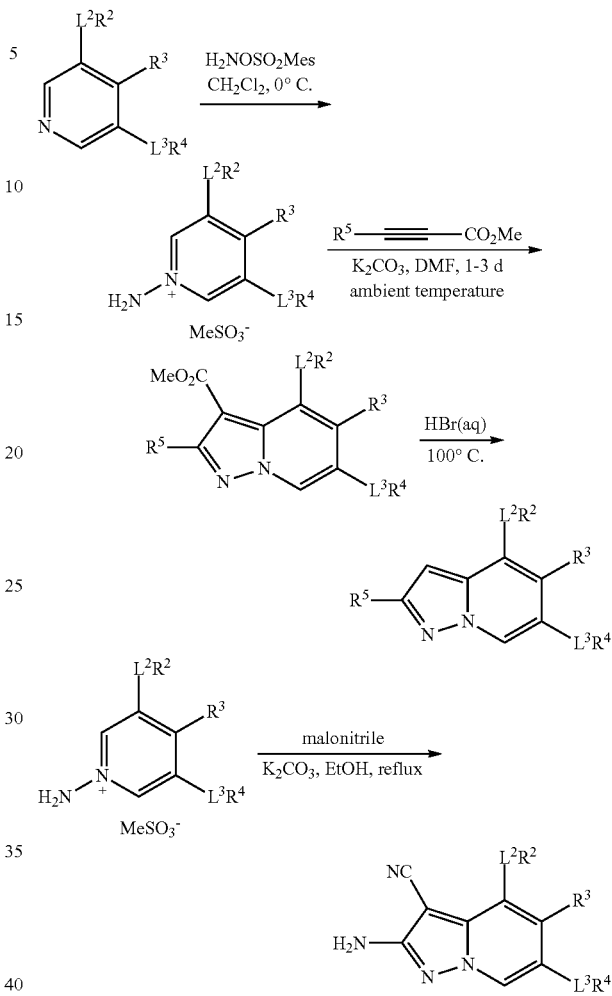

The following compounds were prepared as described in Scheme 1 using the procedure described in Miki, Y. et. al.; *Heterocycles* 1996, 43, 2249-2256

EXAMPLES 1

Representative Compounds 1-1, 1-3 and 1-4 and Preparative Compound 1-2

Compound 1-1

6-bromo-4-methoxypyrazolo[1,5-a]pyridine

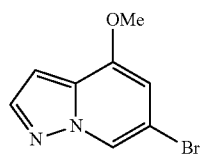 [SMILES: COc1cc(Br)cn2nccc12]

Preparative Compound 1-2

4-bromo-6-methoxypyrazolo[1,5-a]pyridine

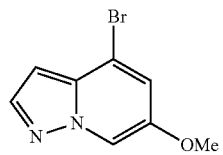 [SMILES: COc1cc(Br)c2ccnn2c1]

Step 1: 1-amino-3-bromo-5-methoxypyridinium 2,4,6-trimethylbenzenesulfonate (Adapted from: Miki, Y. et. al.; *Heterocycles* 1996, 43, 2249-2256; 2-[(aminooxy)sulfonyl]-1,3,5-trimethylbenzene was prepared using the procedure described in Krause, J. G. *Synthesis*, 1972, 3, 140). A solution of 3-bromo-5-methoxypyridine (8.72 g, 46.4 mmol) in dichloromethane (93 ml) was cooled to 0° C. A solution of 2-[(aminooxy)sulfonyl]-1,3,5-trimethylbenzene (13.31 g, 46.4 mmol) in dichloromethane (93 ml) was added in a steady stream via canula and the mixture was allowed to stir for 1 h at 0° C. At this time, 460 mL of ether was added dropwise via addition funnel over 5 minutes. The precipitated solid was collected via filtration, and washed with cold ether. The solid was placed under vacuum for 30 minutes to afford 1-amino-3-bromo-5-methoxypyridinium 2,4,6-trimethylbenzenesulfonate as a colorless solid.

Step 2: methyl 6-bromo-4-methoxypyrazolo[1,5-a]pyridine-3-carboxylate and methyl 4-bromo-6-methoxypyrazolo[1,5-a]pyridine-3-carboxylate To a solution of 1-amino-3-bromo-5-methoxypyridinium 2,4,6-trimethylbenzenesulfonate (11.0 g, 27.3 mmol) in DMF (280 ml) at 0° C. was added potassium carbonate (7.54 g, 54.6 mmol). After stirring for 10 minutes, methyl priopiolate (4.85 ml, 54.6 mmol) was added via syringe and the mixture was allowed to warm to ambient temperature. After 4 days, the reaction mixture was diluted in diethyl ether, washed with saturated aqueous sodium hydrogen carbonate and brine then dried over magnesium sulfate, filtered and concentrated. The residue was purified by column chromatography on silica gel (Ethyl acetate/isohexane gradient) to give an inseparable mixture of methyl 6-bromo-4-methoxypyrazolo[1,5-a]pyridine-3-carboxylate and methyl 4-bromo-6-methoxypyrazolo[1,5-a]pyridine-3-carboxylate as a yellow solid. LRMS (ESI) calculated for $C_{10}H_{10}{}^{79}BrN_2O_3$ [M+H]$^+$, 285.0; found 284.9.

Step 3: 6-bromo-4-methoxypyrazolo[1,5-a]pyridine and 4-bromo-6-methoxypyrazolo[1,5-a]pyridine A mixture of methyl 6-bromo-4-methoxypyrazolo[1,5-a]pyridine-3-carboxylate (4.33 g, 15.2 mmol) and methyl 4-bromo-6-methoxypyrazolo[1,5-a]pyridine-3-carboxylate (1.44 g, 5.05 mmol) was suspended in hydrobromic acid (100 ml, 884 mmol) and heated to 100° C. for 60 minutes. The mixture was cooled to 0° C. and carefully quenched via the addition of 1N aqueous sodium hydroxide (152 ml, 909 mmol). The reaction mixture was diluted in ethyl acetate, washed with 1N aqueous sodium hydroxide and brine then dried over sodium sulfate, filtered and concentrated. The residue was purified by column chromatography on silica gel (Ethyl acetate/isohexane gradient) to give 6-bromo-4-methoxypyrazolo[1,5-a]pyridine (faster eluting isomer) and 4-bromo-6-methoxypyrazolo[1,5-a]pyridine (slower eluting isomer).

6-bromo-4-methoxypyrazolo[1,5-a]pyridine: $^1$H NMR (500 MHz, CDCl$_3$) δ 8.28 (s, 1H); 7.84 (d, 1H); 6.63 (d, 1H); 6.46 (s, 1H); 3.96 (s, 3H). LRMS (ESI) calculated for $C_8H_8{}^{79}BrN_2O$ [M+H]$^+$, 227.0; found 226.9.

4-bromo-6-methoxypyrazolo[1,5-a]pyridine: $^1$H NMR (500 MHz, CDCl$_3$) δ 8.04 (s, 1H); 7.87 (d, 1H); 7.19 (d, 1H); 6.57 (s, 1H); 3.83 (s, 3H). LRMS (ESI) calculated for $C_8H_8{}^{79}BrN_2O$ [M+H]$^+$, 227.0; found 226.9.

Compound 1-3

2-amino-6-bromo-4-methoxypyrazolo[1,5-a]pyridine-3-carbonitrile

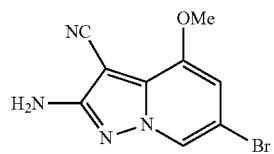 [SMILES: COc1cc(Br)cn2nc(N)c(C#N)c12]

1-amino-3-bromo-5-methoxypyridinium 2,4,6-trimethylbenzenesulfonate (400 mg, 0.992 mmol), malonitrile (0.062 ml, 0.992 mmol), and potassium carbonate (137 mg, 0.992 mmol) were suspended in Ethanol (5 ml) and heated to 75° C. for 1 h. The mixture was cooled to ambient temperature and concentrated to give a red solid. The reaction mixture was diluted in ethyl acetate, washed with saturated aqueous ammonium chloride and brine then dried over sodium sulfate. The residue was purified by column chromatography on silica gel (methanol/dichloromethane gradient) to give 118 mg of a tan solid. This solid was further purified by preparative HPLC Reverse phase (C-18), eluting with acetonitrile/water+0.05% TFA. The fractions containing the desired product were combined and diluted in ethyl acetate, then washed with aqueous sodium bicarbonate and dried over sodium sulfate. The solution was filtered and concentrated under reduced pressure to afford 2-amino-6-bromo-4-methoxypyrazolo[1,5-a]pyridine-3-carbonitrile as a tan solid. $^1$H NMR (500 MHz, DMSO-d$_6$) δ 8.47 (d, 1H); 7.06 (d, 1H); 6.33 (s, 2H); 3.93 (s, 3H). LRMS (ESI) calculated for $C_9H_8{}^{79}BrN_4O$ [M+H]$^+$, 267.0; found 266.9.

The compound in the following table was prepared according to the procedure described in scheme 1 and for compounds 1-1 to 1-3. The compound was prepared as the free base.

TABLE 1

| Compound | Structure | Name | [M + H]+ |
|---|---|---|---|
| 1-4 | MeO$_2$C, OMe, Br (structure) | methyl 6-bromo-4-methoxy-2-methyl-pyrazolo[1,5-a]pyridine-3-carboxylate | Calc'd 299.0 (for $^{79}$Br), found 298.9 |

Scheme 2

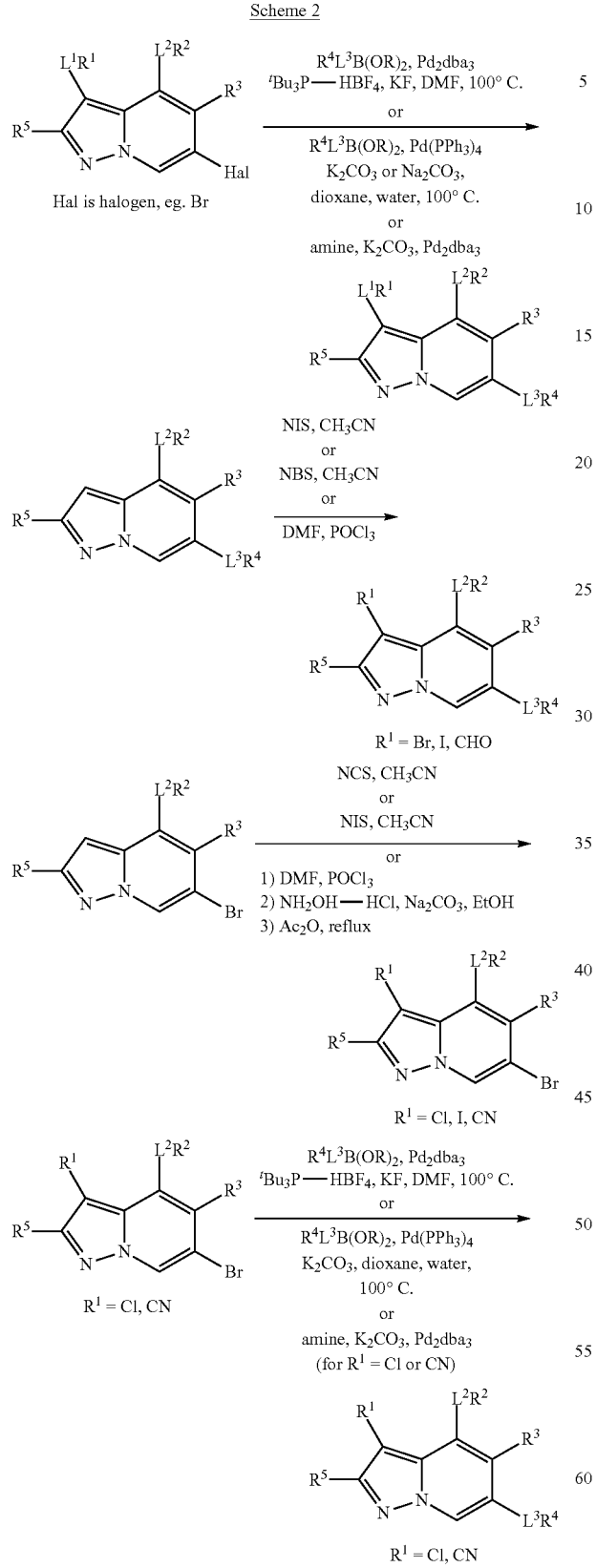

wherein B(OR)₂ is a boron ester such as tetramethyldioxaborolanyl.

EXAMPLES 2

Representative Compounds 2-1 to 2-36

Compound 2-1

3-iodo-4-methoxy-6-(1-methyl-1H-pyrazol-4-yl) pyrazolo[1,5-a]pyridine)

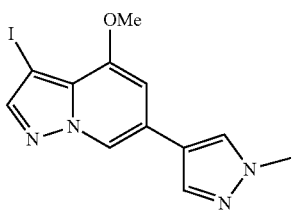 [SMILES: COc1cc(-c2cnn(C)c2)cn2ncc(I)c12]

Step 1: 4-methoxy-6-(1-methyl-1H-pyrazol-4-yl) pyrazolo[1,5-a]pyridine)

Method A: 6-bromo-4-methoxypyrazolo[1,5-a]pyridine (500 mg, 2.20 mmol), 1-methyl-4-(4,4,5,5-tetramethyl-1,3,2-dioxaborolan-2-yl)-1H-pyrazole (1375 mg, 6.61 mmol), tetrakis(triphenylphosphine)palladium (0) (254 mg, 0.220 mmol), and sodium carbonate (700 mg, 6.61 mmol) were suspended in a mixture of 1,4-dioxane (19.8 ml) and water (2.2 ml). The mixture was sparged with argon for 10 minutes, then heated to 90° C. After 2 h, the reaction mixture was diluted in ethyl acetate, washed with saturated aqueous sodium hydrogen carbonate and brine then dried over sodium sulfate, filtered and concentrated. The residue was purified by column chromatography on silica gel (methanol/ethyl acetate gradient) to give 4-methoxy-6-(1-methyl-1H-pyrazol-4-yl) pyrazolo[1,5-a]pyridine as a tan solid contaminated with trace amounts of triphenylphosphine oxide. Analytically pure material could be obtained by purification by preparative HPLC Reverse phase (C-18), eluting with acetonitrile/water+ 0.05% TFA.

Method B: 6-bromo-4-methoxypyrazolo[1,5-a]pyridine (500 mg, 2.20 mmol), 1-methyl-4-(4,4,5,5-tetramethyl-1,3,2-dioxaborolan-2-yl)-1H-pyrazole (916 mg, 4.40 mmol), tris(dibenzylideneacetone)dipalladium (0) (101 mg, 0.110 mmol), potassium fluoride (422 mg, 7.27 mmol), and tri-t-butylphosphonium tetrafluoroborate (63.9 mg, 0.220 mmol) were suspended in DMF (22 ml), sparged with argon for 10 minutes, then heated to 100° C. After 2.5 h, the mixture was cooled to ambient temperature, diluted in ethyl acetate, washed with saturated aqueous sodium hydrogen carbonate and brine then dried over sodium sulfate, filtered and concentrated. The residue was purified by column chromatography on silica gel (methanol/ethyl acetate gradient) to give 4-methoxy-6-(1-methyl-1H-pyrazol-4-yl)pyrazolo[1,5-a]pyridine as a tan solid.

$^1$H NMR (500 MHz, DMSO-$d_6$) δ 8.61 (s, 1H); 8.26 (s, 1H); 8.00 (s, 1H); 7.87 (d, 1H); 6.85 (s, 1H); 6.56 (d, 1H); 3.98 (s, 3H); 3.86 (s, 3H). LRMS (ESI) calculated for $C_{12}H_{13}N_4O$ [M+H]$^+$, 229.1; found 229.0.

Step 2: 3-iodo-4-methoxy-6-(1-methyl-1H-pyrazol-4-yl)pyrazolo[1,5-a]pyridine 4-methoxy-6-(1-methyl-1H-pyrazol-4-yl)pyrazolo[1,5-a] pyridine (486 mg, 2.13 mmol) was suspended in acetonitrile (30 ml). N-iodosuccinimide (958 mg, 4.26 mmol) was added and the mixture was allowed to stir for 1 h. The reaction mixture was diluted in dichloromethane, washed with water, 1N aqueous sodium hydroxide and brine. The combined organic layers were dried over sodium sulfate, filtered, and concentrated to afford 3-iodo-4-methoxy-6-(1-methyl-1H-pyrazol-4-yl)pyrazolo[1,5-a]pyridine as a tan solid. $^1$H NMR (500 MHz, DMSO-d$_6$) δ 8.67 (s, 1H); 8.28 (s, 1H); 8.01 (s, 1H); 7.92 (1, 1H); 6.89 (s, 1H); 3.96 (s, 3H); 3.85 (s, 3H). LRMS (ESI) calculated for $C_{12}H_{12}IN_4O$ [M+H]$^+$, 355.0; found 354.9.

Compound 2-2

3-Chloro-4-methoxy-6-(4-methyl-3-thienyl)pyrazolo[1,5-a]pyridine

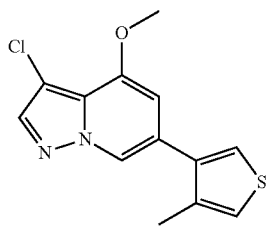 [SMILES: COc1cc(-c2cscc2C)cn2ncc(Cl)c12]

Step 1: 6-bromo-3-chloro-4-methoxypyrazolo[1,5-a]pyridine

To a solution of 6-bromo-4-methoxypyrazolo[1,5-a]pyridine (1010 mg, 4.43 mmol) in acetonitrile (40 ml) was added N-chlorosuccinimide (1180 mg, 8.86 mmol). The reaction mixture was stirred at room temperature for 6 hours. The reaction mixture was partitioned between dichloromethane (100 ml) and 1N aqueous sodium hydroxide (100 ml). The organic layer was washed with brine (100 ml). The organic layer was dried over sodium sulfate, filtered and concentrated to afford 6-bromo-3-chloro-4-methoxypyrazolo[1,5-a]pyridine as a white solid. $^1$H NMR (500 MHz, DMSO-d$_6$) δ 8.66 (s, 1H); 8.03 (s, 1H); 6.84 (s, 1H); 3.94 (s, 1H). LRMS (ESI) calculated for $C_8H_6BrClN_2O$ [M+H]$^+$, 260.9; found 261.0.

Step 2: 3-chloro-4-methoxy-6-(4-methyl-3-thienyl)pyrazolo[1,5-a]pyridine

To a solution of 6-bromo-3-chloro-4-methoxypyrazolo[1,5-a]pyridine (39.0 mg, 0.149 mmol) in DMF (3 ml) was added a 2M solution of sodium carbonate in water (45 µL, 0.089 mmol), (4-methyl-3-thienyl)boronic acid (21.0 mg, 0.149 mmol), and polystyrene triphenylphosphine palladium (0) (104 mg, 10.44 mmol). The reaction mixture was heated in the Biotage Initiator Series at 120° C. for 30 minutes. The mixture was filtered, and purified directly by reverse phase chromatography (Water/Acetonitrile gradient) to afford the TFA salt of 3-chloro-4-methoxy-6-(4-methyl-3-thienyl)pyrazolo[1,5-a]pyridine. $^1$H NMR (500 MHz, DMSO-d$_6$) δ 8.32 (s, 1H); 8.04 (s, 1H); 7.67 (s, 1H); 7.31 (s, 1H); 6.73 (s, 1H); 3.95 (s, 3H); 3.31 (s, 3H). LRMS calculated for: $C_{13}H_{11}ClN_2OS$ [M+H]$^+$, 279.0; found 279.1.

Compound 2-3

3-Chloro-4-methoxy-N-4-pyridinylpyrazolo[1,5-a]pyridin-6-amine

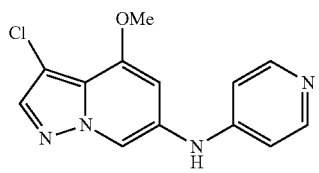 [SMILES: COc1cc(Nc2ccncc2)cn2ncc(Cl)c12]

To a solution of 6-bromo-3-chloro-4-methoxypyrazolo[1,5-a]pyridine (57.0 mg, 0.228 mmol) in t-amyl alcohol (0.76 ml) was added 4-pyridinamine (21.0 mg, 0.228 mmol), potassium carbonate (35.0 mg, 0.251 mmol), 2-dicyclohexylphosphino-2',4',6'-triisopropyl-1,1'-biphenyl (54.0 mg, 0.114 mmol), and tris(dibenzylideneacetone)dipalladium (0) (21.0 mg, 0.023 mmol). The vial was capped, evacuated, and backfilled with argon. The reaction mixture was heated in the microwave at 120° C. for 20 minutes, filtered, and concentrated. The formate salt of 3-chloro-4-methoxy-N-4-pyridinylpyrazolo[1,5-a]pyridin-6-amine was obtained by purification by preparative HPLC reverse phase (C-18), eluting with acetonitrile/water+0.05% formic acid. LRMS (ESI) calculated for $C_{13}H_{11}ClN_4O$ [M+H]$^+$, 275.1; found 275.1.

Compound 2-4

4-methoxy-6-(1-methyl-1H-pyrazol-4-yl)pyrazolo[1,5-a]pyridine-3-carbonitrile

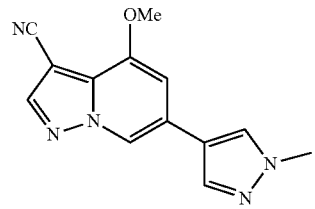 [SMILES: COc1cc(-c2cnn(C)c2)cn2ncc(C#N)c12]

Step 1: 6-bromo-4-methoxypyrazolo[1,5-a]pyridine-3-carbaldehyde

Phosphorous oxychloride (513 µl, 5.51 mmol) was added to DMF (8.52 ml, 110 mmol) at 0° C. The bath was removed and the solution was allowed the solution to warm to ambient temperature. After 30 minutes, 6-bromo-4-methoxypyrazolo[1,5-a]pyridine (500 mg, 2.202 mmol) was added, and the mixture was allowed to stir at ambient temperature. After 3.5 h, the reaction was quenched by the addition of saturated aqueous sodium bicarbonate (30 mL) and stirred for 60 minutes. The reaction mixture was diluted in ethyl acetate, washed with saturated aqueous sodium hydrogen carbonate and brine then dried over sodium sulfate, filtered and concentrated. The solid was placed under vacuum overnight to remove excess DMF and afford 6-bromo-4-methoxypyrazolo[1,5-a]pyridine-3-carbaldehyde contaminated with about 9% of the starting material.

Step 2: 6-bromo-4-methoxypyrazolo[1,5-a]pyridine-3-carbaldehyde oxime 6-bromo-4-methoxypyrazolo[1,5-a]pyridine-3-carbaldehyde (100 mg, 0.365 mmol), hydroxylamine hydrochloride (27.9 mg, 0.401 mmol) and sodium bicarbonate (33.7 mg, 0.401 mmol) were suspended in absolute ethanol (4 ml) and stirred for 1 h (heavy colorless precipitate forms). The mixture was concentrated to dryness, then diluted in 8 mL of water and stirred for 5 minutes. The solid was filtered, washed with water, then placed under vacuum overnight to afford 6-bromo-4-methoxypyrazolo[1,5-a]pyridine-3-carbaldehyde oxime as a mixture of oxime isomers.

Step 3: 6-bromo-4-methoxypyrazolo[1,5-a]pyridine-3-carbonitrile

The oxime isomer mixture of 6-bromo-4-methoxypyrazolo[1,5-a]pyridine-3-carbaldehyde oxime (85.0 mg, 0.315 mmol) was suspended in acetic anhydride (3.0 ml, 31.8 mmol) and heated to 50° C. for 3 h to give a pale blue solution. The solution was then heated to 75° C. for 2 h to give a dark blue solution. The solution was then heated to 100° C. overnight to give a dark purple mixture. The reaction mixture was concentrated and the residue was diluted in ethyl acetate, washed with saturated aqueous sodium hydrogen carbonate and brine then dried over sodium sulfate, filtered and concentrated. The residue was purified by column chromatography on silica gel (ethyl acetate/isohexane gradient) to give 6-bromo-4-methoxypyrazolo[1,5-a]pyridine-3-carbonitrile.

Step 4: 4-methoxy-6-(1-methyl-1H-pyrazol-4-yl)pyrazolo[1,5-a]pyridine-3-carbonitrile 6-bromo-4-methoxypyrazolo[1,5-a]pyridine-3-carbonitrile (50.0 mg, 0.198 mmol), 1-methyl-4-(4,4,5,5-tetramethyl-1,3,2-dioxaborolan-2-yl)-1H-pyrazole (61.9 mg, 0.298 mmol), tri-t-butylphosphonium tetrafluoroborate (5.8 mg, 0.02 mmol), tris(dibenzylideneacetone)dipalladium (0) (9.1 mg, 9.9 μmol), and potassium fluoride (38.0 mg, 0.655 mmol) were suspended in DMF (2 ml) and sparged with argon for 10 minutes. The mixture was heated to 100° C. for 2 h. The reaction mixture was cooled to ambient temperature, diluted in ethyl acetate, washed with saturated aqueous sodium hydrogen carbonate and brine then dried over sodium sulfate, filtered and concentrated. The residue was purified by preparative HPLC Reverse phase (C-18), eluting with Acetonitrile/Water+0.05%. The fractions containing product were combined and diluted in ethyl acetate, then washed with aqueous sodium bicarbonate and dried over sodium sulfate. The solution was filtered and concentrated under reduced pressure to give an off-white solid. The residue was further purified by column chromatography on silica gel (methanol/dichloromethane gradient) to give 4-methoxy-6-(1-methyl-1H-pyrazol-4-yl)pyrazolo[1,5-a]pyridine-3-carbonitrile as an off-white solid. $^1$H NMR (500 MHz, DMSO-$d_6$) δ 8.86 (s, 1H); 8.53 (s, 1H); 8.36 (s, 1H); 8.08 (s, 1H); 7.26 (s, 1H); 4.05 (s, 3H); 3.87 (s, 3H). LRMS (ESI) calculated for $C_{13}H_{12}N_5O$ [M+H]$^+$, 254.1; found 254.1.

Compound 2-5

4-methoxy-6-phenylpyrazolo[1,5-a]pyridine-3-carbonitrile

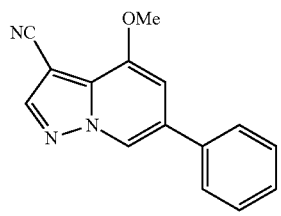 [SMILES: COc1cc(-c2ccccc2)cn2ncc(C#N)c12]

3-iodo-4-methoxy-6-phenylpyrazolo[1,5-a]pyridine (25.0 mg, 0.071 mmol), sodium cyanide (7.0 mg, 0.14 mmol), tetrakis(triphenylphosphine)palladium (0) (4.1 mg, 0.004 mmol), and copper (I) iodide (1.4 mg, 0.007 mmol) were added to a dry flask. Acetonitrile (2 ml) was added and the mixture was sparged with argon for 3 minutes, then heated to 65° C. After 16 h, the reaction mixture cooled and purified by preparative HPLC Reverse phase (C-18), eluting with acetonitrile/water+0.05% TFA to give 4-methoxy-6-phenylpyrazolo[1,5-a]pyridine-3-carbonitrile. $^1$H NMR (600 MHz, DMSO-$d_6$) δ 8.66 (d, 1H); 8.58 (s, 1H); 7.82 (d, 2H); 7.49 (d, 2H); 7.41 (m, 1H); 7.31 (s, 1H); 4.08 (s, 3H). LRMS (ESI) calculated for $C_{15}H_{12}N_3O$ [M+H]$^+$, 250.1; found 250.0.

Compound 2-6

6-bromo-3-iodo-4-methoxypyrazolo[1,5-a]pyridine

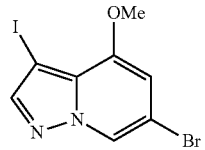 [SMILES: COc1cc(Br)cn2ncc(I)c12]

6-bromo-4-methoxypyrazolo[1,5-a]pyridine (50.0 mg, 0.220 mmol) was dissolved in acetonitrile (2 ml). N-iodosuccinimide (49.5 mg, 0.220 mmol) was added and the mixture was stirred for 1 h, at which time LCMS indicated about 60% conversion. Additional N-iodosuccinimide (9.9 mg, 0.044 mmol) was added and the mixture was stirred for 30 minutes, at which time LCMS indicated about 80% conversion. Additional N-iodosuccinimide (9.9 mg, 0.044 mmol) was added and the mixture was stirred for 30 minutes, at which time LCMS indicated about 80% conversion. Additional N-iodosuccinimide (14.9 mg, 0.066 mmol) was added and the mixture was stirred for 30 minutes, at which time LCMS indicated complete conversion. The reaction mixture was diluted in ethyl acetate, washed with 1N aqueous sodium hydroxide and brine then dried over sodium sulfate, filtered and concentrated. The residue was purified by column chromatography on silica gel (ethyl acetate/isohexane gradient) to give 6-bromo-3-iodo-4-methoxypyrazolo[1,5-a]pyridine as a colorless solid (faster eluting), along with recovered starting material 6-bromo-4-methoxypyrazolo[1,5-a]pyridine (slower eluting). $^1$H NMR (600 MHz, CDCl$_3$) δ 8.25 (d, 1H); 7.80 (s, 1H); 6.47 (s, 1H); 3.93 (s, 3H). LRMS (ESI) calculated for $C_8H_7^{79}BrIN_2O$ [M+H]$^+$, 352.9; found 352.8.

Compound 2-7 tert-Butyl ((2E)-3-(3-chloro-4-methoxypyrazolo[1,5-a]pyridine-6-yl)-2-propen-1-yl)carbamate

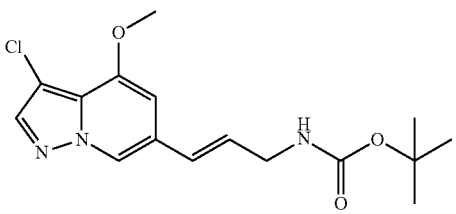 [SMILES: COc1cc(/C=C/CNC(=O)OC(C)(C)C)cn2ncc(Cl)c12]

To a solution of 6-bromo-3-chloro-4-methoxypyrazolo[1,5-a]pyridine in toluene (2.0 ml)/water (0.6 ml)/ethanol (2.0 ml) in a microwave vial was added potassium carbonate (15.86 mg, 0.115 mmol), trans-3-methoxy-1-propenylboronic acid pinacol ester (45.4 mg, 0.229 mmol), and polymer-bound tetrakis(triphenylphosphine)palladium (191 mg, 0.019 mmol). The vial was capped and heated in the Biotage Initiator Series microwave at 120° C. for 10 min. The reaction mixture was filtered, dried in vacuo, and dissolved in DMSO (1 ml). Analytically pure material was obtained by purification by preparative HPLC Reverse phase (C-18), eluting with acetonitrile/water+0.05% formic acid. Lyophilization afforded the formate salt of tert-butyl ((2E)-3-(3-chloro-4-methoxypyrazolo[1,5-a]pyridine-6-yl)-2-propen-1-yl) carbamate as a solid. LRMS (ESI) calculated for $C_{16}H_{20}ClN_3O_3$ [M+H]$^+$: 338.1, Found: 338.1.

Compound 2-8

(2E)-3-(3-Chloro-4-methoxypyrazolo[1,5-a]pyridine-6-yl)-2-propen-1-amine

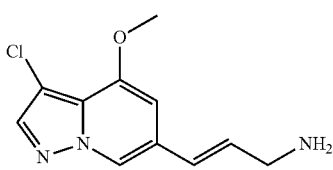 [SMILES: COc1cc(/C=C/CN)cn2ncc(Cl)c12]

To a solution of tert-butyl ((2E)-3-(3-chloro-4-methoxypyrazolo[1,5-a]pyridine-6-yl)-2-propen-1-yl)carbamate (22 mg, 0.066 mmol) in dichloromethane (0.2 ml) was added TFA (76.0 0.986 mmol). After stirring at room temperature for 1 hr, the reaction mixture was quenched with triethylamine, dried in vacuo, and dissolved in DMSO (1 ml). Purification by preparative HPLC Reverse phase (C-18), eluting with acetonitrile/water+0.05% formic acid, followed by lyophilization afforded the formate salt of (2E)-3-(3-chloro-4-methoxypyrazolo[1,5-a]pyridine-6-yl)-2-propen-1-amine as a solid.

LRMS (ESI) calculated for $C_{12}H_{13}ClN_2O_2$ [M+H]$^+$: 238.1, Found: 238.1.

Compound 2-9

3-Chloro-6-ethyl-4-methoxypyrazolo[1,5-a]pyridine

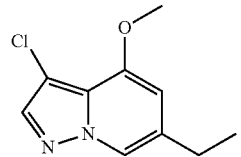

To a solution of 6-bromo-3-chloro-4-methoxypyrazolo[1,5-a]pyridine (50 mg, 0.191 mmol) in toluene (382 µl)/water (172 µl) was added cesium carbonate (187 mg, 0.574 mmol), potassium ethyltrifluoroborate (34.0 mg, 0.191 mmol), palladium acetate (4.29 mg, 0.019 mmol), and 1,1'-bis(di-tert-butylphosphino)ferrocene (9.07 mg, 0.019 mmol) in a microwave vial. The vial was capped and heated at 80° C. overnight. The reaction mixture was cooled to room temperature, filtered through Celite, dried in vacuo, and dissolved in DMSO (1 ml). Purification by preparative HPLC Reverse phase (C-18), eluting with acetonitrile/water+0.05% TFA, followed but lyophilization afforded the TFA salt of 3-chloro-6-ethyl-4-methoxypyrazolo[1,5-a]pyridine as a solid. LRMS (ESI) calculated for $C_{10}H_{11}ClN_2O$ [M+H]$^-$: 211.1, Found: 211.1.

The compounds in the following table were prepared according to the procedure described in scheme 2 and for compounds 2-1 to 2-9. The compounds were prepared as free bases or salts.

TABLE 2

| Compound | Structure | Name | [M + H]+ | Free base or salt form |
|---|---|---|---|---|
| 2-10 | 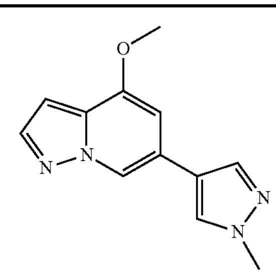 | 4-methoxy-6-(1-methyl-1H-pyrazol-4-yl)pyrazolo[1,5-a]pyridine | Calc'd 229.1, found 229.1 | Free base |

TABLE 2-continued

| Compound | Structure | Name | [M + H]+ | Free base or salt form |
|---|---|---|---|---|
| 2-11 | 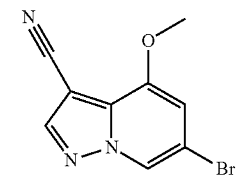 | 6-bromo-4-methoxy-pyrazolo[1,5-a]pyridine-3-carbonitrile | Calc'd 252.0 (for $^{79}$Br), found 252.0 | Free base |
| 2-12 | 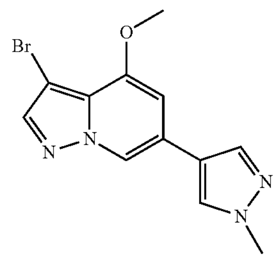 [SMILES: COc1cc(-c2cnn(C)c2)cn2ncc(Br)c12] | 3-bromo-4-methoxy-6-(1-methyl-1H-pyrazol-4-yl)pyrazolo[1,5-a]pyridine | Calc'd 307.0, found 306.9 | Free base |
| 2-13 | 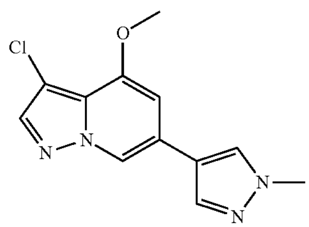 [SMILES: COc1cc(-c2cnn(C)c2)cn2ncc(Cl)c12] | 3-chloro-4-methoxy-6-(1-methyl-1H-pyrazol-4-yl)pyrazolo[1,5-a]pyridine | Calc'd 263.1, found 262.9 | Formate salt |
| 2-14 | 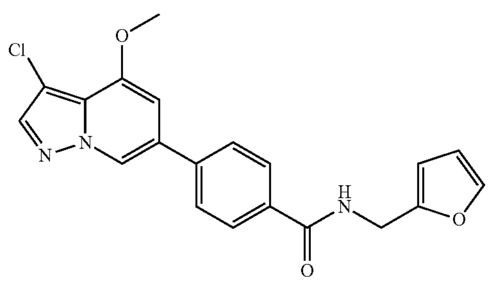 [SMILES: COc1cc(-c2ccc(C(=O)NCc3ccco3)cc2)cn2ncc(Cl)c12] | 4-(3-chloro-4-methoxy-pyrazolo[1,5-a]pyridin-6-yl)-N-(2-furylmethyl)benzamide | Calc'd 382.1, found 382.1 | TFA salt |
| 2-15 | 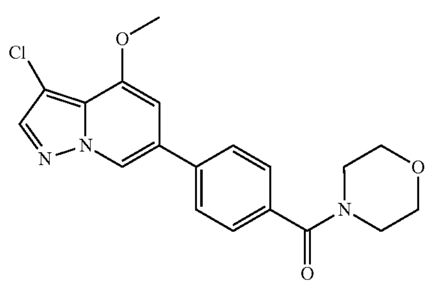 [SMILES: COc1cc(-c2ccc(C(=O)N3CCOCC3)cc2)cn2ncc(Cl)c12] | 3-chloro-4-methoxy-6-[4-(morpholin-4-ylcarbonyl)phenyl]pyrazolo[1,5-a]pyridine | Calc'd 372.1, found 372.1 | TFA salt |
| 2-16 | 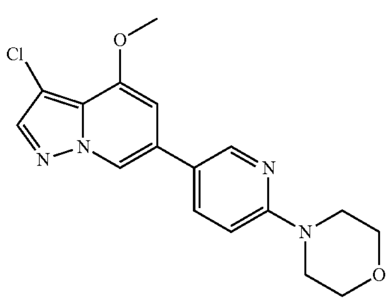 [SMILES: COc1cc(-c2ccc(N3CCOCC3)nc2)cn2ncc(Cl)c12] | 3-chloro-4-methoxy-6-(6-morpholin-4-ylpyridin-3-yl)pyrazolo[1,5-a]pyridine | Calc'd 345.1, found 345.1 | TFA salt |

TABLE 2-continued

| Compound | Structure | Name | [M + H]+ | Free base or salt form |
|---|---|---|---|---|
| 2-17 | 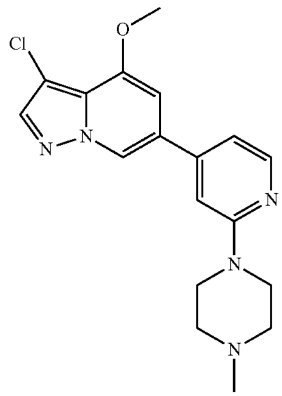 [SMILES: COc1cc(-c2ccnc(N3CCN(C)CC3)c2)cn2ncc(Cl)c12] | 3-chloro-4-methoxy-6-[2-(4-methylpiperazin-1-yl)pyridin-4-yl]pyrazolo[1,5-a]pyridine | Calc'd 358.1, found 358.1 | TFA salt |
| 2-18 | 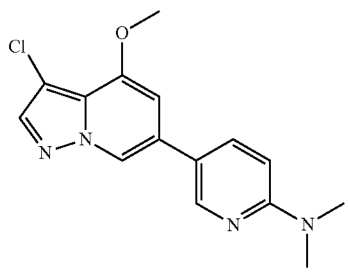 [SMILES: COc1cc(-c2ccc(N(C)C)nc2)cn2ncc(Cl)c12] | 5-(3-chloro-4-methoxypyrazolo[1,5-a]pyridin-6-yl)-N,N-dimethylpyridin-2-amine | Calc'd 303.1, found 303.1 | TFA salt |
| 2-19 | 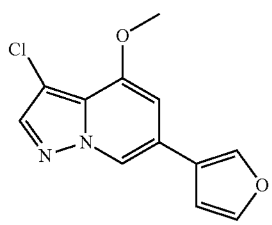 [SMILES: COc1cc(-c2ccoc2)cn2ncc(Cl)c12] | 3-chloro-6-(3-furyl)-4-methoxypyrazolo[1,5-a]pyridine | Calc'd 249.0, found 249.1 | TFA salt |
| 2-20 | 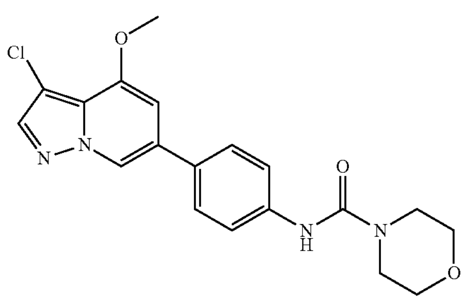 [SMILES: COc1cc(-c2ccc(NC(=O)N3CCOCC3)cc2)cn2ncc(Cl)c12] | N-[4-(3-chloro-4-methoxypyrazolo[1,5-a]pyridin-6-yl)phenyl]morpholine-4-carboxamide | Calc'd 387.1, found 387.1 | TFA salt |
| 2-21 | 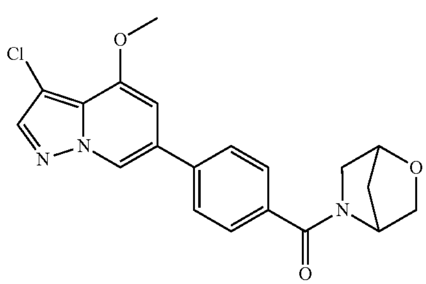 [SMILES: COc1cc(-c2ccc(C(=O)N3CC4CC3CO4)cc2)cn2ncc(Cl)c12] | 3-chloro-4-methoxy-6-[4-(2-oxa-5-azabicyclo[2.2.1]hept-5-ylcarbonyl)phenyl]pyrazolo[1,5-a]pyridine | Calc'd 384.1, found 384.1 | TFA salt |

TABLE 2-continued

| Compound | Structure | Name | [M + H]+ | Free base or salt form |
|---|---|---|---|---|
| 2-22 | 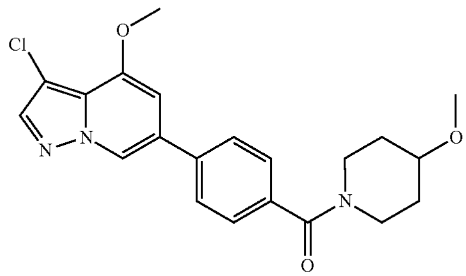 [SMILES: COc1cc(-c2ccc(C(=O)N3CCC(OC)CC3)cc2)cn2ncc(Cl)c12] | 3-chloro-4-methoxy-6-{4-[(4-methoxypiperidin-1-yl)carbonyl]phenyl}pyrazolo[1,5-a]pyridine | Calc'd 400.1, found 400.1 | TFA salt |
| 2-23 | 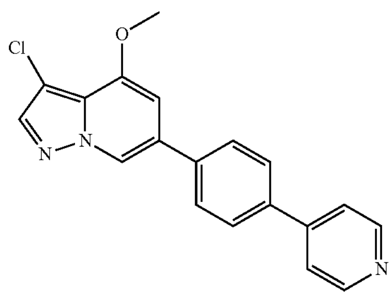 [SMILES: COc1cc(-c2ccc(-c3ccncc3)cc2)cn2ncc(Cl)c12] | 3-chloro-4-methoxy-6-(4-pyridin-4-ylphenyl)pyrazolo[1,5-a]pyridine | Calc'd 336.1, found 336.1 | TFA salt |
| 2-24 | 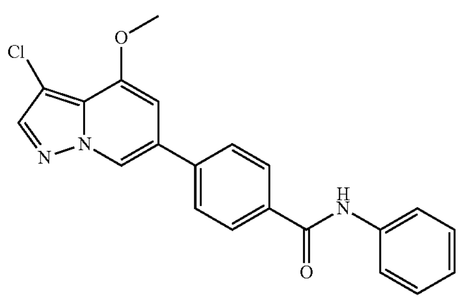 [SMILES: COc1cc(-c2ccc(C(=O)Nc3ccccc3)cc2)cn2ncc(Cl)c12] | 4-(3-chloro-4-methoxypyrazolo[1,5-a]pyridin-6-yl)-N-phenylbenzamide | Calc'd 378.1, found 378.1 | TFA salt |
| 2-25 | 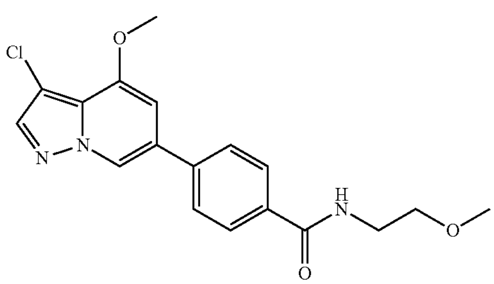 [SMILES: COCCNC(=O)c1ccc(-c2cc(OC)c3c(Cl)cnn3c2)cc1] | 4-(3-chloro-4-methoxypyrazolo[1,5-a]pyridin-6-yl)-N-(2-methoxyethyl)benzamide | Calc'd 360.1, found 360.1 | TFA salt |
| 2-26 | 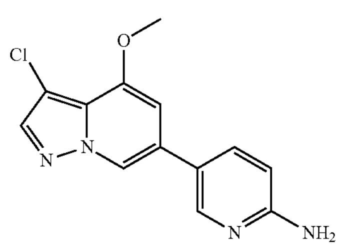 [SMILES: COc1cc(-c2ccc(N)nc2)cn2ncc(Cl)c12] | 5-(3-chloro-4-methoxypyrazolo[1,5-a]pyridin-6-yl)pyridin-2-amine | Calc'd 275.1, found 275.1 | Formate salt |

TABLE 2-continued

| Compound | Structure | Name | [M + H]+ | Free base or salt form |
|---|---|---|---|---|
| 2-27 | 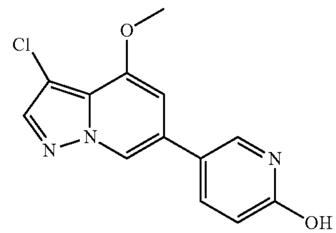 [SMILES: COc1cc(-c2ccc(O)nc2)cn2ncc(Cl)c12] | 5-(3-chloro-4-methoxypyrazolo[1,5-a]pyridin-6-yl)pyridin-2-ol | Calc'd 276.1, found 276.1 | TFA salt |
| 2-28 | 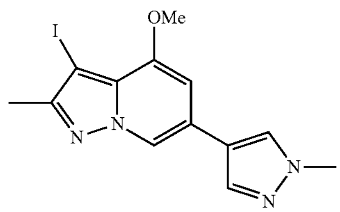 | 3-iodo-4-methoxy-2-methyl-6-(1-methyl-1H-pyrazol-4-yl)pyrazolo[1,5-α]pyridine | Calc'd 369.1, found 368.9 | Free base |
| 2-29 | 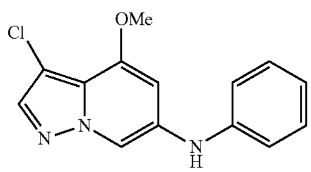 [SMILES: COc1cc(Nc2ccccc2)cn2ncc(Cl)c12] | 3-chloro-4-methoxy-phenylpyrazolo[1,5-a]pyridin-6-amine | Calc'd 274.1, found 274.1 | Formate salt |
| 2-30 | 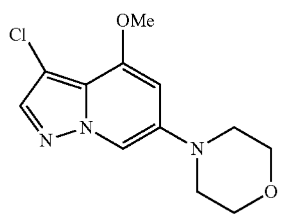 [SMILES: COc1cc(N2CCOCC2)cn2ncc(Cl)c12] | 3-chloro-4-methoxy-6-(4-morpholinyl)pyrazolo[1,5-a]pyridine | Calc'd 268.1, found 268.1 | Formate salt |
| 2-31 | 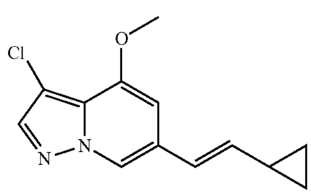 [SMILES: COc1cc(/C=C/C2CC2)cn2ncc(Cl)c12] | 3-chloro-6((E)-2-cycloprpoylvinyl)-4-methoxypyrazolo[1,5-a]pyridine | Calc'd 249.1, found 249.1 | Formate salt |
| 2-32 | 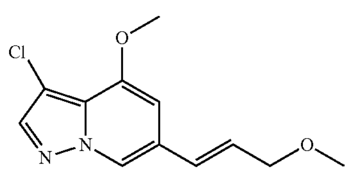 [SMILES: COC/C=C/c1cc(OC)c2c(Cl)cnn2c1] | 3-chloro-4-methoxy-6((1E)-3methoxyvinyl)-4-methoxypyrazolo[1,5-a]pyridine | Calc'd 253.1, found 253.1 | Formate salt |
| 2-33 | 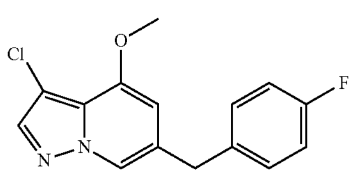 [SMILES: COc1cc(Cc2ccc(F)cc2)cn2ncc(Cl)c12] | 3-chloro-6-(4-fluorobenzyl)-4-methoxypyrazolo[1,5-a]pyridine | Calc'd 291.1, found 291.1 | Formate salt |

TABLE 2-continued
| Compound | Structure | Name | [M + H]+ | Free base or salt form |
|---|---|---|---|---|
| 2-34 | 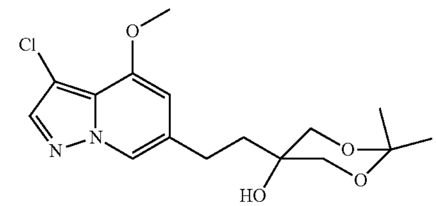 [SMILES: COc1cc(CCC2(O)COC(C)(C)OC2)cn2ncc(Cl)c12] | 5-(2-(3-chloro-4-methoxypyrazolo[1,5-a]pyridn-6-yl)ethyl)-2,2-dimethyl-1,3-dioxan-5-ol | Calc'd 341.1, found 341.1 | Formate salt |
| 2-35 | 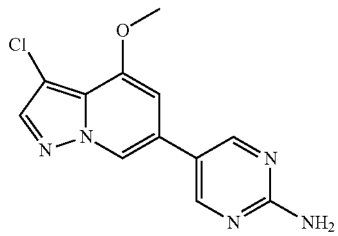 [SMILES: COc1cc(-c2cnc(N)nc2)cn2ncc(Cl)c12] | 5-(3-chloro-4-methoxypyrazolo[1,5-a]pyridin-6-yl)pyrimidin-2-amine | Calc'd 276.1, found 276.1 | Formate salt |
| 2-36 | 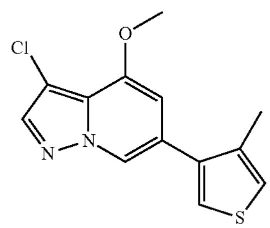 [SMILES: COc1cc(-c2cscc2C)cn2ncc(Cl)c12] | 3-chloro-4-methoxy-6-(4-methyl-3-thienyl)pyrazolo[1,5-a]pyridine | Calc'd 279.0, found 279.1 | Formate salt |
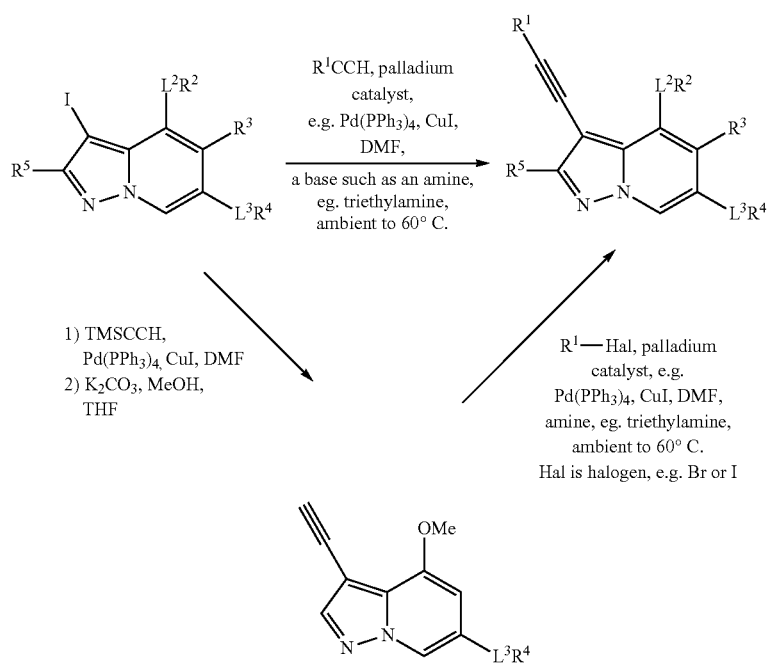
Scheme 3

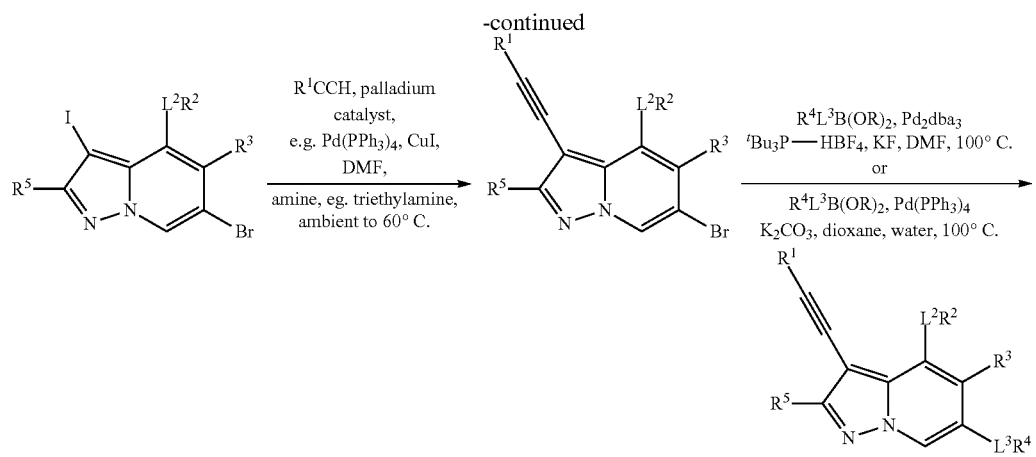

wherein B(OR)$_2$ is a boron ester such as tetramethyldioxaborolanyl.

EXAMPLES 3

Representative Compounds 3-1 to 3-14 and 3-23 to 3-135, and Preparative Compounds 3-15 to 3-22

Compound 3-1

4-methoxy-6-(1-methyl-1H-pyrazol-4-yl)-3-(pyridin-3-ylethynyl)pyrazolo[1,5-a]pyridine

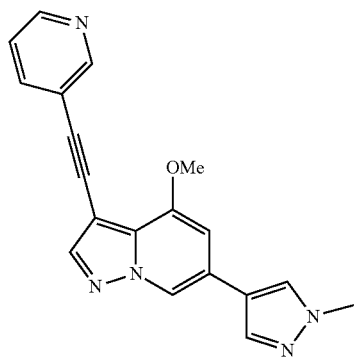 [SMILES: COc1cc(-c2cnn(C)c2)cn2ncc(C#Cc3cccnc3)c12]

3-iodo-4-methoxy-6-(1-methyl-1H-pyrazol-4-yl)pyrazolo[1,5-a]pyridine (20.0 mg, 0.056 mmol), 3-ethynylpyridine (17.5 mg, 0.169 mmol), tetrakis(triphenylphosphine)palladium (0) (6.5 mg, 5.7 mmol), and copper (I) iodide (6.5 mg, 0.034 mmol) were suspended in DMF (1 ml). Triethylamine (0.016 ml, 0.113 mmol) was added, the mixture was sparged with argon for 10 minutes then allowed to stir at ambient temperature. After 1 h, the reaction mixture was diluted in ethyl acetate, washed with saturated aqueous sodium hydrogen carbonate and brine then dried over sodium sulfate, filtered and concentrated. The residue was purified by preparative HPLC Reverse phase (C-18), eluting with Acetonitrile/Water+0.05% TFA. The fractions containing product were combined and diluted in ethyl acetate, then washed with aqueous sodium bicarbonate and dried over sodium sulfate, filtered and concentrated to give 4-methoxy-6-(1-methyl-1H-pyrazol-4-yl)-3-(pyridin-3-ylethynyl)pyrazolo[1,5-a]pyridine. $^1$H NMR (600 MHz, DMSO-d$_6$) δ 8.68 (s, 1H); 8.65 (d, 1H); 8.51 (dd, 1H); 8.30 (s, 1H); 8.17 (s, 1H); 8.03 (s, 1H); 7.85-7.88 (m, 1H); 7.40-7.43 (m, 1H); 7.02 (s, 1H); 4.02 (s, 3H); 3.85 (s, 3H). LRMS (ESI) calculated for C$_{19}$H$_{16}$N$_5$O [M+H]$^+$, 330.1; found 330.0.

Compound 3-2

3-(cyclopropylethynyl)-4-methoxy-6-(1-methyl-1H-pyrazol-4-yl)pyrazolo[1,5-a]pyridine

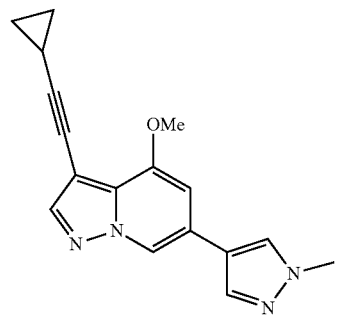 [SMILES: COc1cc(-c2cnn(C)c2)cn2ncc(C#CC3CC3)c12]

Step 1: 6-bromo-3-(cyclopropylethynyl)-4-methoxy-pyrazolo[1,5-a]pyridine 6-bromo-3-iodo-4-methoxypyrazolo[1,5-a]pyridine (50.0 mg, 0.142 mmol), cyclopropyl acetylene (0.018 ml, 0.212 mmol), tetrakis(triphenylphosphine)palladium (0) (16.4 mg, 0.014 mmol), and copper(I) iodide (4.1 mg, 0.02 mmol) were suspended in DMF (2 ml). Triethylamine (0.039 ml, 0.283 mmol) was added, the mixture was sparged with argon for 10 minutes, then heated to 60° C. overnight. LCMS analysis indicated incomplete reaction conversion. Cyclopropyl acetylene (0.018 ml, 0.212 mmol) was added and the mixture was stirred for 6 h, at which time, LCMS analysis indicated the reaction has proceeded further, but still conversion was still incomplete. Cyclopropyl acetylene (0.036 ml, 0.426 mmol) was added and the mixture was stirred overnight. The reaction mixture was diluted in ethyl acetate, washed with saturated aqueous sodium hydrogen carbonate and brine then dried over sodium sulfate, filtered and concentrated. The residue was purified by column chromatography on silica gel (ethyl acetate/isohexane gradient) to afford recovered 6-bromo-3-iodo-4-methoxypyrazolo[1,5-a]pyridine (faster eluting) along with 6-bromo-3-(cyclopropylethynyl)-4-methoxypyrazolo[1,5-a]pyridine (slower eluting).

Step 2: 3-(cyclopropylethynyl)-4-methoxy-6-(1-methyl-1H-pyrazol-4-yl)pyrazolo[1,5-a]pyridine 6-bromo-3-(cyclopropylethynyl)-4-methoxypyrazolo[1,5-a]pyridine (10.0 mg, 0.034 mmol), 1-methyl-4-(4,4,5,5-tetramethyl-1,3,2-dioxaborolan-2-yl)-1H-pyrazole (21.4 mg, 0.103 mmol), tetrakis(triphenylphosphine)palladium (0) (4.0 mg, 3.4 mmol), sodium carbonate (10.9 mg, 0.103 mmol) was suspended in 1,4-dioxane (900 µl/Water (100 µl). The mixture was sparged with Ar for 10 minutes, then heated to 90° C. for 4 h. The reaction mixture was cooled to ambient temperature, diluted in ethyl acetate, washed with saturated aqueous sodium hydrogen carbonate and brine then dried over sodium sulfate, filtered and concentrated. The residue was purified by preparative HPLC Reverse phase (C-18), eluting with Acetonitrile/Water+0.05% TFA. The fractions containing product were combined and diluted in ethyl acetate, then washed with aqueous sodium bicarbonate and dried over sodium sulfate. The solution was filtered and concentrated under reduced pressure to give 3-(cyclopropylethynyl)-4-methoxy-6-(1-methyl-1H-pyrazol-4-yl)pyrazolo[1,5-a]pyridine. $^1$H NMR (600 MHz, CDCl$_3$) δ 8.16 (s, 1H); 7.86 (s, 1H); 7.71 (s, 1H); 7.59 (s, 1H); 6.46 (s, 1H); 3.98 (s, 3H); 3.95 (s, 3H); 1.43-1.46 (m, 1H); 0.78-0.89 (m, 4H). LRMS (ESI) calculated for C$_{17}$H$_{17}$N$_4$O [M+H]$^+$, 293.1; found 293.1.

Compound 3-3

3-{4-[3-(cyclopropylethynyl)-4-methoxypyrazolo[1,5-a]pyridin-6-yl]-1H-pyrazol-1-yl}-2-fluoropropan-1-ol

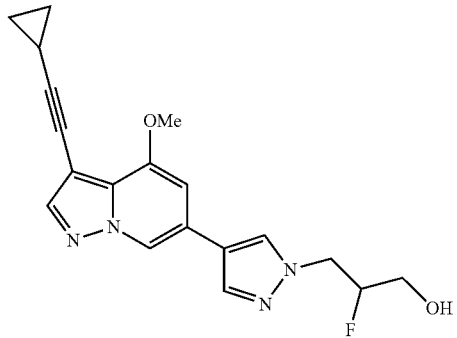 [SMILES: COc1cc(-c2cnn(CC(F)CO)c2)cn2ncc(C#CC3CC3)c12]

Step 1: 3-{[tert-butyl(dimethyl)silyl]oxy}-2-fluoropropyl trifluoromethanesulfonate 3-{[tert-butyl(dimethyl)silyl]oxy}-2-fluoropropan-1-ol (990 mg, 4.75 mmol) [could be prepared in a manner similar to that described in WO2006078598A2, substituting tert-butyl(dimethyl)silylchloride for tert-butyl(diphenyl)silylchloride] and 2,6-lutidine (1.11 ml, 9.50 mmol) were dissolved in dichloromethane (23.8 ml) at 0° C. Triflic anhydride (0.92 ml, 5.46 mmol) was added dropwise via syringe and the solution was allowed to stir for 1 h at 0° C. The reaction mixture was diluted in ethyl acetate, washed with saturated aqueous sodium hydrogen carbonate and brine then dried over sodium sulfate, filtered and concentrated. The residue was purified by column chromatography on silica gel (ethyl acetate/isohexane gradient) to give 3-{[tert-butyl(dimethyl)silyl]oxy}-2-fluoropropyl trifluoromethanesulfonate.

Step 2: 1-(3-{[tert-butyl(dimethyl)silyl]oxy}-2-fluoropropyl-4-(4,4,5,5-tetramethyl-1,3,2-dioxaborolan-2-yl)-1H-pyrazole NaH (0.247 g, 6.17 mmol) was suspended in 10 mL of DMF. 4-(4,4,5,5-tetramethyl-1,3,2-dioxaborolan-2-yl)-1H-pyrazole (0.958 g, 4.94 mmol) was added in 5 mL of DMF dropwise via syringe and the mixture was stirred at room temperature for 30 minutes. Then 3-{[tert-butyl(dimethyl)silyl]oxy}-2-fluoropropyl trifluoromethanesulfonate (1.40 g, 4.11 mmol) was added in 5 mL of DMF dropwise via syringe. After 20 minutes, the reaction mixture was diluted in diethyl ether, washed with water (3×50 mL) and brine then dried over magnesium sulfate, filtered and concentrated to afford 1-(3-{[tert-butyl(dimethyl)silyl]oxy}-2-fluoropropyl)-4-(4,4,5,5-tetramethyl-1,3,2-dioxaborolan-2-yl)-1H-pyrazole.

Step 3: 3-{4-[3-(cyclopropylethynyl)-4-methoxypyrazolo[1,5-a]pyridin-6-yl]-1H-pyrazol-1-yl}-2-fluoropropan-1-ol 6-bromo-3-(cyclopropylethynyl)-4-methoxypyrazolo[1,5-a]pyridine (36.0 mg, 0.124 mmol), 1-(3-{[tert-butyl(dimethyl)silyl]oxy}-2-fluoropropyl)-4-(4,4,5,5-tetramethyl-1,3,2-dioxaborolan-2-yl)-1H-pyrazole (95.0 mg, 0.247 mmol), tris(dibenzylideneacetone)dipalladium (11.3 mg, 0.012 mmol), potassium fluoride (38.1 mg, 0.655 mmol), and tri-t-butylphosphonium tetrafluoroborate (7.2 mg, 0.025 mmol) were suspended in 1.3 mL of DMF and sparged with Ar for 10 minutes. The mixture was heated to 100° C. for 1 h, then allowed to cool to ambient temperature. Tetra-n-butylammonium fluoride (247 µl 0.247 mmol, 1M in THF) was added and the mixture was allowed to stir for 30 minutes, then additional tetra-n-butylammonium fluoride (247 µl, 0.247 mmol, 1M in THF) was added and the mixture was stirred for 30 minutes more. The reaction mixture was diluted in ethyl acetate, washed with saturated aqueous sodium hydrogen carbonate and brine then dried over sodium sulfate, filtered and concentrated. The residue was purified by preparative HPLC Reverse phase (C-18), eluting with Acetonitrile/Water+0.05% TFA (20-100%). The fractions containing product were combined and diluted in ethyl acetate, then washed with aqueous sodium bicarbonate and dried over sodium sulfate. The solution was filtered and concentrated under reduced pressure to give a yellow solid that was slightly impure. The residue was purified by column chromatography on silica gel (methanol/ethylacetate gradient) to give 3-{4-[3-(cyclopropylethynyl)-4-methoxypyrazolo[1,5-a]pyridin-6-yl]-1H-pyrazol-1-yl}-2-fluoropropan-1-ol. $^1$H NMR (500 MHz, DMSO-d$_6$) δ 8.63 (s, 1H); 8.36 (s, 1H); 8.09 (s, 1H); 7.94 (s, 1H); 6.92 (s, 1H); 5.15 (t, 1H); 4.78-4.93 (m, 1H); 4.34-4.46 (m, 2H); 3.96 (s, 3H); 3.50-3.72 (m, 2H); 1.48-1.54 (m, 1H); 0.80-0.87 (m, 2H); 0.66-0.70 (m, 2H). LRMS (ESI) calculated for C$_{19}$H$_{20}$FN$_4$O$_2$ [M+H]$^+$, 355.1; found 355.0.

Compound 3-4

4-methoxy-3-[(5-methyl-1-phenyl-1H-pyrazol-4-yl)ethynyl]-6-(1-methyl-1H-pyrazol-4-yl)pyrazolo[1,5-a]pyridine

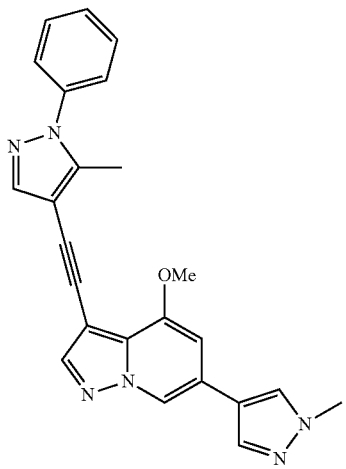 [SMILES: COc1cc(-c2cnn(C)c2)cn2ncc(C#Cc3cnn(-c4ccccc4)c3C)c12]

Step 1: 4-methoxy-6-(1-methyl-1H-pyrazol-4-yl)-3-[(trimethylsilyl)ethynyl]pyrazolo[1,5-a]pyridine 3-iodo-4-methoxy-6-(1-methyl-1H-pyrazol-4-yl)pyrazolo[1,5-a]pyridine (860. mg, 2.43 mmol), tetrakis(triphenylphosphine)palladium(0) (281 mg, 0.243 mmol), trimethylsilylacetylene (1.01 ml, 7.29 mmol) and copper (I) iodide (277 mg, 1.46 mmol) were combined in a round bottom flask. DMF (25 mL) and triethylamine (0.677 mL, 4.86 mmol) were added, then the flask was wrapped with aluminum foil and sparged with nitrogen for 5 minutes. The reaction was stirred at ambient temperature for 30 mins, then diluted with ethyl acetate and washed with saturated aqueous sodium bicarbonate. The organic layer was separated and the aqueous layer was back extracted two times with ethyl acetate. The combined organic layers were dried over sodium sulfate, filtered and concentrated. The liquid was purified by column chromatography on silica gel (methanol/ethyl acetate gradient) to give 4-methoxy-6-(1-methyl-1H-pyrazol-4-yl)-3-[(trimethylsilyl)ethynyl]pyrazolo[1,5-a]pyridine LRMS (ESI) calculated for $C_{17}H_{21}N_4OSi$ [M+H]$^+$, 325.1; found 325.1.

Step 2: 3-ethynyl-4-methoxy-6-(1-methyl-1H-pyrazol-4-yl)pyrazolo[1,5-a]pyridine To a 0.10 M solution of 4-methoxy-6-(1-methyl-1H-pyrazol-4-yl)-3-[(trimethylsilyl)ethynyl]pyrazolo[1,5-a]pyridine (788 mg, 2.43 mmol) in tetrahydrofuran and methanol (1:1, v/v) was added potassium carbonate (336 mg, 2.43 mmol). The reaction mixture was stirred at ambient temperature for two hours, and then diluted with ethyl acetate. The mixture was washed with saturated aqueous ammonium chloride and brine. The organic layer was separated, and the aqueous layer was back extracted with ethyl acetate three times. The combined organic layers was dried over sodium sulfate, filtered and concentrated to give 3-ethynyl-4-methoxy-6-(1-methyl-1H-pyrazol-4-yl)pyrazolo[1,5-a]pyridine. LRMS (ESI) calculated for $C_{14}H_{13}N_4O$ [M+H]$^+$, 252.1; found 253.0.

Step 3: 4-methoxy-3-[(5-methyl-1-phenyl-1H-pyrazol-4-yl)ethynyl]-6-(1-methyl-1H-pyrazol-4-yl)pyrazolo[1,5-a]pyridine Method A: 3-ethynyl-4-methoxy-6-(1-methyl-1H-pyrazol-4-yl)pyrazolo[1,5-a]pyridine (30.0 mg, 0.119 mmol), 4-iodo-5-methyl-1-phenyl-1H-pyrazole (33.8 mg, 0.119 mmol), tetrakis(triphenylphosphine)palladium(0) (14.0 mg, 0.012 mmol) and copper (I) iodide (6.79 mg, 0.036 mmol) were suspended in DMF (1 mL) and triethylamine (0.033 mL, 0.238 mmol) was added. The flask was wrapped with aluminum foil and sparged with nitrogen for 5 minutes. The reaction was stirred at ambient temperature for 1 hour, then diluted with ethyl acetate and washed with saturated aqueous sodium bicarbonate. The organic layer was separated and the aqueous layer was back extracted with ethyl acetate two times. The combined organic layers were dried over sodium sulfate, filtered and concentrated. The residue was purified by preparative HPLC reverse phase (C-18), eluting with acetonitrile/water+0.05% TFA. The fractions containing product were combined and diluted in ethyl acetate, then washed with aqueous sodium bicarbonate and dried over sodium sulfate. The solution was filtered and concentrated under reduced pressure to give 4-methoxy-3-[(5-methyl-1-phenyl-1H-pyrazol-4-yl)ethynyl]-6-(1-methyl-1H-pyrazol-4-yl)pyrazolo[1,5-a]pyridine.

Method B: 3-ethynyl-4-methoxy-6-(1-methyl-1H-pyrazol-4-yl)pyrazolo[1,5-a]pyridine (30.0 mg, 0.119 mmol), 4-iodo-5-methyl-1-phenyl-1H-pyrazole (67.6 mg, 0.238 mmol), and bis(triphenylphosphine)palladium(II) chloride (8.4 mg, 0.012 mmol) were combined into one vial fitted with a Teflon septum. The vial was flushed with nitrogen and tetra-n-butylammonium fluoride (0.36 mL, 0.36 mmol, 1M in THF) and tetrahydrofuran (0.2 mL) were added. After sparging with nitrogen for 5 minutes, the reaction was heated to 80° C. for one hour. The reaction was cooled to ambient temperature, then diluted with ethyl acetate, and washed with saturated aqueous sodium bicarbonate. The organic layer was separated, and the aqueous layer was back extracted with ethyl acetate two times. The combined organic layers were dried over sodium sulfate, filtered and concentrated. The residue was purified by preparative HPLC reverse phase (C-18), eluting with acetonitrile/water+0.05% TFA. The fractions containing product were combined and diluted in ethyl acetate, then washed with aqueous sodium bicarbonate and dried over sodium sulfate. The solution was filtered and concentrated under reduced pressure to give 4-methoxy-3-[(5-methyl-1-phenyl-1H-pyrazol-4-yl)ethynyl]-6-(1-methyl-1H-pyrazol-4-yl)pyrazolo[1,5-a]pyridine Method C: 3-ethynyl-4-methoxy-6-(1-methyl-1H-pyrazol-4-yl)pyrazolo[1,5-a]pyridine (20.0 mg, 0.079 mmol), 4-iodo-5-methyl-1-phenyl-1H-pyrazole (33.8 mg, 0.119 mmol), allylpalladium chloride dimer (2.9 mg, 7.93 mmol), tri(2-furyl)phosphine (3.7 mg, 0.016 mmol) and copper (I) iodide (0.8 mg, 4 mmol) were combined into one vial fitted with a Teflon septum. The vial was and flushed with nitrogen and acetonitrile (0.8 mL) and diisopropylamine (0.034 mL, 0.238 mmol) were added. After sparging with nitrogen for 5 minutes, the reaction was heated to 45° C. for one hour. The mixture was cooled to ambient temperature, diluted with ethyl acetate and washed with saturated aqueous sodium bicarbonate. The organic layer was separated, and the aqueous layer was back extracted with ethyl acetate two times. The combined organic layers were dried over sodium sulfate, filtered and concentrated. The residue was purified by preparative HPLC reverse phase (C-18), eluting with acetonitrile/water+0.05% TFA. The fractions containing product were combined and diluted in ethyl acetate, then washed with aqueous sodium bicarbonate and dried over sodium sulfate. The solution was filtered and concentrated under reduced pressure to give 4-methoxy-3-[(5-methyl-1-phenyl-1H-pyrazol-4-yl)ethynyl]-6-(1-methyl-1H-pyrazol-4-yl)pyrazolo[1,5-a]pyridine.

$^1$H NMR (500 MHz, DMSO-$d_6$) δ 8.66 (s, 1H), 8.31 (s, 1H), 8.12 (s, 1H), 8.04 (s, 1H), 7.83 (s, 1H), 7.52-7.60 (m, 4H), 7.43-7.48 (m, 1H), 4.00 (s, 3H), 3.86 (s, 3H), 2.47 (s, 3H). LRMS (ESI) calculated for $C_{24}H_{21}N_6O$ [M+H]$^-$, 409.2; found 409.2.

Compound 3-5

4-methoxy-6-(1-methyl-1H-pyrazol-4-yl)-3-[(5-methyl-1-pyridin-2-yl-1H-pyrazol-4-yl)ethynyl]pyrazolo[1,5-a]pyridine

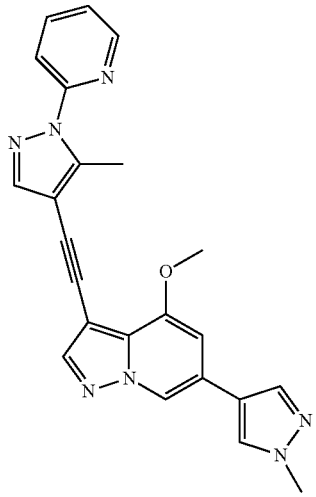 [SMILES: COc1cc(-c2cnn(C)c2)cn2ncc(C#Cc3cnn(-c4ccccn4)c3C)c12]

Step 1: (3E)-4-(dimethylamino)but-3-en-2-one

To N,N-dimethylformamide (10.0 ml, 74.7 mmol) was added acetone (32.9 ml, 448 mmol) and the mixture was heated to 80° C. in a sealed vessel. After 16 hours the reaction mixture was cooled and concentrated to afford (3E)-4-(dimethylamino)but-3-en-2-one which was used without further purification. $^1$H NMR (500 MHz, DMSO-$d_6$) δ 7.43 (d, 1H); 4.89 (d, 1H); 2.96-3.08 (bs, 3H); 2.64-2.78 (bs, 3H); 1.93 (s, 3H).

Step 2: 2-(3-methyl-1H-pyrazol-1-yl)pyridine and 2(5-methyl-1H-pyrazol-1-yl)pyridine (3E)-4-(dimethylamino)but-3-en-2-one (255 mg, 2.25 mmol) and 2-hydrazinopyridine (369 mg, 3.38 mmol) were added to ethanol (3 ml). The reaction mixture was heated to 150° C. in the Biotage Initiator Series microwave reactor. After 30 minutes, the reaction mixture was cooled and concentrated. The residue was purified by column chromatography on silica gel, (ethyl acetate/isohexane gradient) to afford 2-(3-methyl-1H-pyrazol-1-yl)pyridine (faster eluting isomer) and 2-(5-methyl-1H-pyrazol-1-yl)pyridine (slower eluting isomer).

2-(3-methyl-1H-pyrazol-1-yl)pyridine: LRMS (ESI) calculated for $C_9H_{10}N_3$ [M+H]$^+$, 160.1; found 160.1.

2-(5-methyl-1H-pyrazol-1-yl)pyridine: $^1$H NMR (500 MHz, DMSO-$d_6$) δ 8.47 (s, 1H); 7.99-7.94 (m, 1H); 7.82 (d, 1H); 7.61 (s, 1H); 7.33-7.35 (m, 1H); 6.29 (s, 1H); 2.60 (s, 3H). LRMS (ESI) calculated for $C_9H_{10}N_3$ [M+H]$^+$, 160.1; found 160.1.

Step 3: 2-(4-iodo-5-methyl-1H-pyrazol-1-yl)pyridine 2-(5-methyl-1H-pyrazol-1-yl)pyridine (100 mg, 0.63 mmol) and N-iodosuccinimide (212 mg, 0.942 mmol) were added to acetonitrile (5 ml). The reaction mixture was heated to 60° C. After 1 hour, the reaction mixture was diluted with ethyl acetate, washed with 1N aqueous sodium hydroxide and brine, then dried over magnesium sulfate, filtered, and concentrated. The residue was purified by column chromatography on silica gel (ethyl acetate/isohexane gradient) to afford 2-(4-iodo-5-methyl-1H-pyrazol-1-yl)pyridine. LRMS (ESI) calculated for $C_9H_9IN_3$ [M+H]$^+$, 286.0; found 286.0.

Step 4: 4-methoxy-6-(1-methyl-1H-pyrazol-4-yl)-3-[(5-methyl-1-pyridin-2-yl-1H-pyrazol-4-yl)ethynyl]pyrazolo[1,5-a]pyridine To a mixture of 3-ethynyl-4-methoxy-6-(1-methyl-1H-pyrazol-4-yl)pyrazolo[1,5-a]pyridine (30.0 mg, 0.12 mmol), 2-(4-iodo-5-methyl-1H-pyrazol-1-yl)pyridine (51.0 mg, 0.18 mmol), copper (I) iodide (6.8 mg, 0.036 mmol), and tetrakis(triphenylphosphine)palladium (0) (14 mg, 0.012 mmol) in N,N-dimethylformamide (2 ml), was added triethylamine (0.033 ml, 0.24 mmol). The mixture was sparged with argon for 3 minutes and heated to 60° C. After 1 h, reaction mixture was purified directly by preparative HPLC Reverse phase (C-18), eluting with acetonitrile/water+0.05% TFA to give 4-methoxy-6-(1-methyl-1H-pyrazol-4-yl)-3-[(5-methyl-1-pyridin-2-yl-1H-pyrazol-4-yl)ethynyl]pyrazolo[1,5-a]pyridine.

$^1$H NMR (500 MHz, DMSO-$d_6$) δ 8.67 (s, 1H); 8.53-8.50 (m, 1H); 8.31 (s, 1H); 8.13 (s, 1H); 8.00-8.04 (m, 2H); 7.90 (s, 1H); 7.87 (d, 1H); 7.39-7.42 (m, 1H); 6.98 (s, 1H); 4.01 (s, 3H); 3.86 (s, 3H); 2.77 (s, 3H). LRMS (ESI) calculated for $C_{23}H_{20}N_7O$ [M+H]$^+$, 410.2; found 410.1.

Compound 3-6

4-methoxy-6-(1-methyl-1H-pyrazol-4-yl)-3-[(3-methyl-1-pyridin-2-yl-1H-pyrazol-4-yl)ethynyl]pyrazolo[1,5-a]pyridine

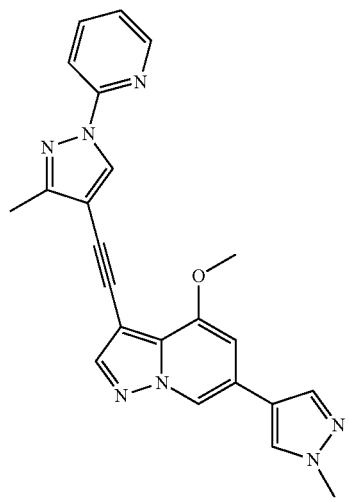 [SMILES: COc1cc(-c2cnn(C)c2)cn2ncc(C#Cc3cn(-c4ccccn4)nc3C)c12]

Title compound was prepared from 2-(3-methyl-1H-pyrazol-1-yl)pyridine isolated from Step 2 of synthesis of Compound 3-5 using the methods used for Compound 3-5.

$^1$H NMR (500 MHz, DMSO-$d_6$) δ 8.68 (s, 1H); 8.66 (s, 1H); 8.44 (d, 1H); 8.31 (s, 1H); 8.11 (s, 1H); 8.04 (s, 1H); 8.00-7.95 (m, 1H); 7.87 (d, 1H); 7.36-7.32 (m, 1H); 7.00 (s,

1H); 4.02 (s, 3H); 3.86 (s, 3H); 2.41 (s, 3H). LRMS (ESI) calculated for $C_{23}H_{20}N_7O$ [M+H]$^+$, 410.2; found 410.2.

Compound 3-7

3-[(3,5-dimethyl-1-phenyl-1H-pyrazol-4-yl)ethynyl]-4-methoxy-6-(1-methyl-1H-pyrazol-4-yl)pyrazolo[1,5-a]pyridine

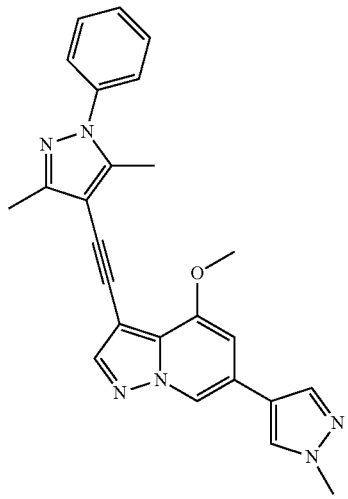 [SMILES: COc1cc(-c2cnn(C)c2)cn2ncc(C#Cc3c(C)nn(-c4ccccc4)c3C)c12]

Title compound was prepared from commercially available 3,5-dimethyl-1-phenyl-1H-pyrazole using Steps 3 and 4 of the synthesis of compound 3-5.

$^1$H NMR (500 MHz, DMSO-$d_6$) δ 8.65 (d, 1H); 8.31 (s, 1H); 8.10 (s, 1H); 8.04 (s, 1H); 7.56-7.50 (m, 4H); 7.43-7.40 (m, 1H); 6.97 (s, 1H); 4.00 (s, 3H); 3.87 (s, 3H); 2.43 (s, 3H); 2.31 (s, 3H). LRMS (ESI) calculated for $C_{25}H_{23}N_6O$ [M+H]$^+$, 423.2; found 423.2.

Compound 3-8

3-[(5-ethyl-1-phenyl-1H-pyrazol-4-yl)ethynyl]-4-methoxy-6-(1-methyl-1H-pyrazol-4-yl)pyrazolo[1,5-a]pyridine

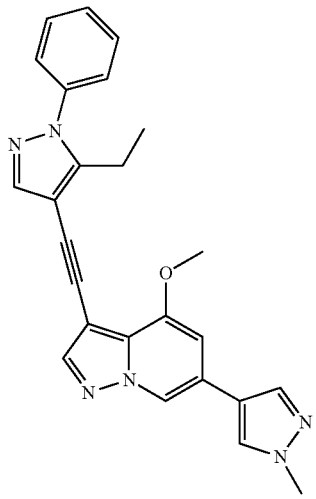 [SMILES: CCc1c(C#Cc2cnn3cc(-c4cnn(C)c4)cc(OC)c23)cnn1-c1ccccc1]

Step 1: methyl (2Z)-2-[(dimethylamino)methylene]-3-oxopentanoate

To N,N-dimethylformamide dimethyl acetal (0.384 ml, 2.88 mmol) was added methyl-3-oxo-pentanoate (250 mg, 1.92 mmol) and the mixture was heated to 110° C. in a sealed vessel. After 30 minutes the reaction mixture was cooled and concentrated to afford methyl (2Z)-2-[(dimethylamino)methylene]-3-oxopentanoate which was used without further purification.

Step 2: methyl 5-ethyl-1-phenyl-1H-pyrazole-4-carboxylate

Methyl (2Z)-2-[(dimethylamino)methylene]-3-oxopentanoate (383 mg, 2.07 mmol) and phenylhydrazine (0.308 ml, 3.10 mmol) were added to ethanol (4 ml). The reaction mixture was heated to 150° C. in the Biotage Initiator Series microwave. After 30 minutes, the reaction mixture was cooled and concentrated. The residue was purified by column chromatography on silica gel (ethyl acetate/hexanes gradient) to afford methyl 5-ethyl-1-phenyl-1H-pyrazole-4-carboxylate.

$^1$H NMR (500 MHz, DMSO-$d_6$) δ 7.99 (s, 1H); 7.59-7.51 (m, 3H); 7.50-7.46 (m, 2H); 3.77 (s, 3H); 2.86 (q, 2H); 1.03 (t, 3H). LRMS (ESI) calculated for $C_{13}H_{15}N_2O_2$ [M+H]$^+$, 231.1; found 231.2.

Step 3: 5-ethyl-1-phenyl-1H-pyrazole-4-carboxylic acid

To a solution of methyl 5-ethyl-1-phenyl-1H-pyrazole-4-carboxylate (315 mg, 1.37 mmol) in ethanol (5 ml) was added 10M sodium hydroxide (0.410 ml, 4.10 mmol). The reaction mixture was heated to 80° C. After 3 hours, the reaction mixture was cooled and quenched with 1N HCl until the pH ~1. The reaction mixture was diluted with chloroform and water, the organics were separated, then dried over magnesium sulfate, filtered, and concentrated to afford 5-ethyl-1-phenyl-1H-pyrazole-4-carboxylic acid.

$^1$H NMR (500 MHz, DMSO-$d_6$) δ 12.42 (s, 1H); 7.93 (s, 1H); 7.59-7.50 (m, 3H); 7.49-7.45 (m, 2H); 2.86 (q, 2H); 1.02 (t, 3H). LRMS (ESI) calculated for $C_{12}H_{13}N_2O_2$ [M+H]$^+$, 217.1; found 217.1.

Step 4: 5-ethyl-1-phenyl-1H-pyrazole 5-ethyl-1-phenyl-1H-pyrazole-4-carboxylic acid (210 mg, 0.971 mmol) was heated neat to 210° C. After 6 hours, the residue was cooled and purified by column chromatography on silica gel (ethyl acetate/hexanes gradient) to afford 5-ethyl-1-phenyl-1H-pyrazole.

$^1$H NMR (500 MHz, DMSO-$d_6$) δ 7.55 (d, 1H); 7.54-7.40 (m, 5H); 6.28 (d, 1H); 2.65 (q, 2H); 1.12 (t, 3H).

Step 5: 5-ethyl-4-iodo-1-phenyl-1H-pyrazole 5-ethyl-1-phenyl-1H-pyrazole (21 mg, 0.12 mmol) and N-iodosuccinimide (41 mg, 0.18 mmol) were added to acetonitrile (5 ml). The reaction mixture was heated to 60° C. After 1 hour, the reaction mixture was diluted with ethyl acetate, washed with 1N aqueous sodium hydroxide and brine, then dried over magnesium sulfate, filtered, and concentrated. The residue was purified by column chromatography on silica gel (ethyl acetate/hexanes gradient) to afford 5-ethyl-4-iodo-1-phenyl-1H-pyrazole.

¹H NMR (500 MHz, DMSO-d₆) δ 7.68 (s, 1H); 7.56-7.52 (m, 2H); 7.50-7.43 (m, 3H); 2.65 (q, 2H); 0.97 (t, 3H). LRMS (ESI) calculated for $C_{11}H_{12}IN_2$ [M+H]⁺, 299.0; found 299.0.

Step 6: 3-[(5-ethyl-1-phenyl-1H-pyrazol-4-yl)ethynyl]-4-methoxy-6-(1-methyl-1H-pyrazol-4-yl)pyrazolo[1,5-a]pyridine To a mixture of 3-ethynyl-4-methoxy-6-(1-methyl-1H-pyrazol-4-yl)pyrazolo[1,5-a]pyridine (20 mg, 0.080 mmol), 5-ethyl-4-iodo-1-phenyl-1H-pyrazole (24 mg, 0.08 mmol), copper (I) iodide (4.5 mg, 0.024 mmol), and tetrakis(triphenylphosphine)palladium (0) (9.2 mg, 0.0079 mmol) in N,N-dimethylformamide (2 ml), was added triethylamine (0.022 ml, 0.16 mmol). The mixture was sparged with argon for 3 minutes and heated to 70° C. After 1 h, reaction mixture was purified directly by preparative HPLC Reverse phase (C-18), eluting with acetonitrile/water+0.05% TFA to give 3-[(5-ethyl-1-phenyl-1H-pyrazol-4-yl)ethynyl]-4-methoxy-6-(1-methyl-1H-pyrazol-4-yl)pyrazolo[1,5-a]pyridine.

¹H NMR (500 MHz, DMSO-d₆) δ 8.66 (d, 1H); 8.31 (s, 1H); 8.11 (s, 1H); 8.04 (s, 1H); 7.81 (s, 1H); 7.58-7.47 (m, 5H); 6.98 (s, 1H); 3.99 (s, 3H); 3.87 (s, 3H); 2.85 (q, 2H); 1.14 (t, 3H). LRMS (ESI) calculated for $C_{25}H_{23}N_6O$ [M+H]⁻, 423.2; found 423.2.

Compound 3-9

3-[(5-cyclopropyl-1-phenyl-1H-pyrazol-4-yl)ethynyl]-4-methoxy-6-(1-methyl-1H-pyrazol-4-yl)pyrazolo[1,5-a]pyridine

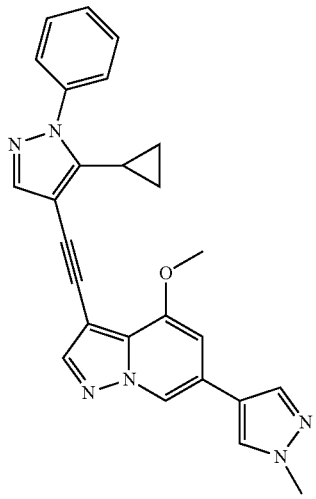 [SMILES: COc1cc(-c2cnn(C)c2)cn2ncc(C#Cc3cnn(-c4ccccc4)c3C3CC3)c12]

Step 1: (2E)-1-cyclopropyl-3-(dimethylamino)prop-2-en-1-one

To N,N-dimethylformamide dimethyl acetal (9.51 ml, 71.3 mmol) was added cyclopropyl methyl ketone (3.34 ml, 35.7 mmol) and the mixture was heated to 150° C. in a sealed vessel. After 16 hours, the reaction mixture was cooled and concentrated to afford (2E)-1-cyclopropyl-3-(dimethylamino)prop-2-en-1-one which was used without further purification.

¹H NMR (500 MHz, DMSO-d₆) δ 7.48 (d, 1H); 5.10 (d, 1H); 3.09-2.96 (bs, 3H); 2.80-2.72 (bs, 3H); 1.90-1.82 (bs, 1H); 0.71-0.67 (m, 2H); 0.63-0.59 (m, 2H).

Step 2: 3-cyclopropyl-1-phenyl-1H-pyrazole and 5-cyclopropyl-1-phenyl-1H-pyrazole (2E)-1-cyclopropyl-3-(dimethylamino)prop-2-en-1-one (327 mg, 2.35 mmol) and phenylhydrazine (0.35 ml, 3.5 mmol) were added to ethanol (5 ml). The reaction mixture was heated to 150° C. in the Biotage Initiator Series microwave reactor. After 30 minutes, the reaction mixture was cooled and concentrated. The residue was purified by column chromatography on silica gel (ethyl acetate/hexanes gradient) to afford 3-cyclopropyl-1-phenyl-1H-pyrazole (faster eluting isomer) and 5-cyclopropyl-1-phenyl-1H-pyrazole (slower eluting isomer).

3-cyclopropyl-1-phenyl-1H-pyrazole: ¹H NMR (500 MHz, DMSO-d₆) δ 8.31 (d, 1H); 7.76-7.72 (m, 2H); 7.46-7.40 (m, 2H); 7.24-7.20 (m, 1H); 6.22 (d, 1H); 1.97-1.93 (m, 1H); 0.92-0.88 (m, 2H); 0.73-0.69 (m, 2H). LRMS (ESI) calculated for $C_{12}H_{13}N_2$ [M+H]⁺, 185.1; found 185.2.

5-cyclopropyl-1-phenyl-1H-pyrazole: ¹H NMR (500 MHz, DMSO-d₆) δ 7.63-7.60 (m, 2H); 7.53-7.49 (m, 3H); 7.40 (t, 1H); 6.10 (d, 1H); 1.86-1.80 (m, 1H); 0.95-0.91 (m, 2H); 0.72-0.69 (m, 2H). LRMS (ESI) calculated for $C_{12}H_{13}N_2$ [M+H]⁺, 185.1; found 185.1.

Step 3: 5-cyclopropyl-4-iodo-1-phenyl-1H-pyrazole 5-cyclopropyl-1-phenyl-1H-pyrazole (200 mg, 1.09 mmol) and N-iodosuccinimide (366 mg, 1.63 mmol) were added to acetonitrile (5 ml). The reaction mixture was heated to 70° C. After 6 hours, the reaction mixture was diluted with ethyl acetate, washed with 1N aqueous sodium hydroxide and brine, then dried over magnesium sulfate, filtered, and concentrated. The residue was purified by column chromatography on silica gel (ethyl acetate/hexanes gradient) to afford 5-cyclopropyl-4-iodo-1-phenyl-1H-pyrazole.

¹H NMR (500 MHz, DMSO-d₆) δ 7.67 (s, 1H); 7.58-7.54 (m, 2H); 7.52-7.48 (m, 2H); 7.44-7.40 (m, 1H); 1.99-1.92 (m, 1H); 0.85-0.80 (m, 2H); 0.43-0.40 (m, 2H). LRMS (ESI) calculated for $C_{12}H_{12}IN_2$ [M+H]⁺, 311.0; found 311.0.

Step 4: 3-[(5-cyclopropyl-1-phenyl-1H-pyrazol-4-yl)ethynyl]-4-methoxy-6-(1-methyl-1H-pyrazol-4-yl)pyrazolo[1,5-a]pyridine To a mixture of 3-ethynyl-4-methoxy-6-(1-methyl-1H-pyrazol-4-yl)pyrazolo[1,5-a]pyridine (40 mg, 0.160 mmol), 5-cyclopropyl-4-iodo-1-phenyl-1H-pyrazole (62 mg, 0.20 mmol), copper (I) iodide (9.1 mg, 0.048 mmol), and tetrakis(triphenylphosphine)palladium (0) (18.3 mg, 0.016 mmol) in N,N-dimethylformamide (2 ml), was added triethylamine (0.044 ml, 0.32 mmol). The mixture was sparged with argon for 3 minutes and heated to 70° C. After 1 h, reaction mixture was purified directly by preparative HPLC Reverse phase (C-18), eluting with acetonitrile/water+0.05% TFA to give 3-[(5-cyclopropyl-1-phenyl-1H-pyrazol-4-yl)ethynyl]-4-methoxy-6-(1-methyl-1H-pyrazol-4-yl)pyrazolo[1,5-a]pyridine.

¹H NMR (500 MHz, DMSO-d₆) δ 8.66 (d, 1H); 8.31 (s, 1H); 8.10 (s, 1H); 8.04 (s, 1H); 7.77 (s, 1H); 7.63-7.61 (m, 2H); 7.57-7.53 (m, 2H); 7.48-7.44 (m, 1H); 6.99 (d, 1H); 4.02 (s, 3H); 3.87 (s, 3H); 1.99-1.95 (m, 1H); 1.21-1.17 (m, 2H); 0.98-0.94 (m, 2H). LRMS (ESI) calculated for $C_{26}H_{23}N_6O$ [M+H]⁺, 435.2; found 435.2.

Compound 3-10

4-methoxy-6-(1-methyl-1H-pyrazol-4-yl)-3-{[5-methyl-1-(2-thienyl)-1H-pyrazol-4-yl]ethynyl}pyrazolo[1,5-a]pyridine

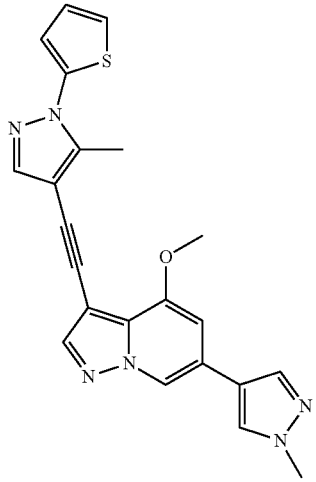 [SMILES: COc1cc(-c2cnn(C)c2)cn2ncc(C#Cc3cnn(-c4cccs4)c3C)c12]

Step 1: 3-methyl-1-(2-thienyl)-1H-pyrazole and 5-methyl-1-(2-thienyl)-1H-pyrazole A mixture of 3-methylpyrazole (500 mg, 6.09 mmol), salicylaldoxime (167 mg, 1.22 mmol), copper (I) oxide (44 mg, 0.30 mmol), and cesium carbonate (3.97 g, 12.2 mmol) was sparged with argon for 3 minutes. To this mixture was added acetonitrile (3 ml) and 2-bromothiophene (0.88 ml, 9.1 mmol). The reaction mixture was sparged with argon for 3 minutes and heated to 82° C. After 16 hours, the reaction mixture was diluted with ethyl acetate, washed with water and brine, then dried over magnesium sulfate, filtered, and concentrated. The residue was purified by column chromatography on silica gel (ethyl acetate/hexanes gradient) to afford 3-methyl-1-(2-thienyl)-1H-pyrazole (faster eluting isomer) and 5-methyl-1-(2-thienyl)-1H-pyrazole (slower eluting isomer).

3-methyl-1-(2-thienyl)-1H-pyrazole: $^1$H NMR (500 MHz, DMSO-$d_6$) δ 8.23 (d, 1H); 7.21-7.19 (m, 2H); 6.97-6.95 (m, 1H); 6.29 (d, 1H); 2.21 (s, 3H). LRMS (ESI) calculated for $C_8H_9N_2S$ [M+H]$^+$, 165.0; found 165.1.

5-methyl-1-(2-thienyl)-1H-pyrazole: $^1$H NMR (500 MHz, DMSO-$d_6$) δ 7.54 (d, 1H); 7.41 (dd, 1H); 7.14 (dd, 1H); 7.04 (dd, 1H); 6.26 (bs, 1H); 2.37 (s, 3H). LRMS (ESI) calculated for $C_8H_9N_2S$ [M+H]$^+$, 165.0; found 165.1.

Step 2: 1-(5-iodo-2-thienyl)-5-methyl-1H-pyrazole and 4-iodo-5-methyl-1-(2-thienyl)-1H-pyrazole 5-methyl-1-(2-thienyl)-1H-pyrazole (64 mg, 0.39 mmol) and N-iodosuccinimide (88 mg, 0.39 mmol) were added to acetonitrile (5 ml). The reaction mixture was heated to 70° C. After 6 hours, the reaction mixture was diluted with ethyl acetate, washed with 1N aqueous sodium hydroxide and brine, then dried over magnesium sulfate, filtered, and concentrated. The residue was purified by column chromatography on silica gel (ethyl acetate/hexanes gradient) to afford 1-(5-iodo-2-thienyl)-5-methyl-1H-pyrazole and 4-iodo-5-methyl-1-(2-thienyl)-1H-pyrazole.

1-(5-iodo-2-thienyl)-5-methyl-1H-pyrazole: $^1$H NMR (500 MHz, DMSO-$d_6$) δ 7.55 (d, 1H); 7.30 (d, 1H); 6.88 (d, 1H); 6.27 (bs, 1H); 2.37 (s, 3H).

4-iodo-5-methyl-1-(2-thienyl)-1H-pyrazole: $^1$H NMR (500 MHz, DMSO-$d_6$) δ 7.18 (s, 1H); 7.48 (dd, 1H); 7.20 (dd, 1H); 7.06 (dd, 1H); 2.36 (s, 3H).

Step 3: 4-methoxy-6-(1-methyl-1H-pyrazol-4-yl)-3-{[5-methyl-1-(2-thienyl)-1H-pyrazol-4-yl]ethynyl}pyrazolo[1,5-a]pyridine To a mixture of 3-ethynyl-4-methoxy-6-(1-methyl-1H-pyrazol-4-yl)pyrazolo[1,5-a]pyridine (20 mg, 0.08 mmol), 4-iodo-5-methyl-1-(2-thienyl)-1H-pyrazole (23 mg, 0.08 mmol), copper (I) iodide (4.5 mg, 0.024 mmol), and tetrakis(triphenylphosphine)palladium (0) (9.1 mg, 0.008 mmol) in N,N-dimethylformamide (2 ml), was added triethylamine (0.022 ml, 0.16 mmol). The mixture was sparged with argon for 3 minutes and heated to 70° C. After 1 h, reaction mixture was purified directly by preparative HPLC Reverse phase (C-18), eluting with acetonitrile/water+0.05% TFA to give 4-methoxy-6-(1-methyl-1H-pyrazol-4-yl)-3-{[5-methyl-1-(2-thienyl)-1H-pyrazol-4-yl]ethynyl}pyrazolo[1,5-a]pyridine.

$^1$H NMR (500 MHz, DMSO-$d_6$) δ 8.67 (d, 1H); 8.31 (s, 1H); 8.12 (s, 1H); 8.04 (s, 1H); 7.84 (s, 1H); 7.48 (dd, 1H); 7.27 (dd, 1H); 7.08 (dd, 1H); 6.99 (bs, 1H); 4.00 (s, 3H); 3.87 (s, 3H); 2.53 (s, 3H). LRMS (ESI) calculated for $C_{22}H_{19}N_6OS$ [M+H]$^+$, 415.1; found 415.1.

Compound 3-11

4-methoxy-6-(1-methyl-1H-pyrazol-4-yl)-3-{[1-methyl-2-(2-thienyl)-1H-imidazol-5-yl]ethynyl}pyrazolo[1,5-a]pyridine

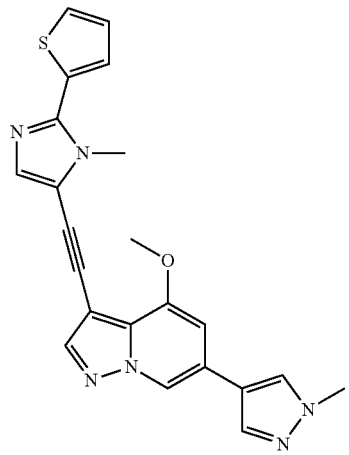 [SMILES: COc1cc(-c2cnn(C)c2)cn2ncc(C#Cc3cnc(-c4cccs4)n3C)c12]

Step 1: 1-methyl-2-(2-thienyl)-1H-imidazole

Methylaminoacetaldehyde dimethyl acetal (0.50 ml, 3.9 mmol), thiophene-2-carbonitrile (0.36 ml, 3.9 mmol) and copper(I) chloride (481 mg, 4.86 mmol) were combined in a sealed tube and heated to 85° C. for 12 hours. The mixture was allowed to reach ambient temperature, and methanol (2 ml) was added, followed with hydrochloric acid (4.8 M, 2.0 ml, 9.7 mmol). The resulting mixture was refluxed for 4 hours and concentrated under reduced pressure to remove methanol. The mixture was placed over an ice bath and 50% aqueous sodium hydroxide (1.24 g, 31.1 mmol) was added slowly to keep the temperature below 20° C. Then the mixture was diluted with ethyl acetate, stirred for 5 mins, filtered and washed with ethyl acetate. The filtrate was washed with brine, separated, dried over sodium sulfate, filtered and concentrated and taken forward without additional purification. LRMS (ESI) calculated for $C_8H_9N_2S$ [M+H]$^+$, 165.0; found 165.1.

Step 2: 5-iodo-1-methyl-2-(2-thienyl)-1H-imidazole

To a solution of 1-methyl-2-(2-thienyl)-1H-imidazole (116 mg, 0.706 mmol) in acetonitrile (5 ml) was added NIS (159 mg, 0.706 mmol) at room temperature. The reaction mixture was heated in the Biotage Initiator Series microwave for 1 hour at 120° C. The reaction mixture was diluted in ethyl acetate, washed with 1N aqueous sodium hydroxide and brine then dried over sodium sulfate, filtered and concentrated to give 5-iodo-1-methyl-2-(2-thienyl)-1H-imidazole. The material was taken forward without any additional purification. LRMS (ESI) calculated for $C_8H_8N_2SI$ [M+H]$^+$, 290.9; found 291.0.

Step 3: 4-methoxy-6-(1-methyl-1H-pyrazol-4-yl)-3-{[1-methyl-2-(2-thienyl)-1H-imidazol-5-yl]ethynyl}pyrazolo[1,5-a]pyridine The compound was synthesized with the same way as Method C in Step 3 of Compound 3-4.
$^1$H NMR (500 MHz, CDCl$_3$) δ 8.24 (s, 1H), 8.02 (s, 1H), 7.75 (s, 1H), 7.64 (s, 1H), 7.39-7.43 (m, 2H), 7.37 (s, 1H), 7.12-7.15 (m, 1H), 6.58 (s, 1H), 4.03 (s, 3H), 3.98 (s, 3H), 3.95 (s, 3H). LRMS (ESI) calculated for $C_{22}H_{19}N_6OS$ [M+H]$^+$, 415.1; found 415.1.

Compound 3-12

3-methoxy-N-(4-{[4-methoxy-6-(1-methyl-1H-pyrazol-4-yl)pyrazolo[1,5-a]pyridin-3-yl]ethynyl}pyridin-2-yl)benzenesulfonamide

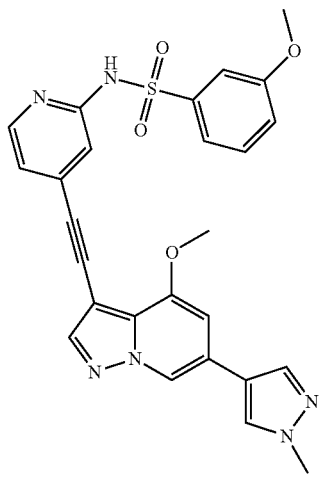 [SMILES: COc1cccc(S(=O)(=O)Nc2cc(C#Cc3cnn4cc(-c5cnn(C)c5)cc(OC)c34)ccn2)c1]

To a solution of 4-{[4-methoxy-6-(1-methyl-1H-pyrazol-4-yl)pyrazolo[1,5-a]pyridin-3-yl]ethynyl}pyridin-2-amine (24 mg, 0.070 mmol) in pyridine (1400 μl), was added 3-methoxybenzenesulfonyl chloride (29 μl, 0.203 mmol). The reaction mixture was stirred for 72 hours at room temperature. The precipitated solid was filtered and the solid washed with 10 mL of dichloromethane. The solid was dried in vacuo to afford 3-methoxy-N-(4-{[4-methoxy-6-(1-methyl-1H-pyrazol-4-yl)pyrazolo[1,5-a]pyridin-3-yl]ethynyl}pyridin-2-yl)benzenesulfonamide an off-white solid. $^1$H NMR (500 MHz, DMSO-d$_6$) δ 8.75 (s, 1H); 8.34 (s, 1H); 8.26 (s, 1H); 8.06 (s, 1H); 7.99 (bs, 2H); 7.49-7.42 (m, 2H); 7.38 (s, 1H); 7.16-7.15 (m, 2H); 7.11 (s, 1H); 6.85 (bs, 1H); 4.07 (s, 3H); 3.87 (s, 3H); 3.79 (s, 3H). LRMS (ESI) calculated for $C_{26}H_{22}N_6O_3S$ [M+H]$^+$, 515.1; found 515.1.

Compound 3-13

N-(4-{[4-methoxy-6-(1-methyl-1H-pyrazol-4-yl)pyrazolo[1,5-a]pyridin-3-yl]ethynyl}pyridin-2-yl)-N'-phenylurea

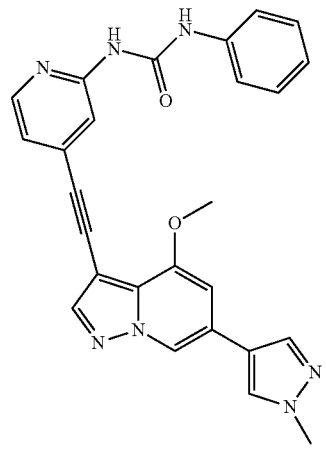 [SMILES: COc1cc(-c2cnn(C)c2)cn2ncc(C#Cc3ccnc(NC(=O)Nc4ccccc4)c3)c12]

To a solution of 4-{[4-methoxy-6-(1-methyl-1H-pyrazol-4-yl)pyrazolo[1,5-a]pyridin-3-yl]ethynyl}pyridin-2-amine (24 mg, 0.07 mmol) in dichloromethane (1400 μl) was added phenyl isocyanate (9.09 μl, 0.084 mmol) and the mixture was allowed to stir for 72 hours at room temperature. The precipitated solid was filtered was filtered and the washed with 10 mL of dichloromethane. The solid was dried in vacuo to afford N-(4-{[4-methoxy-6-(1-methyl-1H-pyrazol-4-yl)pyrazolo[1,5-a]pyridin-3-yl]ethynyl}pyridin-2-yl)-N'-phenylurea. $^1$H NMR (500 MHz, DMSO-d$_6$) δ 10.28 (s, 1H); 9.46 (s, 1H); 8.69 (s, 1H); 8.28 (s, 1H); 8.23-8.21 (m, 2H); 8.01 (s, 1H); 7.56 (s, 1H); 7.47 (d, 2H); 7.26 (t, 2H); 7.04 (s, 1H); 6.98-6.96 (m, 2H); 4.05 (s, 3H); 3.82 (s, 3H). LRMS (ESI) calculated for $C_{26}H_{21}N_7O_2$ [M+H]$^+$, 464.2; found 464.1.

Compound 3-14 pyridin-3-ylmethyl 3-{[4-methoxy-6-(1-methyl-1H-pyrazol-4-yl)pyrazolo[1,5-a]pyridin-3-yl]ethynyl}azetidine-1-carboxylate

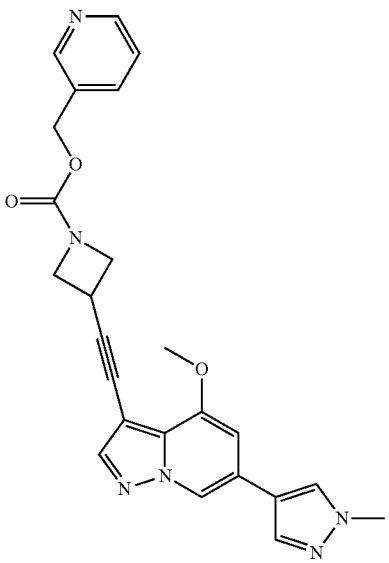 [SMILES: COc1cc(-c2cnn(C)c2)cn2ncc(C#CC3CN(C(=O)OCc4cccnc4)C3)c12]

Step 1: 3-ethynylazetidine (TFA Salt)

To a solution tert-butyl 3-ethynylazetidine-1-carboxylate (506 mg, 2.79 mmol) in methylene chloride (20 ml) was added TFA (2.15 ml, 27.9 mmol) at 0° C. The reaction was stirred at 0° C. for 30 mins and then the solvent was removed under reduced pressure to give 3-ethynylazetidine (TFA salt).

Step 2: pyridin-3-ylmethyl 3-ethynylazetidine-1-carboxylate

To a solution of CDI (1.14 g, 7.02 mmol) in THF (15 ml) was added pyridine-3-methanol (0.68 ml, 7.0 mmol) at 0° C., and the reaction was stirred at room temperature for 1 hour. A solution of 3-ethynylazetidine (TFA salt) (250 mg, 1.40 mmol) and triethylamine (0.98 ml, 7.0 mmol) in THF (3 ml) was added to the reaction mixture, followed with DBU (0.42 ml, 2.8 mmol). After 3 hours, the reaction mixture was diluted with ethyl acetate, washed with saturated aqueous sodium bicarbonate, then dried over sodium sulfate, filtered, and concentrated. The residue was purified by column chromatography on silica gel, eluting with methanol/ethyl acetate to give pyridin-3-ylmethyl 3-ethynylazetidine-1-carboxylate. LRMS (ESI) calculated for $C_{12}H_{13}N_2O_2$ [M+H]$^+$, 217.1; found 217.1.

Step 3: pyridin-3-ylmethyl 3-{[4-methoxy-6-(1-methyl-1H-pyrazol-4-yl)pyrazolo[1,5-a]pyridin-3-yl]ethynyl}azetidine-1-carboxylate Pyridin-3-ylmethyl 3-ethynylazetidine-1-carboxylate (50 mg, 0.23 mmol), 3-iodo-4-methoxy-6-(1-methyl-1H-pyrazol-4-yl)pyrazolo[1,5-a]pyridine (40 mg, 0.11 mmol), allylpalladium chloride dimer (12 mg, 0.03 mmol), tri(2-furyl)phosphine (16 mg, 0.07 mmol) and copper (I) iodide (2.1 mg, 0.011 mmol) were combined into one vial fitted with a Teflon septum. The vial was flushed with nitrogen and acetonitrile (1.6 ml) and diisopropylamine (0.048 mL, 0.34 mmol) were added. After sparging with nitrogen for 5 minutes, the reaction was heated to 45° C. for two hours. The mixture was cooled to ambient temperature, diluted with ethyl acetate and washed with saturated aqueous sodium bicarbonate. The organic layer was separated and the aqueous layer was back extracted with ethyl acetate two times. The combined organic layers were dried over sodium sulfate, filtered and concentrated. The residue was purified by preparative HPLC reverse phase (C-18), eluting with acetonitrile/water+0.05% TFA. The fractions containing product were combined and diluted in ethyl acetate, then washed with aqueous sodium bicarbonate and dried over sodium sulfate. The solution was filtered and concentrated under reduced pressure to give pyridin-3-ylmethyl 3-{[4-methoxy-6-(1-methyl-1H-pyrazol-4-yl)pyrazolo[1,5-a]pyridin-3-yl]ethynyl}azetidine-1-carboxylate. $^1$H NMR (500 MHz, DMSO-d$_6$) δ 8.63 (s, 1H), 8.58 (s, 1H), 8.50-8.54 (m, 1H), 8.29 (s, 1H), 8.02 (s, 2H), 7.74-7.82 (m, 1H), 7.35-7.43 (m, 1H), 6.94 (s, 1H), 5.09 (s, 2H), 4.12-4.38 (br, 2H), 3.80-3.98 (m, 8H), 3.67-3.76 (m, 1H). LRMS (ESI) calculated for $C_{24}H_{23}N_6O_3$ [M+H]$^+$, 443.2; found 443.2.

Preparative compounds 3-15 to 3-22 were used to synthesize the compounds in Table 3.

Preparative Compound 3-15 tert-butyl 2-prop-2-yn-1-ylpyrrolidine-1-carboxylate

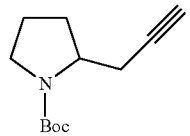

Step 1: ethyl prolinate

Into a 500 ml 3-necked roundbottom flask, was placed a solution of proline (20.0 g, 174. mmol) in EtOH (100 ml). To the above was added thinyl chloride (40 ml). The resulting solution was heated to 70° C., with stirring, for 12 hours. The mixture was concentrated by evaporation. To afford ethyl prolinate that was used without further purification.

Step 2: ethyl 1-benzylprolinate

Into a 500 ml 3-necked roundbottom flask, was placed ethyl prolinate (20.0 g, 140. mmol). This was followed by the addition of a solution of benzaldehyde (14.8 g, 140. mmol) in dichloromethane (100 ml). This was followed by the addition of a solution of sodium triacetoxyborohydride (60.0 g, 280. mmol) in acetic acid (20 ml). The resulting solution was allowed to stirring for 12 hours at room temperature. Adjustment of the pH to 7 was accomplished by the addition of solid potassium carbonate. The resulting solution was extracted one time with 500 ml of EtOAc and concentrated by evaporation to afford ethyl 1-benzylprolinate that was used without further purification.

Step 3: (1-benzylpyrrolidin-2-yl)methanol

Into a 5,000 ml 3-necked roundbottom flask purged and maintained with an inert atmosphere of nitrogen, was placed a solution of lithium aluminum hydride (54.0 g, 1.42 mol) in tetrahydrofuran (3,500 ml) at 0° C. This was followed by the dropwise addition of a solution of ethyl 1-benzylprolinate (330 g, 1.42 mol) in tetrahydrofuran (500 ml), maintaining an internal temperature of 0° C. (2 hours total addition time). The resulting solution was allowed to stir for 2 hours while the temperature was maintained at 0° C. The reaction mixture was then quenched by the addition of water. The solution was filtered, and the filtration residue was washed once with 500 ml of tetrahydrofuran. The filtrate was concentrated by evaporation under vacuum using a rotary evaporator. The residue was dissolved in 3,000 ml of ethyl acetate, dried over sodium sulfate, filtered and concentrated to afford 1-benzylpyrrolidin-2-yl)methanol, which was used without further purification.

Step 4: 1-benzyl-2-(chloromethyl)pyrrolidine

Into a 5,000 ml 3-necked roundbottom flask, was placed a solution of (1-benzylpyrrolidin-2-yl)methanol (250. g, 1.30 mol) in chloroform (2,500 ml). This was followed by the dropwise addition of a solution of thionyl chloride (232. g, 1.95 mol) in chloroform (500 ml), while maintaining the internal temperature at room temperature (60 minute addition time). The resulting solution was heated to reflux for 2 hours. After cooling to ambient temperature, the mixture was concentrated, and the resulting residue was dissolved in 3,000 ml of ethyl acetate. Adjustment of the pH to 7 was accomplished by the addition of triethylamine. The resulting mixture was filtered and the filtrate was concentrated and the residue was purified by flash column chromatography (ethylacetate/petroleum ether gradient) to afford 1-benzyl-2-(chloromethyl) pyrrolidine.

Step 5: (1-benzylpyrrolidin-2-yl)acetonitrile

Into a 3,000 ml 3-necked roundbottom flask, was placed a solution of 1-benzyl-2-(chloromethyl)pyrrolidine (150. g, 714 mmol) in N,N-dimethylformamide (1,500 ml). This was followed by the addition of a solution of NaCN (54.2 g, 834 mmol) in water (300 ml). The resulting solution was heated to reflux for 2 hours. After cooling to ambient temperature, the solution was dissolved in 6,000 ml of water. The resulting solution was extracted with ethyl acetate (3×3,000 ml) and the combined organic layers were dried over sodium sulfate, filtered and concentrated. The residue was purified by flash column chromatography (ethylacetate/petroleum ether gradient) to afford 2-(1-benzylpyrrolidin-2-yl)acetonitrile.

Step 6: ethyl (1-benzylpyrrolidin-2-yl)acetate

Into a 3,000 ml roundbottom flask, was placed ethanol (479. g, 10.4 mol), followed by concentrated sulfuric acid (417 g, 4.17 mol). To the mixture was added 2-(1-benzylpyrrolidin-2-yl)acetonitrile (139. g, 695. mmol). The resulting solution was heated to reflux for 4 hours. After cooling to ambient temperature, the solution was diluted with 3,000 ml of water. Adjustment of the pH to 9 was accomplished by the addition of solid sodium carbonate. The resulting solution was extracted three times with 2,000 ml of ethyl acetate and the combined organic layers were concentrated to afford ethyl 2-(1-benzylpyrrolidin-2-yl)acetate, which was used without additional purification.

Step 7: tert-butyl 2-(2-ethoxy-2-oxoethyl)pyrrolidine-1-carboxylate.

A 5,000 ml roundbottom flask was purged, flushed and maintained with a hydrogen atmosphere, then a solution of ethyl 2-(1-benzylpyrrolidin-2-yl) acetate (120. g, 486 mmol) in ethanol (3,000 ml) was added. To the mixture was added di-tert-butyl-dicarbonate (159 g, 729 mmol). The resulting solution was allowed to stir overnight. The solution was filtered and concentrated. The residue was purified by flash column chromatography (ethylacetate/petroleum ether gradient) to afford tert-butyl 2-(2-ethoxy-2-oxoethyl)pyrrolidine-1-carboxylate.

Step 8: tert-butyl 2-(2-oxoethyl)pyrrolidine-1-carboxylate

Into a 3,000 ml 3-necked roundbottom flask purged and maintained with an inert atmosphere of nitrogen was placed a solution of tert-butyl 2-(2-ethoxy-2-oxoethyl)pyrrolidine-1-carboxylate (119 g, 463 mmol) in dichloromethane (1,200 ml). The solution was cooled to −80° C. and diisobutylaluminum hydride (362 g, 510 mmol) was added dropwise, while maintaining an internal temperature of −80° C. (3 hours total addition time). The resulting solution was allowed to stir for 2 hours while the temperature was maintained at −80° C. The reaction mixture was then quenched by the adding 500 ml of methanol. After warming to ambient temperature, the mixture was washed with 1,000 ml of NaOH (20% w/w aqueous) and 6 times with 1,000 ml of water. The organic layer was dried over sodium sulfate, filtered and concentrated to afford tert-butyl 2-(2-oxoethyl)pyrrolidine-1-carboxylate, which was used without additional purification.

Step 9: tert-butyl 2-(3,3-dibromoprop-2-en-1-yl) pyrrolidine-1-carboxylate

Into a 10 L 3-necked roundbottom flask purged and maintained with an inert atmosphere of nitrogen, was placed a solution of triphenylphosphine (516.6 g, 1.970 mol) in dichloromethane (2,000 ml). The solution was cooled to −15° C. and a solution of carbontetrabromide (327.3 g, 985.8 mmol) in dichloromethane (1,000 ml) was added over a period of 120 minutes. Then a solution of tert-butyl 2-(2-oxoethyl)pyrrolidine-1-carboxylate (105 g, 493 mmol) in dichloromethane (1,000 ml) was added dropwise over a period of 120 minutes. The resulting solution was allowed warm to warm to 0° C., and stir for 20 minutes. The resulting solution was diluted with 4,000 ml of petroleum ether. The mixture was filtered and concentrated. The residue was purified by flash column chromatography (ethylacetate/petroleum ether gradient) to afford tert-butyl 2-(3,3-dibromoprop-2-en-1-yl)pyrrolidine-1-carboxylate.

Step 10: tert-butyl 2-prop-2-yn-1-ylpyrrolidine-1-carboxylate

Into a 3,000 ml 3-necked roundbottom flask purged and maintained with an inert atmosphere of nitrogen, was placed a solution of tert-butyl 2-(3,3-dibromoprop-2-en-1-yl)pyrrolidine-1-carboxylate (103 g, 279 mmol) in tetrahydrofuran (1,000 ml). The solution was cooled to −80° C. and n-butyl lithium (231 mL, 2.00 equiv, 155 g/L) was added dropwise such that the internal temperature was maintained at −80° C. (180 minute addition time). The resulting solution was allowed to warm to ambient temperature and then allowed to stir for 1 h. The reaction mixture was quenched by the addition of 500 mL of water. The resulting solution was extracted three times with 500 mL of diethyl ether and the combined organic layers were dried over sodium sulfate, filtered and concentrated. The residue was purified by flash column chromatography (ethylacetate/petroleum ether gradient) to afford tert-butyl 2-prop-2-yn-1-ylpyrrolidine-1-carboxylate.

Preparative Compound 3-16 tert-butyl 3-ethynylazetidine-1-carboxylate

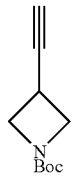

Step 1:
1-(tert-butoxycarbonyl)azetidine-3-carboxylic acid

To a solution of azetidine-3-carboxylic acid (18. g, 0.18 mol), NaOH (21.4 g, 0.534 mol) in 180 mL of tetragydrofuran and 334 mL of water was added di-tert-butyl-dicarbonate (46.6 g, 0.214 mol), and the mixture was stirred overnight at room temperature. The mixture was diluted with 250 mL of ethyl acetate, the biphasic solution obtained was separated, and the basic aqueous layer was acidified to pH=2 by slow addition of concentrated HCl. The aqueous layer was extracted with dichloromethane (3×250 mL). The combined organic layers were dried over magnesium sulfate, filtered and concentrated to afford 1-(tert-butoxycarbonyl)azetidine-3-carboxylic acid.

Step 2: tert-butyl 3-{[methoxy(methyl)amino]carbonyl}azetidine-1-carboxylate

To a solution containing 1-(tert-butoxycarbonyl)azetidine-3-carboxylic acid (60.4 g, 0.30 mol), hydroxybenzotriazole (49 g, 0.36 mol), EDC (69.4 g, 0.36 mol), and triethyamine (142 ml) in 620 ml of dichloromethane was added N,O-dimethylhydroxyl-amine hydrochloride (35.4 g, 0.36 mol). The mixture obtained was stirred overnight at room temperature. The solution was partitioned between 500 ml of water and 200 ml of dichloromethane, and the aqueous layer was washed with 200 ml of dichloromethane. The combined organic layers were washed with 250 ml of brine, dried over magnesium sulfate, filtered and concentrated to afford tert-butyl 3-{[methoxy(methyl)amino]carbonyl}azetidine-1-carboxylate, which was used without additional purification.

Step 3: tert-butyl 3-formylazetidine-1-carboxylate

To a solution tert-butyl 3-{[methoxy(methyl)amino]carbonyl}azetidine-1-carboxylate (93.8 g, 0.3 mol) in tetrahydrofuran at −70° C. was added dropwise lithium aluminum hydride (12.3 g in 320 ml THF). After the addition was complete, the reaction mixture was stirred for 1 h at −70° C. The reaction was quenched by the addition of 13 ml of water, followed by 39 ml of 1N aqueous NaOH solution and 13 ml of water. The mixture was stirred for 1 h, filtered and concentrated. The residue was partitioned between 300 ml of ethyl acetate and 100 ml of water. The layers were separated and the organic layers were washed with 100 ml of brine. The organic layer was dried over magnesium sulfate, filtered and concentrated to afford tert-butyl 3-formylazetidine-1-carboxylate, which was used without additional purification.

Step 4: tert-butyl 3-ethynylazetidine-1-carboxylate

To a solution of tert-butyl 3-formylazetidine-1-carboxylate (96 g, 0.46 mol) and potassium carbonate (128 g, 0.924 mol) in methanol was added dropwise dimethyl-1-diazo-2-oxo-propylphosphonate (67 g, 0.35 mol) in 1.6 L of methanol. The mixture was stirred for 2 h and filtered. The filtrate was concentrated and the residue was diluted with 800 ml of methyl-tert-butyl ether and 1 L of 5% w/w aqueous sodium bicarbonate. The layers were separated and the aqueous layer was washed with methyl-tert-butyl ether (2×500 ml). The combined organic layers were dried over magnesium sulfate, filtered and concentrated. The residue was purified by flash column chromatography to afford tert-butyl 3-ethynylazetidine-1-carboxylate.

Preparative Compound 3-17

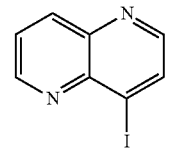 [SMILES: Ic1ccnc2cccnc12]

4-iodo-1,5-naphthyridine

Step 1:
diethyl[(E)-(pyridin-3-ylimino)methyl]malonate

A 250 ml flask was charged with 3-Aminopyridine (8 g, 85 mmol) and diethyl 2-(ethoxymethylene)malonate (18.5 g, 85.6 mmol). The mixture was heated to 110° C. for 30 min, and then cooled to ambient temperature to give diethyl [(E)-(pyridin-3-ylimino)methyl]malonate.

Step 2: ethyl 4-hydroxy-3,4-dihydro-1,5-naphthyridine-3-carboxylate

Diethyl [(E)-(pyridin-3-ylimino)methyl]malonate (9 g, 34 mmol) was dissolved in 1,1'-oxydibenzene (150 ml). The mixture was heated at 250° C. for 2 hours, and then cooled to room temperature. The reaction mixture was filtered to give ethyl 4-hydroxy-3,4-dihydro-1,5-naphthyridine-3-carboxylate.

Step 3: 4-hydroxy-3,4-dihydro-1,5-naphthyridine-3-carboxylic acid

Ethyl 4-hydroxy-3,4-dihydro-1,5-naphthyridine-3-carboxylate (1.8 g, 8.2 mmol) was dissolved in 4% aqueous sodium hydroxide (80 ml). The reaction mixture was heated to reflux for 4 hours, cooled to room temperature, and then adjusted to pH=4 with 2N hydrochloric acid. The reaction mixture was filtered to give 4-hydroxy-3,4-dihydro-1,5-naphthyridine-3-carboxylic acid.

Step 4: 1,5-naphthyridin-4-ol 4-hydroxy-3,4-dihydro-1,5-naphthyridine-3-carboxylic acid (1.4 g, 7.3 mmol) was dissolved in quinoline (50 ml). The mixture was heated to 200° C. for 2 hours, and then cooled to room temperature. The reaction mixture was filtered to give 1,5-naphthyridin-4-ol.

Step 5: 4-bromo-1,5-naphthyridine

A flask was charged with 1,5-naphthyridin-4-ol (1 g, 6.7 mmol) and phosphorousoxybromide (5 g, 17 mmol). The mixture was heated to 150° C., stirred for 1 hour, and then cooled to room temperature. The mixture was poured into ice-water and extracted with toluene. The combined organic extracts were washed with brine, dried over sodium sulfate, filtered and concentrated to give crude product, which was re-crystallized from petroleum ether to give 4-bromo-1,5-naphthyridine.

Step 6: 4-iodo-1,5-naphthyridine 4-bromo-1,5-naphthyridine (99 mg, 0.47 mmol), copper(I) iodide (4.5 mg, 0.024 mmol) and sodium iodide (142 mg, 0.947 mmol) were combined into one vial fitted with a Teflon septum. The vial was flushed with nitrogen and 1,4-dioxane (4 ml) was added. After sparging with nitrogen for 5 minutes, rac-trans-N,N'-dimethylcyclohexane-1,2-diamine (7.5 µl, 0.047 mmol) was added and the reaction was heated to 100° C. for 12 hours. The mixture was cooled to ambient temperature, and saturated aqueous ammonium chloride (2 ml) was added to quench the reaction. After stirring for 10 minutes, the mixture was diluted with ethyl acetate and washed with saturated aqueous sodium bicarbonate. The organic layer was separated, and the aqueous layer was back extracted with ethyl acetate one more time. The combined organic layers were dried over sodium sulfate, filtered and concentrated. The residue was purified by column chromatography on silica gel (methanol/dichloromethane gradient) to afford 4-iodo-1,5-naphthyridine.

Preparative Compound 3-18

2-bromo-5-tert-butyl-1,3,4-thiadiazole

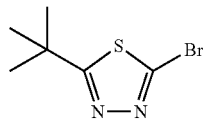

Step 1: 5-tert-butyl-1,3,4-thiadiazol-2-amine

To a solution of pivalic acid (85.1 g, 0.833 mol) in concentrated sulfuric acid (280 ml) was slowly added hydrazinecarbothioamide (76.0 g, 0.833 mol) such that the internal temperature was maintained at 0-4° C. After addition was complete, the resulting mixture was heated to 80° C. and monitored by TLC. After the reaction was complete, the resulting yellow solution was cooled to room temperature, poured into ice, and then adjusted the pH to 7 by the addition of aqueous ammonium hydroxide. The resulting precipitate was filtered to obtain 5-tert-butyl-1,3,4-thiadiazol-2-amine which was used directly without purification.

Step 2: 2-bromo-5-tert-butyl-1,3,4-thiadiazole

To a solution of crude 5-tert-butyl-1,3,4-thiadiazol-2-amine (120.8 g) in glacial acetic acid (800 ml) was added aqueous hydrobromic acid (≧40%, 218 ml) at room temperature. The resulting solution was heated to 65° C., and a solution of sodium nitrite (167 g, 2.42 mol) in water (300 ml) was added dropwise such that the internal temperature was maintained at 65~75° C. After addition was complete, the resulting yellow solution was cooled to room temperature, poured into ice and then extracted with ethyl acetate. The combined organic layer was washed with saturated aqueous sodium carbonate solution until the pH was neutral, dried over magnesium sulfate, filtered and concentrated. The resulting oil was purified via flash column chromatography (ethyl acetate/petroleum ether) to obtain 2-bromo-5-tert-butyl-1,3,4-thiadiazole.

Preparative Compound 3-19 tert-butyl 3-ethynylpyrrolidine-1-carboxylate

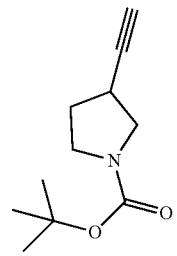

Step 1: 1-benzyl-5-oxopyrrolidine-3-carboxylic acid

A mixture of itaconic acid (130 g, 1.00 mol) and benzylamine (107 g, 1.00 mol) were heated to 130° C. After 30 minutes, the reaction mixture was cooled and diluted with water (200 mL). The resulting slurry was filtered, washed with cold water, dissolved in aqueous sodium hydroxide, and treated with active carbon. The slurry was filtered to remove the carbon, and the aqueous solution was acidified with hydrochloric acid to precipitate solids. The solids were recrystallized from ethanol to afford 1-benzyl-5-oxopyrrolidine-3-carboxylic acid that was used without additional purification.

Step 2: (1-benzylpyrrolidin-3-yl)methanol

To a solution of 5-oxopyrrolidine-3-carboxylic acid (109.5 g, 0.5000 mol) in tetrahydrofuran (1000 mL) was added lithium aluminum hydride (38 g, 1.0 mol) in portions sufficient to keep the reaction mixture refluxing. After the addition was complete, the reaction mixture was stirred at ambient temperature. After 3 hours, the reaction mixture was carefully diluted with water (110 mL) and ethanol (500 mL). After 30 minutes, the reaction mixture was filtered, and the filtrate was concentrated in vacuo, extracted with ethyl acetate (3×200 mL), dried over magnesium sulfate, filtered, and concentrated in vacuo to afford (1-benzylpyrrolidin-3-yl)methanol that was used without additional purification.

Step 3: pyrrolidin-3-ylmethanol

A solution of (1-benzylpyrrolidin-3-yl)methanol (100 g, 0.52 mol) in ethanol (250 mL) was degassed with argon for 5 minutes, charged with palladium on carbon (15 g), then hydrogen gas (1 atm), and heated to 40-50° C. When hydrogen gas was no longer absorbed, the reaction mixture was filtered and concentrated in vacuo to afford pyrrolidin-3-ylmethanol that was used without additional purification.

Step 4: tert-butyl 3-(hydroxymethyl)pyrrolidine-1-carboxylate

To a solution of sodium hydroxide (60 g, 1.5 mol) in water (200 mL) at 0° C. was added tetrahydrofuran (200 mL). The solution was warmed to ambient temperature and charged with pyrrolidin-3-ylmethanol (50 g, 0.50 mol). To this mixture was slowly added a solution of di-tert-butyl dicarbonate (163.5 g, 0.750 mol) in tetrahydrofuran (200 mL). The internal reaction temperature was not allowed to exceed 25° C. After the addition was complete, the reaction mixture was stirred for 5 hours, then diluted with water (200 mL), extracted with ethyl acetate (3×200 mL), dried over sodium sulfate, filtered, and concentrated in vacuo, to afford tert-butyl 3-(hydroxymethyl)pyrrolidine-1-carboxylate that was used without additional purification.

Step 5: tert-butyl 3-formylpyrrolidine-1-carboxylate

To a solution of pyridine (9.5 g, 0.12 mol) in dichloromethane (150 mL) was added chromium trioxide (6.0 g, 0.06 mol). The internal reaction temperature was not allowed to exceed 20° C. during the addition. After 15 minutes, the stirred mixture was charged with a solution of tert-butyl 3-(hydroxymethyl)pyrrolidine-1-carboxylate (2.0 g, 10 mmol) in dichloromethane (30 mL). After 15 minutes, the solution was decanted from the reaction vessel which was washed with dichloromethane (200 mL). The organics were combined, washed with 5% aqueous sodium hydroxide (3×100 mL), then washed with 5% hydrochloric acid (100 mL), then washed with 5% aqueous sodium bicarbonate (100 mL), and finally washed with 5% aqueous sodium chloride (100 mL). The organics were dried over magnesium sulfate, filtered, and concentrated in vacuo to afford tert-butyl 3-formylpyrrolidine-1-carboxylate that was used without additional purification.

Step 6: tert-butyl 3-ethynylpyrrolidine-1-carboxylate

Dimethyl-1-diazo-2-oxypropylphosphonate (11.5 g, 60 mmol) was added to a solution of tert-butyl 3-formylpyrrolidine-1-carboxylate (10 g, 50 mmol) and potassium carbonate (13.8 g, 100 mmol) in dry methanol (150 mL). After 16 hours, the reaction mixture was filtered and washed with methanol. The filtrate was extracted with diethyl ether, and the organic layer was washed with 5% aqueous sodium bicarbonate, dried over sodium sulfate, filtered, and concentrated in vacuo. The residue was purified by column chromatography on silica gel to afford tert-butyl 3-ethynylpyrrolidine-1-carboxylate.

Preparative Compound 3-20

4-bromo-1,8-naphthyridine

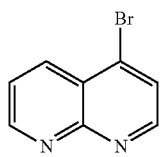

Step 1: diethyl {[(3-methylphenyl)amino]methylene}malonate 6-methylpyridine-2-amine (200 g, 1.87 mol) was added to diethyl ethoxymethylenemalonate (520 g, 2.41 mol). The reaction mixture was heated to 110° C. After 30 minutes, the reaction mixture was cooled to 80° C., diluted with petroleum ether (800 mL), and filtered to afford diethyl {[(3-methylphenyl)amino]methylene}malonate.

Step 2: ethyl 4-hydroxy-7-methyl-1,8-naphthyridine-3-carboxylate

Diethyl {[(3-methylphenyl)amino]methylene}malonate (70 g, 0.25 mol) was added to refluxing diphenyl ether (750 ml). After 10 min, the reaction mixture was cooled to ambient temperature. The resulting suspension was filtered and the filtrate was concentrated in vacuo. The residue was purified by column chromatography on silica gel (methanol/dichloromethane gradient) to afford ethyl 4-hydroxy-7-methyl-1,8-naphthyridine-3-carboxylate.

Step 3: 6-(ethoxycarbonyl)-5-hydroxy-1,8-naphthyridine-2-carboxylic acid

To a mixture of water (65 ml) and pyridine (130 ml) was added ethyl 4-hydroxy-7-methyl-1,8-naphthyridine-3-carboxylate (30 g, 130 mmol) and selenium dioxide (40 g, 360 mmol). The reaction mixture was heated to reflux. After 16 hours, the reaction mixture was diluted with pyridine (350 ml), heated to reflux, then filtered while hot. The filtrate was concentrated in vacuo to afford 6-(ethoxycarbonyl)-5-hydroxy-1,8-naphthyridine-2-carboxylic acid.

Step 4: 5-hydroxy-1,8-naphthyridine-2,6-dicarboxylic acid

To a solution of 6-(ethoxycarbonyl)-5-hydroxy-1,8-naphthyridine-2-carboxylic acid (70 g, 270 mmol) in water (700 mL) was added potassium hydroxide (100 g, 560 mmol). The reaction mixture was heated to reflux. After 2 hours, the reaction mixture was cooled and acidified with hydrochloric acid (5 M) to pH 2.5. The yellow precipitates were filtered and washed with water and pyridine to afford 5-hydroxy-1,8-naphthyridine-2,6-dicarboxylic acid.

Step 5: 1,8-naphthyridin-4-ol

To quinoline (500 ml) was added 5-hydroxy-1,8-naphthyridine-2,6-dicarboxylic acid (50 g, 340 mmol). The reaction mixture was heated to reflux. After 8 hours, the reaction mixture was cooled and concentrated in vacuo to afford 1,8-naphthyridin-4-ol.

Step 6: 4-bromo-1,8-naphthyridine

To a solution of 1,8-naphthyridin-4-ol (59 g, 400 mmol) in acetonitrile (500 ml) was added phosphorus oxide tribromide. The reaction mixture was heated to reflux. After 1 hour, the reaction mixture was carefully diluted with ice and the resulting solution was basified with ammonia solution (25%) to pH>7. The reaction mixture was partially concentrated in vacuo, then extracted with chloroform (4×500 ml). The organics were dried over sodium sulfate, filtered, and concentrated in vacuo. The residue was purified by column chromatography on silica gel (ethyl acetate/petroleum ether gradient) to afford 4-bromo-1,8-naphthyridine.

Preparative Compound 3-21

N-but-3-yn-1-ylmethanesulfonamide

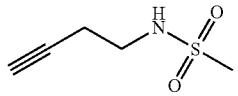

Step 1: 2-but-3-yn-1-yl-1H-isoindole-1,3(2H)-dione

Diethyl azodicarboxylate (410 g, 2.354 mol) was added dropwise to a solution of butyl-3-yn-1-ol (160 g, 2.283 mol), triphenylphosphine (599 g, 2.283 mol), and phthalimide (370 g, 2.52 mol) in toluene. The temperature during addition was kept at 15 to 25° C. After 1 hour, methanol (1000 mL) was added and the reaction mixture was stirred. After 30 minutes, the reaction mixture was filtered to afford 2-but-3-yn-1-yl-1H-isoindole-1,3(2H)-dione.

Step 2: tert-butyl but-3-yn-1-ylcarbamate

To a solution of 2-but-3-yn-1-yl-1H-isoindole-1,3(2H)-dione (470. g, 2.359 mol) in methanol (4600 mL) was added 80% hydrazine monohydrate (180 mL, 3.715 mol). After 16 hours, the reaction mixture was diluted with ice water (1,400 mL) and acidified to pH 3-4. The white precipitate was filtered and washed with methanol. The filtrate was concentrated in vacuo and diluted with tetrahydrofuran (1,500 mL). To this solution was added triethylamine (400 mL, 2.85 mol) and di-tert-butyl dicarbonate (400. g, 1.83 mol). After 16 hours, the reaction mixture was diluted with ethyl acetate, and the organics were separated, dried over magnesium sulfate, filtered, and concentrated in vacuo. The residue was purified by column chromatography on silica gel to afford tert-butyl but-3-yn-1-ylcarbamate.

Step 3: N-but-3-yn-1-ylmethanesulfonamide

To a 5-10° C. solution of tert-butyl but-3-yn-1-ylcarbamate (115 g, 0.675 mol) in dichloromethane (500 mL) was added 4N hydrochloric acid in dioxane (650 mL, 2.60 mol). After 3 hours at ambient temperature, the reaction mixture was concentrated in vacuo. The residue was washed with dichloromethane, then with diethyl ether, and then dried in vacuo to afford but-3-yn-1-amine hydrochloride as an intermediate. To a −5 to −10° C. solution of but-3-yn-1-amine hydrochloride and triethylamine (206 mL, 1.47 mol) in dichloromethane (500 mL) was added methanesulfonyl chloride (68.4 mL, 0.88 mol). After 3 hours at ambient temperature, the reaction mixture was diluted with 1N hydrochloric acid (150 mL). The organics were separated, washed with saturated aqueous sodium bicarbonate (150 mL) and with brine, then dried over magnesium sulfate, filtered, and concentrated in vacuo to afford N-but-3-yn-1-ylmethanesulfonamide.

Preparative Compound 3-22 tert-butyl 3-prop-2-yn-1-ylpyrrolidine-1-carboxylate

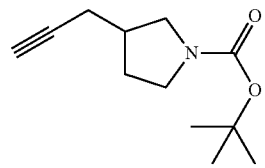

Step 1: pyrrolidin-3-ol

To a solution of 4-hydroxypyrrolidine-2-carboxylic acid (100 g, 763 mmol) in cyclohexanol (500 mL) was added acetophenone (10 g, 83 mmol). The reaction mixture was heated to reflux. After 16 hours, the reaction mixture was cooled, diluted with 2.5M hydrochloric acid (300 mL), and extracted with toluene (3×600 mL). The aqueous layer was basified to pH 9 with 4M sodium hydroxide which resulted in the precipitation of pyrrolidin-3-ol as a brown oil.

Step 2: tert-butyl 3-hydroxypyrrolidine-1-carboxylate

A flask was charged with pyrrolidin-3-ol from the last step (60.0 g, 414 mmol, 60%), di-tert-butyl oxalate (165 g, 414 mmol and 1,4-dioxane (300 ml). The resulting solution was allowed to stir overnight. The solution was extracted with dichloromethane (3×300 ml) and the combined organic layers were dried over sodium sulfate, filtered and concentrated. The residue was purified by column chromatography on silica gel (ethyl acetate/petroleum ether gradient) to afford tert-butyl 3-hydroxypyrrolidine-1-carboxylate as white solid.

Step 3: tert-butyl 3-oxopyrrolidine-1-carboxylate

A flask was charged with a solution of oxalyl chloride (3.2 ml, 33 mmol) in dichloromethane (60 ml). The solution was cooled to −60° C., and a solution of dimethylsulfoxide (5.1 ml, 66 mmol) in dichloromethane (10 ml) was added dropwise, such that the internal temperature was maintained at −60° C. This was followed by the dropwise addition of a solution of tert-butyl 3-hydroxypyrrolidine-1-carboxylate (5.6 g, 30 mmol) in dichloromethane (25 ml). The resulting solution was allowed to stir for 1 hour −60° C., then triethyamine (21 ml) was added and the mixture was allowed to warm to room temperature. The solution was diluted with 150 ml of water and extracted with dichloromethane (2×150 ml). The combined organic layers were washed with brine, dried over sodium sulfate, filtered and concentrated to afford tert-butyl 3-oxopyrrolidine-1-carboxylate as a white solid.

Step 4: tert-butyl-3-(2-ethoxy-2-oxoethylidene)pyrrolidine-1-carboxylate

A flask was charged with NaH (50 g, 1.25 mol, 60% in mineral oil) and tetrahydrofuran (2,500 ml) and cooled to 0° C. A solution of ethyl 2-(diethoxyphosphoryl)acetate (260 g, 1.16 mol) in tetrahydrofuran F (200 ml) was added dropwise. The resulting solution was allowed stir for 1 h at 0° C. Then a solution of tert-butyl 3-oxopyrrolidine-1-carboxylate (215 g, 1.16 mol) in tetrahydrofuran (300 ml) was added dropwise. The resulting solution was allowed to stir for 0.5 hours at 0° C. The reaction mixture was quenched by the addition of 1,000 ml of saturated aqueous ammonium chloride. The resulting mixture was extracted with ethyl acetate (3×2,000 ml) and the combined organic layers were dried over sodium sulfate, filtered and concentrated. The residue was purified by column chromatography on silica gel (ethyl acetate/petroleum ether gradient) to afford tert-butyl-3-(2-ethoxy-2-oxo-ethylidene)pyrrolidine-1-carboxylate as colorless oil.

Step 5: tert-butyl 3-(2-ethoxy-2-oxoethyl)pyrrolidine-1-carboxylate

A flask was charged with EtOH (700 ml), tert-butyl 3-(2-ethoxy-2-oxoethylidene)pyrrolidine-1-carboxylate (246 g, 965 mmol) and Pd/C (40 g). Then the flask was charged with $H_2$ (3 L). The resulting solution was stirred overnight. The reaction mixture was filtered and concentrated to afford tert-butyl 3-(2-ethoxy-2-oxoethyl)pyrrolidine-1-carboxylate as a colorless oil.

Step 6: tert-butyl 3-(2-oxoethyl)pyrrolidine-1-carboxylate

A flask was charged with tert-butyl 3-(2-ethoxy-2-oxoethyl)pyrrolidine-1-carboxylate (160 g, 623 mmol) and dichloromethane (2,500 ml) and cooled to −78° C. A solution of diisobutylaluminum hydride (800 ml, 1.10 equiv) was added dropwise, such that the internal temperature was maintained at −78° C. After 1 h at 78° C., the reaction mixture was quenched by the addition of 30 ml of methanol. After warming to ambient temperature, the mixture was filtered and the filter cake was washed with dichloromethane (3×1,000 mL). The filtrate was dried over sodium sulfate, filtered and concentrated. The residue was purified by column chromatography on silica gel (ethyl acetate/petroleum ether gradient) to afford tert-butyl 3-(2-oxoethyl)pyrrolidine-1-carboxylate as light yellow oil.

Step 7: tert-butyl 3-(3,3-dibromoprop-2-en-1-yl) pyrrolidine-1-carboxylate

A flask was charged with triphenylphosphine (477 g, 1.82 mol) and dichloromethane (2,500 ml) was cooled to 0° C. A solution of carbon tetrabromide (302 g, 910 mmol) in dichloromethane (300 ml) was added dropwise, followed by the dropwise addition of a solution of tert-butyl 3-(2-oxoethyl) pyrrolidine-1-carboxylate (97 g, 455.40 mmol, 1.00 equiv) in dichloromethane (200 ml). The resulting solution was allowed stir for 1.5 hours at 0° C. The reaction mixture was washed with 4,000 ml of petroleum ether, and filtered. The filtrate was concentrated and the residue was purified by column chromatography on silica gel (ethyl acetate/petroleum ether gradient) to afford tert-butyl 3-(3,3-dibromoprop-2-en-1-yl)pyrrolidine-1-carboxylate as light yellow oil.

Step 8: tert-butyl 3-prop-2-yn-1-ylpyrrolidine-1-carboxylate

A flask was charged with tert-butyl 3-(3,3-dibromoprop-2-en-1-yl)pyrrolidine-1-carboxylate (155 g, 420. mmol) and (1,800 ml) and cooled to −80° C. A solution of butyllithium (370 ml, 2.20 equiv) was added dropwise such that the internal temperature was maintained at −80° C. After stirring for an addition hour at −80° C., the reaction mixture was quenched by the addition of 1,000 mL of saturated aqueous ammonium chloride. The resulting mixture was extracted with diethyl ether (3×1,000 mL). The combined organic layers were washed with brine (3×800 mL), then dried over sodium sulfate, filtered and concentrated. The residue was purified by column chromatography on silica gel (ethyl acetate/petroleum ether gradient) to afford tert-butyl 3-(prop-2-ynyl)pyrrolidine-1-carboxylate as light yellow oil.

The compounds in the following table were prepared according to the procedure described in scheme 3 and for compounds 3-1 to 3-14. The compounds were prepared as free bases. Preparative compounds 3-15 to 3-22 were used in their synthesis.

TABLE 3

| Compound | Structure | Name | [M + H]+ |
|---|---|---|---|
| 3-23 | 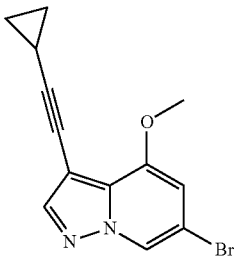 [SMILES: COc1cc(Br)cn2ncc(C#CC3CC3)c12] | 6-bromo-3-(cyclopropylethynyl)-4-methoxypyrazolo[1,5-a]pyridine | Calc'd 291.0 (for $^{79}Br$), found 290.9 |

TABLE 3-continued

| Compound | Structure | Name | [M + H]+ |
|---|---|---|---|
| 3-24 | 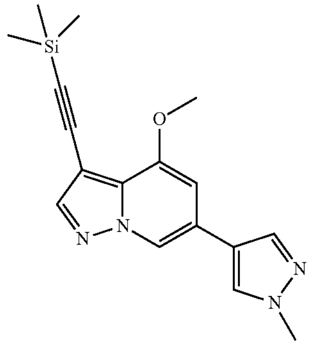 [SMILES: COc1cc(-c2cnn(C)c2)cn2ncc(C#C[Si](C)(C)C)c12] | 4-methoxy-6-(1-methyl-1H-pyrazol-4-yl)-3-[(trimethylsilyl)ethynyl]pyrazolo[1,5-a]pyridine | Calc'd 325.1, found 325.1 |
| 3-25 | 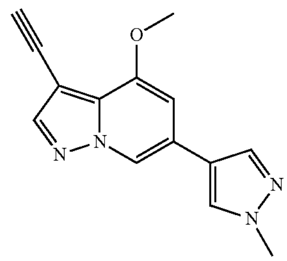 [SMILES: C#Cc1cnn2cc(-c3cnn(C)c3)cc(OC)c12] | 3-ethynyl-4-methoxy-6-(1-methyl-1H-pyrazol-4-yl)pyrazolo[1,5-a]pyridine | Calc'd 253.1, found 253.0 |
| 3-26 | 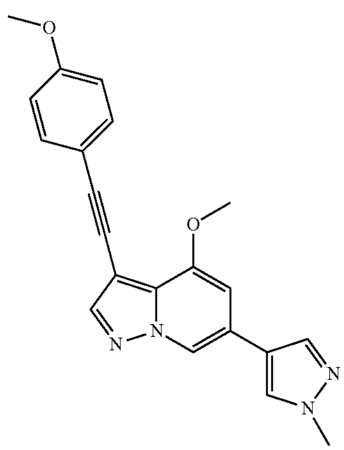 [SMILES: COc1ccc(C#Cc2cnn3cc(-c4cnn(C)c4)cc(OC)c23)cc1] | 4-methoxy-3-[(4-methoxyphenyl)ethynyl]-6-(1-methyl-1H-pyrazol-4-yl)pyrazolo[1,5-a]pyridine | Calc'd 359.2, found 359.0 |
| 3-27 | 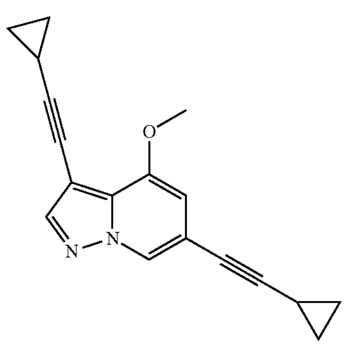 [SMILES: COc1cc(C#CC2CC2)cn2ncc(C#CC3CC3)c12] | 3,6-bis(cyclopropylethynyl)-4-methoxypyrazolo[1,5-a]pyridine | Calc'd 277.1, found 277.0 |

TABLE 3-continued

| Compound | Structure | Name | [M + H]+ |
|---|---|---|---|
| 3-28 | 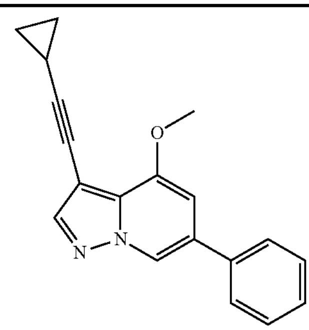 | 3-(cyclopropylethynyl)-4-methoxy-6-phenylpyrazolo[1,5-a]pyridine | Calc'd 289.1, found 289.0 |
| 3-29 | 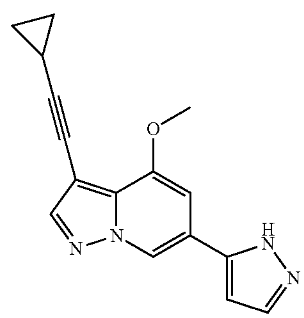 [SMILES: COc1cc(-c2ccn[nH]2)cn2ncc(C#CC3CC3)c12] | 3-(cyclopropylethynyl)-4-methoxy-6-(1H-pyrazol-5-yl)pyrazolo[1,5-a]pyridine | Calc'd 279.1, found 279.0 |
| 3-30 | 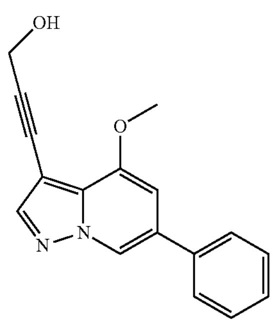 [SMILES: COc1cc(-c2ccccc2)cn2ncc(C#CCO)c12] | 3-(4-methoxy-6-phenylpyrazolo[1,5-a]pyridine-3-yl)prop-2-yn-1-ol | Calc'd 279.1, found 279.0 |
| 3-31 | 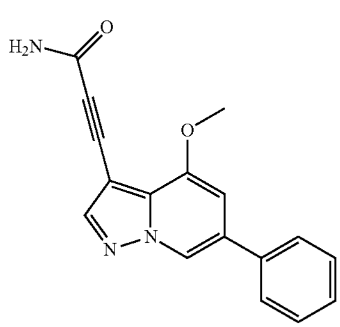 [SMILES: COc1cc(-c2ccccc2)cn2ncc(C#CC(N)=O)c12] | 3-(4-methoxy-6-phenylpyrazolo[1,5-a]pyridine-3-yl)prop-2-ynamide | Calc'd 292.1, found 292.0 |

TABLE 3-continued

| Compound | Structure | Name | [M + H]+ |
|---|---|---|---|
| 3-32 | 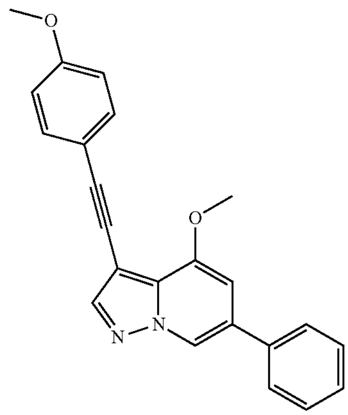 [SMILES: COc1ccc(C#Cc2cnn3cc(-c4ccccc4)cc(OC)c23)cc1] | 4-methoxy-3-[(4-methoxyphenyl)ethynyl]-6-phenylpyrazolo[1,5-a]pyridine | Calc'd 355.1, found 355.0 |
| 3-33 | 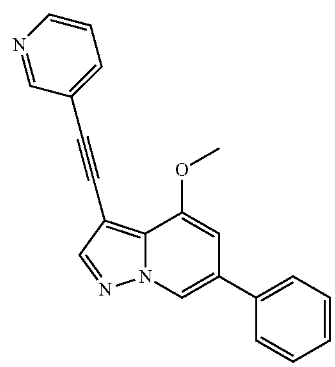 [SMILES: COc1cc(-c2ccccc2)cn2ncc(C#Cc3cccnc3)c12] | 4-methoxy-6-phenyl-3-(pyridine-3-ylethynyl)pyrazolo[1,5-a]pyridine | Calc'd 326.1, found 326.0 |
| 3-34 | 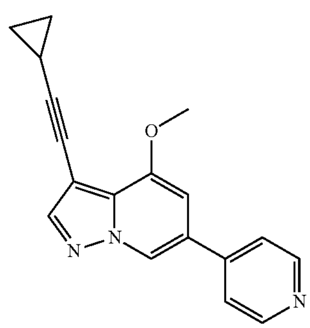 [SMILES: COc1cc(-c2ccncc2)cn2ncc(C#CC3CC3)c12] | 3-(cyclopropylethynyl)-4-methoxy-6-pyridin-4-ylpyrazolo[1,5-a]pyridine | Calc'd 290.1, found 290.0 |
| 3-35 | 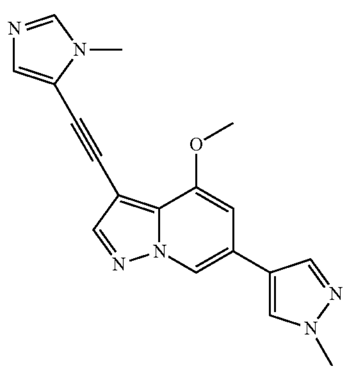 [SMILES: COc1cc(-c2cnn(C)c2)cn2ncc(C#Cc3cncn3C)c12] | 4-methoxy-3-[(1-methyl-1H-imidazol-5-yl)ethynyl]-6-(1-methyl-1H-pyrazol-4-yl)pyrazolo[1,5-a]pyridine | Calc'd 333.1, found 333.0 |

TABLE 3-continued

| Compound | Structure | Name | [M + H]+ |
| --- | --- | --- | --- |
| 3-36 | 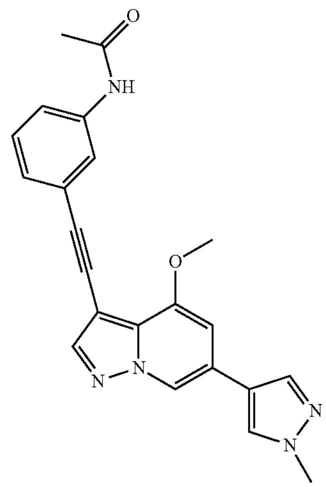 [SMILES: COc1cc(-c2cnn(C)c2)cn2ncc(C#Cc3cccc(NC(C)=O)c3)c12] | N-(3-{[4-methoxy-6-(1-methyl-1H-pyrazol-4-yl)pyrazolo[1,5-a]pyridine-3-yl]ethynyl}phenyl)acetamide | Calc'd 386.2, found 386.0 |
| 3-37 | 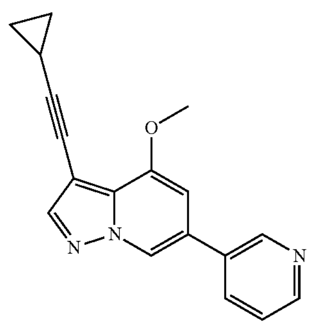 [SMILES: COc1cc(-c2cccnc2)cn2ncc(C#CC3CC3)c12] | 3-(cyclopropylethynyl)-4-methoxy-6-pyridin-3-ylpyrazolo[1,5-a]pyridine | Calc'd 290.1, found 290.0 |
| 3-38 | 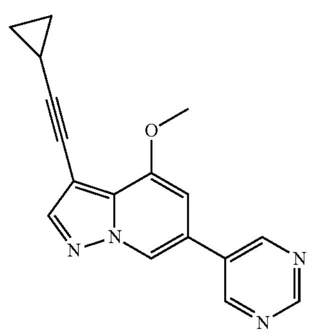 [SMILES: COc1cc(-c2cncnc2)cn2ncc(C#CC3CC3)c12] | 3-(cyclopropylethynyl)-4-methoxy-6-pyrimidin-5-ylpyrazolo[1,5-a]pyridine | Calc'd 291.1, found 291.0 |
| 3-39 | 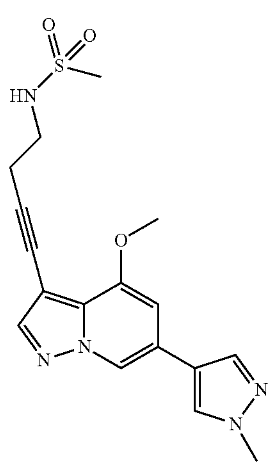 [SMILES: COc1cc(-c2cnn(C)c2)cn2ncc(C#CCCNS(C)(=O)=O)c12] | N-{4-[4-methoxy-6-(1-methyl-1H-pyrazol-4-yl)pyrazolo[1,5-a]pyridine-3-yl]but-3-yn-1-yl}methanesulfonamide | Calc'd 374.1, found 374.0 |

TABLE 3-continued

| Compound | Structure | Name | [M + H]+ |
|---|---|---|---|
| 3-40 | 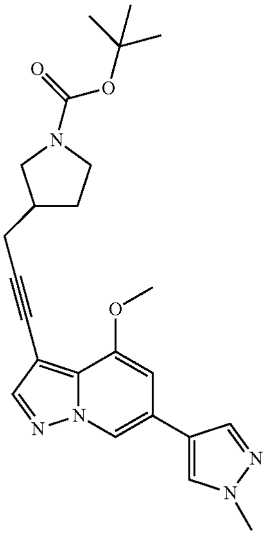 [SMILES: COc1cc(-c2cnn(C)c2)cn2ncc(C#CCC3CCN(C(=O)OC(C)(C)C)C3)c12] | tert-butyl 3-{3-[4-methoxy-6-(1-methyl-1H-pyrazol-4-yl)pyrazolo[1,5-a]pyridine-3-yl]prop-2-yn-1-yl}pyrrolidine-1-carboxylate | Calc'd 436.2, found 436.1 |
| 3-41 | 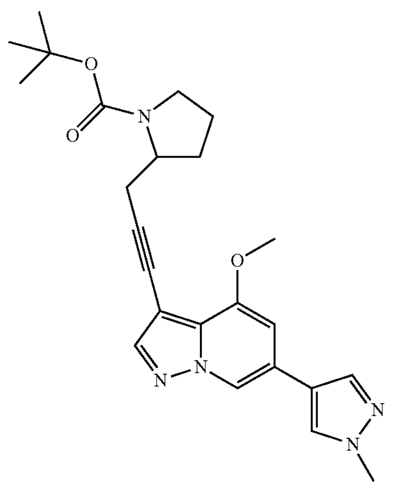 [SMILES: COc1cc(-c2cnn(C)c2)cn2ncc(C#CCC3CCCN3C(=O)OC(C)(C)C)c12] | tert-butyl 2-{3-[4-methoxy-6-(1-methyl-1H-pyrazol-4-yl)pyrazolo[1,5-a]pyridine-3-yl]prop-2-yn-1-yl}pyrrolidine-1-carboxylate | Calc'd 436.2, found 436.1 |
| 3-42 | 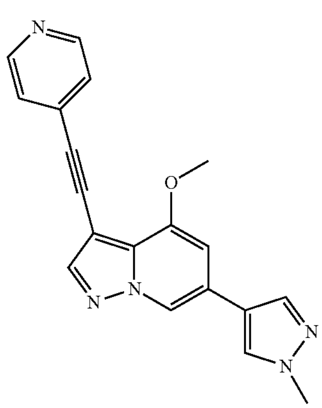 [SMILES: COc1cc(-c2cnn(C)c2)cn2ncc(C#Cc3ccncc3)c12] | 4-methoxy-6-(1-methyl-1H-pyrazol-4-yl)-3-(pyridine-4-ylethynyl)pyrazolo[1,5-a]pyridine | Calc'd 330.1, found 330.0 |

TABLE 3-continued

| Compound | Structure | Name | [M + H]+ |
|---|---|---|---|
| 3-43 | 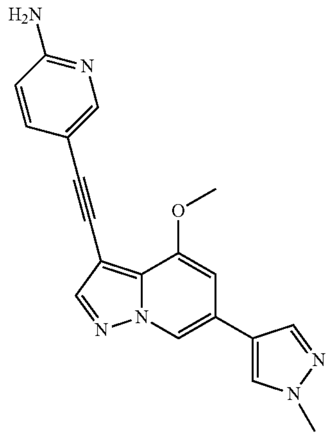 [SMILES: COc1cc(-c2cnn(C)c2)cn2ncc(C#Cc3ccc(N)nc3)c12] | 5-{[4-methoxy-6-(1-methyl-1H-pyrazol-4-yl)pyrazolo[1,5-a]pyridine-3-yl]ethynyl}pyridine-2-amine | Calc'd 345.1, found 345.0 |
| 3-44 | 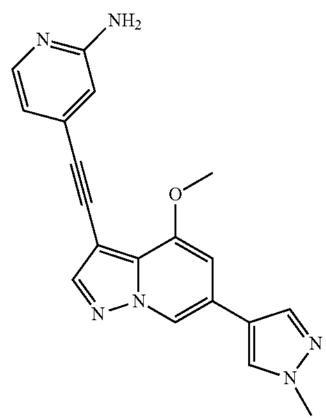 [SMILES: COc1cc(-c2cnn(C)c2)cn2ncc(C#Cc3ccnc(N)c3)c12] | 4-{[4-methoxy-6-(1-methyl-1H-pyrazol-4-yl)pyrazolo[1,5-a]pyridine-3-yl]ethynyl}pyridine-2-amine | Calc'd 345.1, found 345.0 |
| 3-45 | 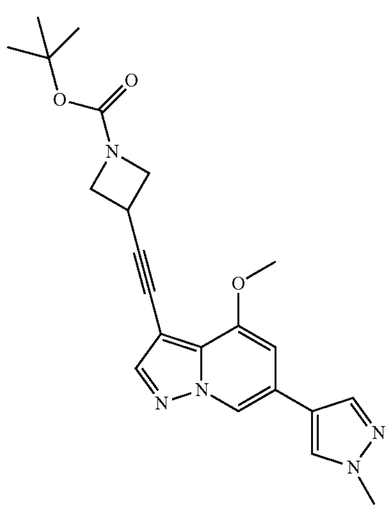 [SMILES: COc1cc(-c2cnn(C)c2)cn2ncc(C#CC3CN(C(=O)OC(C)(C)C)C3)c12] | tert-butyl 3-{[4-methoxy-6-(1-methyl-1H-pyrazol-4-yl)pyrazolo[1,5-a]pyridine-3-yl]ethynyl}azetidine-1-carboxylate | Calc'd 408.2, found 408.1 |

TABLE 3-continued
| Compound | Structure | Name | [M + H]+ |
|---|---|---|---|
| 3-46 | 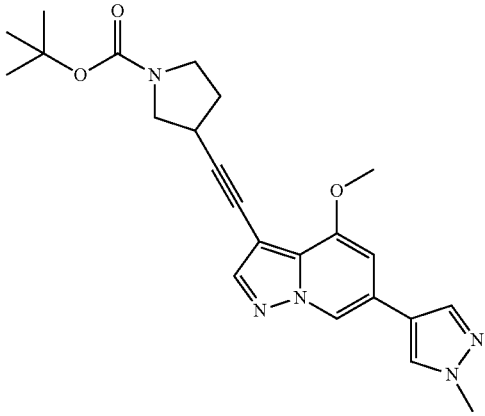 [SMILES: COc1cc(-c2cnn(C)c2)cn2ncc(C#CC3CCN(C(=O)OC(C)(C)C)C3)c12] | tert-butyl 3-{[4-methoxy-6-(1-methyl-1H-pyrazol-4-yl)pyrazolo[1,5-a]pyridine-3-yl]ethynyl}pyrrolidine-1-carboxylate | Calc'd 422.2, found 422.1 |
| 3-47 | 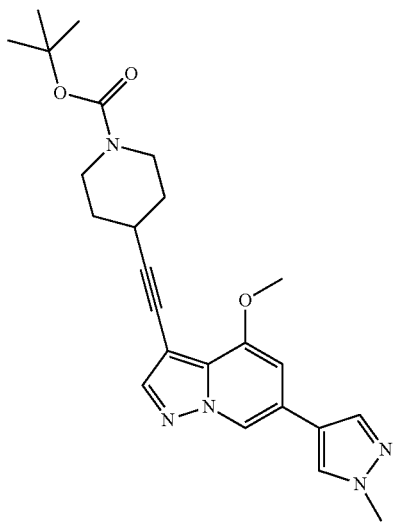 [SMILES: COc1cc(-c2cnn(C)c2)cn2ncc(C#CC3CCN(C(=O)OC(C)(C)C)CC3)c12] | tert-butyl 4-{[4-methoxy-6-(1-methyl-1H-pyrazol-4-yl)pyrazolo[1,5-a]pyridine-3-yl]ethynyl}piperidine-1-carboxylate | Calc'd 436.2, found 436.1 |
| 3-48 | 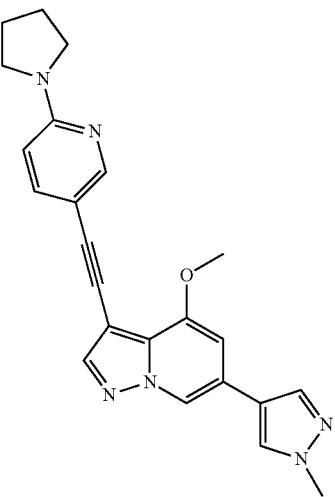 [SMILES: COc1cc(-c2cnn(C)c2)cn2ncc(C#Cc3ccc(N4CCCC4)nc3)c12] | 4-methoxy-6-(1-methyl-1H-pyrazol-4-yl)-3-[(6-pyrrolidin-1-ylpyridin-3-yl)ethynyl]pyrazolo[1,5-a]pyridine | Calc'd 399.2, found 399.1 |

TABLE 3-continued

| Compound | Structure | Name | [M + H]+ |
|---|---|---|---|
| 3-49 | 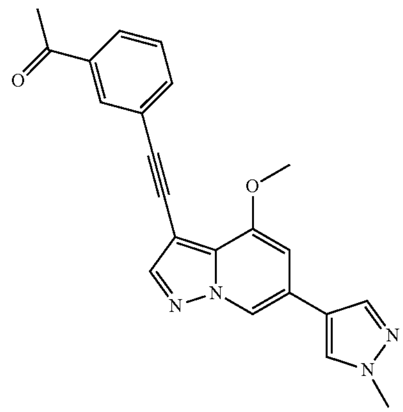 [SMILES: COc1cc(-c2cnn(C)c2)cn2ncc(C#Cc3cccc(C(C)=O)c3)c12] | 1-(3-{[4-methoxy-6-(1-methyl-1H-pyrazol-4-yl)pyrazolo[1,5-a]pyridine-3-yl]ethynyl}phenyl)ethanone | Calc'd 371.2, found 371.0 |
| 3-50 | 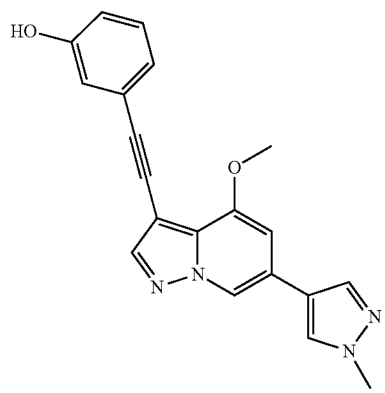 [SMILES: COc1cc(-c2cnn(C)c2)cn2ncc(C#Cc3cccc(O)c3)c12] | 3-{[4-methoxy-6-(1-methyl-1H-pyrazol-4-yl)pyrazolo[1,5-a]pyridine-3-yl]ethynyl}phenol | Calc'd 345.1, found 345.0 |
| 3-51 | 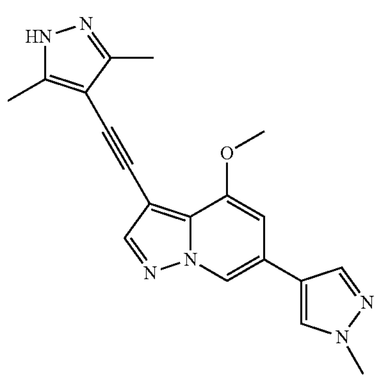 [SMILES: COc1cc(-c2cnn(C)c2)cn2ncc(C#Cc3c(C)n[nH]c3C)c12] | 3-[(3,5-dimethyl-1H-pyrazol-4-yl)ethynyl]-4-methoxy-6-(1-methyl-1H-pyrazol-4-yl)pyrazolo[1,5-a]pyridine | Calc'd 347.2, found 347.1 |
| 3-52 | 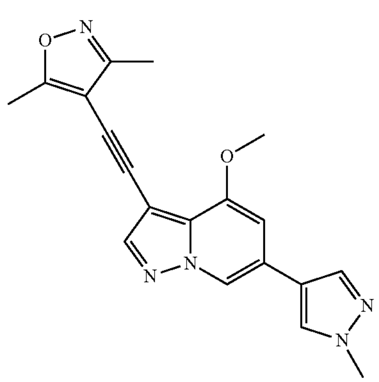 [SMILES: COc1cc(-c2cnn(C)c2)cn2ncc(C#Cc3c(C)noc3C)c12] | 3-[(3,5-dimethylisoxazol-4-yl)ethynyl]-4-methoxy-6-(1-methyl-1H-pyrazol-4-yl)pyrazolo[1,5-a]pyridine | Calc'd 348.1, found 348.0 |

TABLE 3-continued

| Compound | Name | [M + H]+ |
|---|---|---|
| 3-53 | 4-{[4-methoxy-6-(1-methyl-1H-pyrazol-4-yl)pyrazolo[1,5-a]pyridine-3-yl]ethynyl}-N,N-dimethyl-1H-imidazole-1-sulfonamide | Calc'd 426.1, found 426.0 |
| 3-54 | 4-methoxy-6-(1-methyl-1H-pyrazol-4-yl)-3-[(1-methyl-1H-pyrazol-4-yl)ethynyl]pyrazolo[1,5-a]pyridine | Calc'd 333.1, found 333.0 |
| 3-55 | 4-{[4-methoxy-6-(1-methyl-1H-pyrazol-4-yl)pyrazolo[1,5-a]pyridine-3-yl]ethynyl}pyridine-2-carboxamide | Calc'd 373.1, found 373.0 |

TABLE 3-continued

| Compound | Structure | Name | [M + H]+ |
|---|---|---|---|
| 3-56 | 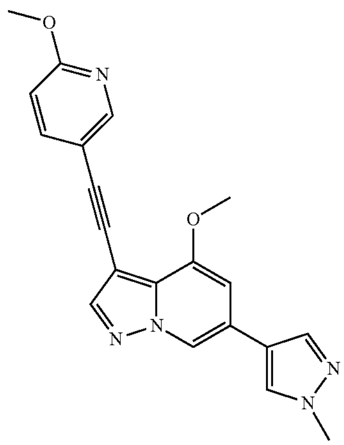 [SMILES: COc1ccc(C#Cc2cnn3cc(-c4cnn(C)c4)cc(OC)c23)cn1] | 4-methoxy-3-[(6-methoxypyridin-3-yl)ethynyl]-6-(1-methyl-1H-pyrazol-4-yl)pyrazolo[1,5-a]pyridine | Calc'd 360.1, found 360.0 |
| 3-57 | 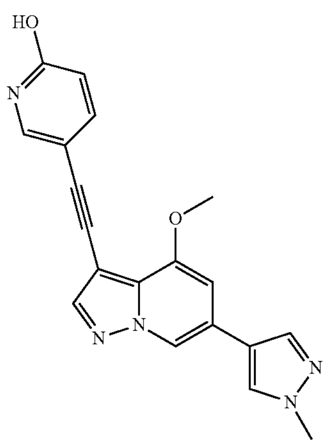 [SMILES: COc1cc(-c2cnn(C)c2)cn2ncc(C#Cc3ccc(O)nc3)c12] | 5-{[4-methoxy-6-(1-methyl-1H-pyrazol-4-yl)pyrazolo[1,5-a]pyridine-3-yl]ethynyl}pyridine-2-ol | Calc'd 346.1, found 346.0 |
| 3-58 | 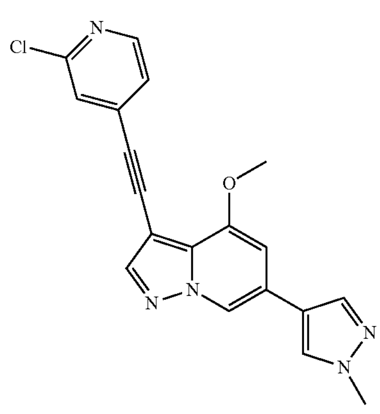 [SMILES: COc1cc(-c2cnn(C)c2)cn2ncc(C#Cc3ccnc(Cl)c3)c12] | 3-[(2-chloropyridin-4-yl)ethynyl]-4-methoxy-6-(1-methyl-1H-pyrazol-4-yl)pyrazolo[1,5-a]pyridine | Calc'd 364.1, found 364.0 |

TABLE 3-continued

| Compound | Structure | Name | [M + H]+ |
|---|---|---|---|
| 3-59 | 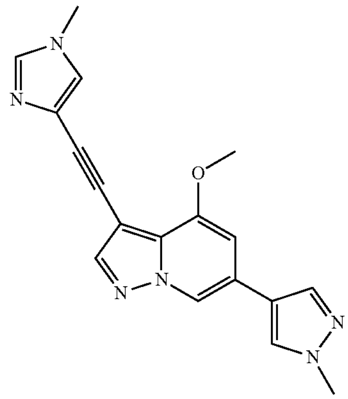 [SMILES: COc1cc(-c2cnn(C)c2)cn2ncc(C#Cc3cn(C)cn3)c12] | 4-methoxy-3-[(1-methyl-1H-imidazol-4-yl)ethynyl]-6-(1-methyl-1H-pyrazol-4-yl)pyrazolo[1,5-a]pyridine | Calc'd 333.1, found 333.1 |
| 3-60 | 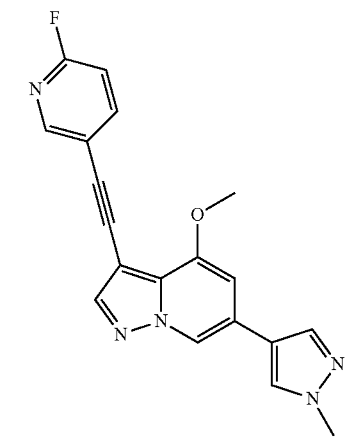 [SMILES: COc1cc(-c2cnn(C)c2)cn2ncc(C#Cc3ccc(F)nc3)c12] | 3-[(6-fluoropyridin-3-yl)ethynyl]-4-methoxy-6-(1-methyl-1H-pyrazol-4-yl)pyrazolo[1,5-a]pyridine | Calc'd 348.1, found 348.0 |
| 3-61 | 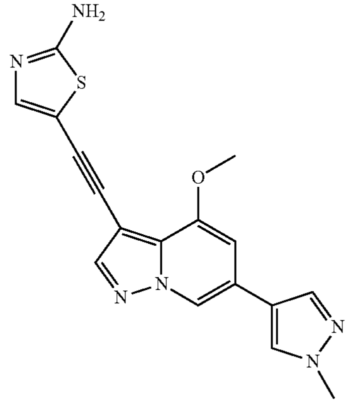 [SMILES: COc1cc(-c2cnn(C)c2)cn2ncc(C#Cc3cnc(N)s3)c12] | 5-{[4-methoxy-6-(1-methyl-1H-pyrazol-4-yl)pyrazolo[1,5-a]pyridine-3-yl]ethynyl}-1,3-thiazol-2-amine | Calc'd 351.1, found 351.0 |

TABLE 3-continued

| Compound | Structure | Name | [M + H]+ |
|---|---|---|---|
| 3-62 | 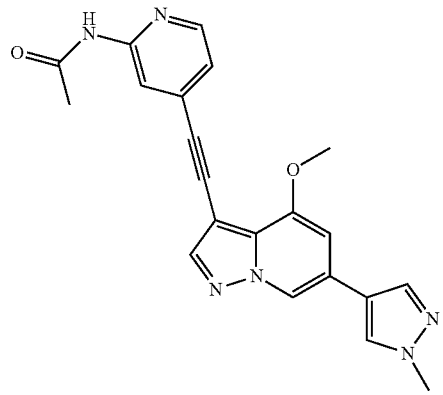 [SMILES: COc1cc(-c2cnn(C)c2)cn2ncc(C#Cc3ccnc(NC(C)=O)c3)c12] | N-(4-{[4-methoxy-6-(1-methyl-1H-pyrazol-4-yl)pyrazolo[1,5-a]pyridin-3-yl]ethynyl}pyridin-2-yl)acetamide | Calc'd 387.2, found 387.1 |
| 3-63 | 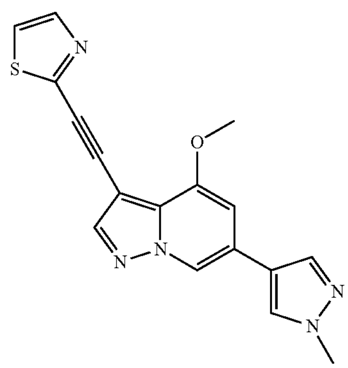 [SMILES: COc1cc(-c2cnn(C)c2)cn2ncc(C#Cc3nccs3)c12] | 4-methoxy-6-(1-methyl-1H-pyrazol-4-yl)-3-(1,3-thiazol-2-ylethynyl)pyrazolo[1,5-a]pyridine | Calc'd 336.1, found 336.0 |
| 3-64 | 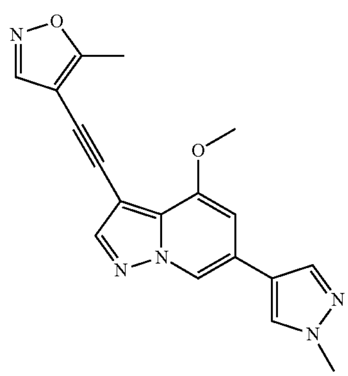 [SMILES: COc1cc(-c2cnn(C)c2)cn2ncc(C#Cc3cnoc3C)c12] | 4-methoxy-3-[(5-methylisoxazol-4-yl)ethynyl]-6-(1-methyl-1H-pyrazol-4-yl)pyrazolo[1,5-a]pyridine | Calc'd 334.1, found 334.0 |
| 3-65 | 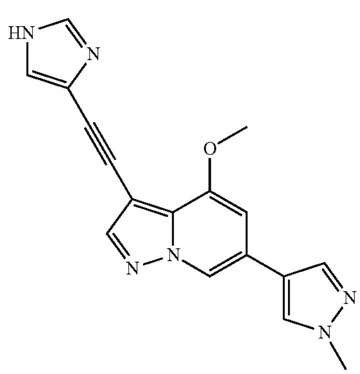 [SMILES: COc1cc(-c2cnn(C)c2)cn2ncc(C#Cc3c[nH]cn3)c12] | 3-(1H-imidazol-4-ylethynyl)-4-methoxy-6-(1-methyl-1H-pyrazol-4-yl)pyrazolo[1,5-a]pyridine | Calc'd 319.1, found 319.0 |

TABLE 3-continued

| Compound | Structure | Name | [M + H]+ |
| --- | --- | --- | --- |
| 3-66 | 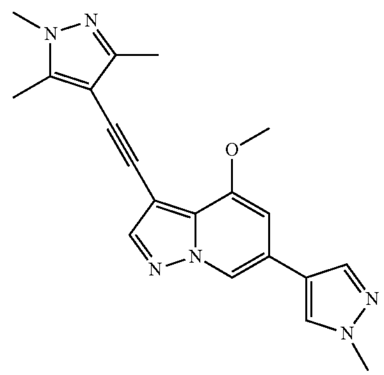 [SMILES: COc1cc(-c2cnn(C)c2)cn2ncc(C#Cc3c(C)nn(C)c3C)c12] | 4-methoxy-6-(1-methyl-1H-pyrazol-4-yl)-3-[(1,3,5-trimethyl-1H-pyrazol-4-yl)ethynyl]pyrazolo[1,5-a]pyridine | Calc'd 361.2, found 361.1 |
| 3-67 | 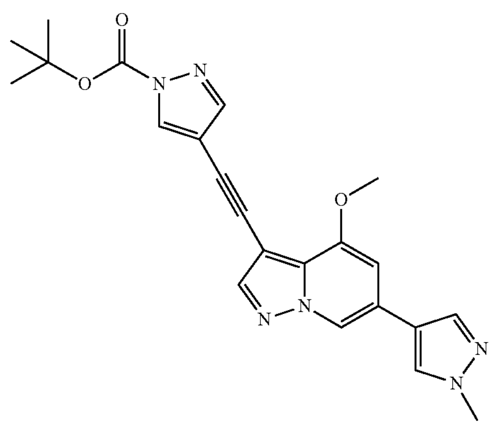 [SMILES: COc1cc(-c2cnn(C)c2)cn2ncc(C#Cc3cnn(C(=O)OC(C)(C)C)c3)c12] | tert-butyl 4-{[4-methoxy-6-(1-methyl-1H-pyrazol-4-yl)pyrazolo[1,5-a]pyridin-3-yl]ethynyl}-1H-pyrazole-1-carboxylate | Calc'd 419.2, found 419.1 |
| 3-68 | 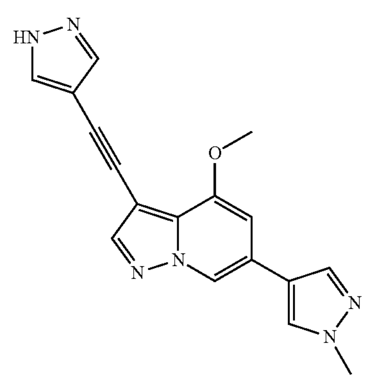 [SMILES: COc1cc(-c2cnn(C)c2)cn2ncc(C#Cc3cn[nH]c3)c12] | 4-methoxy-6-(1-methyl-1H-pyrazol-4-yl)-3-(1H-pyrazol-4-ylethynyl)pyrazolo[1,5-a]pyridine | Calc'd 319.1, found 319.0 |
| 3-69 | 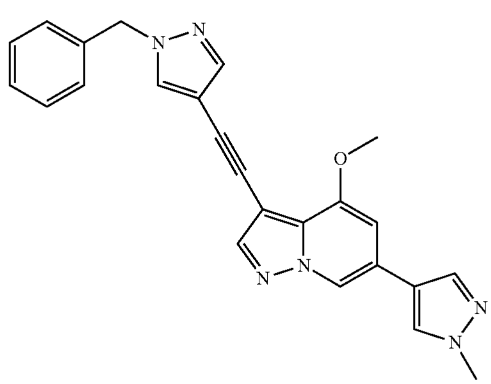 [SMILES: COc1cc(-c2cnn(C)c2)cn2ncc(C#Cc3cnn(Cc4ccccc4)c3)c12] | 3-[(1-benzyl-1H-pyrazol-4-yl)ethynyl]-4-methoxy-6-(1-methyl-1H-pyrazol-4-yl)pyrazolo[1,5-a]pyridine | Calc'd 409.2, found 409.1 |

TABLE 3-continued

| Compound | Structure | Name | [M + H]+ |
|---|---|---|---|
| 3-70 | 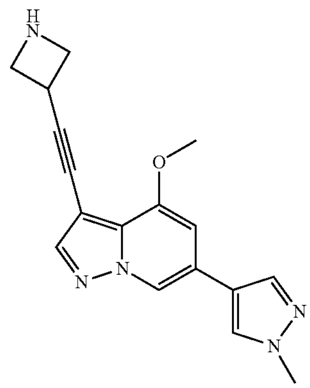 [SMILES: COc1cc(-c2cnn(C)c2)cn2ncc(C#CC3CNC3)c12] | 3-(azetidin-3-ylethynyl)-4-methoxy-6-(1-methyl-1H-pyrazol-4-yl)pyrazolo[1,5-a]pyridine | Calc'd 308.2, found 308.1 |
| 3-71 | 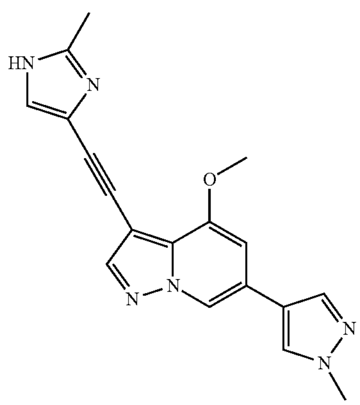 [SMILES: COc1cc(-c2cnn(C)c2)cn2ncc(C#Cc3c[nH]c(C)n3)c12] | 4-methoxy-3-[(2-methyl-1H-imidazol-4-yl)ethynyl]-6-(1-methyl-1H-pyrazol-4-yl)pyrazolo[1,5-a]pyridine | Calc'd 333.1, found 333.1 |
| 3-72 | 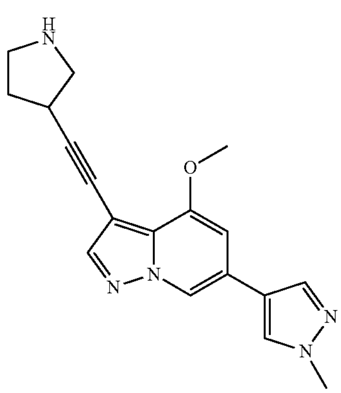 [SMILES: COc1cc(-c2cnn(C)c2)cn2ncc(C#CC3CCNC3)c12] | 4-methoxy-6-(1-methyl-1H-pyrazol-4-yl)-3-(pyrrolidin-3-ylethynyl)pyrazolo[1,5-a]pyridine | Calc'd 322.2, found 322.1 |

TABLE 3-continued

| Compound | Structure | Name | [M + H]+ |
|---|---|---|---|
| 3-73 | 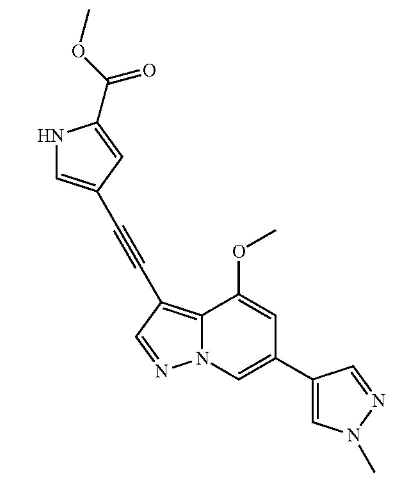 [SMILES: COC(=O)c1cc(C#Cc2cnn3cc(-c4cnn(C)c4)cc(OC)c23)c[nH]1] | methyl 4-{[4-methoxy-6-(1-methyl-1H-pyrazol-4-yl)pyrazolo[1,5-a]pyridin-3-yl]ethynyl}-1H-pyrrole-2-carboxylate | Calc'd 376.1, found 376.0 |
| 3-74 | 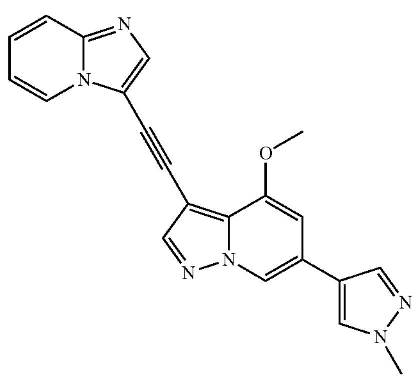 [SMILES: COc1cc(-c2cnn(C)c2)cn2ncc(C#Cc3cnc4ccccn34)c12] | 3-{[4-methoxy-6-(1-methyl-1H-pyrazol-4-yl)pyrazolo[1,5-a]pyridin-3-yl]ethynyl}imidazo[1,2-a]pyridine | Calc'd 369.1, found 369.0 |
| 3-75 | 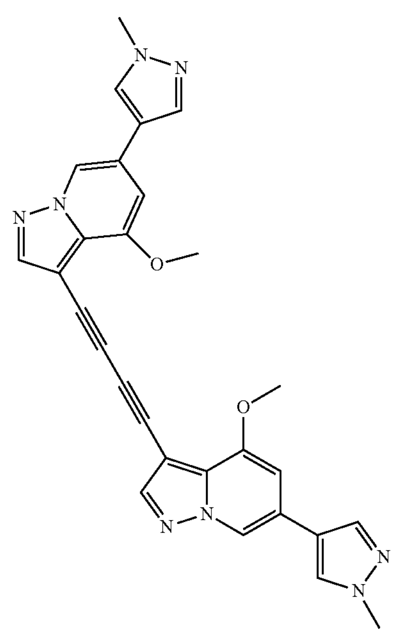 [SMILES: COc1cc(-c2cnn(C)c2)cn2ncc(C#CC#Cc3cnn4cc(-c5cnn(C)c5)cc(OC)c34)c12] | 3,3'-buta-1,3-diyne-1,4-diylbis[4-methoxy-6-(1-methyl-1H-pyrazol-4-yl)pyrazolo[1,5-a]pyridine] | Calc'd 503.0, found 503.0 |

TABLE 3-continued

| Compound | Structure | Name | [M + H]+ |
|---|---|---|---|
| 3-76 | 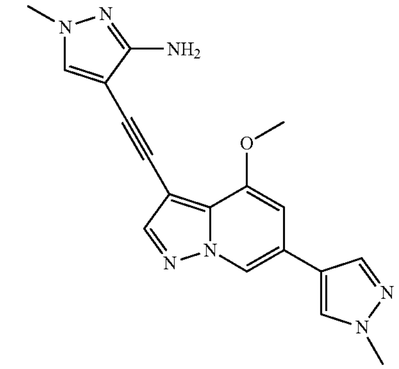 [SMILES: COc1cc(-c2cnn(C)c2)cn2ncc(C#Cc3cn(C)nc3N)c12] | 4-{[4-methoxy-6-(1-methyl-1H-pyrazol-4-yl)pyrazolo[1,5-a]pyridin-3-yl]ethynyl}-1-methyl-1H-pyrazol-3-amine | Calc'd 348.2, found 348.1 |
| 3-77 | 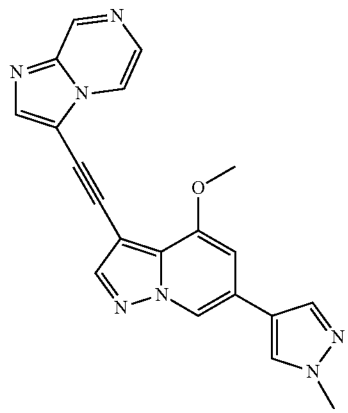 [SMILES: COc1cc(-c2cnn(C)c2)cn2ncc(C#Cc3cnc4cnccn34)c12] | 3-{[4-methoxy-6-(1-methyl-1H-pyrazol-4-yl)pyrazolo[1,5-a]pyridin-3-yl]ethynyl}imidazo[1,2-a]pyrazine | Calc'd 370.1, found 370.0 |
| 3-78 | 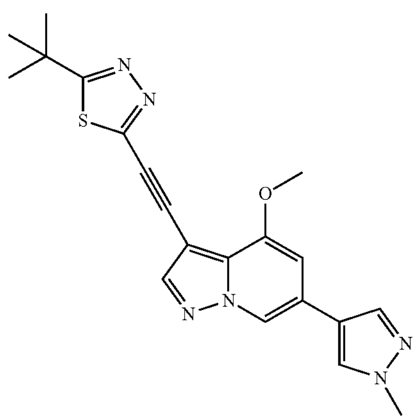 [SMILES: COc1cc(-c2cnn(C)c2)cn2ncc(C#Cc3nnc(C(C)(C)C)s3)c12] | 3-[(5-tert-butyl-1,3,4-thiadiazol-2-yl)ethynyl]-4-methoxy-6-(1-methyl-1H-pyrazol-4-yl)pyrazolo[1,5-a]pyridine | Calc'd 393.1, found 393.0 |
| 3-79 | 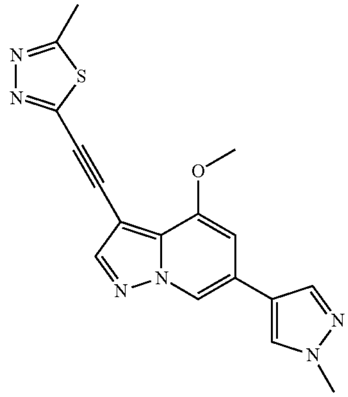 [SMILES: COc1cc(-c2cnn(C)c2)cn2ncc(C#Cc3nnc(C)s3)c12] | 4-methoxy-6-(1-methyl-1H-pyrazol-4-yl)-3-[(5-methyl-1,3,4-thiadiazol-2-yl)ethynyl]pyrazolo[1,5-a]pyridine | Calc'd 351.1, found 351.0 |

TABLE 3-continued

| Compound | Structure | Name | [M + H]+ |
|---|---|---|---|
| 3-80 | 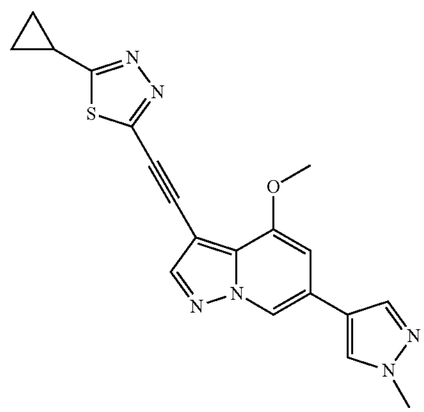 [SMILES: COc1cc(-c2cnn(C)c2)cn2ncc(C#Cc3nnc(C4CC4)s3)c12] | 3-[(5-cyclopropyl-1,3,4-thiadiazol-2-yl)ethynyl]-4-methoxy-6-(1-methyl-1H-pyrazol-4-yl)pyrazolo[1,5-a]pyridine | Calc'd 377.1, found 377.0 |
| 3-81 | 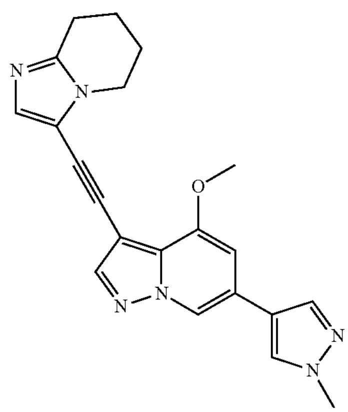 [SMILES: COc1cc(-c2cnn(C)c2)cn2ncc(C#Cc3cnc4n3CCCC4)c12] | 3-{[4-methoxy-6-(1-methyl-1H-pyrazol-4-yl)pyrazolo[1,5-a]pyridin-3-yl]ethynyl}-5,6,7,8-tetrahydroimidazo[1,2-a]pyridine | Calc'd 373.2, found 373.2 |
| 3-82 | 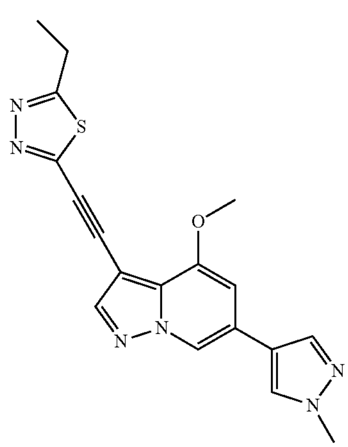 [SMILES: CCc1nnc(C#Cc2cnn3cc(-c4cnn(C)c4)cc(OC)c23)s1] | 3-[(5-ethyl-1,3,4-thiadiazol-2-yl)ethynyl]-4-methoxy-6-(1-methyl-1H-pyrazol-4-yl)pyrazolo[1,5-a]pyridine | Calc'd 365.1, found 365.1 |

TABLE 3-continued

| Compound | Structure | Name | [M + H]+ |
|---|---|---|---|
| 3-83 | 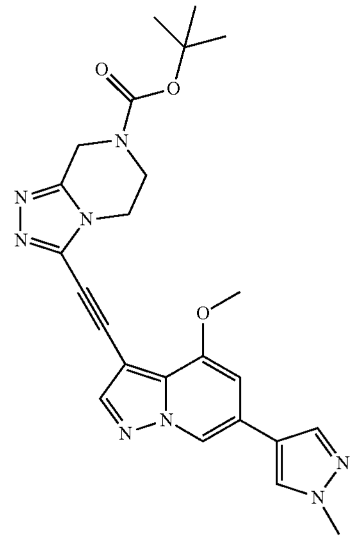 [SMILES: COc1cc(-c2cnn(C)c2)cn2ncc(C#Cc3nnc4n3CCN(C(=O)OC(C)(C)C)C4)c12] | tert-butyl 3-{[4-methoxy-6-(1-methyl-1H-pyrazol-4-yl)pyrazolo[1,5-a]pyridin-3-yl]ethynyl}-5,6-dihydro[1,2,4]triazolo[4,3-a]pyrazine-7(8H)-carboxylate | Calc'd 475.2, found 475.2 |
| 3-84 | 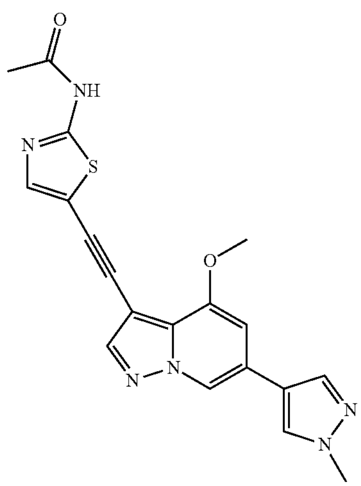 [SMILES: COc1cc(-c2cnn(C)c2)cn2ncc(C#Cc3cnc(NC(C)=O)s3)c12] | N-(5-{[4-methoxy-6-(1-methyl-1H-pyrazol-4-yl)pyrazolo[1,5-a]pyridin-3-yl]ethynyl}-1,3-thiazol-2-yl)acetamide | Calc'd 393.1, found 393.1 |
| 3-85 | 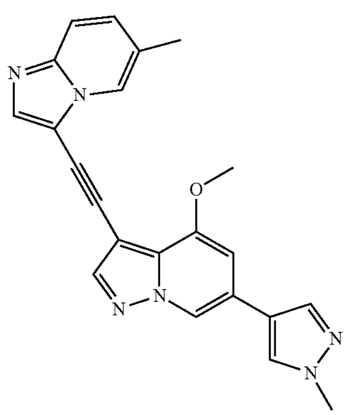 [SMILES: COc1cc(-c2cnn(C)c2)cn2ncc(C#Cc3cnc4ccc(C)cn34)c12] | 3-{[4-methoxy-6-(1-methyl-1H-pyrazol-4-yl)pyrazolo[1,5-a]pyridin-3-yl]ethynyl}-6-methylimidazo[1,2-a]pyridine | Calc'd 383.2, found 383.1 |

TABLE 3-continued

| Compound | Structure | Name | [M + H]+ |
|---|---|---|---|
| 3-86 | 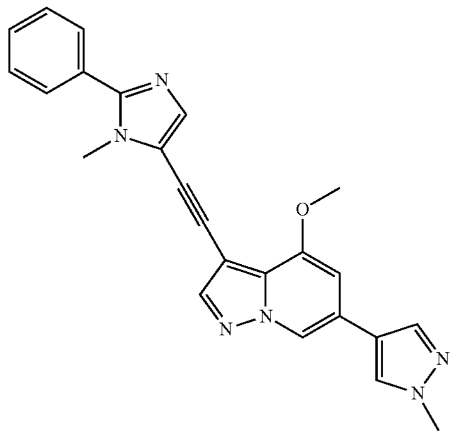 [SMILES: COc1cc(-c2cnn(C)c2)cn2ncc(C#Cc3cnc(-c4ccccc4)n3C)c12] | 4-methoxy-3-[(1-methyl-2-phenyl-1H-imidazol-5-yl)ethynyl]-6-(1-methyl-1H-pyrazol-4-yl)pyrazolo[1,5-a]pyridine | Calc'd 409.2, found 409.2 |
| 3-87 | 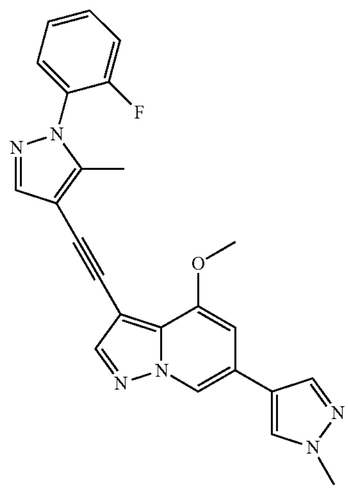 [SMILES: COc1cc(-c2cnn(C)c2)cn2ncc(C#Cc3cnn(-c4ccccc4F)c3C)c12] | 3-{[1-(2-fluorophenyl)-5-methyl-1H-pyrazol-4-yl]ethynyl}-4-methoxy-6-(1-methyl-1H-pyrazol-4-yl)pyrazolo[1,5-a]pyridine | Calc'd 427.2, found 427.1 |
| 3-88 | 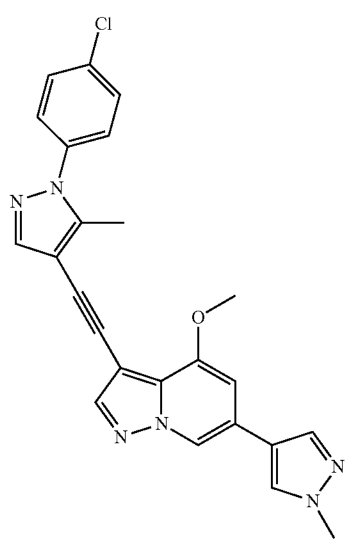 | 3-{[1-(4-chlorophenyl)-5-methyl-1H-pyrazol-4-yl]ethynyl}-4-methoxy-6-(1-methyl-1H-pyrazol-4-yl)pyrazolo[1,5-a]pyridine | Calc'd 443.1, found 443.1 |

TABLE 3-continued

| Compound | Structure | Name | [M + H]+ |
|---|---|---|---|
| 3-89 | 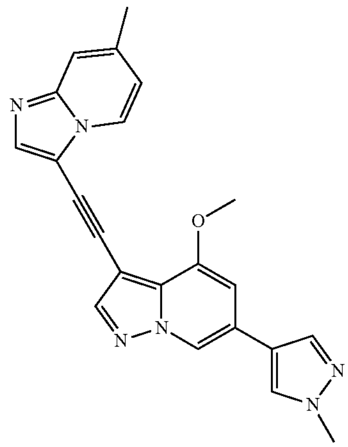 [SMILES: COc1cc(-c2cnn(C)c2)cn2ncc(C#Cc3cnc4cc(C)ccn34)c12] | 3-{[4-methoxy-6-(1-methyl-1H-pyrazol-4-yl)pyrazolo[1,5-a]pyridin-3-yl]ethynyl}-7-methylimidazo[1,2-a]pyridine | Calc'd 383.2, found 383.1 |
| 3-90 | 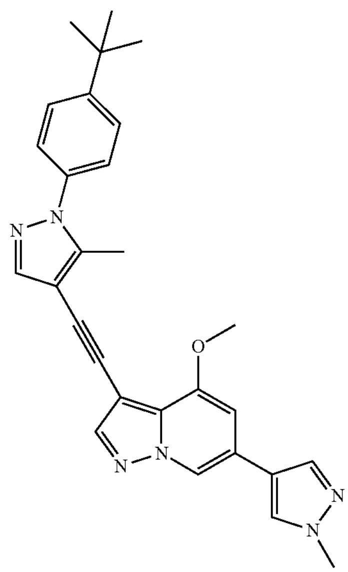 [SMILES: COc1cc(-c2cnn(C)c2)cn2ncc(C#Cc3cnn(-c4ccc(C(C)(C)C)cc4)c3C)c12] | 3-{[1-(4-tert-butylphenyl)-5-methyl-1H-pyrazol-4-yl]ethynyl}-4-methoxy-6-(1-methyl-1H-pyrazol-4-yl)pyrazolo[1,5-a]pyridine | Calc'd 465.2, found 465.2 |
| 3-91 | 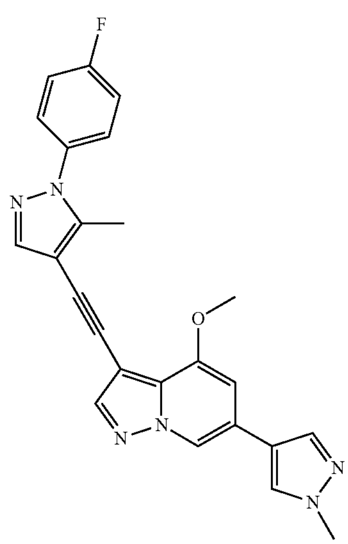 [SMILES: COc1cc(-c2cnn(C)c2)cn2ncc(C#Cc3cnn(-c4ccc(F)cc4)c3C)c12] | 3-{[1-(4-fluorophenyl)-5-methyl-1H-pyrazol-4-yl]ethynyl}-4-methoxy-6-(1-methyl-1H-pyrazol-4-yl)pyrazolo[1,5-a]pyridine | Calc'd 427.2, found 427.1 |

TABLE 3-continued

| Compound | Structure | Name | [M + H]+ |
|---|---|---|---|
| 3-92 | 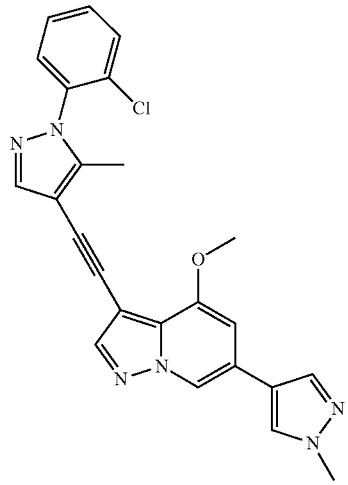 [SMILES: COc1cc(-c2cnn(C)c2)cn2ncc(C#Cc3cnn(-c4ccccc4Cl)c3C)c12] | 3-{[1-(2-chlorophenyl)-5-methyl-1H-pyrazol-4-yl]ethynyl}-4-methoxy-6-(1-methyl-1H-pyrazol-4-yl)pyrazolo[1,5-a]pyridine | Calc'd 443.1, found 443.1 |
| 3-93 | 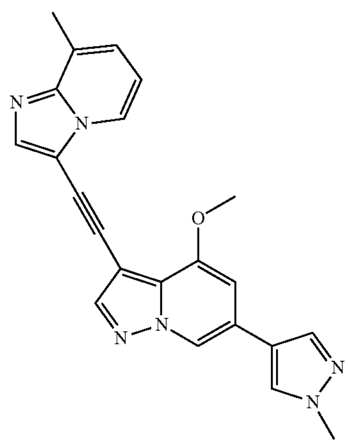 [SMILES: COc1cc(-c2cnn(C)c2)cn2ncc(C#Cc3cnc4c(C)cccn34)c12] | 3-{[4-methoxy-6-(1-methyl-1H-pyrazol-4-yl)pyrazolo[1,5-a]pyridin-3-yl]ethynyl}-8-methylimidazo[1,2-a]pyridine | Calc'd 383.2, found 383.1 |
| 3-94 | 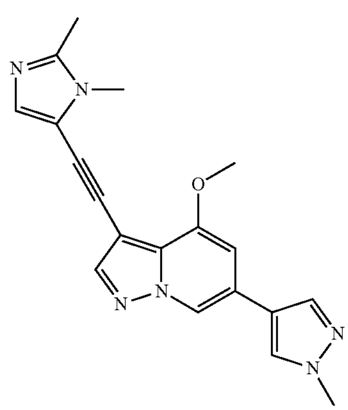 [SMILES: COc1cc(-c2cnn(C)c2)cn2ncc(C#Cc3cnc(C)n3C)c12] | 3-[(1,2-dimethyl-1H-imidazol-5-yl)ethynyl]-4-methoxy-6-(1-methyl-1H-pyrazol-4-yl)pyrazolo[1,5-a]pyridine | Calc'd 347.2, found 347.1 |

TABLE 3-continued

| Compound | Structure | Name | [M + H]+ |
|---|---|---|---|
| 3-95 | 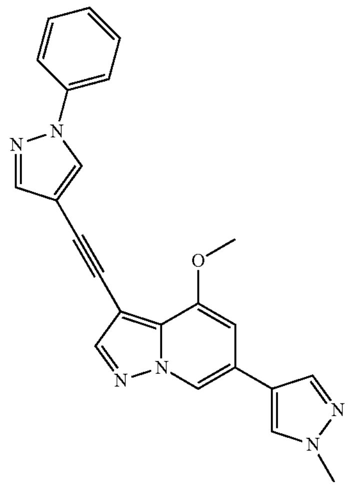 [SMILES: COc1cc(-c2cnn(C)c2)cn2ncc(C#Cc3cnn(-c4ccccc4)c3)c12] | 4-methoxy-6-(1-methyl-1H-pyrazol-4-yl)-3-[(1-phenyl-1H-pyrazol-4-yl)ethynyl]pyrazolo[1,5-a]pyridine | Calc'd 395.2, found 395.1 |
| 3-96 | 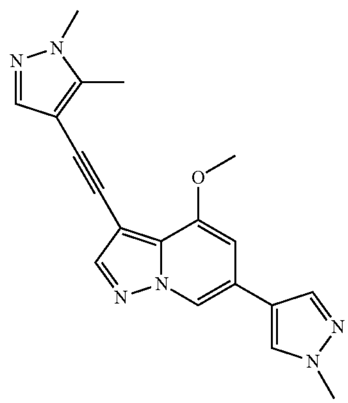 [SMILES: COc1cc(-c2cnn(C)c2)cn2ncc(C#Cc3cnn(C)c3C)c12] | 3-[(1,5-dimethyl-1H-pyrazol-4-yl)ethynyl]-4-methoxy-6-(1-methyl-1H-pyrazol-4-yl)pyrazolo[1,5-a]pyridine | Calc'd 347.2, found 347.1 |
| 3-97 | 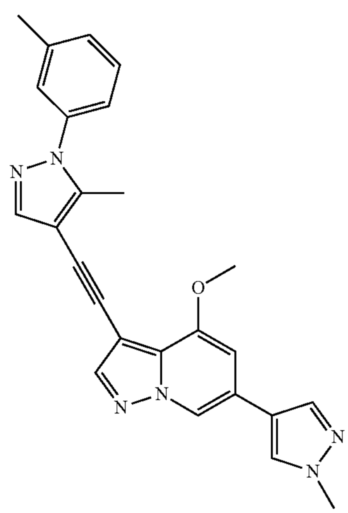 [SMILES: COc1cc(-c2cnn(C)c2)cn2ncc(C#Cc3cnn(-c4cccc(C)c4)c3C)c12] | 4-methoxy-3-{[5-methyl-1-(3-methylphenyl)-1H-pyrazol-4-yl]ethynyl}-6-(1-methyl-1H-pyrazol-4-yl)pyrazolo[1,5-a]pyridine | Calc'd 423.2, found 423.2 |

TABLE 3-continued

| Compound | Structure | Name | [M + H]+ |
|---|---|---|---|
| 3-98 | 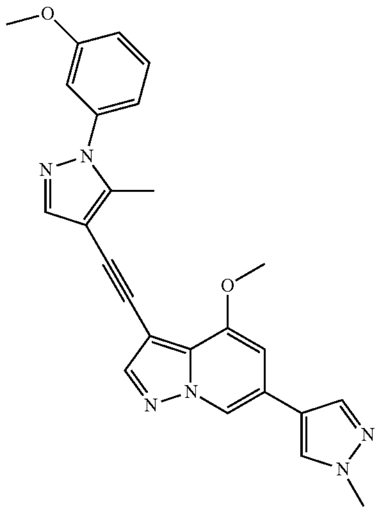 [SMILES: COc1cccc(-n2ncc(C#Cc3cnn4cc(-c5cnn(C)c5)cc(OC)c34)c2C)c1] | 4-methoxy-3-{[1-(3-methoxyphenyl)-5-methyl-1H-pyrazol-4-yl]ethynyl}-6-(1-methyl-1H-pyrazol-4-yl)pyrazolo[1,5-a]pyridine | Calc'd 439.2, found 439.2 |
| 3-99 | 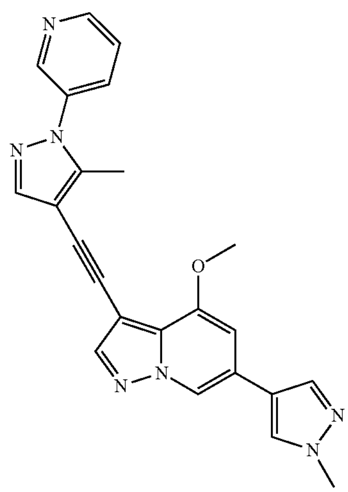 [SMILES: COc1cc(-c2cnn(C)c2)cn2ncc(C#Cc3cnn(-c4cccnc4)c3C)c12] | 4-methoxy-6-(1-methyl-1H-pyrazol-4-yl)-3-[(5-methyl-1-pyridin-3-yl-1H-pyrazol-4-yl)ethynyl]pyrazolo[1,5-a]pyridine | Calc'd 410.2, found 410.1 |
| 3-100 | 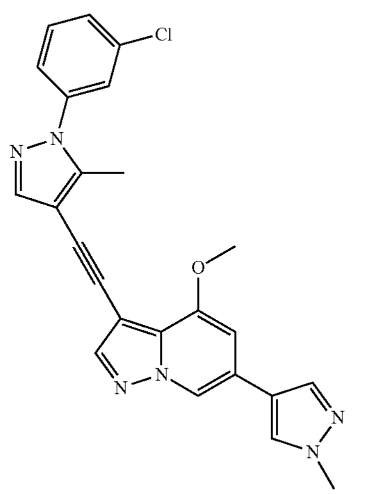 [SMILES: COc1cc(-c2cnn(C)c2)cn2ncc(C#Cc3cnn(-c4cccc(Cl)c4)c3C)c12] | 3-{[1-(3-chlorophenyl)-5-methyl-1H-pyrazol-4-yl]ethynyl}-4-methoxy-6-(1-methyl-1H-pyrazol-4-yl)pyrazolo[1,5-a]pyridine | Calc'd 443.1, found 443.1 |

TABLE 3-continued

| Compound | Structure | Name | [M + H]+ |
|---|---|---|---|
| 3-101 | 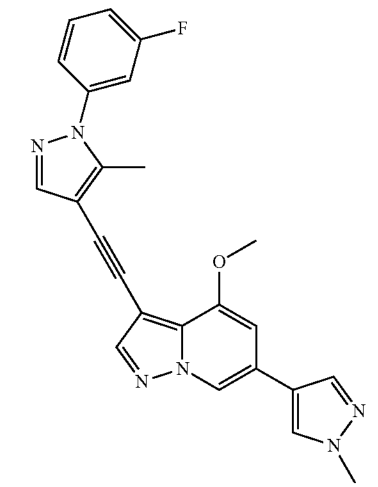 [SMILES: COc1cc(-c2cnn(C)c2)cn2ncc(C#Cc3cnn(-c4cccc(F)c4)c3C)c12] | 3-{[1-(3-fluorophenyl)-5-methyl-1H-pyrazol-4-yl]ethynyl}-4-methoxy-6-(1-methyl-1H-pyrazol-4-yl)pyrazolo[1,5-a]pyridine | Calc'd 427.2, found 427.1 |
| 3-102 | 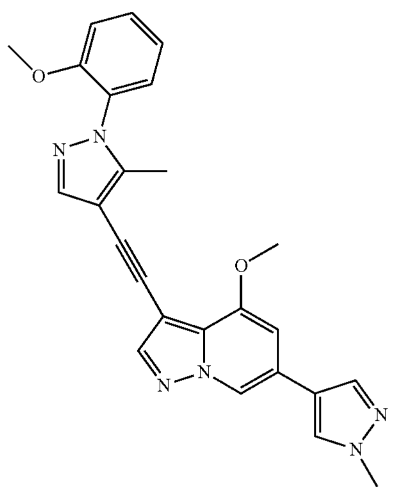 [SMILES: COc1ccccc1-n1ncc(C#Cc2cnn3cc(-c4cnn(C)c4)cc(OC)c23)c1C] | 4-methoxy-3-{[1-(2-methoxyphenyl)-5-methyl-1H-pyrazol-4-yl]ethynyl}-6-(1-methyl-1H-pyrazol-4-yl)pyrazolo[1,5-a]pyridine | Calc'd 439.2, found 439.2 |
| 3-103 | 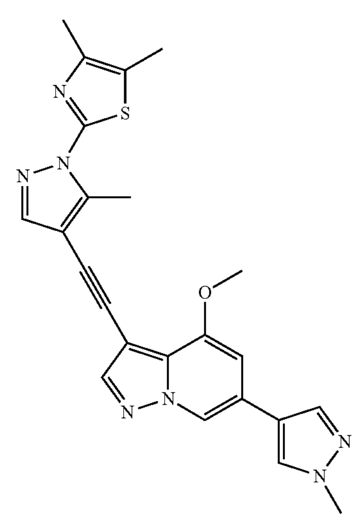 [SMILES: COc1cc(-c2cnn(C)c2)cn2ncc(C#Cc3cnn(-c4nc(C)c(C)s4)c3C)c12] | 3-{[1-(4,5-dimethyl-1,3-thiazol-2-yl)-5-methyl-1H-pyrazol-4-yl]ethynyl}-4-methoxy-6-(1-methyl-1H-pyrazol-4-yl)pyrazolo[1,5-a]pyridine | Calc'd 444.2, found 444.2 |

TABLE 3-continued

| Compound | Structure | Name | [M + H]+ |
|---|---|---|---|
| 3-104 | 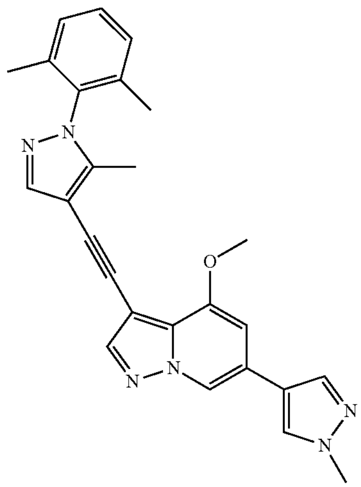 [SMILES: COc1cc(-c2cnn(C)c2)cn2ncc(C#Cc3cnn(-c4c(C)cccc4C)c3C)c12] | 3-{[1-(2,6-dimethylphenyl)-5-methyl-1H-pyrazol-4-yl]ethynyl}-4-methoxy-6-(1-methyl-1H-pyrazol-4-yl)pyrazolo[1,5-a]pyridine | Calc'd 437.2, found 437.2 |
| 3-105 | 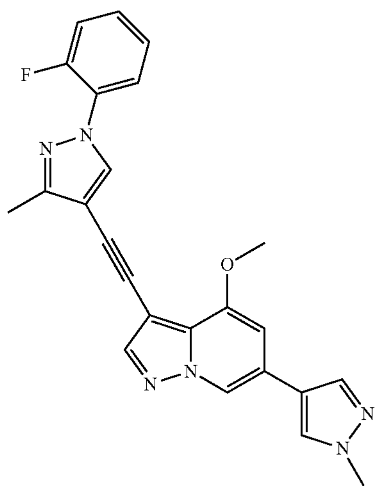 [SMILES: COc1cc(-c2cnn(C)c2)cn2ncc(C#Cc3cn(-c4ccccc4F)nc3C)c12] | 3-{[1-(2-fluorophenyl)-3-methyl-1H-pyrazol-4-yl]ethynyl}-4-methoxy-6-(1-methyl-1H-pyrazol-4-yl)pyrazolo[1,5-a]pyridine | Calc'd 427.2, found 427.2 |
| 3-106 | 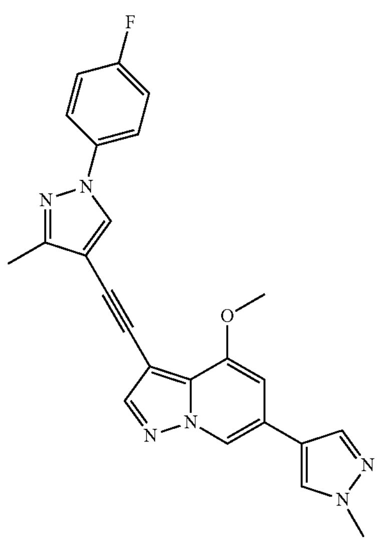 [SMILES: COc1cc(-c2cnn(C)c2)cn2ncc(C#Cc3cn(-c4ccc(F)cc4)nc3C)c12] | 3-{[1-(4-fluorophenyl)-3-methyl-1H-pyrazol-4-yl]ethynyl}-4-methoxy-6-(1-methyl-1H-pyrazol-4-yl)pyrazolo[1,5-a]pyridine | Calc'd 427.2, found 427.2 |

TABLE 3-continued

| Compound | Structure | Name | [M + H]+ |
|---|---|---|---|
| 3-107 | 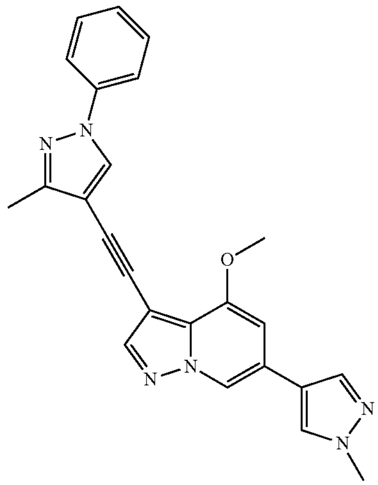 [SMILES: COc1cc(-c2cnn(C)c2)cn2ncc(C#Cc3cn(-c4ccccc4)nc3C)c12] | 4-methoxy-3-[(3-methyl-1-phenyl-1H-pyrazol-4-yl)ethynyl]-6-(1-methyl-1H-pyrazol-4-yl)pyrazolo[1,5-a]pyridine | Calc'd 409.2, found 409.2 |
| 3-108 | 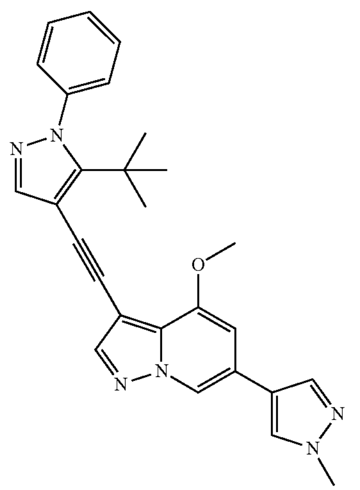 [SMILES: COc1cc(-c2cnn(C)c2)cn2ncc(C#Cc3cnn(-c4ccccc4)c3C(C)(C)C)c12] | 3-[(5-tert-butyl-1-phenyl-1H-pyrazol-4-yl)ethynyl]-4-methoxy-6-(1-methyl-1H-pyrazol-4-yl)pyrazolo[1,5-a]pyridine | Calc'd 451.2, found 451.2 |
| 3-109 | 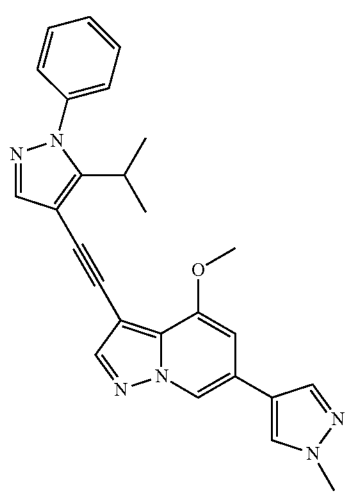 [SMILES: COc1cc(-c2cnn(C)c2)cn2ncc(C#Cc3cnn(-c4ccccc4)c3C(C)C)c12] | 3-[(5-isopropyl-1-phenyl-1H-pyrazol-4-yl)ethynyl]-4-methoxy-6-(1-methyl-1H-pyrazol-4-yl)pyrazolo[1,5-a]pyridine | Calc'd 437.2, found 437.2 |

TABLE 3-continued

| Compound | Structure | Name | [M + H]+ |
|---|---|---|---|
| 3-110 | 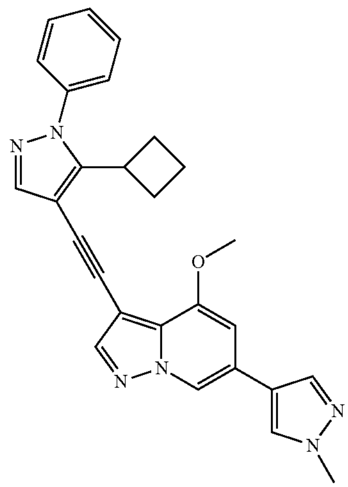 [SMILES: COc1cc(-c2cnn(C)c2)cn2ncc(C#Cc3cnn(-c4ccccc4)c3C3CCC3)c12] | 3-[(5-cyclobutyl-1-phenyl-1H-pyrazol-4-yl)ethynyl]-4-methoxy-6-(1-methyl-1H-pyrazol-4-yl)pyrazolo[1,5-a]pyridine | Calc'd 449.2, found 449.2 |
| 3-111 | 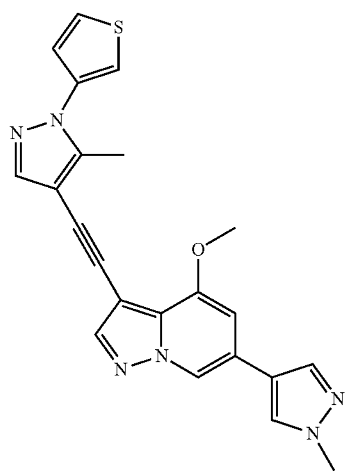 [SMILES: COc1cc(-c2cnn(C)c2)cn2ncc(C#Cc3cnn(-c4ccsc4)c3C)c12] | 4-methoxy-6-(1-methyl-1H-pyrazol-4-yl)-3-{[5-methyl-1-(3-thienyl)-1H-pyrazol-4-yl]ethynyl}pyrazolo[1,5-a]pyridine | Calc'd 415.1, found 415.1 |
| 3-112 | 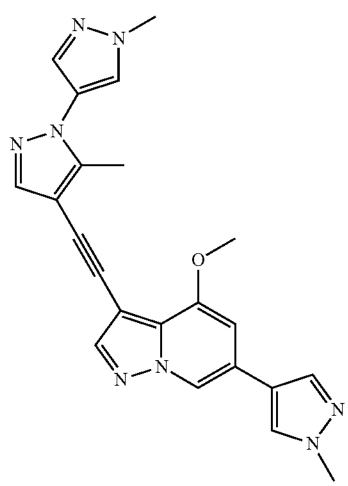 [SMILES: COc1cc(-c2cnn(C)c2)cn2ncc(C#Cc3cnn(-c4cnn(C)c4)c3C)c12] | 4-{[4-methoxy-6-(1-methyl-1H-pyrazol-4-yl)pyrazolo[1,5-a]pyridin-3-yl]ethynyl}-1',5-dimethyl-1'H-1,4'-bipyrazole | Calc'd 413.2, found 413.2 |

TABLE 3-continued

| Compound | Structure | Name | [M + H]+ |
|---|---|---|---|
| 3-113 | 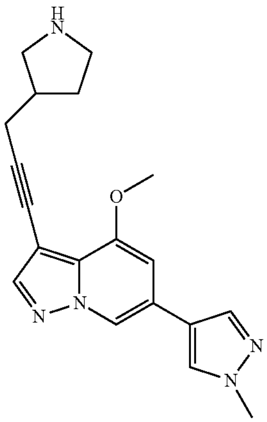 [SMILES: COc1cc(-c2cnn(C)c2)cn2ncc(C#CCC3CCNC3)c12] | 4-methoxy-6-(1-methyl-1H-pyrazol-4-yl)-3-(3-pyrrolidin-3-ylprop-1-yn-1-yl)pyrazolo[1,5-a]pyridine | Calc'd 336.2, found 336.1 |
| 3-114 | 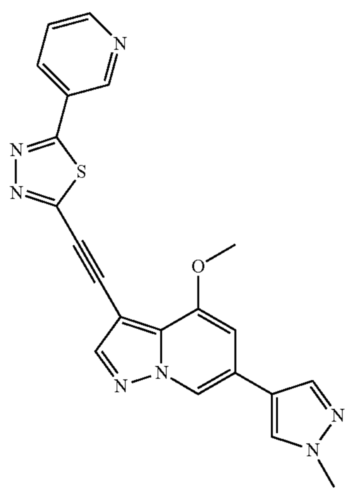 [SMILES: COc1cc(-c2cnn(C)c2)cn2ncc(C#Cc3nnc(-c4cccnc4)s3)c12] | 4-methoxy-6-(1-methyl-1H-pyrazol-4-yl)-3-[(5-pyridin-3-yl-1,3,4-thiadiazol-2-yl)ethynyl]pyrazolo[1,5-a]pyridine | Calc'd 414.1, found 414.1 |
| 3-115 | 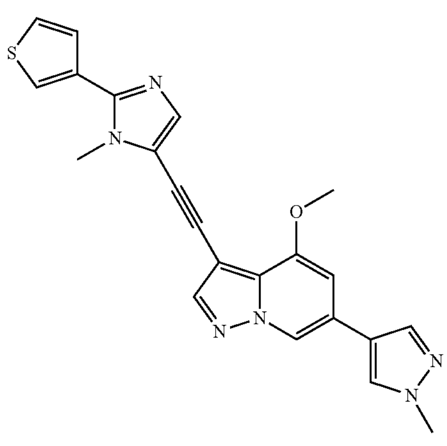 [SMILES: COc1cc(-c2cnn(C)c2)cn2ncc(C#Cc3cnc(-c4ccsc4)n3C)c12] | 4-methoxy-6-(1-methyl-1H-pyrazol-4-yl)-3-{[1-methyl-2-(3-thienyl)-1H-imidazol-5-yl]ethynyl}pyrazolo[1,5-a]pyridine | Calc'd 415.1, found 415.1 |

TABLE 3-continued

| Compound | Structure | Name | [M + H]+ |
|---|---|---|---|
| 3-116 | 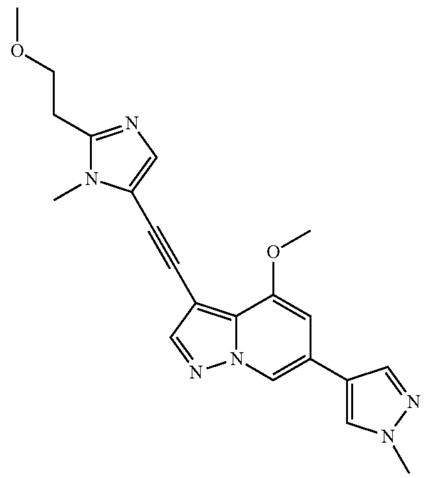 [SMILES: COCCc1ncc(C#Cc2cnn3cc(-c4cnn(C)c4)cc(OC)c23)n1C] | 4-methoxy-3-{[2-(2-methoxyethyl)-1-methyl-1H-imidazol-5-yl]ethynyl}-6-(1-methyl-1H-pyrazol-4-yl)pyrazolo[1,5-a]pyridine | Calc'd 391.2, found 391.2 |
| 3-117 | 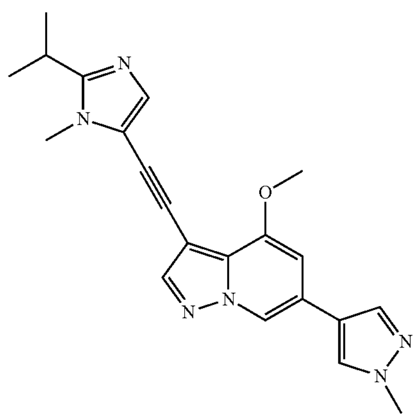 [SMILES: COc1cc(-c2cnn(C)c2)cn2ncc(C#Cc3cnc(C(C)C)n3C)c12] | 3-[(2-isopropyl-1-methyl-1H-imidazol-5-yl)ethynyl]-4-methoxy-6-(1-methyl-1H-pyrazol-4-yl)pyrazolo[1,5-a]pyridine | Calc'd 375.2, found 375.2 |
| 3-118 | 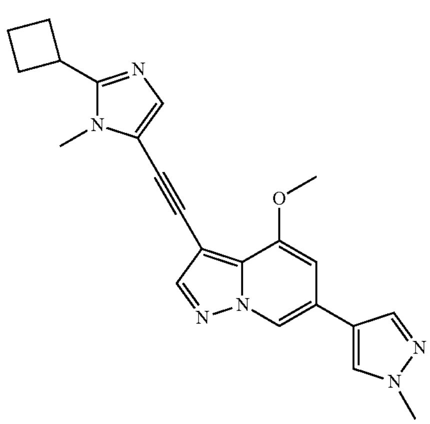 [SMILES: COc1cc(-c2cnn(C)c2)cn2ncc(C#Cc3cnc(C4CCC4)n3C)c12] | 3-[(2-cyclobutyl-1-methyl-1H-imidazol-5-yl)ethynyl]-4-methoxy-6-(1-methyl-1H-pyrazol-4-yl)pyrazolo[1,5-a]pyridine | Calc'd 387.2, found 387.2 |

TABLE 3-continued

| Compound | Structure | Name | [M + H]+ |
|---|---|---|---|
| 3-119 | 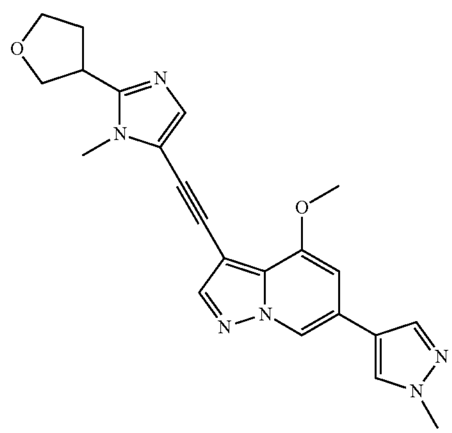 [SMILES: COc1cc(-c2cnn(C)c2)cn2ncc(C#Cc3cnc(C4CCOC4)n3C)c12] | 4-methoxy-6-(1-methyl-1H-pyrazol-4-yl)-3-{[1-methyl-2-(tetrahydrofuran-3-yl)-1H-imidazol-5-yl]ethynyl}pyrazolo[1,5-a]pyridine | Calc'd 403.2, found 403.2 |
| 3-120 | 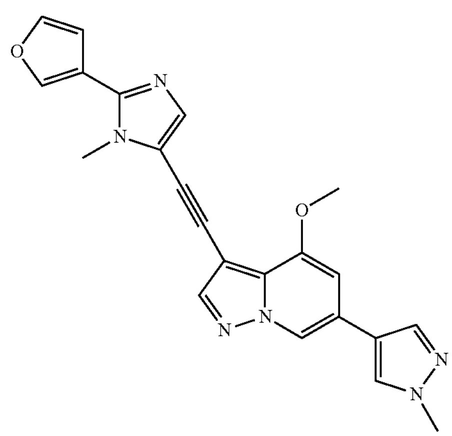 [SMILES: COc1cc(-c2cnn(C)c2)cn2ncc(C#Cc3cnc(-c4ccoc4)n3C)c12] | 3-{[2-(3-furyl)-1-methyl-1H-imidazol-5-yl]ethynyl}-4-methoxy-6-(1-methyl-1H-pyrazol-4-yl)pyrazolo[1,5-a]pyridine | Calc'd 399.2, found 399.2 |
| 3-121 | 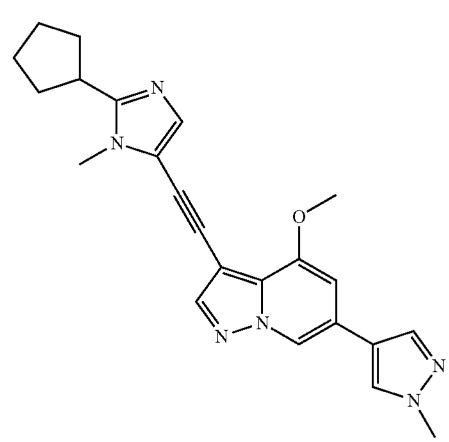 [SMILES: COc1cc(-c2cnn(C)c2)cn2ncc(C#Cc3cnc(C4CCCC4)n3C)c12] | 3-[(2-cyclopentyl-1-methyl-1H-imidazol-5-yl)ethynyl]-4-methoxy-6-(1-methyl-1H-pyrazol-4-yl)pyrazolo[1,5-a]pyridine | Calc'd 401.2, found 401.2 |

TABLE 3-continued
| Compound | Structure | Name | [M + H]+ |
|---|---|---|---|
| 3-122 | 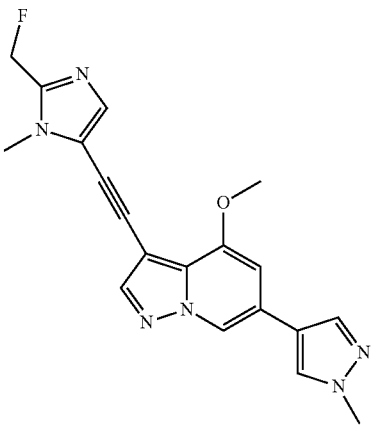 [SMILES: COc1cc(-c2cnn(C)c2)cn2ncc(C#Cc3cnc(CF)n3C)c12] | 3-{[2-(fluoromethyl)-1-methyl-1H-imidazol-5-yl]ethynyl}-4-methoxy-6-(1-methyl-1H-pyrazol-4-yl)pyrazolo[1,5-a]pyridine | Calc'd 365.2, found 365.1 |
| 3-123 | 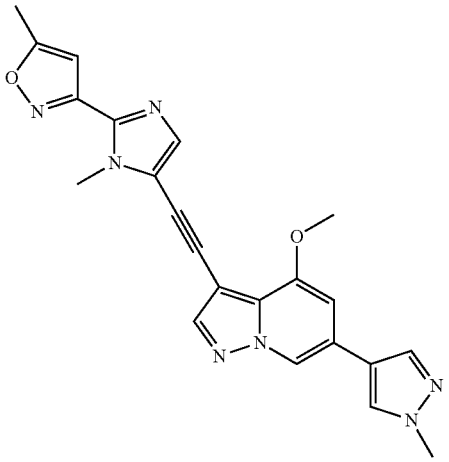 [SMILES: COc1cc(-c2cnn(C)c2)cn2ncc(C#Cc3cnc(-c4cc(C)on4)n3C)c12] | 4-methoxy-3-{[1-methyl-2-(5-methylisoxazol-3-yl)-1H-imidazol-5-yl]ethynyl}-6-(1-methyl-1H-pyrazol-4-yl)pyrazolo[1,5-a]pyridine | Calc'd 414.2, found 414.2 |
| 3-124 | 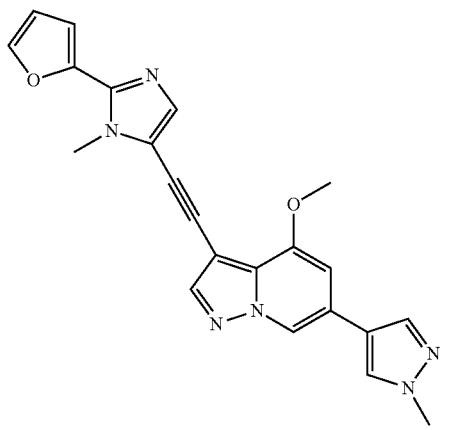 [SMILES: COc1cc(-c2cnn(C)c2)cn2ncc(C#Cc3cnc(-c4ccco4)n3C)c12] | 3-{[2-(2-furyl)-1-methyl-1H-imidazol-5-yl]ethynyl}-4-methoxy-6-(1-methyl-1H-pyrazol-4-yl)pyrazolo[1,5-a]pyridine | Calc'd 399.2, found 399.2 |

TABLE 3-continued

| Compound | Structure | Name | [M + H]+ |
|---|---|---|---|
| 3-125 | 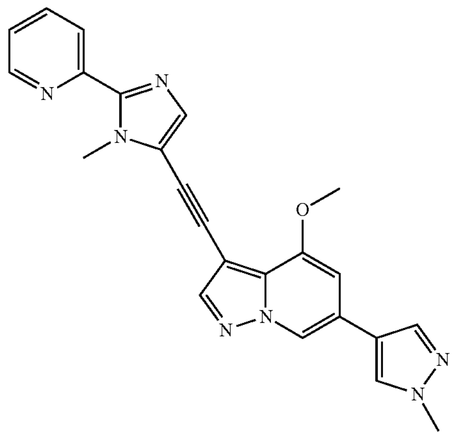 [SMILES: COc1cc(-c2cnn(C)c2)cn2ncc(C#Cc3cnc(-c4ccccn4)n3C)c12] | 4-methoxy-6-(1-methyl-1H-pyrazol-4-yl)-3-[(1-methyl-2-pyridin-2-yl-1H-imidazol-5-yl)ethynyl]pyrazolo[1,5-a]pyridine | Calc'd 410.2, found 410.2 |
| 3-126 | 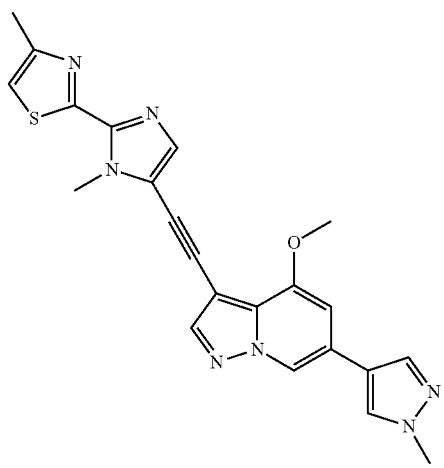 [SMILES: COc1cc(-c2cnn(C)c2)cn2ncc(C#Cc3cnc(-c4nc(C)cs4)n3C)c12] | 4-methoxy-3-{[1-methyl-2-(4-methyl-1,3-thiazol-2-yl)-1H-imidazol-5-yl]ethynyl}-6-(1-methyl-1H-pyrazol-4-yl)pyrazolo[1,5-a]pyridine | Calc'd 430.1, found 430.1 |
| 3-127 | 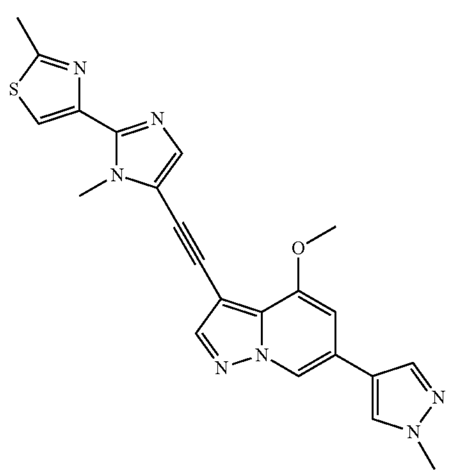 [SMILES: COc1cc(-c2cnn(C)c2)cn2ncc(C#Cc3cnc(-c4csc(C)n4)n3C)c12] | 4-methoxy-3-{[1-methyl-2-(2-methyl-1,3-thiazol-4-yl)-1H-imidazol-5-yl]ethynyl}-6-(1-methyl-1H-pyrazol-4-yl)pyrazolo[1,5-a]pyridine | Calc'd 430.1, found 430.1 |

TABLE 3-continued

| Compound | Structure | Name | [M + H]+ |
|---|---|---|---|
| 3-128 | 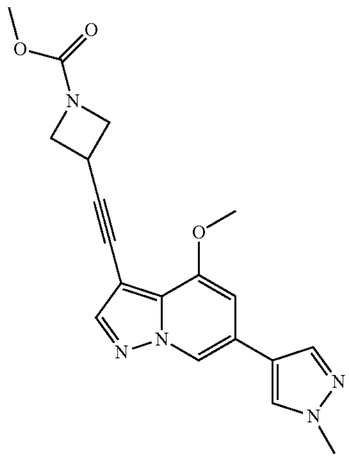 [SMILES: COC(=O)N1CC(C#Cc2cnn3cc(-c4cnn(C)c4)cc(OC)c23)C1] | methyl 3-{[4-methoxy-6-(1-methyl-1H-pyrazol-4-yl)pyrazolo[1,5-a]pyridin-3-yl]ethynyl}azetidine-1-carboxylate | Calc'd 366.2, found 366.2 |
| 3-129 | 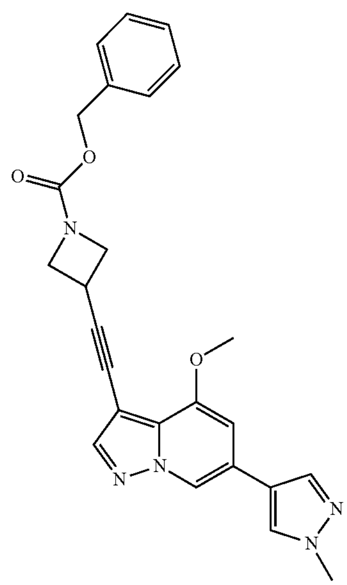 [SMILES: COc1cc(-c2cnn(C)c2)cn2ncc(C#CC3CN(C(=O)OCc4ccccc4)C3)c12] | benzyl 3-{[4-methoxy-6-(1-methyl-1H-pyrazol-4-yl)pyrazolo[1,5-a]pyridin-3-yl]ethynyl}azetidine-1-carboxylate | Calc'd 464.2 (+Na+), found 464.2 |
| 3-130 | 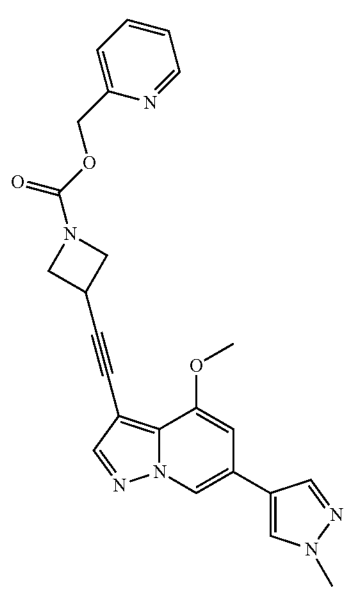 [SMILES: COc1cc(-c2cnn(C)c2)cn2ncc(C#CC3CN(C(=O)OCc4ccccn4)C3)c12] | pyridin-2-ylmethyl 3-{[4-methoxy-6-(1-methyl-1H-pyrazol-4-yl)pyrazolo[1,5-a]pyridin-3-yl]ethynyl}azetidine-1-carboxylate | Calc'd 443.2, found 443.2 |

TABLE 3-continued

| Compound | Structure | Name | [M + H]+ |
|---|---|---|---|
| 3-131 | 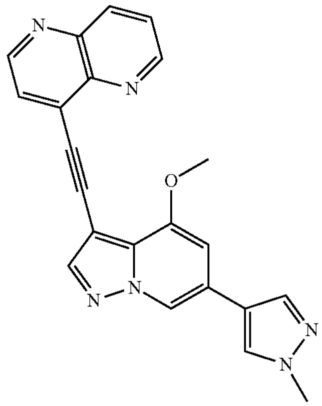 [SMILES: COc1cc(-c2cnn(C)c2)cn2ncc(C#Cc3ccnc4cccnc34)c12] | 4-{[4-methoxy-6-(1-methyl-1H-pyrazol-4-yl)pyrazolo[1,5-a]pyridin-3-yl]ethynyl}-1,5-naphthyridine | Calc'd 381.1, found 381.1 |
| 3-132 | 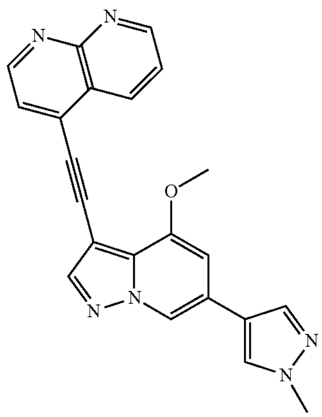 [SMILES: COc1cc(-c2cnn(C)c2)cn2ncc(C#Cc3ccnc4ncccc34)c12] | 4-{[4-methoxy-6-(1-methyl-1H-pyrazol-4-yl)pyrazolo[1,5-a]pyridin-3-yl]ethynyl}-1,8-naphthyridine | Calc'd 381.1, found 381.1 |
| 3-133 | 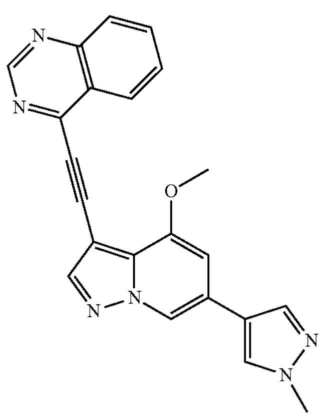 [SMILES: COc1cc(-c2cnn(C)c2)cn2ncc(C#Cc3ncnc4ccccc34)c12] | 4-{[4-methoxy-6-(1-methyl-1H-pyrazol-4-yl)pyrazolo[1,5-a]pyridin-3-yl]ethynyl}quinazoline | Calc'd 381.1, found 381.1 |

TABLE 3-continued

| Compound | Structure | Name | [M + H]+ |
|---|---|---|---|
| 3-134 | 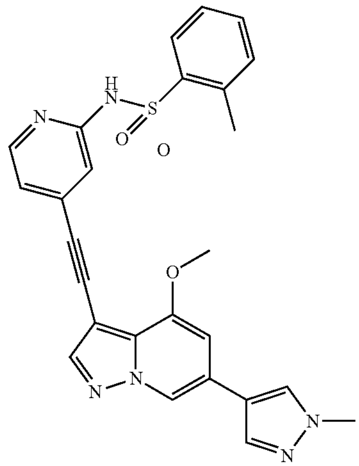 | N-(4-{[4-methoxy-6-(1-methyl-1H-pyrazol-4-yl)pyrazolo[1,5-a]pyridin-3-yl]ethynyl}pyridin-2-yl)-2-methylbenzenesulfonamide | Calc'd 499.2, found 499.1 |
| 3-135 | 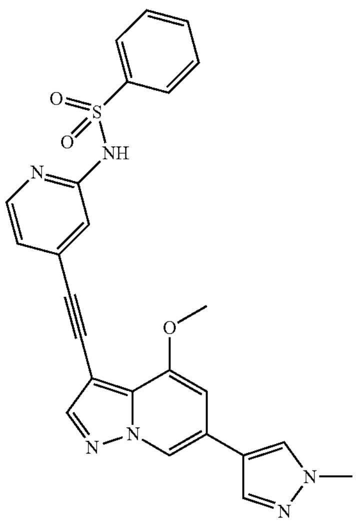 [SMILES: COc1cc(-c2cnn(C)c2)cn2ncc(C#Cc3ccnc(NS(=O)(=O)c4ccccc4)c3)c12] | N-(4-{[4-methoxy-6-(1-methyl-1H-pyrazol-4-yl)pyrazolo[1,5-a]pyridin-3-yl]ethynyl}pyridin-2-yl)benzenesulfonamide | Calc'd 485.1, found 485.1 |

Scheme 4

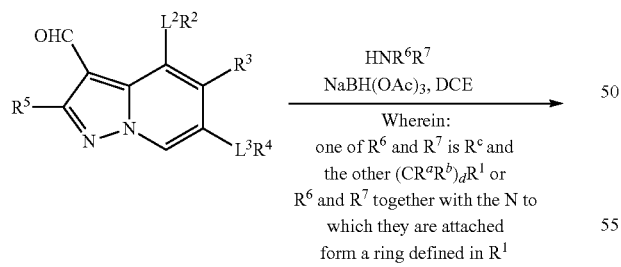

Wherein:
one of $R^6$ and $R^7$ is $R^c$ and
the other $(CR^aR^b)_dR^1$ or
$R^6$ and $R^7$ together with the N to
which they are attached
form a ring defined in $R^1$

EXAMPLES 4

Representative Compounds 4-1, 4-2 and 4-4 to 4-31, and Preparative Compound 4-3

Compound 4-1

3-(2,7-diazaspiro[3.5]non-2-ylmethyl)-4-methoxy-6-(1-methyl-1H-pyrazol-4-yl)pyrazolo[1,5-a]pyridine

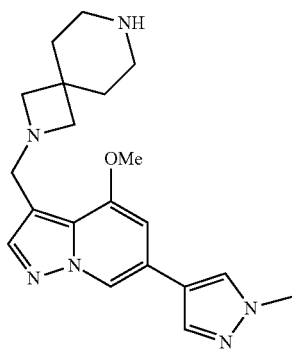 [SMILES: COc1cc(-c2cnn(C)c2)cn2ncc(CN3CC4(CCNCC4)C3)c12]

Step 1: tert-butyl 2-{[4-methoxy-6-(1-methyl-1H-pyrazol-4-yl)pyrazolo[1,5-a]pyridin-3-yl]methyl}-2,7-diazaspiro[3.5]nonane-7-carboxylate)

To a solution of 4-methoxy-6-(1-methyl-1H-pyrazol-4-yl) pyrazolo[1,5-a]pyridine-3-carbaldehyde (25.0 mg, 0.098 mmol), 7-(tert-butoxycarbonyl)-7-aza-2-azoniaspiro[3.5] nonane chloride (39.0 mg, 0.15 mmol), and triethylamine (0.054 mL, 0.39 mmol) in 1,2-dichloroethane (2 ml) was added sodium triacetoxyborohydride (41.0 mg, 0.20 mmol). After 2 h, the reaction was quenched with saturated aqueous sodium hydrogen carbonate, diluted with ethyl acetate, dried over magnesium sulfate, filtered and concentrated. The residue was purified by column chromatography on silica gel (ethyl acetate/isohexane gradient) to give tert-butyl 2-{[4-methoxy-6-(1-methyl-1H-pyrazol-4-yl)pyrazolo[1,5-a]pyridin-3-yl]methyl}-2,7-diazaspiro[3.5]nonane-7-carboxylate. LRMS (ESI) calculated for $C_{25}H_{35}N_6O_3$ [M+H]$^+$, 467.3; found 467.1.

Step 2: 3-(2,7-diazaspiro[3.5]non-2-ylmethyl)-4-methoxy-6-(1-methyl-1H-pyrazol-4-yl)pyrazolo[1,5-a]pyridine To a solution of tert-butyl 2-{[4-methoxy-6-(1-methyl-1H-pyrazol-4-yl)pyrazolo[1,5-a]pyridin-3-yl]methyl}-2,7-diazaspiro[3.5]nonane-7-carboxylate (47 mg, 0.10 mmol) in dichloromethane (2 ml) was added trifluoroacetic acid (0.008 mL, 0.1 mmol). After 30 minutes, the reaction mixture was concentrated. The residue was dissolved in methanol and eluted through a bicarbonate resin cartridge (StratoSpheres SPE, PL-HCO$_3$ MP SPE) to give 3-(2,7-diazaspiro[3.5]non-2-ylmethyl)-4-methoxy-6-(1-methyl-1H-pyrazol-4-yl)pyrazolo[1,5-a]pyridine as a solid. $^1$H NMR (500 MHz, DMSO-d$_6$) δ 8.51 (s, 1H); 8.24 (s, 1H); 7.97 (s, 1H); 7.12 (s, 1H); 6.77 (s, 1H); 3.95 (s, 3H); 3.85 (s, 3H); 3.79 (s, 2H); 2.89 (s, 4H); 2.50-2.54 (m, 4H); 1.47-1.50 (m, 4H). LRMS (ESI) calculated for $C_{20}H_{27}N_6O$ [M+H]$^+$, 367.3; found 367.1.

Compound 4-2

N-{[4-methoxy-6-(1-methyl-1H-pyrazol-4-yl)pyrazolo[1,5-a]pyridin-3-yl]methyl}pyridin-3-amine

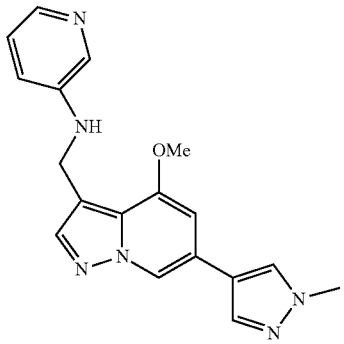 [SMILES: COc1cc(-c2cnn(C)c2)cn2ncc(CNc3cccnc3)c12]

A solution of 4-methoxy-6-(1-methyl-1H-pyrazol-4-yl) pyrazolo[1,5-a]pyridine-3-carbaldehyde (10.0 mg, 0.039 mmol), 3-aminopyridine (5.5 mg, 0.059 mmol), and acetic acid (50 µl) in 1,2-dichloroethane (1 ml) was stirred for 2 d. Sodium triacetoxyborohydride (24.8 mg, 0.117 mmol) was added and the mixture was stirred for 1 d. The mixture was diluted with dichloromethane and washed with saturated aqueous sodium bicarbonate. The organic layer was filtered with isoElute and concentrated. The residue was purified by column chromatography on silica gel (methanol/ethyl acetate gradient) to give N-{[4-methoxy-6-(1-methyl-1H-pyrazol-4-yl)pyrazolo[1,5-a]pyridin-3-yl]methyl}pyridin-3-amine $^1$H NMR (500 MHz, CDCl$_3$) δ 8.52 (s, 1H); 8.21 (s, 1H); 8.00 (d, 1H); 7.96 (s, 1H), 7.80 (s, 1H), 7.69 (d, 1H), 7.02 (d, 1H), 6.95 (d, 1H), 6.81 (s, 1H), 6.08 (t, 1H), 4.47 (s, 2H), 3.98 (s, 3H), 3.82 (s, 3H) LRMS (ESI) calculated for $C_{18}H_{19}N_6O$ [M+H]$^+$, 335.2; found 335.1.

Preparative Compound 4-3 tert-butyl 2,6-diazaspiro[3.3]heptane-2-carboxylate hydrochloride

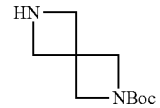

Step 1: 3-bromo-2,2-bis(bromomethyl)propanol-1

A mixture of pentaerythritol (640 g), 48% hydrobromic acid (2370 ml) and glacial acetic acid (470 ml) was refluxed (130-134° C.) for 18 h. Additional amount of 48% hydrobromic acid (2370 mL) was added to the reaction mixture followed by the addition of sulphuric acid (1135 mL). The reaction mixture was refluxed (135-140° C.) for an additional 8 h. The reaction mixture was cooled to 20-25° C. and the layers were separated. The lower layer was dissolved in chloroform, washed with water and dried over anhydrous potassium carbonate. The organic layer was concentrated to afford 1300 g of crude material. The residue was fractionally distilled under reduced pressure to give a colorless liquid, which crystallized during distillation. The solid was refluxed with hexane until the solution was clear. The solution was stirred overnight at ambient temperature and filtered to afford 382 g of 3-bromo-2,2-bis(bromomethyl)propanol-1.

Step 2: 3,3-Bis(bromomethyl)oxetane

A mixture of potassium hydroxide (98.5 g, 1.76 mol) and 3-bromo-2,2-bis(bromomethyl)propanol-1 (382 g, 1.17 mol) in ethanol (500 mL) was refluxed for 30 mins. The solid was filtered and the filtrate was distilled under reduced pressure to afford 235 gm of crude material. Distillation of the crude material under reduced pressure gave 205 gm of pure material of 3,3-Bis(bromomethyl)oxetane as a colorless liquid.

Step 3: 3,3-bis(aminomethyl)oxetane-1,3-dihydrobromide 3,3-Bis(bromomethyl)oxetane (250 g, 1.03 mol) was placed in an autoclave with a pressure gauge and liquid ammonia (900 mL) was added to the pre-cooled compound. The autoclave was heated to 50° C. for 24 h. After cooling to ambient temperature, the excess ammonia was evaporated and the residue was washed with methanol to give 3,3-bis (aminomethyl)oxetane-1,3-dihydrobromide.

Step 4:
2,2-Bis(bromomethyl)-propane-1,3-Dihydrobromide

Phosphorous tribromide (600 mL) was added to 3,3-bis (aminomethyl)oxetane-1,3-dihydrobromide (150 g, 0.54 mol) and the reaction mixture was heated to reflux temperature 60 hours. After the completion of the reaction phosphorous tribromide was distilled off from the reaction mass under vacuum at 100-120° C. until the reaction mass became a thick mass. Then the excess phosphorous tribromide in the reaction mass was quenched by adding the reaction mass to crushed ice and then followed by adding methanol (300 mL). Then the separated solids were filtered and washed with methanol (150 mL) to afford 100.0 g of 2,2-Bis(bromomethyl)-propane-1, 3-Dihydrobromide. The mother liquors were concentrated under vacuum until the reaction mass became a thick syrup. Then methanol (500 mL) was added and then stirred and the solids were separated. The filtered solids were washed with methanol (150 mL) to afford an additional 50.0 g of 2,2-Bis (bromomethyl)-propane-1,3-Dihydrobromide.

Step 5: di-tert-butyl 2,6-diazaspiro[3.3]heptane-2,6-dicarboxylate 2,2-Bis(bromomethyl)-propane-1,3-Dihydrobromide (100 g, 0.24 mol) was dissolved in water (1800 mL). The reaction mixture was heated to 95-100° C. and then a solution of sodium hydroxide (28.4 g, 0.72 mol) in water (200 mL) was added in three lots over about 30 minutes. The reaction mixture was maintained at the same temperature until complete (4 hours). The reaction mixture was cooled to ambient temperature and then 48% aqueous HBr was added until the pH was about 1.0 to 2.0. The reaction mass was filtered on a high flow bed to remove the junky material from it. Then the water was evaporated from the filtered solution under vacuum until the reaction mass became a thick solid. Then the obtained wet solids were dissolved in water (400 mL) and then a sodium carbonate solution (61.2 g dissolved in 100 ml of water) was added, followed by tetrahydrofuran (900 mL). The contents were stirred as such for 10 minutes. Then a solution of di-tert-butyl-dicarbonate in tetrahydrofuran (100 ml) was added and then the mixture was stirred vigorously for 3 hours at ambient temperature. The reaction was quenched by the addition of brine solution (100 mL) and then extracted with 3×200 ml of ethyl acetate. The combined ethyl acetate layer was washed with brine solution and then the obtained organic layer was dried over anhydrous sodium sulfate. The solvent from the organic layer was evaporated under reduced pressure to afford 50.0 g of crude residue. To this was added pentane (100 ml) and stirred for 15 minutes for solids to separate out. The solids were filtered and washed with pentane to afford 40.0 g of di-tert-butyl 2,6-diazaspiro[3.3]heptane-2,6-dicarboxylate.

Step 6: tert-butyl 2,6-diazaspiro[3.3]heptane-2-carboxylate hydrochloride

Acetyl chloride (5.3 g, 0.67 mol) was slowly added (about 5 min) added to methanol (560 mL) and then the solution was allowed to stir for an additional 5 minutes. di-tert-butyl 2,6-diazaspiro[3.3]heptane-2,6-dicarboxylate (20 g, 0.67 mol) was added in portions over about 15 minutes, then the mixture was allowed to stir for 20 hours. Then triethylamine (6.8 g, 0.67 mol) was added slowly over about 5 minutes duration. The reaction mixture was stirred at ambient temperature for 2 hours. The solvents were distilled off from the reaction under reduced pressure to afford 18.0 g of white solids. The solids were treated with pentane (50 mL) and filtered and then washed with ethyl acetate (100 mL) to afford 10.0 g of tert-butyl 2,6-diazaspiro[3.3]heptane-2-carboxylate hydrochloride.

The compounds in the following table were prepared according to the procedure described in scheme 4 and for compounds 4-1 to 4-3. The compounds were prepared as free bases or salts.

TABLE 4

| Compound | Structure | Name | [M + H]+ | Free base or salt form |
|---|---|---|---|---|
| 4-4 | 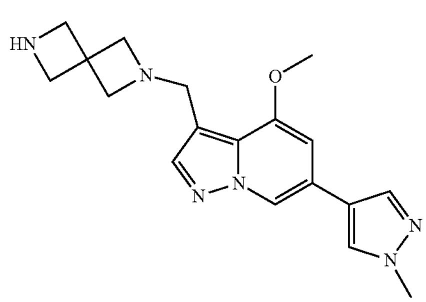 [SMILES: COc1cc(-c2cnn(C)c2)cn2ncc(CN3CC4(CNC4)C3)c12] | 3-(2,6-diazaspiro[3.3]hept-2-ylmethyl)-4-methoxy-6-(1-methyl-1H-pyrazol-4-yl)pyrazolo[1,5-a]pyridine | Calc'd 339.2, found 339.1 | Free base |

TABLE 4-continued

| Compound | Structure | Name | [M + H]+ | Free base or salt form |
|---|---|---|---|---|
| 4-5 | 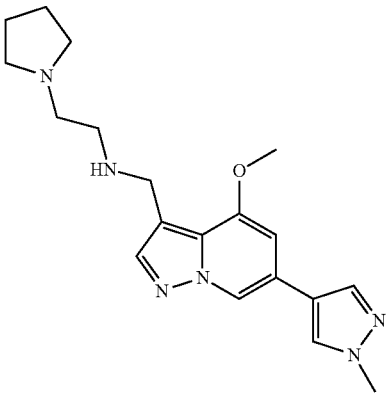 [SMILES: COc1cc(-c2cnn(C)c2)cn2ncc(CNCCN3CCCC3)c12] | N-{[4-methoxy-6-(1-methyl-1H-pyrazol-4-yl)pyrazolo[1,5-a]pyridin-3-yl]methyl}-2-pyrrolidin-1-ylethanamine | Calc'd 355.2, found 355.1 | Free base |
| 4-6 | 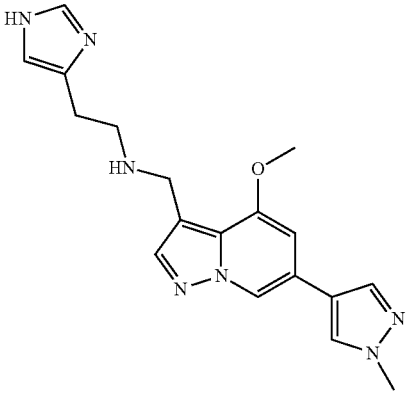 [SMILES: COc1cc(-c2cnn(C)c2)cn2ncc(CNCCc3c[nH]cn3)c12] | 2-(1H-imidazol-4-yl)-N-{[4-methoxy-6-(1-methyl-1H-pyrazol-4-yl)pyrazolo[1,5-a]pyridin-3-yl]methyl}ethanamine | Calc'd 352.2, found 352.1 | Free base |
| 4-7 | 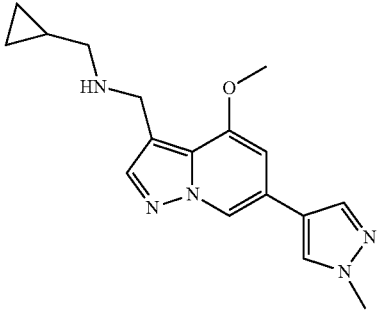 [SMILES: COc1cc(-c2cnn(C)c2)cn2ncc(CNCC3CC3)c12] | 1-cyclopropyl-N-{[4-methoxy-6-(1-methyl-1H-pyrazol-4-yl)pyrazolo[1,5-a]pyridin-3-yl]methyl}methanamine | Calc'd 312.2, found 312.1 | Free base |
| 4-8 | 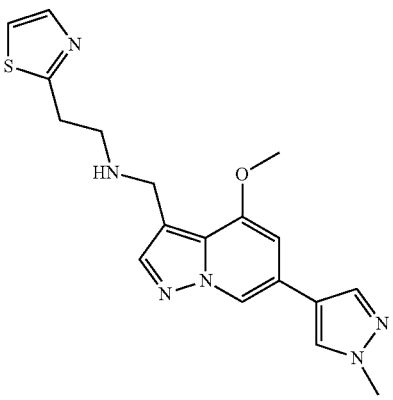 [SMILES: COc1cc(-c2cnn(C)c2)cn2ncc(CNCCc3nccs3)c12] | N-{[4-methoxy-6-(1-methyl-1H-pyrazol-4-yl)pyrazolo[1,5-a]pyridin-3-yl]methyl}-2-(1,3-thiazol-2-yl)ethanamine | Calc'd 369.1, found 241.1 (des-amine fragment) | Free base |

TABLE 4-continued

| Compound | Structure | Name | [M + H]+ | Free base or salt form |
|---|---|---|---|---|
| 4-9 | 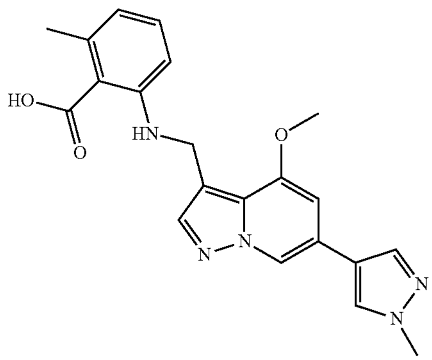 [SMILES: COc1cc(-c2cnn(C)c2)cn2ncc(CNc3cccc(C)c3C(=O)O)c12] | 2-({[4-methoxy-6-(1-methyl-1H-pyrazol-4-yl)pyrazolo[1,5-a]pyridin-3-yl]methyl}amino)-6-methylbenzoic acid | Calc'd 392.2, found 392.2 | TFA salt |
| 4-10 | 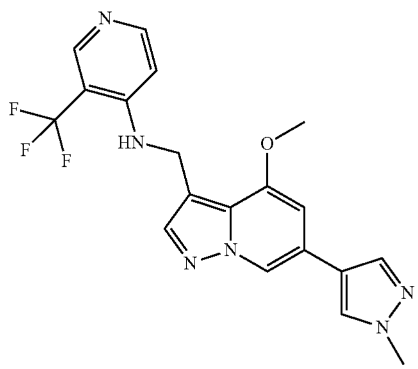 [SMILES: COc1cc(-c2cnn(C)c2)cn2ncc(CNc3ccncc3C(F)(F)F)c12] | N-{[4-methoxy-6-(1-methyl-1H-pyrazol-4-yl)pyrazolo[1,5-a]pyridin-3-yl]methyl}-3-(trifluoromethyl)pyridin-4-amine | Calc'd 403.1, found 403.1 | TFA salt |
| 4-11 | 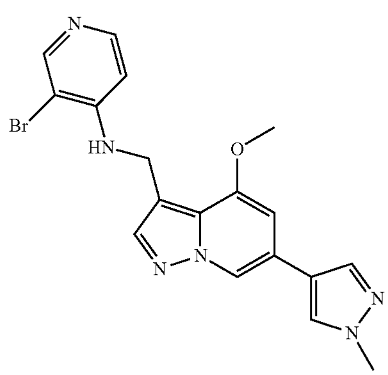 [SMILES: COc1cc(-c2cnn(C)c2)cn2ncc(CNc3ccncc3Br)c12] | 3-bromo-N-{[4-methoxy-6-(1-methyl-1H-pyrazol-4-yl)pyrazolo[1,5-a]pyridin-3-yl]methyl}pyridin-4-amine | Calc'd 413.1 (for [79]Br), found 413.1 | Formate salt |
| 4-12 | 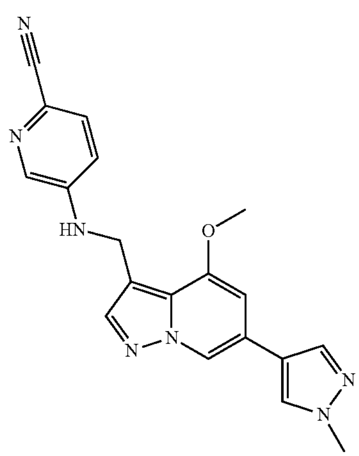 [SMILES: COc1cc(-c2cnn(C)c2)cn2ncc(CNc3ccc(C#N)nc3)c12] | 5-({[4-methoxy-6-(1-methyl-1H-pyrazol-4-yl)pyrazolo[1,5-a]pyridin-3-yl]methyl}amino)pyridine-2-carbonitrile | Calc'd 360.2, found 360.1 | Formate salt |

TABLE 4-continued

| Compound | Structure | Name | [M + H]+ | Free base or salt form |
|---|---|---|---|---|
| 4-13 | 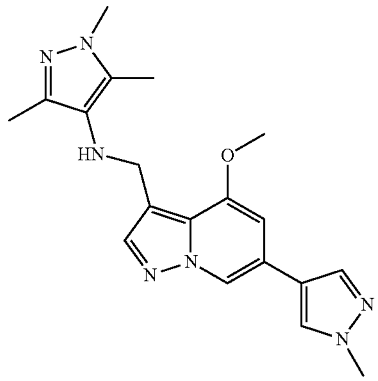 [SMILES: COc1cc(-c2cnn(C)c2)cn2ncc(CNc3c(C)nn(C)c3C)c12] | N-{[4-methoxy-6-(1-methyl-1H-pyrazol-4-yl)pyrazolo[1,5-a]pyridin-3-yl]methyl}-1,3,5-trimethyl-1H-pyrazol-4-amine | Calc'd 366.2, found 366.1 | Formate salt |
| 4-14 | 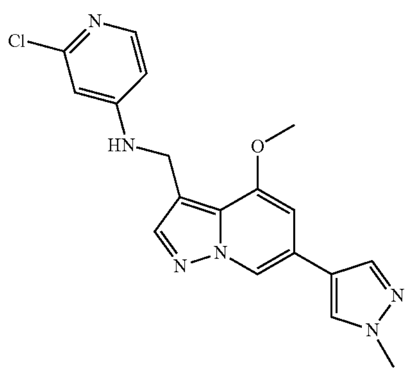 [SMILES: COc1cc(-c2cnn(C)c2)cn2ncc(CNc3ccnc(Cl)c3)c12] | 2-chloro-N-{[4-methoxy-6-(1-methyl-1H-pyrazol-4-yl)pyrazolo[1,5-a]pyridin-3-yl]methyl}pyridin-4-amine | Calc'd 369.1, found 369.1 | Formate salt |
| 4-15 | 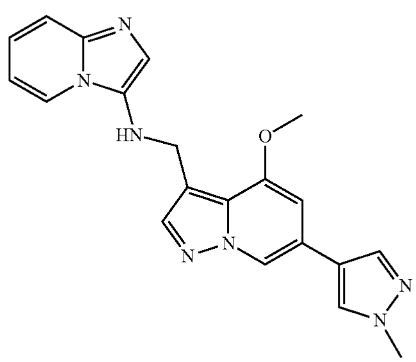 [SMILES: COc1cc(-c2cnn(C)c2)cn2ncc(CNc3cnc4ccccn34)c12] | N-{[4-methoxy-6-(1-methyl-1H-pyrazol-4-yl)pyrazolo[1,5-a]pyridin-3-yl]methyl}imidazo[1,2-a]pyridin-3-amine | Calc'd 374.2, found 374.1 | Formate salt |
| 4-16 | 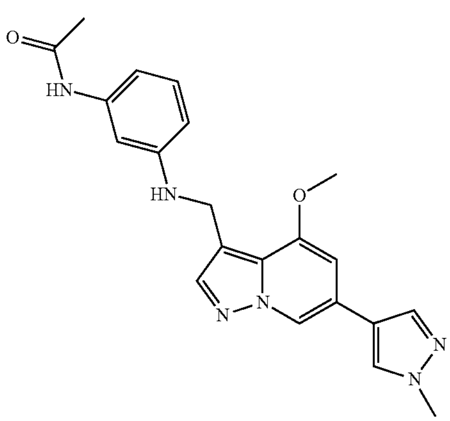 [SMILES: COc1cc(-c2cnn(C)c2)cn2ncc(CNc3cccc(NC(C)=O)c3)c12] | N-[3-({[4-methoxy-6-(1-methyl-1H-pyrazol-4-yl)pyrazolo[1,5-a]pyridin-3-yl]methyl}amino)phenyl]acetamide | Calc'd 391.2, found 391.1 | Formate salt |

TABLE 4-continued

| Compound | Structure | Name | [M + H]+ | Free base or salt form |
|---|---|---|---|---|
| 4-17 | 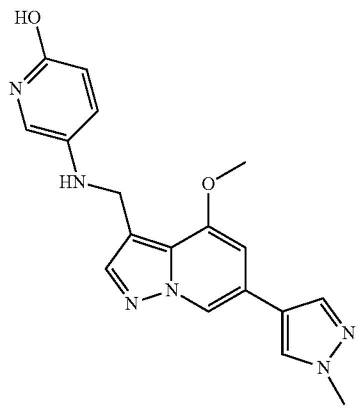 [SMILES: COc1cc(-c2cnn(C)c2)cn2ncc(CNc3ccc(O)nc3)c12] | 5-({[4-methoxy-6-(1-methyl-1H-pyrazol-4-yl)pyrazolo[1,5-a]pyridin-3-yl]methyl}amino)pyridin-2-ol | Calc'd 351.2, found 241.1 (des-amine fragment) | Formate salt |
| 4-18 | 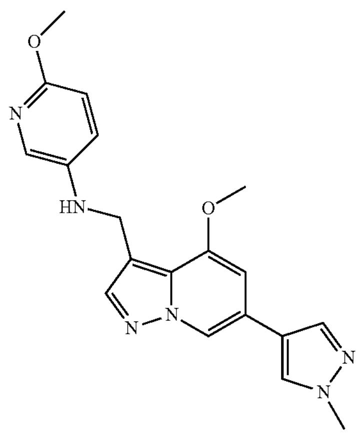 [SMILES: COc1ccc(NCc2cnn3cc(-c4cnn(C)c4)cc(OC)c23)cn1] | 6-methoxy-N-{[4-methoxy-6-(1-methyl-1H-pyrazol-4-yl)pyrazolo[1,5-a]pyridin-3-yl]methyl}pyridin-3-amine | Calc'd 365.2, found 365.2 | Formate salt |
| 4-19 | 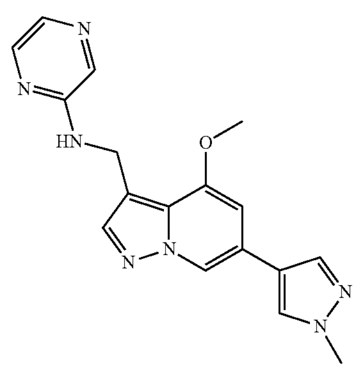 [SMILES: COc1cc(-c2cnn(C)c2)cn2ncc(CNc3cnccn3)c12] | N-{[4-methoxy-6-(1-methyl-1H-pyrazol-4-yl)pyrazolo[1,5-a]pyridin-3-yl]methyl}pyrazin-2-amine | Calc'd 336.2, found 336.2 | Formate salt |
| 4-20 | 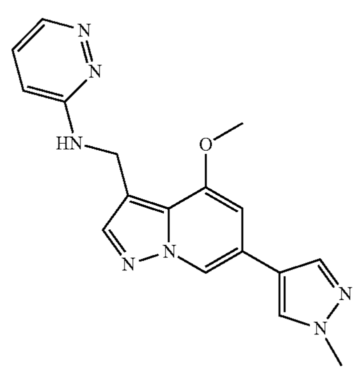 [SMILES: COc1cc(-c2cnn(C)c2)cn2ncc(CNc3cccnn3)c12] | N-{[4-methoxy-6-(1-methyl-1H-pyrazol-4-yl)pyrazolo[1,5-a]pyridin-3-yl]methyl}pyridazin-3-amine | Calc'd 336.2, found 336.1 | Formate salt |

TABLE 4-continued

| Compound | Structure | Name | [M + H]+ | Free base or salt form |
|---|---|---|---|---|
| 4-21 | 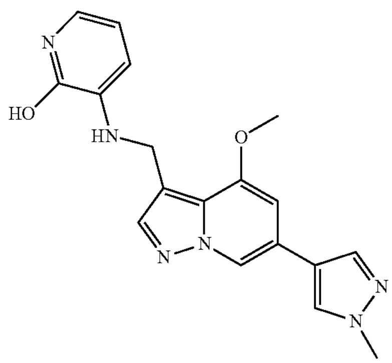 [SMILES: COc1cc(-c2cnn(C)c2)cn2ncc(CNc3cccnc3O)c12] | 3-({[4-methoxy-6-(1-methyl-1H-pyrazol-4-yl)pyrazolo[1,5-a]pyridin-3-yl]methyl}amino)pyridin-2-ol | Calc'd 351.2, found 241.1 (des-amine fragment) | Formate salt |
| 4-22 | 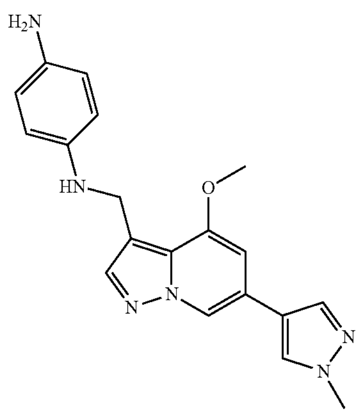 [SMILES: COc1cc(-c2cnn(C)c2)cn2ncc(CNc3ccc(N)cc3)c12] | N-{[4-methoxy-6-(1-methyl-1H-pyrazol-4-yl)pyrazolo[1,5-a]pyridin-3-yl]methyl}benzene-1,4-diamine | Calc'd 349.2, found 349.2 | Formate salt |
| 4-23 | 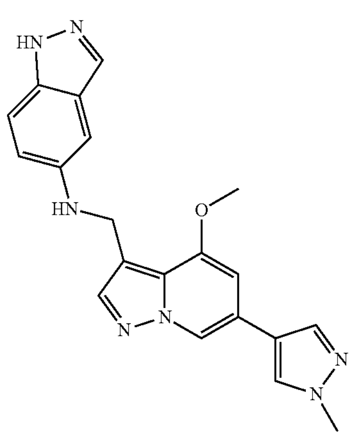 [SMILES: COc1cc(-c2cnn(C)c2)cn2ncc(CNc3ccc4[nH]ncc4c3)c12] | N-{[4-methoxy-6-(1-methyl-1H-pyrazol-4-yl)pyrazolo[1,5-a]pyridin-3-yl]methyl}-1H-indazol-5-amine | Calc'd 374.2, found 241.1 (des-amine fragment) | Formate salt |

TABLE 4-continued

| Compound | Structure | Name | [M + H]+ | Free base or salt form |
|---|---|---|---|---|
| 4-24 | 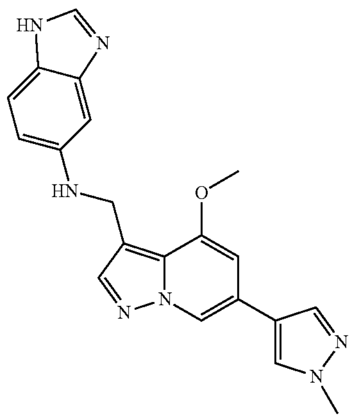 [SMILES: COc1cc(-c2cnn(C)c2)cn2ncc(CNc3ccc4[nH]cnc4c3)c12] | N-{[4-methoxy-6-(1-methyl-1H-pyrazol-4-yl)pyrazolo[1,5-a]pyridin-3-yl]methyl}-1H-benzimidazol-5-amine | Calc'd 374.2, found 374.2 | Formate salt |
| 4-25 | 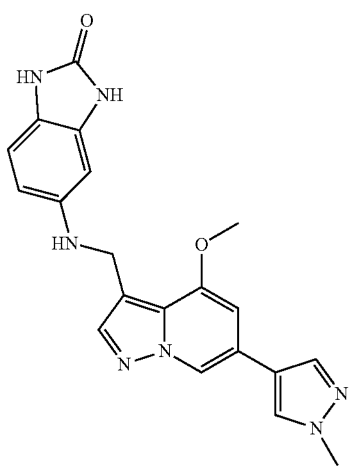 [SMILES: COc1cc(-c2cnn(C)c2)cn2ncc(CNc3ccc4[nH]c(=O)[nH]c4c3)c12] | 5-({[4-methoxy-6-(1-methyl-1H-pyrazol-4-yl)pyrazolo[1,5-a]pyridin-3-yl]methyl}amino)-1,3-dihydro-2H-benzimidazol-2-one | Calc'd 390.2, found 390.1 | Formate salt |
| 4-26 | 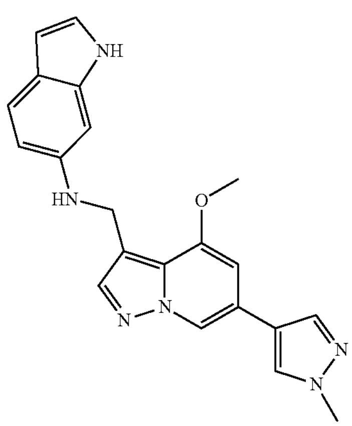 [SMILES: COc1cc(-c2cnn(C)c2)cn2ncc(CNc3ccc4cc[nH]c4c3)c12] | N-{[4-methoxy-6-(1-methyl-1H-pyrazol-4-yl)pyrazolo[1,5-a]pyridin-3-yl]methyl}-1H-indol-6-amine | Calc'd 373.2, found 241.1 (des-amine fragment) | Formate salt |

TABLE 4-continued

| Compound | Structure | Name | [M + H]+ | Free base or salt form |
|---|---|---|---|---|
| 4-27 | 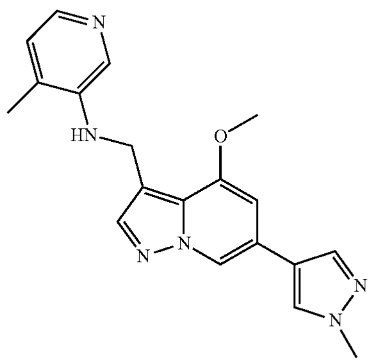 [SMILES: COc1cc(-c2cnn(C)c2)cn2ncc(CNc3cnccc3C)c12] | N-{[4-methoxy-6-(1-methyl-1H-pyrazol-4-yl)pyrazolo[1,5-a]pyridin-3-yl]methyl}-4-methylpyridin-3-amine | Calc'd 349.2, found 349.2 | Formate salt |
| 4-28 | 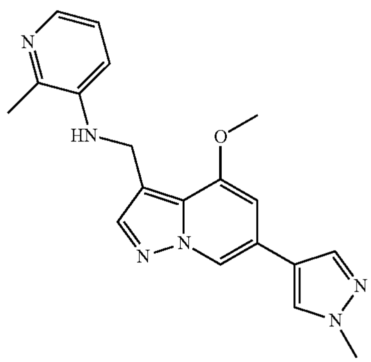 [SMILES: COc1cc(-c2cnn(C)c2)cn2ncc(CNc3cccnc3C)c12] | N-{[4-methoxy-6-(1-methyl-1H-pyrazol-4-yl)pyrazolo[1,5-a]pyridin-3-yl]methyl}-2-methylpyridin-3-amine | Calc'd 349.2, found 349.2 | Formate salt |
| 4-29 | 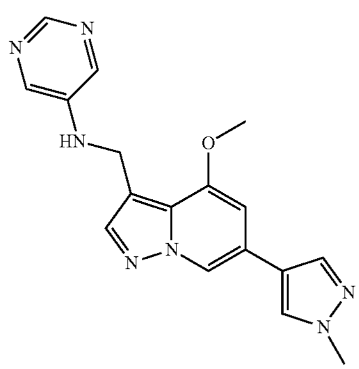 [SMILES: COc1cc(-c2cnn(C)c2)cn2ncc(CNc3cncnc3)c12] | N-{[4-methoxy-6-(1-methyl-1H-pyrazol-4-yl)pyrazolo[1,5-a]pyridin-3-yl]methyl}pyrimidin-5-amine | Calc'd 336.2, found 336.2 | Formate salt |

TABLE 4-continued
| Compound | Structure | Name | [M + H]+ | Free base or salt form |
|---|---|---|---|---|
| 4-30 | 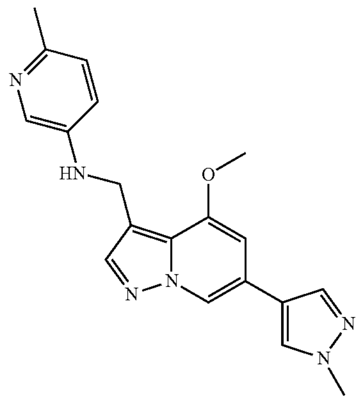 [SMILES: COc1cc(-c2cnn(C)c2)cn2ncc(CNc3ccc(C)nc3)c12] | N-{[4-methoxy-6-(1-methyl-1H-pyrazol-4-yl)pyrazolo[1,5-a]pyridin-3-yl]methyl}-6-methylpyridin-3-amine | Calc'd 349.2, found 349.2 | Formate salt |
| 4-31 | 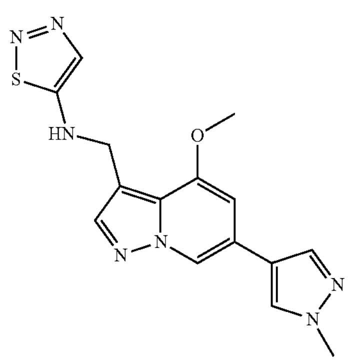 [SMILES: COc1cc(-c2cnn(C)c2)cn2ncc(CNc3cnns3)c12] | N-{[4-methoxy-6-(1-methyl-1H-pyrazol-4-yl)pyrazolo[1,5-a]pyridin-3-yl]methyl}-1,2,3-thiadiazol-5-amine | Calc'd 342.1, found 342.1 | Formate salt |
Scheme 5
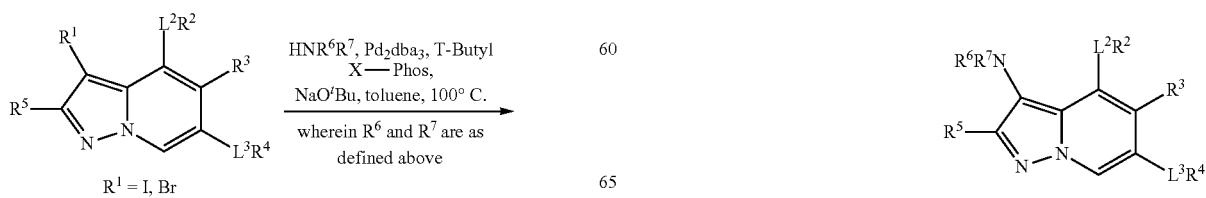

EXAMPLES 5

Representative Compounds 5-1 to 5-14

Compound 5-1

N-benzyl-4-methoxy-6-(1-methyl-1H-pyrazol-4-yl)pyrazolo[1,5-a]pyridin-3-amine

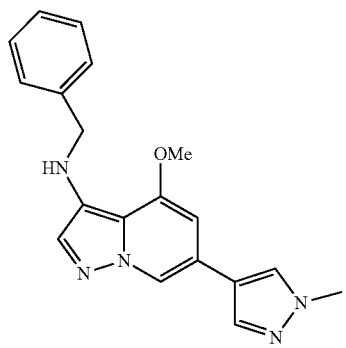

5-1

N-benzyl-4-methoxy-6-(1-methyl-1H-pyrazol-4-yl)pyrazolo[1,5-a]pyridin-3-amine 3-bromo-4-methoxy-6-(1-methyl-1H-pyrazol-4-yl)pyrazolo[1,5-a]pyridine (25.0 mg, 0.081 mmol), benzyl amine (12.0 mg, 0.011 mmol), tris[dibenzylideneacetone]dipalladium (0) (1.9 mg, 0.0020 mmol), and tert-butyl X-phos (3.5 mg, 8.1 mmol) were suspended in toluene (1.6 ml), sparged with argon for 3 minutes, then heated to 100° C. After 12 hours, the reaction mixture was concentrated. The residue was purified by preparative HPLC Reverse phase (C-18), eluting with acetonitrile/water+0.05% TFA to give N-benzyl-4-methoxy-6-(1-methyl-1H-pyrazol-4-yl)pyrazolo[1,5-a]pyridin-3-amine $^1$H NMR (500 MHz, DMSO-$d_6$) δ 8.23 (s, 1H); 8.17 (s, 1H); 7.91 (s, 1H); 7.38 (d, 2H); 7.29 (t, 2H); 7.25 (s, 1H); 7.20 (t, 1H); 6.44 (s, 1H); 4.92 (t, 1H); 4.23 (d, 2H); 3.93 (s, 3H); 3.83 (s, 3H). LRMS (ESI) calculated for $C_{19}H_{20}N_5O$ [M+H]$^+$, 334.2; found 334.1.

The compounds in the following table were prepared according to the procedure described in scheme 5 and for compound 5-1. The compounds were prepared as free bases.

TABLE 5

| Compound | Structure | Name | [M + H]+ |
| --- | --- | --- | --- |
| 5-2 | 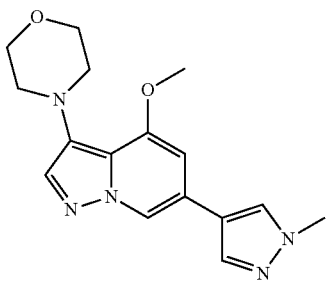 [SMILES: COc1cc(-c2cnn(C)c2)cn2ncc(N3CCOCC3)c12] | 4-methoxy-6-(1-methyl-1H-pyrazol-4-yl)-3-morpholin-4-ylpyrazolo[1,5-a]pyridine | Calc'd 314.2, found 314.1 |
| 5-3 | 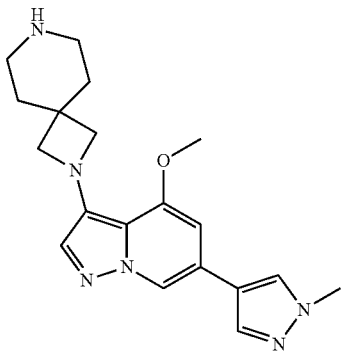 [SMILES: COc1cc(-c2cnn(C)c2)cn2ncc(N3CC4(CCNCC4)C3)c12] | 3-(2,7-diazaspiro[3.5]non-2-yl)-4-methoxy-6-(1-methyl-1H-pyrazol-4-yl)pyrazolo[1,5-a]pyridine | Calc'd 353.2, found 353.1 |

TABLE 5-continued

| Compound | Structure | Name | [M + H]+ |
| --- | --- | --- | --- |
| 5-4 | 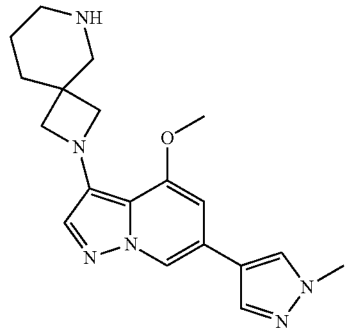 [SMILES: COc1cc(-c2cnn(C)c2)cn2ncc(N3CC4(CCCNC4)C3)c12] | 3-(2,6-diazaspiro[3.5]non-2-yl)-4-methoxy-6-(1-methyl-1H-pyrazol-4-yl)pyrazolo[1,5-a]pyridine | Calc'd 353.2, found 353.1 |
| 5-5 | 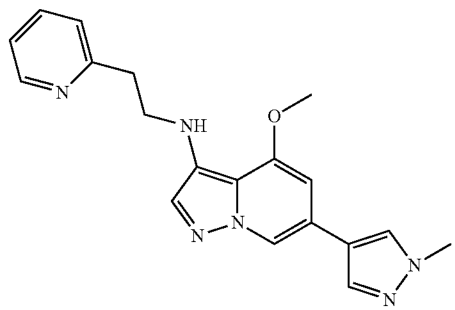 [SMILES: COc1cc(-c2cnn(C)c2)cn2ncc(NCCc3ccccn3)c12] | 4-methoxy-6-(1-methyl-1H-pyrazol-4-yl)-N-(2-pyridin-2-ylethyl)pyrazolo[1,5-a]pyridin-3-amine | Calc'd 349.2, found 349.1 |
| 5-6 | 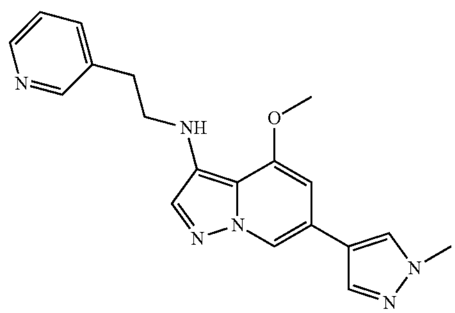 [SMILES: COc1cc(-c2cnn(C)c2)cn2ncc(NCCc3cccnc3)c12] | 4-methoxy-6-(1-methyl-1H-pyrazol-4-yl)-N-(2-pyridin-3-ylethyl)pyrazolo[1,5-a]pyridin-3-amine | Calc'd 349.2, found 349.1 |
| 5-7 | 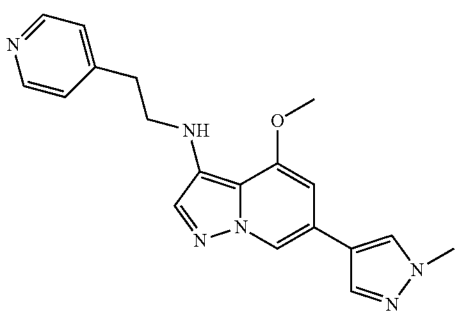 [SMILES: COc1cc(-c2cnn(C)c2)cn2ncc(NCCc3ccncc3)c12] | 4-methoxy-6-(1-methyl-1H-pyrazol-4-yl)-N-(2-pyridin-4-ylethyl)pyrazolo[1,5-a]pyridin-3-amine | Calc'd 349.2, found 349.1 |
| 5-8 | 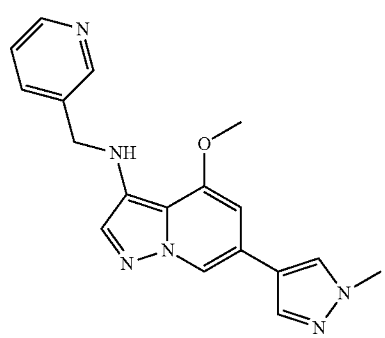 [SMILES: COc1cc(-c2cnn(C)c2)cn2ncc(NCc3cccnc3)c12] | 4-methoxy-6-(1-methyl-1H-pyrazol-4-yl)-N-(pyridin-3-ylmethyl)pyrazolo[1,5-a]pyridin-3-amine | Calc'd 335.2, found 335.1 |

TABLE 5-continued

| Compound | Structure | Name | [M + H]+ |
|---|---|---|---|
| 5-9 | 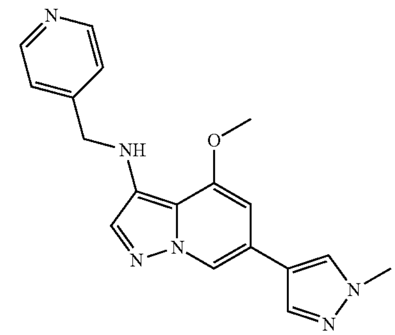 [SMILES: COc1cc(-c2cnn(C)c2)cn2ncc(NCc3ccncc3)c12] | 4-methoxy-6-(1-methyl-1H-pyrazol-4-yl)-N-(pyridin-4-ylmethyl)pyrazolo[1,5-a]pyridin-3-amine | Calc'd 335.2, found 335.1 |
| 5-10 | 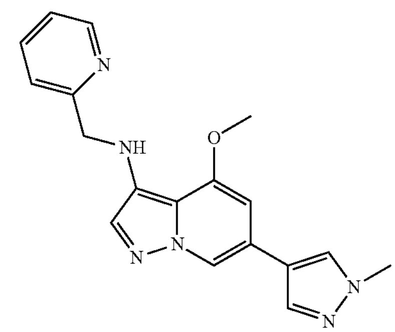 [SMILES: COc1cc(-c2cnn(C)c2)cn2ncc(NCc3ccccn3)c12] | 4-methoxy-6-(1-methyl-1H-pyrazol-4-yl)-N-(pyridin-2-ylmethyl)pyrazolo[1,5-a]pyridin-3-amine | Calc'd 335.2, found 335.1 |
| 5-11 | 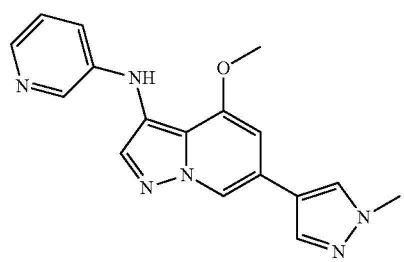 [SMILES: COc1cc(-c2cnn(C)c2)cn2ncc(Nc3cccnc3)c12] | 4-methoxy-6-(1-methyl-1H-pyrazol-4-yl)-N-pyridin-3-ylpyrazolo[1,5-a]pyridin-3-amine | Calc'd 321.1, found 321.1 |
| 5-12 | 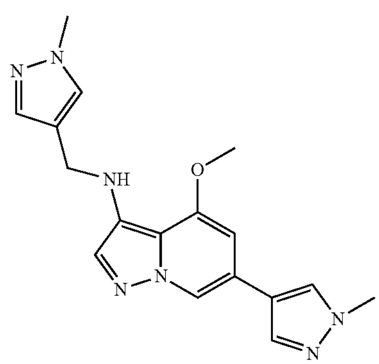 [SMILES: COc1cc(-c2cnn(C)c2)cn2ncc(NCc3cnn(C)c3)c12] | 4-methoxy-6-(1-methyl-1H-pyrazol-4-yl)-N-[(1-methyl-1H-pyrazol-4-yl)methyl]pyrazolo[1,5-a]pyridin-3-amine | Calc'd 338.2, found 338.1 |
| 5-13 | 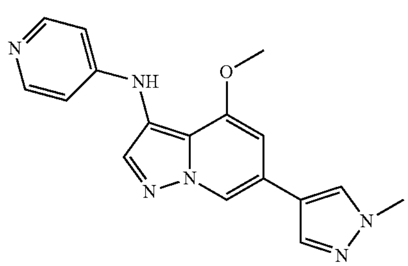 [SMILES: COc1cc(-c2cnn(C)c2)cn2ncc(Nc3ccncc3)c12] | 4-methoxy-6-(1-methyl-1H-pyrazol-4-yl)-N-pyridin-4-ylpyrazolo[1,5-a]pyridin-3-amine | Calc'd 321.1, found 321.1 |

TABLE 5-continued

| Compound | Structure | Name | [M + H]+ |
|---|---|---|---|
| 5-14 | 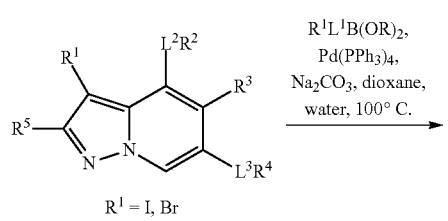 | N'-[4-methoxy-6-(1-methyl-1H-pyrazol-4-yl)pyrazolo[1,5-a]pyridin-3-yl]-N,N-dimethylpropane-1,3-diamine | Calc'd 329.2, found 329.1 |

Scheme 6

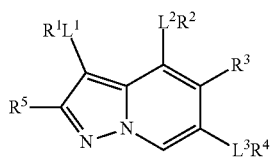

$R^1 = I, Br$

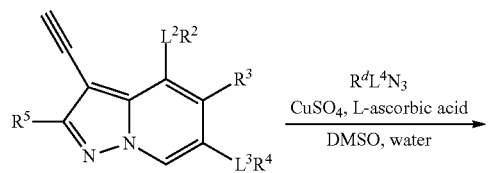

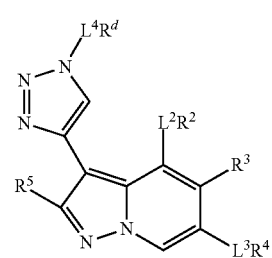

wherein B(OR)$_2$ is a boron ester such as tetramethyldioxaborolanyl.

EXAMPLES 6

Representative Compounds 6-1 to 6-19

Compound 6-1

3-(5-bromo-1-benzothien-2-yl)-4-methoxy-6-(1-methyl-1H-pyrazol-4-yl)pyrazolo[1,5-a]pyridine

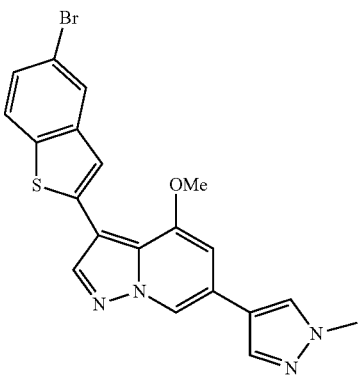 [SMILES: COc1cc(-c2cnn(C)c2)cn2ncc(-c3cc4cc(Br)ccc4s3)c12]

3-iodo-4-methoxy-6-(1-methyl-1H-pyrazol-4-yl)pyrazolo[1,5-a]pyridine (25.0 mg, 0.071 mmol), 5-bromobenzeno[B]thiophene-2-boronic acid (19.0 mg, 0.074 mmol), tetrakis(triphenylphosphine)palladium (0) (8.2 mg, 7.1 µmol), and sodium carbonate (15.0 mg, 0.141 mmol) were suspended in Dioxane (900 µl)/Water (100 µl). The mixture was sparged with argon for 10 minutes, heated to 90° C. and stirred overnight. The reaction mixture was diluted in ethyl acetate, washed with saturated aqueous sodium hydrogen carbonate and brine then dried over sodium sulfate, filtered and concentrated. The residue was purified by column chromatography on silica gel (methanol/ethyl acetate gradient) to afford a tan solid that contained unidentified impurities. The residue was purified by preparative HPLC Reverse phase (C-18), eluting with Acetonitrile/Water+0.05% TFA. The fractions containing product were combined and diluted in ethyl acetate, then washed with aqueous sodium bicarbonate and dried over sodium sulfate. The solution was filtered and concentrated under reduced pressure to afford 3-(5-bromo-1-benzothien-2-yl)-4-methoxy-6-(1-methyl-1H-pyrazol-4-yl)pyrazolo[1,5-a]pyridine. $^1$H NMR (500 MHz, DMSO-d$_6$) δ 8.70 (s, 1H); 8.33 (s, 1H); 8.27 (s, 1H); 8.06 (s, 1H); 8.03 (d, 1H); 7.88 (d, 1H); 7.64 (s, 1H); 7.41 (dd, 1H); 7.03 (s, 1H); 4.05 (s, 3H); 3.88 (s, 3H). LRMS (ESI) calculated for $C_{20}H_{16}{}^{79}BrN_4OS$ [M+H]$^+$, 439.0; found 438.9.

Compound 6-2

3-{1-[2-(3,5-dimethyl-1H-pyrazol-4-yl)ethyl]-1H-1,2,3-triazol-4-yl}-4-methoxy-6-(1-methyl-1H-pyrazol-4-yl)pyrazolo[1,5-a]pyridine

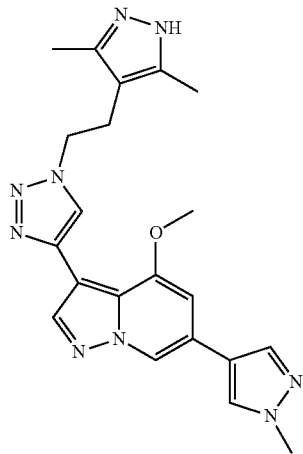 [SMILES: COc1cc(-c2cnn(C)c2)cn2ncc(-c3cn(CCc4c(C)n[nH]c4C)nn3)c12]

To a solution of 3-ethynyl-4-methoxy-6-(1-methyl-1H-pyrazol-4-yl)pyrazolo[1,5-a]pyridine (50 mg, 0.20 mmol) in DMSO (3200 μl), and Water (790 μl) was added L-Ascorbic Acid Sodium Salt (13.0 mg, 0.065 mmol), copper(II)sulfate (3.2 mg, 0.02 mmol) and 4-(2-azidoethyl)-3,5-dimethyl-1H-pyrazole (39 mg, 0.238 mmol). The vial was capped and allowed to stir at room temperature overnight. Purification of the reaction mixture by preparative HPLC Reverse phase (C-18), eluting with acetonitrile/water+0.05% TFA, followed by lyophilization afforded 3-{1-[2-(3,5-dimethyl-1H-pyrazol-4-yl)ethyl]-1H-1,2,3-triazol-4-yl}-4-methoxy-6-(1-methyl-1H-pyrazol-4-yl)pyrazolo[1,5-a]pyridine as the formate salt. $^1$H NMR (500 MHz, DMSO-d$_6$) δ 11.93 (s, 1H); 8.61 (s, 1H); 8.29 (s, 1H); 8.26 (s, 1H); 8.02 (s, 1H); 7.88 (s, 1H); 6.89 (s, 1H); 4.44 (t, 2H); 3.95 (s, 3H); 3.87 (s, 3H); 2.85 (t, 2H); 1.93 (s, 6H). LRMS (ESI) calculated for $C_{21}H_{23}N_9O$ [M+H]$^+$, 418.2; found 418.2.

Compound 6-3

4-Methoxy-6-(1-methyl-1H-pyrazol-4-yl)-3-(1H-pyrazol-4-yl)-pyrazolo[1,5-a]pyridine

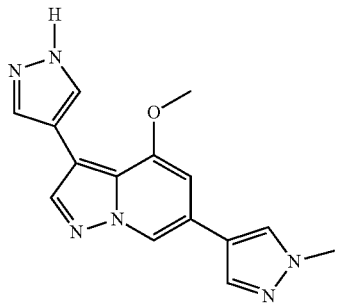 [SMILES: COc1cc(-c2cnn(C)c2)cn2ncc(-c3cn[nH]c3)c12]

4-[4-Methoxy-6-(1-methyl-1H-pyrazol-4-yl)-3,3a-dihydro-pyrazolo[1,5-a]pyridin-3-yl]-pyrazole-1-carboxylic acid tert-butyl ester was prepared by the method described for compound 6-1, substituting tert-butyl 4-(4,4,5,5-tetramethyl-1,3,2-dioxaborolan-2-yl)-1H-pyrazole-1-carboxylate for 5-bromobenzeno[B]thiophene-2-boronic acid. To the solution of 4-[4-Methoxy-6-(1-methyl-1H-pyrazol-4-yl)-3,3a-dihydro-pyrazolo[1,5-a]pyridin-3-yl]-pyrazole-1-carboxylic acid tert-butyl ester (0.030 g, 0.075 mmol) in dichloromethane (3.0 mL) was added TFA (0.017 mL, 0.15 mmol) dropwise at 0° C. and the solution was allowed to warm to ambient temperature. After 3 hours, the solvent was removed under reduced pressure and the crude product thus obtained was purified by flash column chromatography (methanol/dichloromethane gradient) to give 4-Methoxy-6-(1-methyl-1H-pyrazol-4-yl)-3-(1H-pyrazol-4-yl)-pyrazolo[1,5-a]pyridine. $^1$H NMR (400 MHz, DMSO-d$_6$) δ 12.78 (bs, 1H), 8.57 (d, 1H), 8.28 (s, 1H), 8.09 (s, 1H), 8.02 (d, 1H), 7.91-7.86 (m, 2H), 6.83 (s, 1H), 4.00 (s, 3H), 3.88 (s, 3H). LRMS (ESI) calculated for $C_{15}H_{14}N_6O$ [M+H]$^+$, 295.1; found 295.1.

Compound 6-4

4-Methoxy-6-(1-methyl-1H-pyrazol-4-yl)-3-(1-pyridin-2-ylmethyl-1H-pyrazol-4-yl)-pyrazolo[1,5-a]pyridine

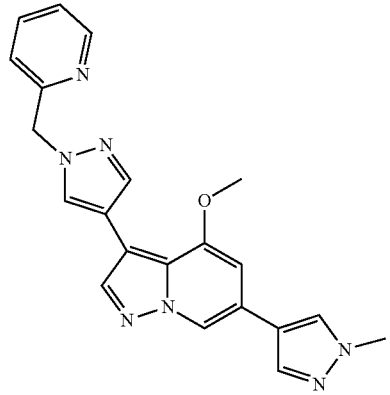 [SMILES: COc1cc(-c2cnn(C)c2)cn2ncc(-c3cnn(Cc4ccccn4)c3)c12]

To a stirred suspension of NaH (60% dispersion in mineral oil, 0.004 g, 0.1 mmol) in tetrahydrofuran (2.0 mL) was added a solution of 4-Methoxy-6-(1-methyl-1H-pyrazol-4-yl)-3-(1H-pyrazol-4-yl)-pyrazolo[1,5-a]pyridine (15 mg, 0.05 mmol) in tetrahydrofuran (1.0 mL) at 0° C. The resultant slurry was then stirred at ambient temperature for 15 min followed by the addition of 2-(chloromethyl)pyridine (0.007 g, 0.055 mmol) in tetrahydrofuran (1.0 mL). The reaction mixture was heated to 60° C. After 8 hours, the reaction mixture was cooled and quenched with ice water and the organic components were extracted with ethyl acetate (2×10 mL) and the combined organic layers were concentrated. The crude material was purified by flash column chromatography (methanol/dichloromethane gradient) to afford 4-Methoxy-6-(1-methyl-1H-pyrazol-4-yl)-3-(1-pyridin-2-ylmethyl-1H-pyrazol-4-yl)-pyrazolo[1,5-a]pyridine. $^1$H NMR (400 MHz, CD$_3$OD) δ 8.56 (bs, 2H), 8.34 (s, 1H), 8.07-8.02 (m, 2H), 7.91 (s, 1H), 7.86-7.83 (m, 2H), 7.38 (bs, 1H), 7.17 (bs, 1H), 6.79 (s, 1H), 5.51 (s, 2H), 4.01 (s, 3H), 3.96 (s, 3H). LRMS (ESI) calculated for $C_{21}H_{19}N_7O$ [M+H]$^+$, 386.2; found 386.5.

The compounds in the following table were prepared according to the procedure described in scheme 6 and for compounds 6-1 to 6-4. The compounds were prepared as free bases.

TABLE 6

| Compound | Structure | Name | [M + H]+ |
|---|---|---|---|
| 6-5 | 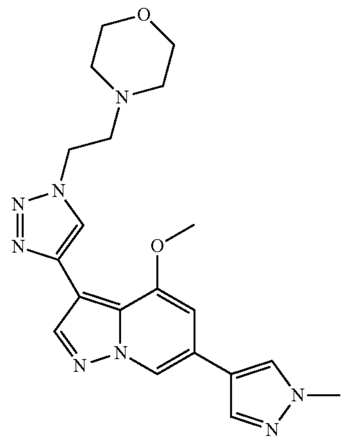 [SMILES: COc1cc(-c2cnn(C)c2)cn2ncc(-c3cn(CCN4CCOCC4)nn3)c12] | 4-methoxy-6-(1-methyl-1H-pyrazol-4-yl)-3-[1-(2-morpholin-4-ylethyl)-1H-1,2,3-triazol-4-yl]pyrazolo[1,5-a]pyridine | Calc'd 409.2, found 409.2 |
| 6-6 | 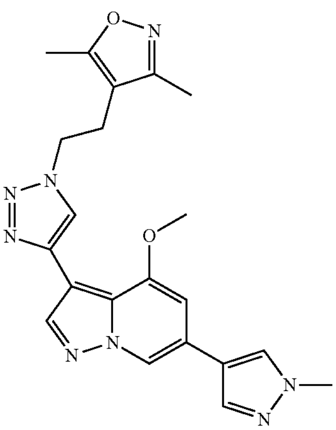 [SMILES: COc1cc(-c2cnn(C)c2)cn2ncc(-c3cn(CCc4c(C)noc4C)nn3)c12] | 3-{1-[2-(3,5-dimethylisoxazol-4-yl)ethyl]-1H-1,2,3-triazol-4-yl}-4-methoxy-6-(1-methyl-1H-pyrazol-4-yl)pyrazolo[1,5-a]pyridine | Calc'd 419.2, found 419.1 |
| 6-7 | 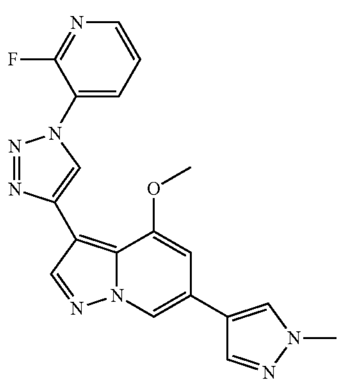 [SMILES: COc1cc(-c2cnn(C)c2)cn2ncc(-c3cn(-c4cccnc4F)nn3)c12] | 3-[1-(2-fluoropyridin-3-yl)-1H-1,2,3-triazol-4-yl]-4-methoxy-6-(1-methyl-1H-pyrazol-4-yl)pyrazolo[1,5-a]pyridine | Calc'd 391.1, found 391.1 |
| 6-8 | 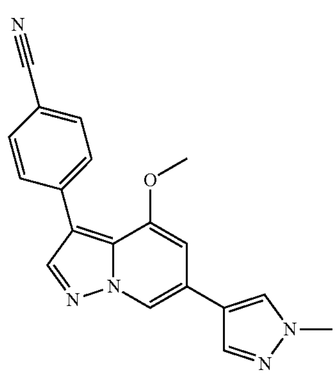 [SMILES: COc1cc(-c2cnn(C)c2)cn2ncc(-c3ccc(C#N)cc3)c12] | 4-[4-methoxy-6-(1-methyl-1H-pyrazol-4-yl)pyrazolo[1,5-a]pyridin-3-yl]benzonitrile | Calc'd 330.1, found 330.1 |

TABLE 6-continued

| Compound | Structure | Name | [M + H]+ |
|---|---|---|---|
| 6-9 | 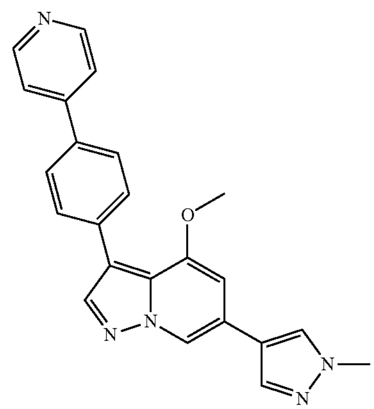 [SMILES: COc1cc(-c2cnn(C)c2)cn2ncc(-c3ccc(-c4ccncc4)cc3)c12] | 4-methoxy-6-(1-methyl-1H-pyrazol-4-yl)-3-(4-pyridin-4-ylphenyl)pyrazolo[1,5-a]pyridine | Calc'd 382.2, found 382.3 |
| 6-10 | 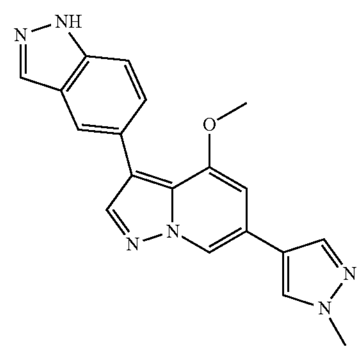 [SMILES: COc1cc(-c2cnn(C)c2)cn2ncc(-c3ccc4[nH]ncc4c3)c12] | 5-[4-methoxy-6-(1-methyl-1H-pyrazol-4-yl)pyrazolo[1,5-a]pyridin-3-yl]-1H-indazole | Calc'd 345.1, found 345.1 |
| 6-11 | 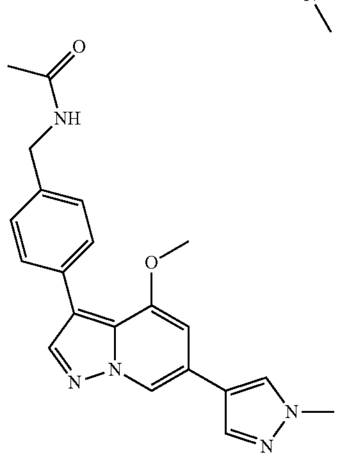 | N-{4-[4-methoxy-6-(1-methyl-1H-pyrazol-4-yl)pyrazolo[1,5-a]pyridin-3-yl]benzyl}acetamide | Calc'd 376.3, found 376.2 |
| 6-12 | 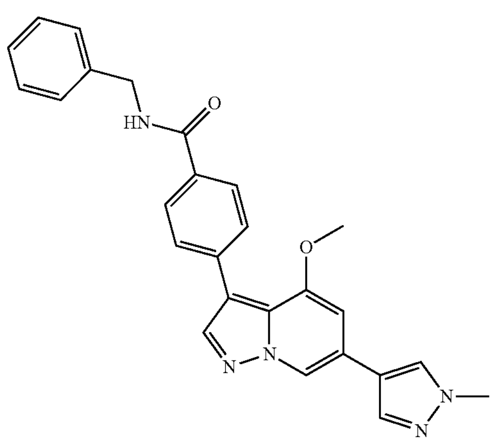 [SMILES: COc1cc(-c2cnn(C)c2)cn2ncc(-c3ccc(C(=O)NCc4ccccc4)cc3)c12] | N-benzyl-4-[4-methoxy-6-(1-methyl-1H-pyrazol-4-yl)pyrazolo[1,5-a]pyridin-3-yl]benzamide | Calc'd 438.2, found 438.0 |

TABLE 6-continued

| Compound | Structure | Name | [M + H]+ |
|---|---|---|---|
| 6-13 | 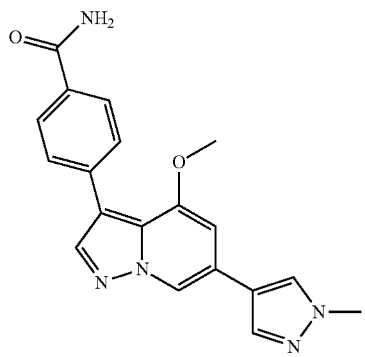 [SMILES: COc1cc(-c2cnn(C)c2)cn2ncc(-c3ccc(C(N)=O)cc3)c12] | 4-[4-methoxy-6-(1-methyl-1H-pyrazol-4-yl)pyrazolo[1,5-a]pyridin-3-yl]benzamide | Calc'd 348.1, found 348.3 |
| 6-14 | 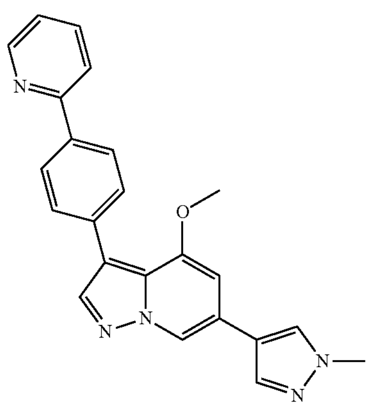 [SMILES: COc1cc(-c2cnn(C)c2)cn2ncc(-c3ccc(-c4ccccn4)cc3)c12] | 4-methoxy-6-(1-methyl-1H-pyrazol-4-yl)-3-(4-pyridin-2-ylphenyl)pyrazolo[1,5-a]pyridine | Calc'd 382.2, found 382.3 |
| 6-15 | 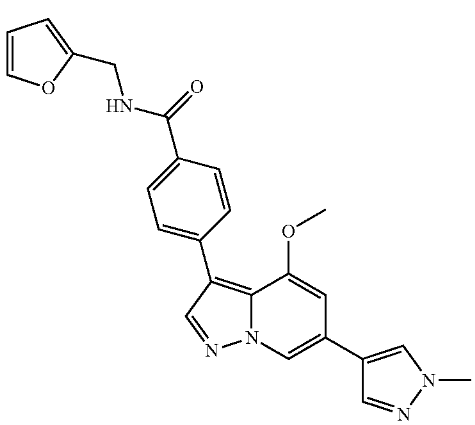 [SMILES: COc1cc(-c2cnn(C)c2)cn2ncc(-c3ccc(C(=O)NCc4ccco4)cc3)c12] | N-(2-furylmethyl)-4-[4-methoxy-6-(1-methyl-1H-pyrazol-4-yl)pyrazolo[1,5-a]pyridin-3-yl]benzamide | Calc'd 428.2, found 428.1 |

TABLE 6-continued

| Compound | Structure | Name | [M + H]+ |
|---|---|---|---|
| 6-16 | 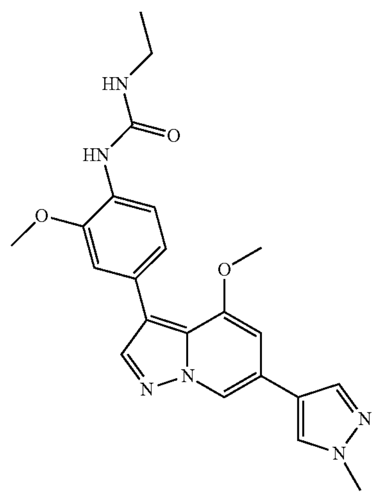 [SMILES: CCNC(=O)Nc1ccc(-c2cnn3cc(-c4cnn(C)c4)cc(OC)c23)cc1OC] | 1-ethyl-3-{2-methoxy-4-[4-methoxy-6-(1-methyl-1H-pyrazol-4-yl)pyrazolo[1,5-a]pyridin-3-yl]phenyl}urea | Calc'd 421.2, found 421.1 |
| 6-17 | 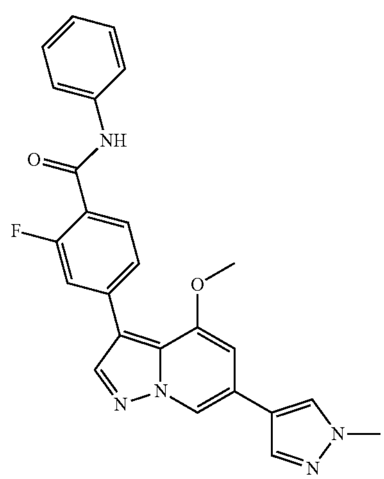 [SMILES: COc1cc(-c2cnn(C)c2)cn2ncc(-c3ccc(C(=O)Nc4ccccc4)c(F)c3)c12] | 2-fluoro-4-[4-methoxy-6-(1-methyl-1H-pyrazol-4-yl)pyrazolo[1,5-a]pyridin-3-yl]-N-phenylbenzamide | Calc'd 442.2, found 442.3 |
| 6-18 | 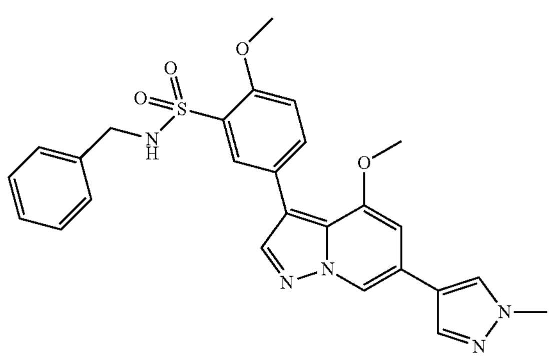 [SMILES: COc1ccc(-c2cnn3cc(-c4cnn(C)c4)cc(OC)c23)cc1S(=O)(=O)NCc1ccccc1] | N-benzyl-2-methoxy-5-[4-methoxy-6-(1-methyl-1H-pyrazol-4-yl)pyrazolo[1,5-a]pyridin-3-yl]benzenesulfonamide | Calc'd 504.2, found 540.0 |

TABLE 6-continued
| Compound | Structure | Name | [M + H]+ |
|---|---|---|---|
| 6-19 | 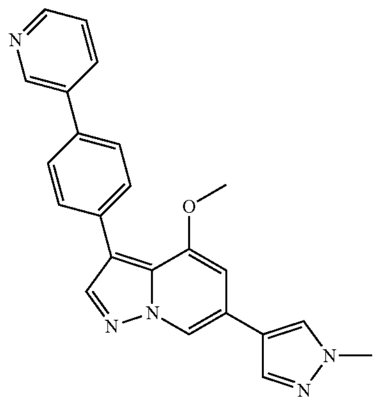 [SMILES: COc1cc(-c2cnn(C)c2)cn2ncc(-c3ccc(-c4cccnc4)cc3)c12] | 4-methoxy-6-(1-methyl-1H-pyrazol-4-yl)-3-(4-pyridin-3-ylphenyl)pyrazolo[1,5-a]pyridine | Calc'd 382.2, found 382.3 |
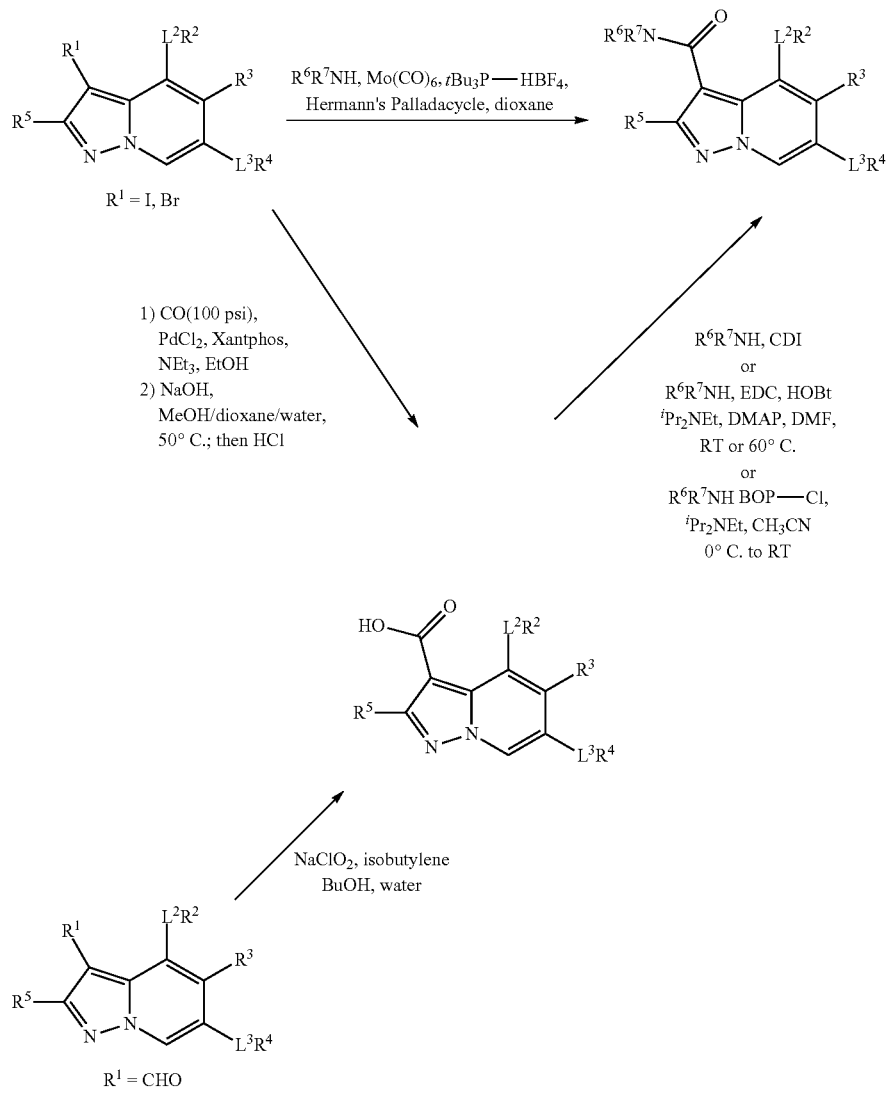
Scheme 7
Wherein R⁶ and R⁷ are as defined above

EXAMPLES 7

Representative Compounds 7-1 to 7-25

Compound 7-1

4-methoxy-6-(1-methyl-1H-pyrazol-4-yl)-N-pyridin-4-ylpyrazolo[1,5-a]pyridine-3-carboxamide

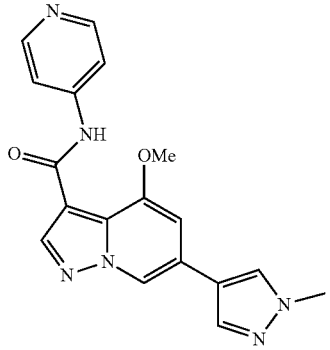 [SMILES: COc1cc(-c2cnn(C)c2)cn2ncc(C(=O)Nc3ccncc3)c12]

4-methoxy-6-(1-methyl-1H-pyrazol-4-yl)-N-pyridin-4-ylpyrazolo[1,5-a]pyridine-3-carboxamide 3-bromo-4-methoxy-6-(1-methyl-1H-pyrazol-4-yl)pyrazolo[1,5-a]pyridine (30 mg, 0.098 mmol), 4-aminopyridine (18 mg, 0.20 mmol), 1,8-diazabicyclo[5.4.0]undec-7-ene (0.059 ml, 0.39 mmol), molybdenum hexacarbonyl (0.013 ml, 0.098 mmol), tri-(tert-butyl)phosphonium hydrogen tetrafluoroborate salt (3.0 mg, 0.01 mmol), trans-di-mu-acetatobis[2-(di-o-tolylphosphino)benzyl]dipalladium (II) (4.6 mg, 0.0049 mmol) were added to dioxane (3.9 ml). The mixture was sparged with argon for 3 minutes and heated to 100° C. After 16 h, the reaction mixture was cooled and purified directly by preparative HPLC Reverse phase (C-18), eluting with acetonitrile/water+0.05% TFA to give 4-methoxy-6-(1-methyl-1H-pyrazol-4-yl)-N-pyridin-4-ylpyrazolo[1,5-a]pyridine-3-carboxamide. $^1$H NMR (500 MHz, DMSO-$d_6$) δ 10.30 (s, 1H); 8.81 (s, 1H); 8.44 (d, 2H); 8.37 (d, 2H); 8.09 (s, 1H); 7.67 (d, 2H); 7.24 (s, 1H); 4.10 (s, 3H); 3.88 (s, 3H). LRMS (ESI) calculated for $C_{18}H_{17}N_6O_2$ $[M+H]^+$, 349.1 found 349.0.

Compound 7-2

N-(2,3-dimethylpyridin-4-O-4-methoxy-6-(1-methyl-1H-pyrazol-4-yl)pyrazolo[1,5-a]pyridine-3-carboxamide

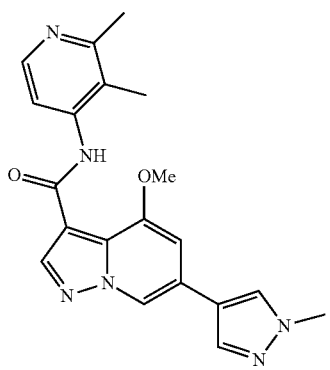 [SMILES: COc1cc(-c2cnn(C)c2)cn2ncc(C(=O)Nc3ccnc(C)c3C)c12]

Step 1: ethyl 4-methoxy-6-(1-methyl-1H-pyrazol-4-yl)pyrazolo[1,5-a]pyridine-3-carboxylate 3-iodo-4-methoxy-6-(1-methyl-1H-pyrazol-4-yl)pyrazolo[1,5-a]pyridine (650.0 mg, 1.835 mmol), palladium (II) chloride (16.3 mg, 0.092 mmol), and Xantphos (53.1 mg, 0.092 mmol) were placed in a 40 mL scintillation vial. Absolute ethanol (6 ml) and triethylamine (0.384 ml, 2.75 mmol) were added and the mixture was sparged with argon for 5 minutes. The vial was transferred to a pressure reactor, which was filled with CO (30 psi) and vented (3×). The vessel was pressurized to 100 psi of CO and heated to 100° C. After 4 h, the system was cooled to ambient temperature. The reaction mixture was diluted in ethyl acetate, washed with saturated aqueous sodium hydrogen carbonate and brine then dried over sodium sulfate, filtered and concentrated. The residue was purified by column chromatography on silica gel (methanol/ethyl acetate gradient) to give ethyl 4-methoxy-6-(1-methyl-1H-pyrazol-4-yl)pyrazolo[1,5-a]pyridine-3-carboxylate.

Step 2: 4-methoxy-6-(1-methyl-1H-pyrazol-4-yl)pyrazolo[1,5-a]pyridine-3-carboxylic acid Ethyl 4-methoxy-6-(1-methyl-1H-pyrazol-4-yl)pyrazolo[1,5-a]pyridine-3-carboxylate (532 mg, 1.77 mmol) was dissolved in methanol (2 ml)/1,4-dioxane (2 ml)/Water (2 ml), then 1 N aqueous sodium hydroxide (1.77 ml, 1.77 mmol) was added and the mixture was heated to 55° C. After 2 h, LCMS analysis indicated incomplete conversion. Additional 1 N aqueous sodium hydroxide (0.18 ml, 0.18 mmol) was added and the reaction mixture was stirred for 1 h. LCMS analysis indicated incomplete conversion, so additional 1 N aqueous sodium hydroxide (0.18 ml, 0.18 mmol) was added and the reaction mixture was stirred overnight at 55° C. The reaction mixture was cooled to ambient temperature and 1N HCl (2.12 ml, 2.12 mmol) was added. The mixture was concentrated to give a tan solid that was suspended in 10 mL of water, filtered, and washed with water. The solid was transferred to a flask as a slurry in methanol and concentrated to give 4-methoxy-6-(1-methyl-1H-pyrazol-4-yl)pyrazolo[1,5-a]pyridine-3-carboxylic acid.

Step 3: (N-(2,3-dimethylpyridin-4-yl)-4-methoxy-6-(1-methyl-1H-pyrazol-4-yl)pyrazolo[1,5-a]pyridine-3-carboxamide 4-methoxy-6-(1-methyl-1H-pyrazol-4-yl)pyrazolo[1,5-a]pyridine-3-carboxylic acid (30.0 mg, 0.110 mmol), 2,3-dimethyl-pyridin-4-ylamine (26.9 mg, 0.220 mmol), N-[3-(dimethylamino)propyl]-N-ethylcarbodiimide hydrochloride (31.7 mg, 0.165 mmol), and 1H-1,2,3-benzotriazol-1-ol hydrate (16.9 mg, 0.110 mmol) were suspended in DMF (1 ml). Diisopropylethylamine (0.058 ml, 0.331 mmol) was added and the reaction mixture was allowed to stir. After 2 h, N,N-dimethylpyridin-4-amine (13.5 mg, 0.110 mmol) was added and the mixture was stirred overnight. After 16 h, the reaction mixture was heated to 60° C. for 4 h, after which additional 2,3-dimethyl-pyridin-4-ylamine (26.9 mg, 0.220 mmol) was added and the mixture was heated to 70° C. overnight. The reaction mixture was diluted in DMSO/water and filter through a 45 μm filter. The filtrate was purified by preparative HPLC Reverse phase (C-18), eluting with Acetonitrile/Water+0.05% TFA to give a solid that was contaminated with trace impurities. Additional purification by column chromatography on silica gel (methanol/ethyl acetate gradient) afforded (N-(2,3-dimethylpyridin-4-yl)-4-methoxy-6-(1-methyl-1H-pyrazol-4-yl)pyrazolo[1,5-a]pyridine-3-carboxamide. $^1$H NMR (500 MHz, DMSO-$d_6$) δ 9.68 (s, 1H); 8.83 (s, 1H); 8.41 (s, 1H); 8.37 (s, 1H); 8.19 (d, 1H); 8.10 (s, 1H); 7.82 (d, 1H); 7.28 (s, 1H); 4.13 (s, 3H); 3.88 (s, 3H); 2.47 (s, 3H); 2.24 (s, 3H). LRMS (ESI) calculated for $C_{20}H_{21}N_6O_2$ [M+H]$^+$, 377.2; found 377.2.

Compound 7-3

N-[4-(acetylamino)phenyl]-4-methoxy-6-(1-methyl-1H-pyrazol-4-yl)pyrazolo[1,5-a]pyridine-3-carboxamide

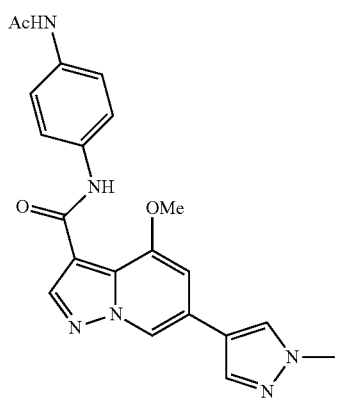 [SMILES: COc1cc(-c2cnn(C)c2)cn2ncc(C(=O)Nc3ccc(NC(C)=O)cc3)c12]

4-methoxy-6-(1-methyl-1H-pyrazol-4-yl)pyrazolo[1,5-a]pyridine-3-carboxylic acid. (30.0 mg, 0.110 mmol) was suspended in acetonitrile (1 ml) at 0° C. Bis(2-oxo-1,3-oxazolidin-3-yl)phosphinic chloride (42.1 mg, 0.165 mmol) was added and the mixture was allowed to stir at 0° C. After 1 h, 4-aminoacetanilide (33.1 mg, 0.220 mmol) was added in one portion followed by diisopropylethylamine (48 µl, 0.28 mmol), then the mixture was allowed to warm to ambient temperature overnight. The reaction mixture was filtered through a 45 µm glass fiber filter and washed with acetonitrile, then the solid was washed off of the filter with methanol. The slurry was concentrated to afford N-[4-(acetylamino)phenyl]-4-methoxy-6-(1-methyl-1H-pyrazol-4-yl)pyrazolo[1,5-a]pyridine-3-carboxamide. $^1$H NMR (500 MHz, DMSO-$d_6$) δ 10.00 (s, 1H); 9.90 (s, 1H); 8.78 (s, 1H); 8.36 (s, 1H); 8.32 (s, 1H); 8.08 (s, 1H); 7.62 (d, 2H); 7.54 (d, 2H); 7.21 (s, 1H); 4.13 (s, 3H); 3.88 (s, 3H); 2.02 (s, 3H). LRMS (ESI) calculated for: $C_{21}H_{21}N_6O_3$ [M+H]$^+$, 405.2; found 405.1.

Compound 7-4

4-methoxy-6-(1-methyl-1H-pyrazol-4-yl)pyrazolo[1,5-a]pyridine-3-carboxamide

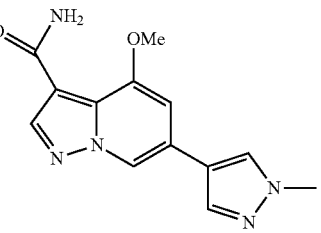

Step 1: 4-methoxy-6-(1-methyl-1H-pyrazol-4-yl)pyrazolo[1,5-a]pyridine-3-carboxylic acid To a suspension of 4-methoxy-6-(1-methyl-1H-pyrazol-4-yl)pyrazolo[1,5-a]pyridine-3-carbaldehyde (25.0 mg, 0.098 mmol) in water (1 ml) was added sodium dihydrogen phosphate (82 mg, 0.68 mmol). After 5 minutes, n-butanol (5 ml), 2-methyl-2-butene (0.145 ml, 1.37 mmol), and sodium chlorite (79 mg, 0.88 mmol) were added. After 3 hours, LCMS indicated incomplete conversion to product. Sodium chlorite (44 mg, 0.49 mmol) and 2-methyl-2-butene (0.104 ml, 0.98 mmol) were added. After 16 hours, reaction mixture was diluted with ethyl acetate, washed with water and brine, then dried over magnesium sulfate, filtered, and concentrated to give 4-methoxy-6-(1-methyl-1H-pyrazol-4-yl)pyrazolo[1,5-a]pyridine-3-carboxylic acid as white solids which were used without further purification. LRMS (ESI) calculated for $C_{13}H_{13}N_4O_3$ [M+H]$^+$, 273.1 found 273.0.

Step 2: 4-methoxy-6-(1-methyl-1H-pyrazol-4-yl)pyrazolo[1,5-a]pyridine-3-carboxamide To a solution of 4-methoxy-6-(1-methyl-1H-pyrazol-4-yl)pyrazolo[1,5-a]pyridine-3-carboxylic acid (14.0 mg, 0.051 mmol) and 1,1'-carbonyldiimidazole (13.0 mg, 0.077 mmol) in N,N-dimethylformamide (2 ml) was added 28% ammonium hydroxide solution (0.072 ml, 0.51 mmol). After 30 minutes the reaction mixture was purified directly by preparative HPLC Reverse phase (C-18), eluting with acetonitrile/water+0.05% TFA to give 4-methoxy-6-(1-methyl-1H-pyrazol-4-yl)pyrazolo[1,5-a]pyridine-3-carboxamide as gray solids. $^1$H NMR (500 MHz, DMSO-$d_6$) δ 8.73 (s, 1H); 8.33 (s, 1H); 8.25 (s, 1H); 8.06 (s, 1H); 7.61 (s, 1H); 7.29 (s, 1H); 7.15 (s, 1H); 4.07 (s, 3H); 3.87 (s, 3H). LRMS (ESI) calculated for $C_{13}K_4N_5O_2$ [M+H]$^-$, 272.1 found 272.0.

The compounds in the following table were prepared according to the procedure described in scheme 7 and for compounds 7-1 to 7-4. The compounds were prepared as free bases or salts.

TABLE 7

| Compound | Structure | Name | [M + H]+ | Free base or salt form |
|---|---|---|---|---|
| 7-5 | 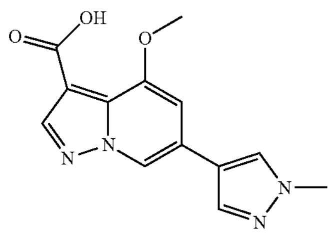 [SMILES: COc1cc(-c2cnn(C)c2)cn2ncc(C(=O)O)c12] | 4-methoxy-6-(1-methyl-1H-pyrazol-4-yl)pyrazolo[1,5-a]pyridine-3-carboxylic acid | Calc'd 273.1, found 273.0 | Free base |
| 7-6 | 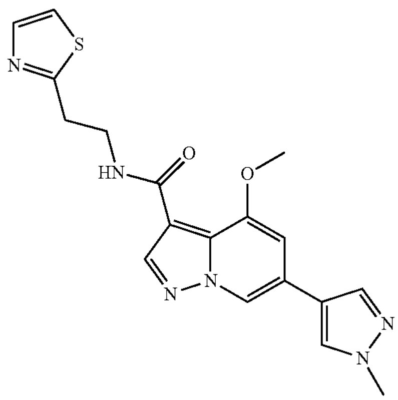 [SMILES: COc1cc(-c2cnn(C)c2)cn2ncc(C(=O)NCCc3nccs3)c12] | 4-methoxy-6-(1-methyl-1H-pyrazol-4-yl)-N-[2-(1,3-thiazol-2-yl)ethyl]pyrazolo[1,5-a]pyridine-3-carboxamide | Calc'd 383.1, found 383.0 | Free base |
| 7-7 | 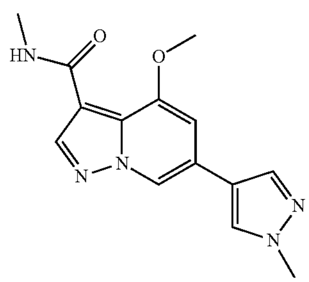 [SMILES: CNC(=O)c1cnn2cc(-c3cnn(C)c3)cc(OC)c12] | 4-methoxy-N-methyl-6-(1-methyl-1H-pyrazol-4-yl)pyrazolo[1,5-a]pyridine-3-carboxamide | Calc'd 286.1, found 286.1 | Free base |
| 7-8 | 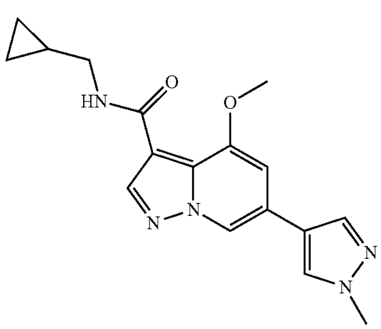 [SMILES: COc1cc(-c2cnn(C)c2)cn2ncc(C(=O)NCC3CC3)c12] | N-(cyclopropylmethyl)-4-methoxy-6-(1-methyl-1H-pyrazol-4-yl)pyrazolo[1,5-a]pyridine-3-carboxamide | Calc'd 326.2, found 326.1 | Free base |

TABLE 7-continued

| Compound | Structure | Name | [M + H]+ | Free base or salt form |
|---|---|---|---|---|
| 7-9 | 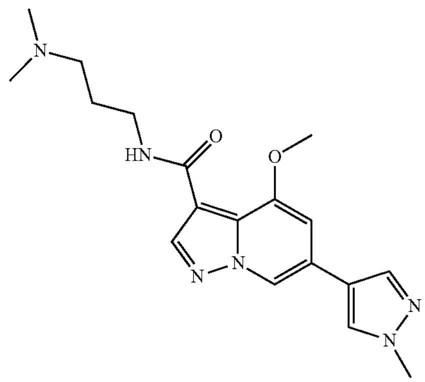 [SMILES: COc1cc(-c2cnn(C)c2)cn2ncc(C(=O)NCCCN(C)C)c12] | N-[3-(dimethylamino)propyl]-4-methoxy-6-(1-methyl-1H-pyrazol-4-yl)pyrazolo[1,5-a]pyridine-3-carboxamide | Calc'd 357.2, found 357.1 | Free base |
| 7-10 | 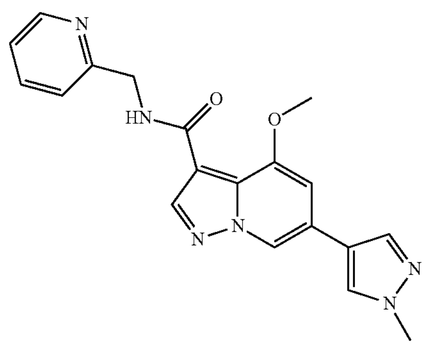 [SMILES: COc1cc(-c2cnn(C)c2)cn2ncc(C(=O)NCc3ccccn3)c12] | 4-methoxy-6-(1-methyl-1H-pyrazol-4-yl)-N-(pyridin-2-ylmethyl)pyrazolo[1,5-a]pyridine-3-carboxamide | Calc'd 363.1, found 363.0 | Free base |
| 7-11 | 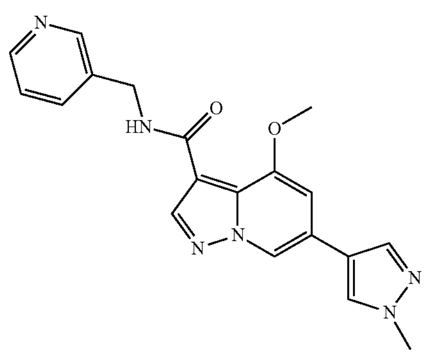 [SMILES: COc1cc(-c2cnn(C)c2)cn2ncc(C(=O)NCc3cccnc3)c12] | 4-methoxy-6-(1-methyl-1H-pyrazol-4-yl)-N-(pyridin-3-ylmethyl)pyrazolo[1,5-a]pyridine-3-carboxamide | Calc'd 363.1, found 363.0 | Free base |
| 7-12 | 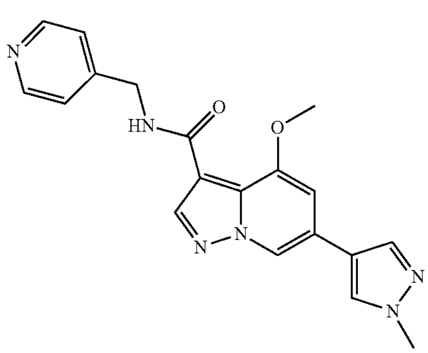 [SMILES: COc1cc(-c2cnn(C)c2)cn2ncc(C(=O)NCc3ccncc3)c12] | 4-methoxy-6-(1-methyl-1H-pyrazol-4-yl)-N-(pyridin-4-ylmethyl)pyrazolo[1,5-a]pyridine-3-carboxamide | Calc'd 363.1, found 363.0 | Free base |

TABLE 7-continued

| Compound | Structure | Name | [M + H]+ | Free base or salt form |
|---|---|---|---|---|
| 7-13 | 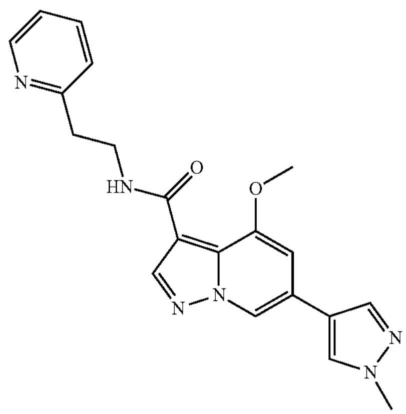 [SMILES: COc1cc(-c2cnn(C)c2)cn2ncc(C(=O)NCCc3ccccn3)c12] | 4-methoxy-6-(1-methyl-1H-pyrazol-4-yl)-N-(2-pyridin-2-ylethyl)pyrazolo[1,5-a]pyridine-3-carboxamide | Calc'd 377.2, found 377.1 | Free base |
| 7-14 | 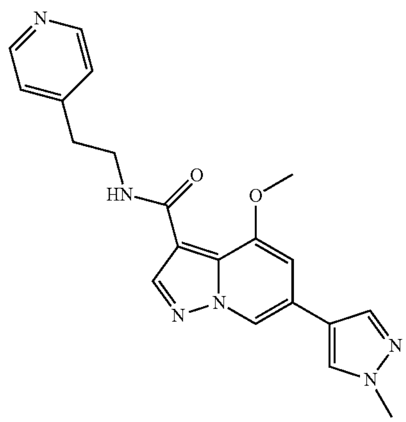 [SMILES: COc1cc(-c2cnn(C)c2)cn2ncc(C(=O)NCCc3ccncc3)c12] | 4-methoxy-6-(1-methyl-1H-pyrazol-4-yl)-N-(2-pyridin-4-ylethyl)pyrazolo[1,5-a]pyridine-3-carboxamide | Calc'd 377.2, found 377.0 | Free base |
| 7-15 | 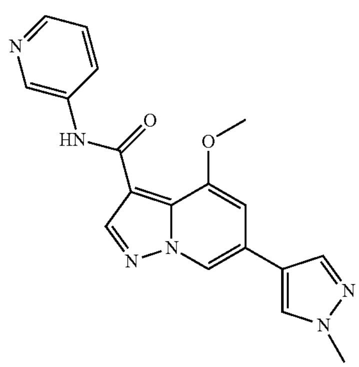 [SMILES: COc1cc(-c2cnn(C)c2)cn2ncc(C(=O)Nc3cccnc3)c12] | 4-methoxy-6-(1-methyl-1H-pyrazol-4-yl)-N-pyridin-3-ylpyrazolo[1,5-a]pyridine-3-carboxamide | Calc'd 349.1, found 349.0 | Free base |
| 7-16 | 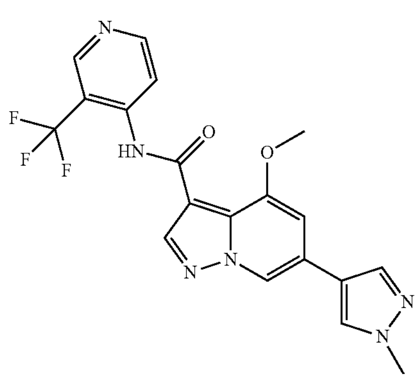 [SMILES: COc1cc(-c2cnn(C)c2)cn2ncc(C(=O)Nc3ccncc3C(F)(F)F)c12] | 4-methoxy-6-(1-methyl-1H-pyrazol-4-yl)-N-[3-(trifluoromethyl)pyridin-4-yl]pyrazolo[1,5-a]pyridine-3-carboxamide | Calc'd 417.1, found 417.1 | Formate salt |

TABLE 7-continued

| Compound | Structure | Name | [M + H]+ | Free base or salt form |
|---|---|---|---|---|
| 7-17 | 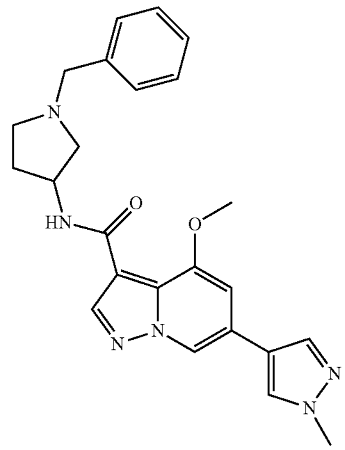 [SMILES: COc1cc(-c2cnn(C)c2)cn2ncc(C(=O)NC3CCN(Cc4ccccc4)C3)c12] | N-(1-benzylpyrrolidin-3-yl)-4-methoxy-6-(1-methyl-1H-pyrazol-4-yl)pyrazolo[1,5-a]pyridine-3-carboxamide | Calc'd 431.2, found 431.1 | Formate salt |
| 7-18 | 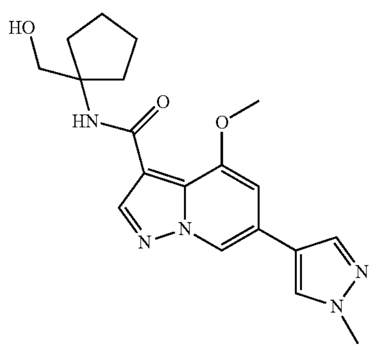 [SMILES: COc1cc(-c2cnn(C)c2)cn2ncc(C(=O)NC3(CO)CCCC3)c12] | N-[1-(hydroxymethyl)cyclopentyl]-4-methoxy-6-(1-methyl-1H-pyrazol-4-yl)pyrazolo[1,5-a]pyridine-3-carboxamide | Calc'd 370.2, found 370.1 | Formate salt |
| 7-19 | 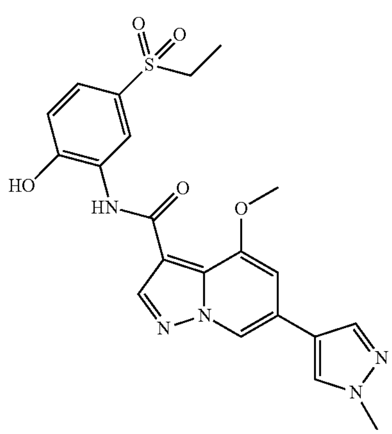 [SMILES: CCS(=O)(=O)c1ccc(O)c(NC(=O)c2cnn3cc(-c4cnn(C)c4)cc(OC)c23)c1] | N-[5-(ethylsulfonyl)-2-hydroxyphenyl]-4-methoxy-6-(1-methyl-1H-pyrazol-4-yl)pyrazolo[1,5-a]pyridine-3-carboxamide | Calc'd 456.1, found 456.0 | Formate salt |

TABLE 7-continued

| Compound | Structure | Name | [M + H]+ | Free base or salt form |
|---|---|---|---|---|
| 7-20 | 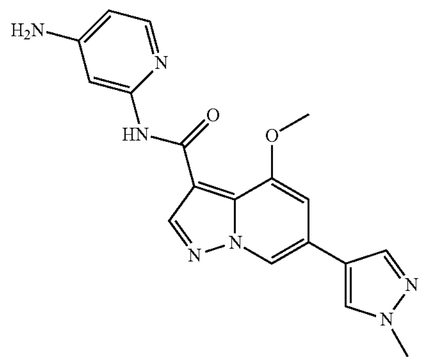 [SMILES: COc1cc(-c2cnn(C)c2)cn2ncc(C(=O)Nc3cc(N)ccn3)c12] | N-(4-aminopyridin-2-yl)-4-methoxy-6-(1-methyl-1H-pyrazol-4-yl)pyrazolo[1,5-a]pyridine-3-carboxamide | Calc'd 364.2, found 364.1 | Free base |
| 7-21 | 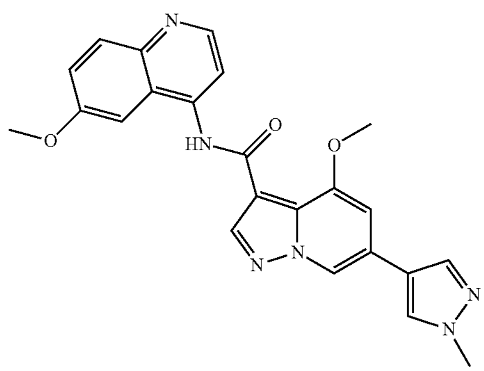 [SMILES: COc1ccc2nccc(NC(=O)c3cnn4cc(-c5cnn(C)c5)cc(OC)c34)c2c1] | 4-methoxy-N-(6-methoxyquinolin-4-yl)-6-(1-methyl-1H-pyrazol-4-yl)pyrazolo[1,5-a]pyridine-3-carboxamide | Calc'd 429.2, found 429.1 | Free base |
| 7-22 | 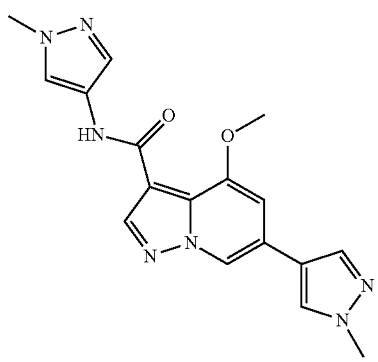 [SMILES: COc1cc(-c2cnn(C)c2)cn2ncc(C(=O)Nc3cnn(C)c3)c12] | 4-methoxy-N,6-bis(1-methyl-1H-pyrazol-4-yl)pyrazolo[1,5-a]pyridine-3-carboxamide | Calc'd 352.2, found 352.1o | Free base |
| 7-23 | 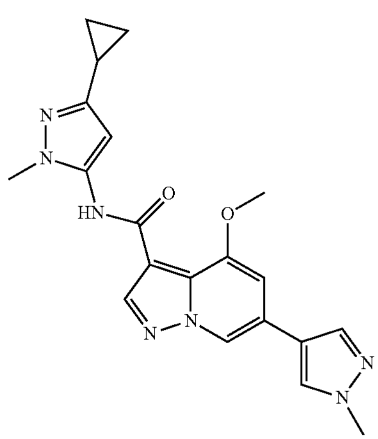 [SMILES: COc1cc(-c2cnn(C)c2)cn2ncc(C(=O)Nc3cc(C4CC4)nn3C)c12] | N-(3-cyclopropyl-1-methyl-1H-pyrazol-5-yl)-4-methoxy-6-(1-methyl-1H-pyrazol-4-yl)pyrazolo[1,5-a]pyridine-3-carboxamide | Calc'd 392.2, found 392.1 | Formate salt |

TABLE 7-continued
| Compound | Structure | Name | [M + H]+ | Free base or salt form |
|---|---|---|---|---|
| 7-24 | 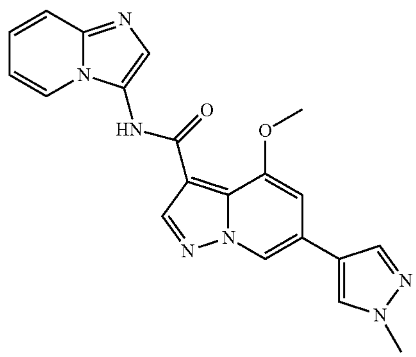 [SMILES: COc1cc(-c2cnn(C)c2)cn2ncc(C(=O)Nc3cnc4ccccn34)c12] | N-imidazo[1,2-a]pyridin-3-yl-4-methoxy-6-(1-methyl-1H-pyrazol-4-yl)pyrazolo[1,5-a]pyridine-3-carboxamide | Calc'd 388.2, found 388.1 | Free base |
| 7-25 | 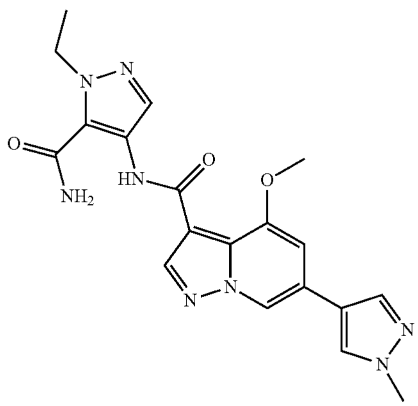 [SMILES: CCn1ncc(NC(=O)c2cnn3cc(-c4cnn(C)c4)cc(OC)c23)c1C(N)=O] | N-[5-(aminocarbonyl)-1-ethyl-1H-pyrazol-4-yl]-4-methoxy-6-(1-methyl-1H-pyrazol-4-yl)pyrazolo[1,5-a]pyridine-3-carboxamide | Calc'd 409.2, found 409.2 | Free base |
Scheme 8
Procedure A
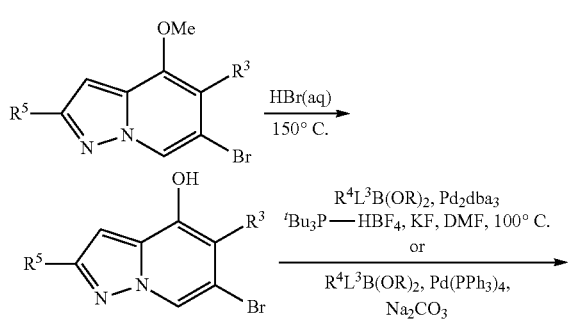
Procedure B
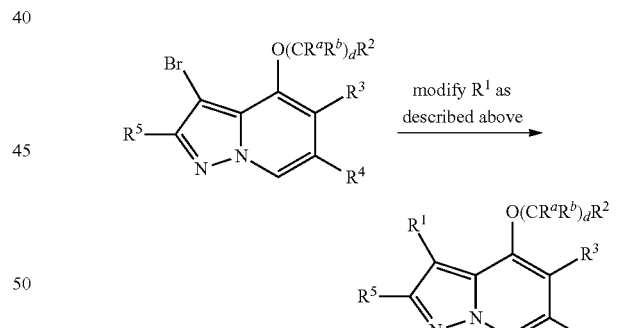
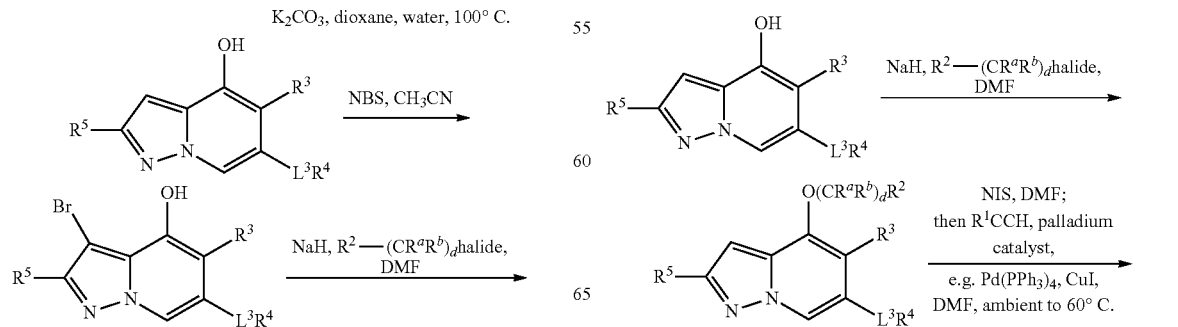

-continued

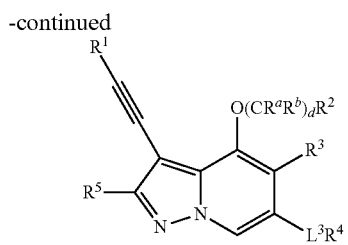

wherein B(OR)₂ is a boron ester such as tetramethyldioxaborolanyl

EXAMPLES 8

Representative Compounds 8-1 to 8-12

Compound 8-1

4-(benzyloxy)-3-bromo-6-(1-methyl-1H-pyrazol-4-yl)pyrazolo[1,5-a]pyridine

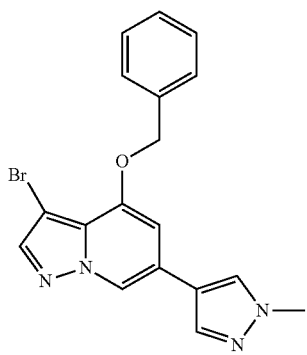 [SMILES: Cn1cc(-c2cc(OCc3ccccc3)c3c(Br)cnn3c2)cn1]

Step 1: 6-bromopyrazolo[1,5-a]pyridin-4-ol 6-bromo-4-methoxypyrazolo[1,5-a]pyridine (1.50 g, 6.61 mmol) was suspended in HBr (15 ml, 133 mmol). The reaction mixture was heated in the Biotage Initiator Series microwave for 80 minutes at 150° C. The reaction mixture was added dropwise via pipette to a mixture of NaOH (5.29 g, 132 mmol) in 50 mL of water and ice. The mixture was diluted in ethyl acetate, washed with saturated aqueous sodium bicarbonate and brine then dried over sodium sulfate, filtered and concentrated to give 6-bromopyrazolo[1,5-a]pyridin-4-ol.

Step 2: 4-(benzyloxy)-6-bromopyrazolo[1,5-a]pyridine 6-bromopyrazolo[1,5-a]pyridin-4-ol (1.10 g, 5.16 mmol) and benzyl bromide (0.676 ml, 5.68 mmol) were dissolved in DMF (20 ml) at 0° C. NaH (413 mg, 10.3 mmol, 60 wt %) was added in one portion and the mixture was allowed to stir at 0° C. After 30 minutes, additional benzyl bromide 0.068 ml, 0.57 mmol was added and the mixture was allowed to stir 30 minutes at 0° C. The reaction mixture was diluted in diethyl ether, washed with saturated aqueous sodium hydrogen carbonate and brine then dried over magnesium sulfate, filtered and concentrated. The residue was purified by column chromatography on silica gel (ethyl acetate/isohexane gradient) to afford 4-(benzyloxy)-6-bromopyrazolo[1,5-a]pyridine.

Step 3: 4-(benzyloxy)-6-(1-methyl-1H-pyrazol-4-yl)pyrazolo[1,5-a]pyridine

Method A: 4-(benzyloxy)-6-bromopyrazolo[1,5-a]pyridine (1.27 g, 4.19 mmol), 1-methyl-4-(4,4,5,5-tetramethyl-1,3,2-dioxaborolan-2-yl)-1H-pyrazole (1.74 g, 8.38 mmol), tris(dibenzylideneacetone)dipalladium (0) (192 mg, 0.209 mmol), potassium fluoride (803 mg, 13.8 mmol), and tri-t-butylphosphonium tetrafluoroborate (122 mg, 0.419 mmol) were suspended in DMF (21 mL), sparged with argon for 10 minutes, then heated to 100° C. After 2 h, the reaction mixture was cooled to ambient temperature, diluted in ethyl acetate, washed with saturated aqueous sodium hydrogen carbonate and brine. The combined aqueous layers were saturated with NaCl and extracted with ethyl acetate (5×50 ml). The combined organic layers were dried over sodium sulfate, filtered and concentrated. The residue was purified by column chromatography on silica gel (methanol/ethyl acetate gradient). Fractions containing pure 4-(benzyloxy)-6-(1-methyl-1H-pyrazol-4-yl)pyrazolo[1,5-a]pyridine were set aside and fractions that were impure by TLC analysis were combined and repurified in a similar manner to afford a second batch of pure 4-(benzyloxy)-6-(1-methyl-1H-pyrazol-4-yl)pyrazolo[1,5-a]pyridine.

Method B: 4-(benzyloxy)-6-bromopyrazolo[1,5-a]pyridine (200 mg, 0.660 mmol), 1-methyl-4-(4,4,5,5-tetramethyl-1,3,2-dioxaborolan-2-yl)-1H-pyrazole (412 mg, 1.979 mmol), tetrakis(triphenylphosphine)palladium (0) (76 mg, 0.066 mmol), and sodium carbonate (210 mg, 1.98 mmol) were suspended in 1,4-dioxane (4 ml)/water (0.444 ml). The mixture was sparged with argon for 10 minutes, then heated to 90° C. for 2 h. After cooling to ambient temperature, the reaction mixture was diluted in ethyl acetate, washed with saturated aqueous sodium hydrogen carbonate and brine then dried over sodium sulfate, filtered and concentrated. The residue was purified by column chromatography on silica gel (methanol/ethyl acetate gradient) to afford 4-(benzyloxy)-6-(1-methyl-1H-pyrazol-4-yl)pyrazolo[1,5-a]pyridine contaminated with triphenylphosphine oxide.

Step 4: 4-(benzyloxy)-3-bromo-6-(1-methyl-1H-pyrazol-4-yl)pyrazolo[1,5-a]pyridine 4-(benzyloxy)-6-bromopyrazolo[1,5-a]pyridine (50.0 mg, 0.164 mmol) was dissolved in acetonitrile (2 ml). N-bromosuccinimide (29.2 mg, 0.164 mmol) was added in one portion and the mixture was allowed to stir. After 30 minutes, additional N-bromosuccinimide (2.9 mg, 0.016 mmol) was added and the mixture was stirred for 1 h. The reaction mixture was diluted in dichloromethane, washed with water, 1N aqueous sodium hydroxide and brine then dried over sodium sulfate, filtered and concentrated to afford 4-(benzyloxy)-3-bromo-6-(1-methyl-1H-pyrazol-4-yl)pyrazolo[1,5-a]pyridine. $^1$H NMR (500 MHz, DMSO-d$_6$) δ 8.66 (s, 1H); 8.28 (s, 1H); 8.02 (s, 1H); 7.99 (s, 1H); 7.58 (app d, 2H); 7.43 (app t, 2H); 7.31-7.36 (m, 1H); 7.08 (s, 1H); 5.35 (s, 2H); 3.87 (s, 3H). LRMS (ESI) calculated for $C_{18}H_{16}{}^{81}BrN_4O$ [M+H]$^+$, 385.0; found 384.9.

Compound 8-2

3-bromo-6-(1-methyl-1H-pyrazol-4-yl)-4-(piperidin-3-ylmethoxy)pyrazolo[1,5-a]pyridine

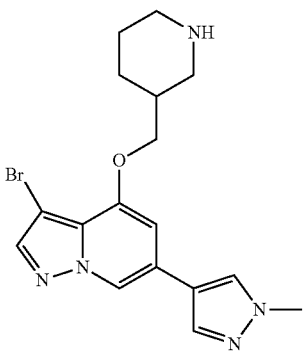 [SMILES: Cn1cc(-c2cc(OCC3CCCNC3)c3c(Br)cnn3c2)cn1]

Step 1: 6-(1-methyl-1H-pyrazol-4-yl)pyrazolo[1,5-a]pyridin-4-ol 4-(benzyloxy)-6-(1-methyl-1H-pyrazol-4-yl)pyrazolo[1,5-a]pyridine (185 mg, 0.608 mmol) and palladium hydroxide on carbon (85 mg, 0.122 mmol, 20 wt %) were suspended in EtOH (10 ml) and placed under an atmosphere of hydrogen (balloon). After 2 h, additional palladium hydroxide on carbon (85 mg, 0.122 mmol, 20 wt %) was added and the mixture was allowed to stir overnight. The reaction mixture was filtered through a 45 μm syringe filter and the filtrate was concentrated. The residue was purified by column chromatography on silica gel (methanol/ethyl acetate gradient) to afford 6-(1-methyl-1H-pyrazol-4-yl)pyrazolo[1,5-a]pyridin-4-ol.

Step 2: 3-bromo-6-(1-methyl-1H-pyrazol-4-yl)pyrazolo[1,5-a]pyridin-4-ol 6-(1-methyl-1H-pyrazol-4-yl)pyrazolo[1,5-a]pyridin-4-ol (75.0 mg, 0.350 mmol) was suspended in acetonitrile (4 ml). N-bromosuccinimide (68.5 mg, 0.385 mmol) was added and the mixture was allowed to stir. After 30 minutes, additional N-bromosuccinimide (6.9 mg, 0.039 mmol) was added and the mixture was allowed to stir for 1 h. The reaction mixture was diluted in dichloromethane, washed with water and 1 N aqueous sodium hydroxide. The pH of the combined aqueous layers was adjusted to pH 7 with 6 N HCl, then the aqueous layers were extracted with ethyl acetate (2×) and the combined organic layers were dried over sodium sulfate, filtered and concentrated. The residue was purified by column chromatography on silica gel (methanol/dichloromethane gradient) to afford 3-bromo-6-(1-methyl-1H-pyrazol-4-yl)pyrazolo[1,5-a]pyridin-4-ol.

Step 3: tert-butyl 3-({[3-bromo-6-(1-methyl-1H-pyrazol-4-yl)pyrazolo[1,5-a]pyridin-4-yl]oxy}methyl)piperidine-1-carboxylate 3-bromo-6-(1-methyl-1H-pyrazol-4-yl)pyrazolo[1,5-a]pyridin-4-ol (60.0 mg, 0.205 mmol), tert-butyl 3-(bromomethyl)piperidine-1-carboxylate (114 mg, 0.410 mmol), and NaH (29.5 mg, 0.737 mmol) were suspended in DMF (2 ml), then heated to 60° C. After 2 h, the reaction mixture was quenched with 1 ml of saturated aqueous ammonium chloride, diluted in ethyl acetate, washed with saturated aqueous sodium bicarbonate and brine. The combined aqueous layers were extracted with ethyl acetate (1×30 mL), and the combined organic layers were dried over sodium sulfate, filtered and concentrated. The residue was purified by column chromatography on silica gel (methanol/ethyl acetate gradient) afford a yellow oil. The residue was purified by preparative HPLC Reverse phase (C-18), eluting with Acetonitrile/Water+0.05% TFA. The fractions containing product were combined and diluted in ethyl acetate, then washed with aqueous sodium bicarbonate and dried over sodium sulfate, filtered and concentrated to afford tert-butyl 3-({[3-bromo-6-(1-methyl-1H-pyrazol-4-yl)pyrazolo[1,5-a]pyridin-4-yl]oxy}methyl)piperidine-1-carboxylate.

Step 4: 3-bromo-6-(1-methyl-1H-pyrazol-4-yl)-4-(piperidin-3-ylmethoxy)pyrazolo[1,5-a]pyridine tert-butyl 3-({[3-bromo-6-(1-methyl-1H-pyrazol-4-yl)pyrazolo[1,5-a]pyridin-4-yl]oxy}methyl)piperidine-1-carboxylate (55.0 mg, 0.112 mmol) was dissolved in dichloromethane (3 ml) at 0° C. Trifluoroacetic acid (1.0 ml) was added and the solution was allowed to stir for 30 minutes. The solution was concentrated to a colorless oil, which was dissolved in 2 ml of methanol and eluted through a bicarbonate resin cartridge (StratoSpheres SPE, PL-HCO$_3$ MP SPE), flushing with 10 mL of methanol. The solution was concentrated and eluted through a second bicarbonate resin cartridge to afford 3-bromo-6-(1-methyl-1H-pyrazol-4-yl)-4-(piperidin-3-ylmethoxy)pyrazolo[1,5-a]pyridine. $^1$H NMR (500 MHz, DMSO-d$_6$) δ 8.62 (s, 1H); 8.28 (s, 1H); 8.01 (s, 1H); 7.96 (s, 1H); 6.89 (s, 1H); 3.98-4.06 (m, 2H); 3.85 (s, 3H), 3.12-3.16 (m, 1H); 2.84-2.89 (m, 1H); 1.92-2.01 (m, 1H); 1.84-1.90 (m, 1H); 1.58-1.64 (m, 1H); 1.20-1.45 (m, 4H). LRMS (ESI) calculated for $C_{17}H_{21}{}^{79}BrN_5O$ [M+H]$^+$, 390.1; found 390.0.

Compound 8-3

3-(cyclopropylethynyl)-6-(1-methyl-1H-pyrazol-4-yl)-4-(pyridin-3-ylmethoxy)pyrazolo[1,5-a]pyridine

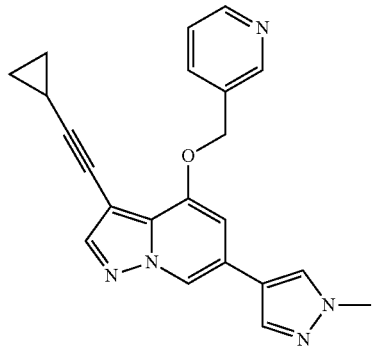 [SMILES: Cn1cc(-c2cc(OCc3cccnc3)c3c(C#CC4CC4)cnn3c2)cn1]

Step 1: 6-(1-methyl-1H-pyrazol-4-yl)-4-(pyridin-3-ylmethoxy)pyrazolo[1,5-a]pyridine 6-bromopyrazolo[1,5-a]pyridin-4-ol (10.0 mg, 0.047 mmol), 3-(bromomethyl)pyridine hydrobromide (14.2 mg, 0.056 mmol), and NaH (6.7 mg, 0.168 mmol, 60 wt %) were suspended in DMF (1 ml) and stirred for 1 h. The reaction mixture was quenched by the addition of saturated aqueous ammonium chloride. The reaction mixture was diluted in ethyl acetate, then washed with water (5 mL) and brine (5 mL). The combined aqueous layers were extracted with ethyl acetate (2×10 mL), and the combined organic layers were dried over magnesium sulfate, filtered and concentrated. The residue was purified by column chromatography on silica gel (methanol/ethyl acetate gradient) to afford 6-(1-methyl-1H-pyrazol-4-yl)-4-(pyridin-3-ylmethoxy)pyrazolo[1,5-a]pyridine.

Step 2: 3-iodo-6-(1-methyl-1H-pyrazol-4-yl)-4-(pyridin-3-ylmethoxy)pyrazolo[1,5-a]pyridine 6-(1-methyl-1H-pyrazol-4-yl)-4-(pyridin-3-ylmethoxy) pyrazolo[1,5-a]pyridine. (12.0 mg, 0.039 mmol) was dissolved in acetonitrile (4 ml). N-iodosuccinimide (17.7 mg, 0.079 mmol) was added and the mixture was stirred for 30 minutes. The reaction mixture was diluted in ethyl acetate, washed with water, 1N aqueous sodium hydroxide, and brine. The combined aqueous layers were extracted with ethyl acetate, and the combined organic layers were dried over sodium sulfate, filtered and concentrated. The residue was purified by column chromatography on silica gel (methanol/ethyl acetate gradient) to give a purple solid. The solid was diluted in dichloromethane, washed with 1 M NaOH and brine then dried over sodium sulfate, filtered and concentrated to afford 3-iodo-6-(1-methyl-1H-pyrazol-4-yl)-4-(pyridin-3-ylmethoxy)pyrazolo[1,5-a]pyridine. contaminated with approximately 10% of the starting -(1-methyl-1H-pyrazol-4-yl)-4-(pyridin-3-ylmethoxy)pyrazolo[1,5-a]pyridine.

Step 3: 3-(cyclopropylethynyl)-6-(1-methyl-1H-pyrazol-4-yl)-4-(pyridin-3-ylmethoxy)pyrazolo[1,5-a]pyridine 3-iodo-6-(1-methyl-1H-pyrazol-4-yl)-4-(pyridin-3-ylmethoxy)pyrazolo[1,5-a]pyridine from Step 2 (11.0 mg, 0.026 mmol), tetrakis(triphenylphosphine)palladium (0) (3.0 mg, 2.6 µmol), and CuI (2.9 mg, 0.02 mmol) were suspended in DMF (1 ml). Triethylamine (11 µl, 0.08 mmol) and cyclopropyl acetylene (5.1 mg, 0.08 mmol) were added and the mixture was sparged with argon for 10 minutes. After stirring at ambient temperature for 1.5 h, the reaction mixture was diluted in ethyl acetate, washed with saturated aqueous sodium hydrogen carbonate and brine then dried over sodium sulfate, filtered and concentrated. The residue was purified by preparative HPLC Reverse phase (C-18), eluting with Acetonitrile/Water+0.05% TFA. The fractions containing product were combined and diluted in ethyl acetate, then washed with aqueous sodium bicarbonate and dried over sodium sulfate. The solution was filtered and concentrated to afford 3-(cyclopropylethynyl)-6-(1-methyl-1H-pyrazol-4-yl)-4-(pyridin-3-ylmethoxy)pyrazolo[1,5-a]pyridine. $^1$H NMR (500 MHz, DMSO-d$_6$) δ 8.79 (s, 1H); 8.65 (s, 1H); 8.57-8.60 (m, 1H); 8.30 (s, 1H); 8.00-8.05 (m, 2H); 7.98 (s, 1H); 7.49 (dd, 1H); 7.12 (s, 1H); 5.37 (s, 2H); 3.87 (s, 3H); 1.39-1.45 (m, 1H); 0.71-0.76 (m, 2H); 0.42-0.46 (m, 2H). LRMS (ESI) calculated for C$_{22}$H$_{20}$N$_5$O [M+H]$^+$, 370.2; found 370.0.

Compound 8-4

3-(cyclopropylethynyl)-6-(1-methyl-1H-pyrazol-4-yl)-4-(pyridin-2-ylmethoxy)pyrazolo[1,5-a]pyridine

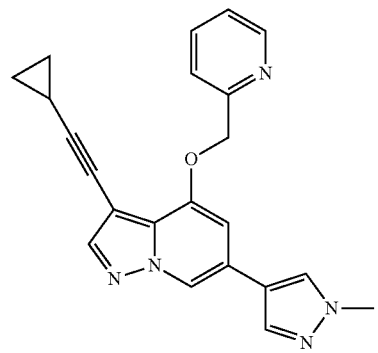 [SMILES: Cn1cc(-c2cc(OCc3ccccn3)c3c(C#CC4CC4)cnn3c2)cn1]

Step 1: 6-(1-methyl-1H-pyrazol-4-yl)-4-(pyridin-2-ylmethoxy)pyrazolo[1,5-a]pyridine 6-(1-methyl-1H-pyrazol-4-yl)-4-(pyridin-2-ylmethoxy) pyrazolo[1,5-a]pyridine was prepared from 6-bromopyrazolo[1,5-a]pyridin-4-ol as described for compound 8-3, Step 1, using 2-(bromomethyl)pyridine hydrobromide in place of .3-(bromomethyl)pyridine hydrobromide.

Step 2: 3-(cyclopropylethynyl)-6-(1-methyl-1H-pyrazol-4-yl)-4-(pyridin-2-ylmethoxy)pyrazolo[1,5-a]pyridine 6-(1-methyl-1H-pyrazol-4-yl)-4-(pyridin-2-ylmethoxy) pyrazolo[1,5-a]pyridine (10.0 mg, 0.033 mmol) and N-iodosuccinimide (8.8 mg, 0.04 mmol) were dissolved in DMF (1 ml). After 20 minutes, LCMS analysis indicated complete conversion to the iodide. At this time, copper (I) iodide (3.7 mg, 0.02 mmol), tetrakis(triphenylphosphine)palladium (0) (3.8 mg, 3.2 µmol), triethylamine (0.014 ml, 0.098 mmol), and cyclopropylacetylene (6.5 mg, 0.10 mmol) was added, followed by 0.5 mL of DMF to wash down the sides of the flask. The mixture was sparged with argon for 10 minutes then allowed to stir at ambient temperature overnight. The reaction mixture was diluted in ethyl acetate, washed with saturated aqueous sodium hydrogen carbonate and brine then dried over sodium sulfate, filtered and concentrated. The residue was purified by preparative HPLC Reverse phase (C-18), eluting with Acetonitrile/Water+0.05% TFA. The fractions containing product were combined and diluted in ethyl acetate, then washed with aqueous sodium bicarbonate and dried over sodium sulfate. The solution was filtered and concentrated to afford 3-(cyclopropylethynyl)-6-(1-methyl-1H-pyrazol-4-yl)-4-(pyridin-2-ylmethoxy)pyrazolo[1,5-a]pyridine. $^1$H NMR (500 MHz, DMSO-d$_6$) δ 8.66 (s, 1H); 8.61 (d, 1H); 8.33 (s, 1H); 8.05 (s, 1H); 8.01 (s, 1H); 7.88-7.95 (m, 2H); 7.36-7.40 (m, 1H); 7.15 (s, 1H); 5.38 (s, 2H); 3.86 (s, 3H), 1.51-1.58 (m, 1H); 0.81-0.88 (m, 2H); 0.56-0.60 (m, 2H). LRMS (ESI) calculated for C$_{22}$H$_{20}$N$_5$O [M+H]$^+$, 370.2; found 370.1.

The compounds in the following table were prepared according to the procedure described in scheme 8 and for compounds 8-1 to 8-4. The compounds were prepared as free bases.

TABLE 8

| Compound | Structure | Name | [M + H]+ |
| --- | --- | --- | --- |
| 8-5 | 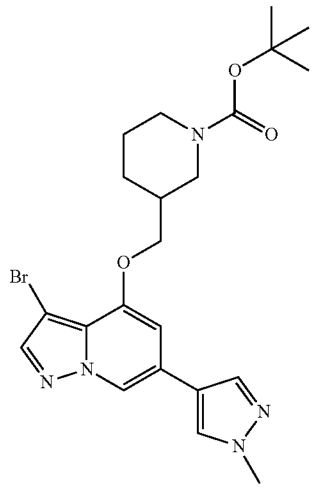 [SMILES: Cn1cc(-c2cc(OCC3CCCN(C(=O)OC(C)(C)C)C3)c3c(Br)cnn3c2)cn1] | tert-butyl 3-({[3-bromo-6-(1-methyl-1H-pyrazol-4-yl)pyrazolo[1,5-a]pyridin-4-yl]oxy}methyl)piperidine-1-carboxylate | Calc'd 490.1 (for $^{79}$Br), found 490.0 |
| 8-6 | 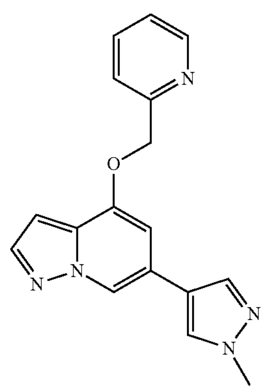 [SMILES: Cn1cc(-c2cc(OCc3ccccn3)c3ccnn3c2)cn1] | 6-(1-methyl-1H-pyrazol-4-yl)-4-(pyridin-2-ylmethoxy)pyrazolo[1,5-a]pyridine | Calc'd 306.1, found 306.1 |
| 8-7 | 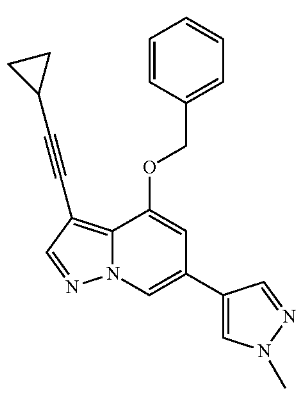 [SMILES: Cn1cc(-c2cc(OCc3ccccc3)c3c(C#CC4CC4)cnn3c2)cn1] | 4-(benzyloxy)-3-(cyclopropylethynyl)-6-(1-methyl-1H-pyrazol-4-yl)pyrazolo[1,5-a]pyridine | Calc'd 369.2 found 369.1 |

TABLE 8-continued

| Compound | Structure | Name | [M + H]+ |
|---|---|---|---|
| 8-8 | 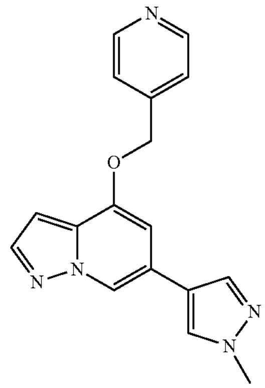 [SMILES: Cn1cc(-c2cc(OCc3ccncc3)c3ccnn3c2)cn1] | 6-(1-methyl-1H-pyrazol-4-yl)-4-(pyridin-4-ylmethoxy)pyrazolo[1,5-a]pyridine | Calc'd 306.1, found 306.0 |
| 8-9 | 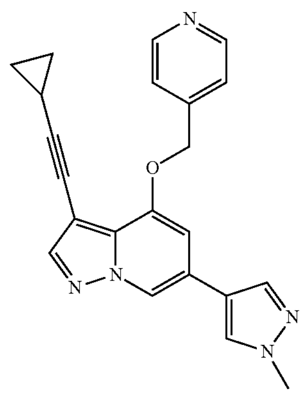 [SMILES: Cn1cc(-c2cc(OCc3ccncc3)c3c(C#CC4CC4)cnn3c2)cn1] | 3-(cyclopropylethynyl)-6-(1-methyl-1H-pyrazol-4-yl)-4-(pyridin-4-ylmethoxy)pyrazolo[1,5-a]pyridine | Calc'd 370.2, found 370.1 |
| 8-10 | 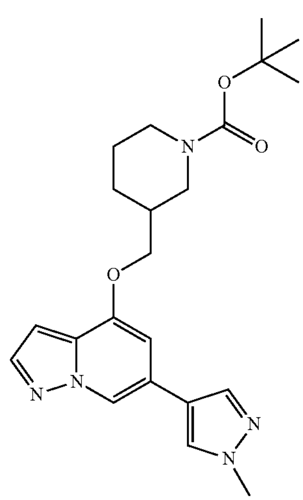 [SMILES: Cn1cc(-c2cc(OCC3CCCN(C(=O)OC(C)(C)C)C3)c3ccnn3c2)cn1] | tert-butyl 3-({[6-(1-methyl-1H-pyrazol-4-yl)pyrazolo[1,5-a]pyridin-4-yl]oxy}methyl)piperidine-1-carboxylate | Calc'd 412.2, found 412.1 |

TABLE 8-continued

| Compound | Structure | Name | [M + H]+ |
|---|---|---|---|
| 8-11 | 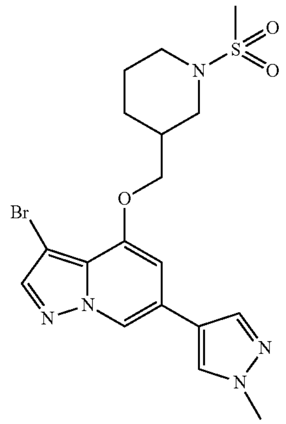 [SMILES: Cn1cc(-c2cc(OCC3CCCN(S(C)(=O)=O)C3)c3c(Br)cnn3c2)cn1] | 3-bromo-6-(1-methyl-1H-pyrazol-4-yl)-4-{[1-(methylsulfonyl)piperidin-3-yl]methoxy}pyrazolo[1,5-a]pyridine | Calc'd 468.1 (for $^{79}$Br), found 467.9 |
| 8-12 | 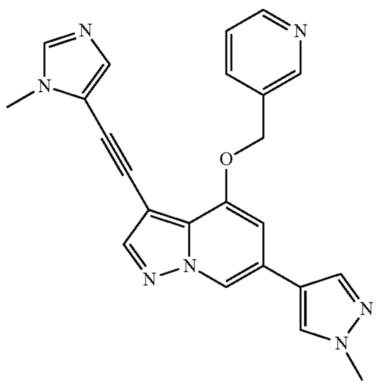 [SMILES: Cn1cc(-c2cc(OCc3cccnc3)c3c(C#Cc4cncn4C)cnn3c2)cn1] | 3-[(1-methyl-1H-imidazol-5-yl)ethynyl]-6-(1-methyl-1H-pyrazol-4-yl)-4-(pyridin-3-ylmethoxy)pyrazolo[1,5-a]pyridine | Calc'd 410.2, found 410.0 |

Scheme 9

Wherein:
one of R$^8$ and R$^9$ is R$^c$ and the other (C=O)$_b$R$^2$;
B(OR)$_2$ is a boron ester such as tetramethyldioxaborolanyl.

EXAMPLE 9

Representative Compound 9-1

Compound 9-1 tert-butyl [6-(1-methyl-1H-pyrazol-4-yl)pyrazolo[1,5-a]pyridin-4-yl]carbamate

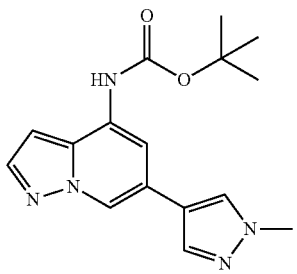 [SMILES: Cn1cc(-c2cc(NC(=O)OC(C)(C)C)c3ccnn3c2)cn1]

Step 1: 4-bromopyrazolo[1,5-a]pyridin-6-ol 4-bromo-6-methoxypyrazolo[1,5-a]pyridine (725 mg, 3.19 mmol) was suspended in HBr (12 ml, 106 mmol). The reaction mixture was heated in the Biotage Initiator Series microwave for 1 h at 150° C. The reaction mixture was slowly added via pipette to a solution of 5N NaOH (22.0 ml, 110 mmol) in 100 mL of saturated aqueous sodium bicarbonate at 0° C. The reaction mixture was diluted in ethyl acetate, washed with saturated aqueous sodium hydrogen carbonate and brine then dried over sodium sulfate, filtered and concentrated to afford 4-bromopyrazolo[1,5-a]pyridin-6-ol.

Step 2:
6-(benzyloxy)-4-bromopyrazolo[1,5-a]pyridine 4-bromopyrazolo[1,5-a]pyridin-6-ol (50.0 mg, 0.235 mmol) was dissolved in DMF (2 ml). NaH (14.1 mg, 0.352 mmol, 60%) was added in one portion, and the mixture was allowed to stir for 10 minutes. Benzyl bromide (0.031 ml, 0.258 mmol) was added and the mixture was allowed to stir for 30 minutes. The reaction mixture was quenched with saturated aqueous ammonium chloride, diluted in ethyl acetate, washed with saturated aqueous sodium hydrogen carbonate and brine then dried over sodium sulfate, filtered and concentrated. The residue was purified by column chromatography on silica gel (ethyl acetate/isohexane gradient) to afford 6-(benzyloxy)-4-bromopyrazolo[1,5-a]pyridine.

Step 3: tert-butyl[6-(benzyloxy)pyrazolo[1,5-a]pyridin-4-yl]carbamate 6-(benzyloxy)-4-bromopyrazolo[1,5-a]pyridine (150 mg, 0.495 mmol), tert-butyl carbamate (116 mg, 0.990 mmol), tris(dibenzylideneacetone)dipalladium (0) (45.3 mg, 0.049 mmol), Xantphos (57.3 mg, 0.099 mmol), and cesium carbonate (484 mg, 1.48 mmol) were suspended in 1,4-dioxane (5 mL). The mixture was sparged with argon for 10 minutes then heated to 95° C. After 2 h, the reaction mixture was diluted in ethyl acetate, washed with saturated aqueous sodium hydrogen carbonate and brine then dried over sodium sulfate, filtered and concentrated. The residue was purified by column chromatography on silica gel (ethyl acetate/isohexane gradient) to afford tert-butyl [6-(benzyloxy)pyrazolo[1,5-a]pyridin-4-yl]carbamate contaminated with tert-butyl carbamate.

Step 4: tert-butyl (6-hydroxypyrazolo[1,5-a]pyridin-4-yl)carbamate tert-butyl [6-(benzyloxy)pyrazolo[1,5-a]pyridin-4-yl]carbamate from Step 3 (140 mg, 0.363 mmol) was dissolved in absolute ethanol (5 ml). Palladium on carbon (77 mg, 0.073 mmol) was added and the mixture was placed under an atmosphere of hydrogen (balloon). After 1 h, the mixture was filtered through a 45 μm syringe filter and the filtrate was concentrated. The residue was purified by column chromatography on silica gel (ethyl acetate/isohexane gradient) to afford tert-butyl (6-hydroxypyrazolo[1,5-a]pyridin-4-yl)carbamate.

Step 5: 4-[(tert-butoxycarbonyl)amino]pyrazolo[1,5-a]pyridin-6-yl trifluoromethanesulfonate tert-butyl (6-hydroxypyrazolo[1,5-a]pyridin-4-yl)carbamate (55.0 mg, 0.221 mmol) and N-phenylbis(trifluoromethanesulfonimide) (87.0 mg, 0.243 mmol) were suspended in dichloromethane (4 ml). Triethylamine (0.062 ml, 0.441 mmol) was added and the mixture was allowed to stir at ambient temperature. After 3 h, the reaction mixture was diluted in ethyl acetate, washed with saturated aqueous sodium hydrogen carbonate and brine then dried over sodium sulfate, filtered and concentrated. The residue was purified by column chromatography on silica gel (ethyl acetate/isohexane gradient) to afford 4-[(tert-butoxycarbonyl)amino]pyrazolo[1,5-a]pyridin-6-yl trifluoromethanesulfonate.

Step 6: tert-butyl [6-(1-methyl-1H-pyrazol-4-yl) pyrazolo[1,5-a]pyridin-4-yl]carbamate 4-[(tert-butoxycarbonyl)amino]pyrazolo[1,5-a]pyridin-6-yl trifluoromethanesulfonate (20.0 mg, 0.052 mmol), 1-methyl-4-(4,4,5,5-tetramethyl-1,3,2-dioxaborolan-2-yl)-1H-pyrazole (21.8 mg, 0.105 mmol), tris(dibenzylideneacetone) dipalladium (0) (4.8 mg, 5.2 μmol), potassium fluoride (10.1 mg, 0.173 mmol), and tri-tert-butylphosphonium tetrafluoroborate (3.0 mg, 10.0 μmol) were suspended in DMF. The mixture was sparged with argon for 10 minutes, then heated to 100° C. for 2 h. The reaction mixture was diluted in ethyl acetate, washed with saturated aqueous sodium hydrogen carbonate and brine then dried over sodium sulfate, filtered and concentrated. The residue was purified by column chromatography on silica gel (methanol/ethyl acetate gradient) to afford a yellow gum. The gum was purified by preparative HPLC Reverse phase (C-18), eluting with Acetonitrile/Water+0.05% TFA. The fractions containing product were combined and diluted in ethyl acetate, then washed with aqueous sodium bicarbonate and dried over sodium sulfate. The solution was filtered and concentrated under reduced pressure to afford tert-butyl [6-(1-methyl-1H-pyrazol-4-yl)pyrazolo[1,5-a]pyridin-4-yl]carbamate. $^1$H NMR (500 MHz, CDCl$_3$) δ 8.35 (s, 1H); 7.89 (s, 2H); 7.76 (s, 1H); 7.66 (s, 1H); 6.73 (s, 1H); 6.47 (s, 1H); 3.94 (s, 3H), 1.56 (s, 9H). LRMS (ESI) calculated for $C_{16}H_{20}N_5O_2$ [M+H]$^+$, 314.2; found 314.1.

Scheme 10

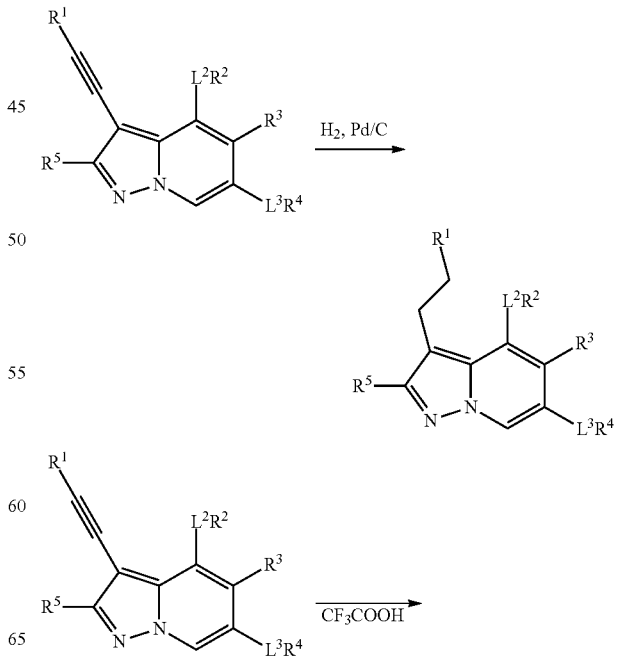

-continued

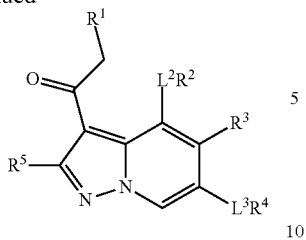

EXAMPLES 10

Representative Compounds 10-1 to 10-3

Compound 10-1

4-{2-[4-methoxy-6-(1-methyl-1H-pyrazol-4-yl)pyrazolo[1,5-a]pyridin-3-yl]ethyl}pyridin-2-amine

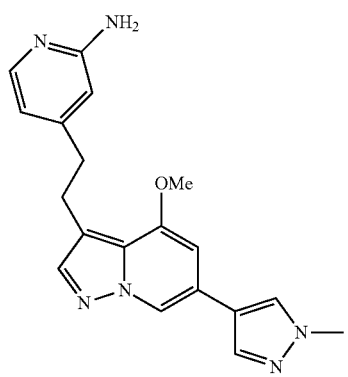 [SMILES: COc1cc(-c2cnn(C)c2)cn2ncc(CCc3ccnc(N)c3)c12]

To a solution of 4-{[4-methoxy-6-(1-methyl-1H-pyrazol-4-yl)pyrazolo[1,5-a]pyridin-3-yl]ethynyl}pyridin-2-amine (8.3 mg, 0.024 mmol) in ethanol (1 ml) was added palladium hydroxide on carbon (8 mg, 5.70 μmmol, 20 wt %). The reaction system was placed under an atmosphere of hydrogen (balloon) and stirred at ambient temperature for 7 hours. The mixture was filtered through a 45 min syringe filter and washed with EtOH. The filtrate was concentrated and the residue was purified by preparative HPLC reverse phase (C-18), eluting with acetonitrile/water+0.05% TFA. The fractions containing product were combined and diluted in ethyl acetate, then washed with aqueous sodium bicarbonate and dried over sodium sulfate. The solution was filtered and concentrated under reduced pressure to afford 4-{2-[4-methoxy-6-(1-methyl-1H-pyrazol-4-yl)pyrazolo[1,5-a]pyridin-3-yl]ethyl}pyridin-2-amine $^1$H NMR (500 MHz, CDCl$_3$) δ 8.18 (s, 1H), 7.87 (d, 1H), 7.73 (s, 1H), 7.56-7.63 (m, 2H), 6.54 (d, 1H), 6.39 (s, 1H), 6.36 (s, 1H), 5.18 (br s, 2H), 3.97 (s, 6H), 3.15 (t, 2H), 2.86 (t, 2H). LRMS (ESI) calculated for C$_{19}$H$_{21}$N$_6$O [M+H]$^+$, 349.2; found 349.1.

Compound 10-2

1-[4-methoxy-6-(1-methyl-1H-pyrazol-4-yl)pyrazolo[1,5-a]pyridin-3-yl]-2-[1-(trifluoroacetyl)azetidin-3-yl]ethanone

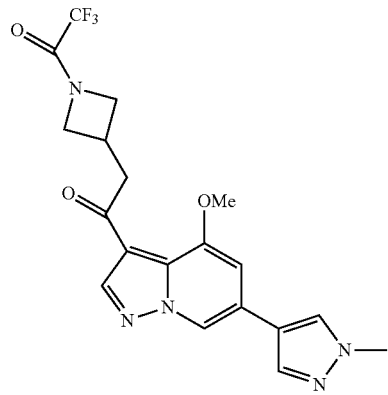 [SMILES: COc1cc(-c2cnn(C)c2)cn2ncc(C(=O)CC3CN(C(=O)C(F)(F)F)C3)c12]

To a solution of tert-butyl 3-{[4-methoxy-6-(1-methyl-1H-pyrazol-4-yl)pyrazolo[1,5-a]pyridin-3-yl]ethynyl}azetidine-1-carboxylate (24 mg, 0.059 mmol) in dichloromethane (0.5 ml), was added trifluoroacetic acid (0.50 ml, 6.49 mmol) at 0° C. The reaction mixture was warmed to room temperature and stirred for 30 mins. The reaction was diluted with ethyl acetate, and washed with saturated aqueous sodium bicarbonate. The organic layer was separated, and the aqueous layer was back extracted two times with ethyl acetate. The combined organic layers were dried over sodium sulfate, filtered and concentrated. The residue was purified by column chromatography on silica gel (methanol/dichloromethane gradient) to afford 1-[4-methoxy-6-(1-methyl-1H-pyrazol-4-yl)pyrazolo[1,5-a]pyridin-3-yl]-2-[1-(trifluoroacetyl)azetidin-3-yl]ethanone. $^1$H NMR (500 MHz, CDCl$_3$) δ 8.35 (s, 1H), 8.32 (s, 1H), 7.77 (s, 1H), 7.67 (s, 1H), 6.81 (s, 1H), 4.68 (app t, 1H), 4.39 (app t, 1H), 4.10-4.16 (m, 1H), 4.06 (s, 3H), 3.98 (s, 3H), 3.85-3.91 (m, 1H), 3.36-3.53 (m, 2H), 3.23-3.33 (m, 1H). LRMS (ESI) calculated for C$_{19}$H$_{19}$F$_3$N$_5$O$_3$ [M+H]$^+$, 422.1; found 422.0.

The compound in the following table was prepared according to the procedure described in scheme 10 and for compounds 10-1 and 10-2. The compound was prepared as the free base.

TABLE 10

| Compound | Structure | Name | [M + H]+ |
|---|---|---|---|
| 10-3 | 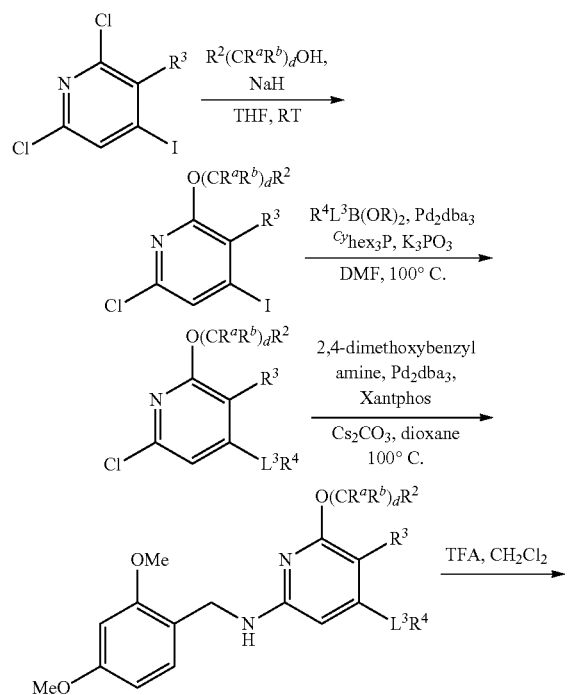 | 3-ethyl-4-methoxy-6-(1-methyl-1H-pyrazol-4-yl)pyrazolo[1,5-a]pyridine | Calc'd 257.1, found 257.1 |

Scheme 11

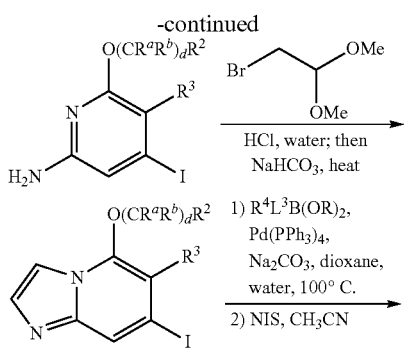

wherein $B(OR)_2$ o is a boron ester such as tetramethyldioxaborolanyl.

EXAMPLES 11

Representative Compounds 11-1 to 11-3

Compound 11-1

5-(benzyloxy)-7-phenylimidazo[1,2-a]pyridine

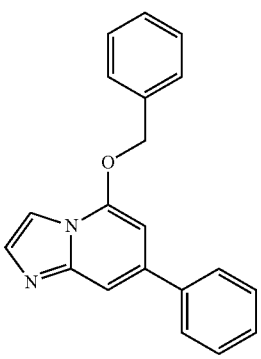 [SMILES: c1ccc(COc2cc(-c3ccccc3)cc3nccn23)cc1]

Step 1: 2-(benzyloxy)-6-chloro-4-iodopyridine

To a solution of sodium hydride (1.24 g, 31.0 mmol, 60 wt % in mineral oil) in THF (30.4 mL) at 0° C. was added benzyl alcohol (2.09 mL, 20.1 mmol) dropwise via syringe. After stirring at 0° C. for 30 mins, 2,6-dichloro-4-iodopyridine (5.00 g, 18.3 mmol) in THF (5 mL) was added dropwise via syringe. The reaction mixture was warmed to room temperature and stirred for 3 hours. The reaction was cooled down to 0° C., and saturated aqueous ammonium chloride was slowly added to quench the reaction. The reaction mixture was allowed to warm to room temperature, diluted with ethyl acetate, and washed with saturated aqueous sodium bicarbonate and saturated aqueous sodium thiosulfate. The organic layer was separated and the aqueous layer was back extracted two times with ethyl acetate. The combined organic layers were dried over sodium sulfate, filtered and concentrated. The residue was purified by column chromatography on silica gel (ethyl acetate/ioshexane gradient) to give 2-(benzyloxy)-6-chloro-4-iodopyridine. LRMS (ESI) calculated for $C_{12}H_{10}ClINO$ [M+H]$^+$, 345.9; found 345.8.

Step 2: 2-(benzyloxy)-6-chloro-4-phenylpyridine

Phenylboronic acid (38.8 mg, 0.318 mmol), tricyclohexylphosphine (22.3 mg, 0.080 mmol), potassium phosphate tribasic (0.24 mL, 1.11 mmol) and tris(dibenzylideneacetone)dipalladium (0) (29.1 mg, 0.032 mmol) were combined into vial fitted with a Teflon septum. The vial was flushed with argon and a solution of 2-(benzyloxy)-6-chloro-4-iodopyridine (110 mg, 0.318 mmol) in DMF (3.2 mL) was added. The reaction was sparged with argon for 10 mins, then heated to 90° C. and stirred for two and a half hours. The reaction mixture was cooled down to room temperature, diluted with ethyl acetate, and washed with saturated aqueous sodium bicarbonate. The organic layer was separated, and the aqueous layer was back extracted two times with ethyl acetate. The combined organic layers were dried sodium sulfate, filtered and concentrated. The residue was purified by column chromatography on silica gel (ethyl acetate/ioshexane gradient) to give the 2-(benzyloxy)-6-chloro-4-phenylpyridine. LRMS (ESI) calculated for $C_{18}H_{15}ClNO$ [M+H]$^+$, 296.1; found 296.0.

Step 3: 6-(benzyloxy)-4-phenylpyridin-2-amine

Cesium carbonate (806 mg, 2.48 mmol), Xantphos (95.0 mg, 0.165 mmol), and tris(dibenzylideneacetone)dipalladium (0) (76.0 mg, 0.082 mmol) were combined into vial fitted with a Teflon septum. The vial was flushed with argon and a solution of 2-(benzyloxy)-6-chloro-4-phenylpyridine (244 mg, 0.825 mmol) in 1,4-dioxane (2 ml) was added, followed by 2,4-dimethoxybenzylamine (0.249 ml 1.65 mmol). The solution was sparged with argon for 10 mins, then heated to 90° C. and stirred for 24 hours. The reaction mixture was cooled down to room temperature, diluted with ethyl acetate, and washed with saturated aqueous sodium bicarbonate. The organic layer was separated, and the aqueous layer was back extracted two times with ethyl acetate. The combined organic layers were dried over sodium sulfate filtered and concentrated. The residue was dissolved in dichloromethane (2.5 mL), and trifluoroacetic acid (2.5 mL, 32.4 mmol) was added. After stirring at room temperature for 1 hour, the solvent was removed under reduced pressure. The residue was dissolved with ethyl acetate, and washed with saturated aqueous sodium bicarbonate. The organic layer was separated, and the aqueous layer was back extracted one time with ethyl acetate. The combined organic layers were dried over sodium sulfate, filtered and concentrated. The residue was purified by column chromatography on silica gel (ethyl acetate/ioshexane gradient) to give 6-(benzyloxy)-4-phenylpyridin-2-amine. LRMS (ESI) calculated for $C_{18}H_{17}N_2O$ [M+H]$^+$, 277.1; found 277.0.

Step 4: 5-(benzyloxy)-7-phenylimidazo[1,2-a]pyridine

To a solution of bromoacetaldehyde dimethyl acetal (0.16 mL, 1.38 mmol) in water (2 mL) was added hydrochloric acid (0.046 mL, 0.276 mmol). After stirring at room temperature for 2 hours, the reaction was heated to 80° C. for 40 mins to give a clear solution. The reaction was cooled down to room temperature, and sodium bicarbonate (147 mg, 1.75 mmol) was added, followed by a solution of 6-(benzyloxy)-4-phenylpyridin-2-amine (254 mg, 0.919 mmol) in 1,4-dioxane (2 mL). The reaction was stirred overnight at ambient temperature, then diluted with ethyl acetate, filtered and concentrated. The residue was purified by column chromatography on silica gel (methanol/ethyl acetate gradient) to give 5-(benzyloxy)-7-phenylimidazo[1,2-a]pyridine. LRMS (ESI) calculated for $C_{20}H_{17}N_2O$ [M+H]$^+$, 301.1; found 301.0.

Compound 11-2

5-(benzyloxy)-3-iodo-7-phenylimidazo[1,2-a]pyridine

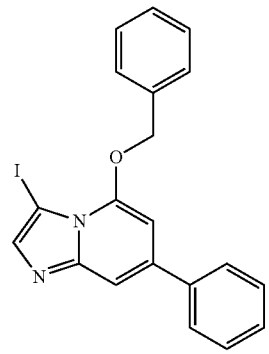 [SMILES: Ic1cnc2cc(-c3ccccc3)cc(OCc3ccccc3)n12]

To a solution of 5-(benzyloxy)-7-phenylimidazo[1,2-a]pyridine (Compound 11-1) (60 mg, 0.20 mmol) in acetonitrile (4 mL) was added N-iodosuccinimide (59 mg, 0.26 mmol) at room temperature. The reaction was stirred at room temperature for 12 h, diluted with ethyl acetate, and washed with 1N aqueous sodium hydroxide. The organic layer was separated, and the aqueous layer was back extracted one time with ethyl acetate. The combined organic layers were dried over sodium sulfate, filtered and concentrated. The residue was purified by column chromatography on silica gel (ethyl acetate/isohexane gradient) to give 5-(benzyloxy)-3-iodo-7-phenylimidazo [1,2-a]pyridine. $^1$H NMR (500 MHz, CDCl$_3$) δ 7.55-7.59 (m, 4H), 7.54 (s, 1H), 7.36-7.47 (m, 7H), 6.34 (s, 1H), 5.34 (s, 2H). LRMS (ESI) calculated for $C_{20}H_{16}IN_2O$ [M+H]$^+$, 427.0; found 426.9.

Compound 11-3

3-iodo-5-methoxy-7-phenylimidazo[1,2-a]pyridine

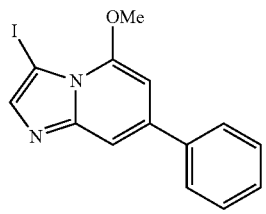 [SMILES: COc1cc(-c2ccccc2)cc2ncc(I)n12]

Step 1: 2,6-difluoro-3-iodopyridine

To a solution of butyllithium (38.8 ml, 97 mmol) in tetrahydrofuran (194 ml) at −78° C. was added diisopropylamine (13.8 ml, 97 mmol) dropwise. After 15 minutes at −78° C., 2,6-difluoropyridine (8.8 ml, 97 mmol) was added slowly. After 1 hour slowly, a solution of iodine (24.6 g, 97 mmol) in tetrahydrofuran (50 ml) was carefully added, keeping the internal temperature at −78° C. Sodium sulfite (3.0 g, 24 mmol) was added and the temperature was allowed to gradually increase to ambient temperature. The reaction mixture was diluted with ethyl ether, washed with water, then dried over magnesium sulfate, filtered, and concentrated. The residue was purified by column chromatography on silica gel, eluting (ethyl acetate/isohexane gradient) to give 2,6-difluoro-3-iodopyridine.

Step 2: 2,6-difluoro-4-iodopyridine

To a solution of butyllithium (35.8 ml, 90.0 mmol) in tetrahydrofuran (170 ml) at −78° C. was added dropwise diisopropylamine (12.8 ml, 90.0 mmol). After 30 minutes at −78° C., 2,6-difluoro-3-iodopyridine (21.6 g, 90.0 mmol) was added slowly. After 30 minutes the reaction mixture was quenched with water (50 ml) and allowed to gradually warm to ambient temperature. The reaction mixture was diluted with ethyl ether, washed with water and brine, then dried over magnesium sulfate, filtered, and concentrated. The residue was purified by column chromatography on silica gel (ethyl acetate/isohexane gradient) to give 2,6-difluoro-4-iodopyridine.

Step 3: 2-fluoro-4-iodo-6-methoxypyridine

To a solution of 2,6-difluoro-4-iodopyridine (7.37 g, 30.6 mmol) in tetrahydrofuran (200 ml) cooled to 0° C. was added a 0.5 M solution of sodium methoxide (61.2 ml, 30.6 mm) in methyl alcohol. After 4 h the reaction mixture was warmed to ambient temperature. LRMS indicated incomplete conversion to product and additional 0.5 M sodium methoxide solution in methyl alcohol (6.12 ml, 3.06 mmol) was added. After 1 hour the reaction mixture was quenched with water (50 ml), partially concentrated, diluted with ethyl ether, washed with water and brine, then dried over magnesium sulfate, filtered, and concentrated to afford 2-fluoro-4-iodo-6-methoxypyridine as a yellow oil which was used without further purification. $^1$H NMR (600 MHz, DMSO-$d_6$) δ 7.19 (s, 1H); 7.16 (d, 1H); 3.78 (s, 3H).

Step 4: 4-iodo-6-methoxypyridin-2-amine

To a solution of 2-fluoro-4-iodo-6-methoxypyridine (7.1 g, 28 mmol) in n-butanol (64 ml) was added 28% solution of ammonium hydroxide (20 ml, 140 mmol). The reaction mixture was heated to 120° C. After 16 hours LRMS indicated incomplete conversion to product. Additional 28% solution of ammonium hydroxide (20 ml, 140 mmol) was added and the reaction mixture was reheated to 120° C. After 16 h LRMS indicated incomplete conversion to product. Additional 28% solution of ammonium hydroxide (8.0 ml, 56 mmol) was added and the reaction mixture was reheated to 120° C. After 24 h the reaction mixture was cooled, partially concentrated, diluted with ethyl ether, washed with water, then dried over magnesium sulfate, filtered, and concentrated. The residue was purified by column chromatography on silica gel (ethyl ether/isohexane gradient) to give 4-iodo-6-methoxypyridin-2-amine LRMS (ESI) calculated for $C_6H_8IN_2O$ [M+H]$^+$, 251.0 found 250.9.

Step 5: 7-iodo-5-methoxyimidazo[1,2-a]pyridine

To a mixture of bromoacetaldehyde dimethylacetal (4.50 ml, 37.1 mmol) in water (126 ml) was added a 1M solution of hydrochloric acid (8.40 ml, 8.40 mmol). After 2.5 h the reaction mixture was heated to 80° C. resulting in a clear solution. After 40 minutes the reaction mixture was cooled to ambient temperature and sodium bicarbonate (3.83 g, 45.6 mmol) and 4-iodo-6-methoxypyridin-2-amine (5.25 g, 21.0 mmol) were added. After 16 hours the reaction mixture was diluted with ethyl acetate, washed with water, then dried over magnesium sulfate, filtered, and concentrated. The residue was purified by column chromatography on silica gel (methanol/dichloromethane gradient) to give 7-iodo-5-methoxyimidazo[1,2-a]pyridine. LRMS (ESI) calculated for $C_8H_8IN_2O$ [M+H]$^+$, 275.0 found 274.9.

Step 6: 5-methoxy-7-phenylimidazo[1,2-a]pyridine 7-iodo-5-methoxyimidazo[1,2-a]pyridine (539 mg, 1.97 mmol), phenylboronic acid (719 mg, 5.90 mmol), tetrakis(triphenylphosphine)palladium (0) (227 mg, 0.197 mmol), and sodium carbonate (625 mg, 5.90 mmol) were added to a dry flask. Dioxane (18 ml) and water (2 ml) were added and the reaction mixture was sparged with argon for 5 minutes. The reaction mixture was heated to 85° C. After 16 h, the reaction mixture was cooled, diluted with ethyl acetate, washed with water, then dried over magnesium sulfate, filtered, and concentrated. The residue was purified by column chromatography on silica gel (methanol/dichloromethane gradient) to give 5-methoxy-7-phenylimidazo[1,2-a]pyridine. LRMS (ESI) calculated for $C_{14}H_{13}N_2O$ [M+H]+, 225.1 found 225.0.

Step 7:
3-iodo-5-methoxy-7-phenylimidazo[1,2-a]pyridine

To a solution of 5-methoxy-7-phenylimidazo[1,2-a]pyridine (397 mg, 1.77 mmol) in acetonitrile (30 ml) was added N-iodosuccinimide (478 mg, 2.12 mmol). After 1 h the reaction mixture was diluted with ethyl acetate, washed with 1N aqueous sodium hydroxide and water, then dried over magnesium sulfate, filtered, and concentrated. The residue was purified by column chromatography on silica gel (ethyl acetate/isohexane gradient) to give 3-iodo-5-methoxy-7-phenylimidazo[1,2-a]pyridine. $^1$H NMR (600 MHz, DMSO-$d_6$) δ 7.86 (d, 1H); 7.83 (d, 1H); 7.52-7.53 (m, 1H); 7.48-7.45 (m, 2H); 7.38-7.40 (m, 1H); 7.33-7.35 (m, 1H); 6.61 (d, 1H); 4.10 (s, 3H). LRMS (ESI) calculated for $C_{14}H_{12}IN_2O$ [M+H]+, 351.0 found 350.9.

Scheme 12

EXAMPLES 12

Representative Compounds 12-1 to 12-34

Compound 12-1

5-methoxy-7-phenyl-3-(pyridin-3-ylethynyl)imidazo[1,2-a]pyridine

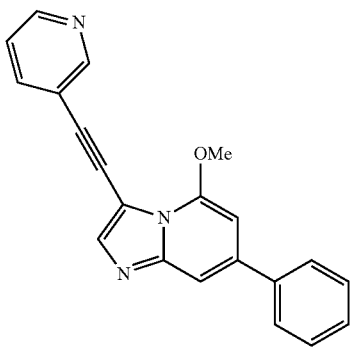 [SMILES: COc1cc(-c2ccccc2)cc2ncc(C#Cc3cccnc3)n12]

5-(benzyloxy)-3-iodo-7-phenylimidazo[1,2-a]pyridine (32.0 mg, 0.091 mmol), tetrakis(triphenylphosphine)palladium(0) (10.6 mg, 9.14 μmol) and copper(I)iodide (10.44 mg, 0.055 mmol) were suspended in DMF (1 mL). Triethylamine (0.025 mL, 0.183 mmol) and 3-ethynylpyridine (28.3 mg, 0.274 mmol) were added, and the mixture was sparged with argon for 5 minutes. The reaction was stirred at room temperature for 1 hour, diluted with acetonitrile, DMSO and water. The solution was directly purified by preparative HPLC Reverse phase (C-18), eluting with acetonitrile/water+ 0.05% TFA. The fractions containing product were combined and diluted in ethyl acetate, then washed with aqueous sodium bicarbonate and dried over sodium sulfate. The solution was filtered and concentrated under reduced pressure to afford impure material, which was additionally purified by column chromatography on silica gel (methanol/dichloromethane gradient) to afford -methoxy-7-phenyl-3-(pyridin-3-ylethynyl)imidazo[1,2-a]pyridine. $^1$H NMR (500 MHz, CDCl$_3$) δ 8.75 (d, 1H), 8.53 (dd, 1H), 7.89 (s, 1H), 7.75-7.79 (m, 1H), 7.62-7.67 (m, 2H), 7.53 (s, 1H), 7.45-7.50 (m, 2H), 7.39-7.43 (m, 1H), 7.27-7.31 (m, 1H), 6.37 (s, 1H), 4.16 (s, 3H). LRMS (ESI) calculated for $C_{21}H_{16}N_3O$ [M+H]+, 326.1; found 326.0.

The compounds in the following table were prepared according to the procedure described in scheme 12 and for compound 12-1. The compounds were prepared as free bases.

TABLE 12

| Compound | Structure | Name | [M + H]+ |
|---|---|---|---|
| 12-2 | 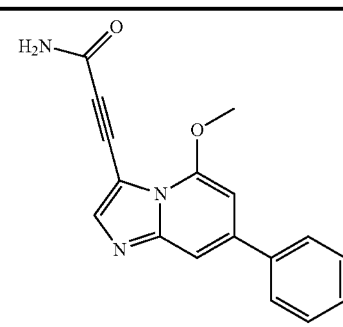 | 3-(5-methoxy-7-phenylimidazo[1,2-a]pyridin-3-yl)prop-2-ynamide | Calc'd 292.1, found 292.1 |

TABLE 12-continued

| Compound | Structure | Name | [M + H]+ |
| --- | --- | --- | --- |
| 12-3 | 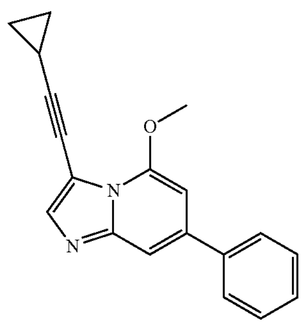 [SMILES: COc1cc(-c2ccccc2)cc2ncc(C#CC3CC3)n12] | 3-(cyclopropylethynyl)-5-methoxy-7-phenylimidazo[1,2-a]pyridine | Calc'd 289.1, found 289.0 |
| 12-4 | 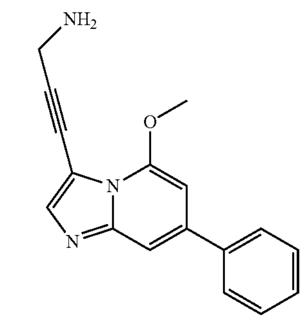 [SMILES: COc1cc(-c2ccccc2)cc2ncc(C#CCN)n12] | 3-(5-methoxy-7-phenylimidazo[1,2-a]pyridin-3-yl)prop-2-yn-1-amine | Calc'd 278.1, found 278.0 |
| 12-5 | 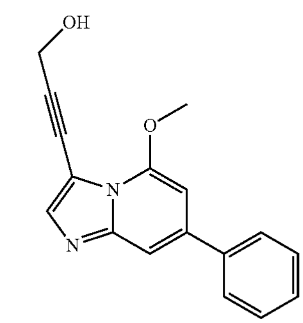 [SMILES: COc1cc(-c2ccccc2)cc2ncc(C#CCO)n12] | 3-(5-methoxy-7-phenylimidazo[1,2-a]pyridin-3-yl)prop-2-yn-1-ol | Calc'd 279.1, found 279.0 |
| 12-6 | 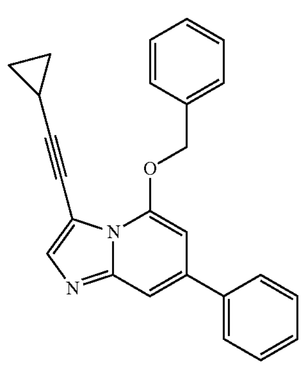 [SMILES: C(#CC1CC1)c1cnc2cc(-c3ccccc3)cc(OCc3ccccc3)n12] | 5-(benzyloxy)-3-(cyclopropylethynyl)-7-phenylimidazo[1,2-a]pyridine | Calc'd 365.2, found 365.1 |

TABLE 12-continued

| Compound | Structure | Name | [M + H]+ |
|---|---|---|---|
| 12-7 | 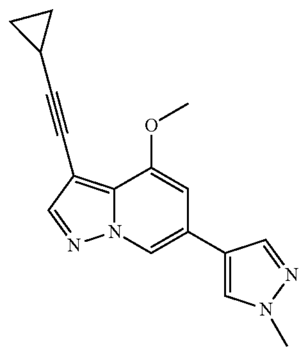 [SMILES: COc1cc(-c2cnn(C)c2)cn2ncc(C#CC3CC3)c12] | 3-(cyclopropylethynyl)-5-methoxy-7-(1-methyl-1H-pyrazol-4-yl)imidazo[1,2-a]pyridine | Calc'd 293.1, found |
| 12-8 | 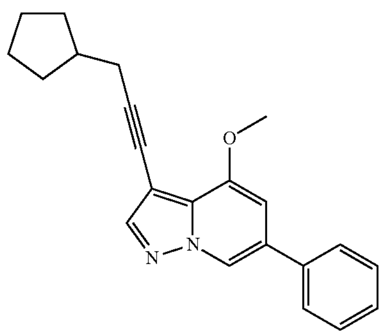 [SMILES: COc1cc(-c2ccccc2)cn2ncc(C#CCC3CCCC3)c12] | 3-(3-cyclopentylprop-1-yn-1-yl)-5-methoxy-7-phenylimidazo[1,2-a]pyridine | Calc'd 331.2, found 331.1 |
| 12-9 | 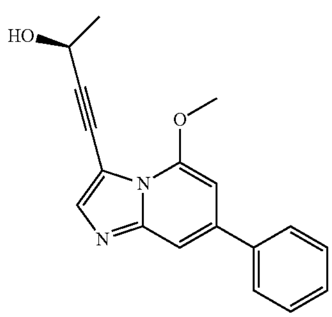 [SMILES: COc1cc(-c2ccccc2)cc2ncc(C#C[C@H](C)O)n12] | (2S)-4-(5-methoxy-7-phenylimidazo[1,2-a]pyridin-3-yl)but-3-yn-2-ol | Calc'd 293.1, found 293.1 |
| 12-10 | 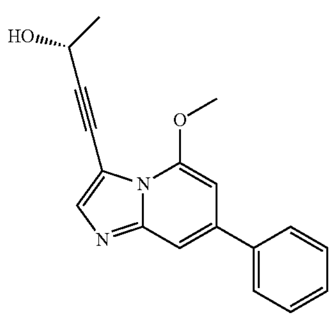 [SMILES: COc1cc(-c2ccccc2)cc2ncc(C#C[C@@H](C)O)n12] | (2R)-4-(5-methoxy-7-phenylimidazo[1,2-a]pyridin-3-yl)but-3-yn-2-ol | Calc'd 293.1, found 293.0 |

TABLE 12-continued

| Compound | Structure | Name | [M + H]+ |
|---|---|---|---|
| 12-11 | 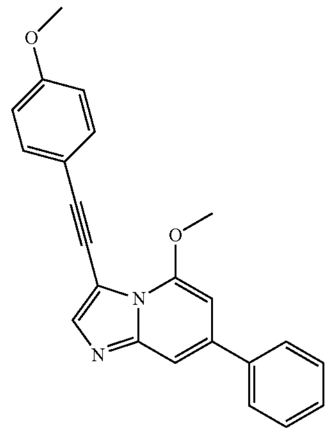 [SMILES: COc1ccc(C#Cc2cnc3cc(-c4ccccc4)cc(OC)n23)cc1] | 5-methoxy-3-[(4-methoxyphenyl)ethynyl]-7-phenylimidazo[1,2-a]pyridine | Calc'd 355.1, found 355.0 |
| 12-12 | 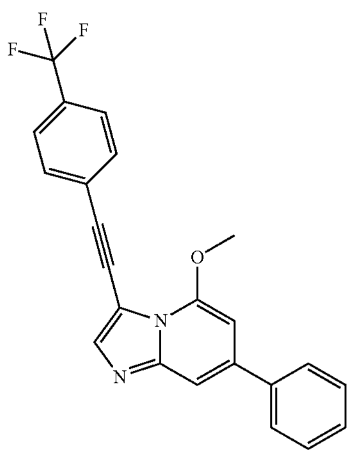 [SMILES: COc1cc(-c2ccccc2)cc2ncc(C#Cc3ccc(C(F)(F)F)cc3)n12] | 5-methoxy-7-phenyl-3-{[4-(trifluoromethyl)phenyl]ethynyl}imidazo[1,2-a]pyridine | Calc'd 393.1, found 393.0 |
| 12-13 | 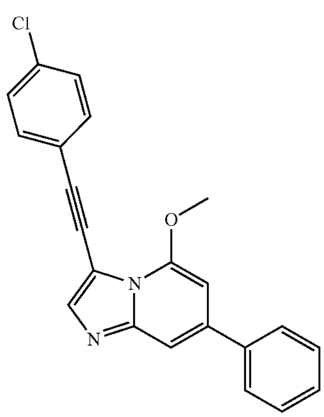 [SMILES: COc1cc(-c2ccccc2)cc2ncc(C#Cc3ccc(Cl)cc3)n12] | 3-[(4-chlorophenyl)ethynyl]-5-methoxy-7-phenylimidazo[1,2-a]pyridine | Calc'd 359.1, found 359.0 |

TABLE 12-continued
| Compound | Structure | Name | [M + H]+ |
|---|---|---|---|
| 12-14 | 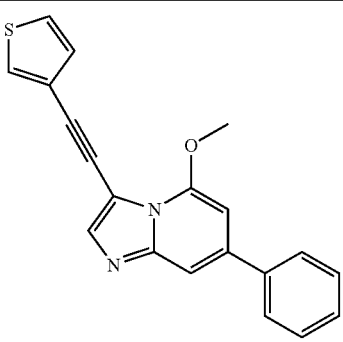 | 5-methoxy-7-phenyl-3-(3-thienylethynyl)imidazo[1,2-a]pyridine | Calc'd 331.1, found 331.0 |
| 12-15 | 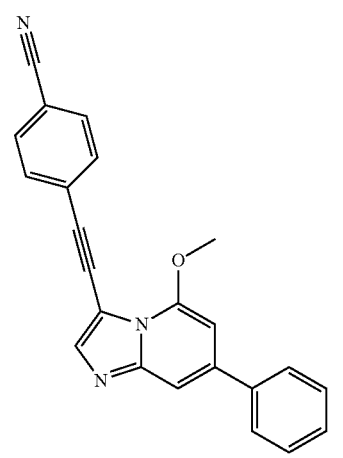 [SMILES: COc1cc(-c2ccccc2)cc2ncc(C#Cc3ccc(C#N)cc3)n12] | 4-[(5-methoxy-7-phenylimidazo[1,2-a]pyridin-3-yl)ethynyl]benzonitrile | Calc'd 350.1, found 350.0 |
| 12-16 | 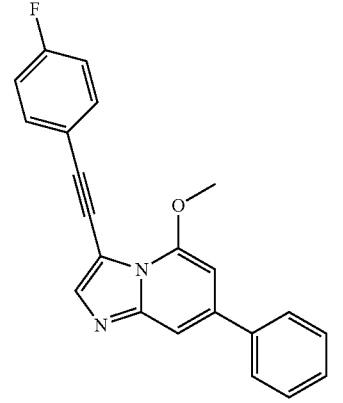 [SMILES: COc1cc(-c2ccccc2)cc2ncc(C#Cc3ccc(F)cc3)n12] | 3-[(4-fluorophenyl)ethynyl]-5-methoxy-7-phenylimidazo[1,2-a]pyridine | Calc'd 343.1, found 343.0 |
| 12-17 | 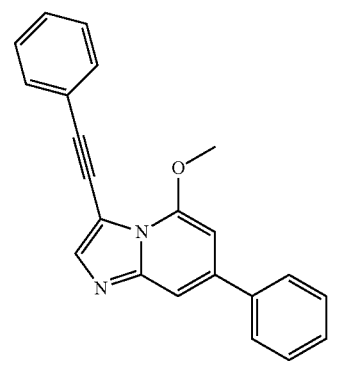 [SMILES: COc1cc(-c2ccccc2)cc2ncc(C#Cc3ccccc3)n12] | 5-methoxy-7-phenyl-3-(phenylethynyl)imidazo[1,2-a]pyridine | Calc'd 325.1, found 325.0 |

TABLE 12-continued

| Compound | Structure | Name | [M + H]+ |
|---|---|---|---|
| 12-18 | 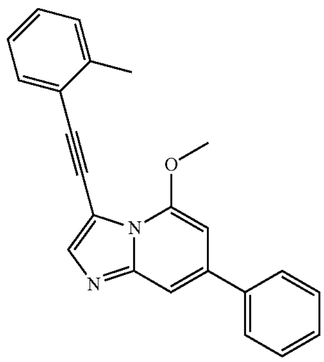 [SMILES: COc1cc(-c2ccccc2)cc2ncc(C#Cc3ccccc3C)n12] | 5-methoxy-3-[(2-methylphenyl)ethynyl]-7-phenylimidazo[1,2-a]pyridine | Calc'd 339.1, found 339.0 |
| 12-19 | 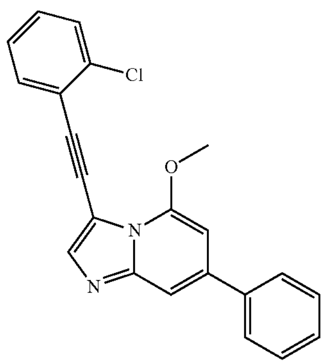 [SMILES: COc1cc(-c2ccccc2)cc2ncc(C#Cc3ccccc3Cl)n12] | 3-[(2-chlorophenyl)ethynyl]-5-methoxy-7-phenylimidazo[1,2-a]pyridine | Calc'd 359.1, found 359.0 |
| 12-20 | 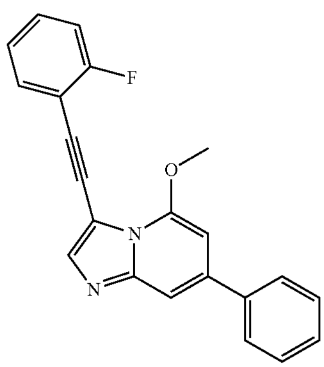 [SMILES: COc1cc(-c2ccccc2)cc2ncc(C#Cc3ccccc3F)n12] | 3-[(2-fluorophenyl)ethynyl]-5-methoxy-7-phenylimidazo[1,2-a]pyridine | Calc'd 343.1, found 343.0 |
| 12-21 | 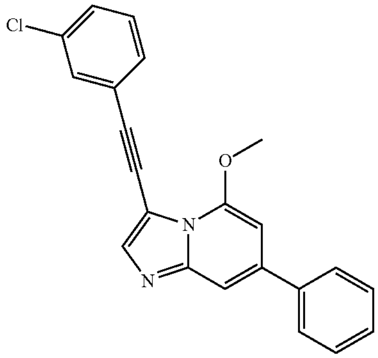 [SMILES: COc1cc(-c2ccccc2)cc2ncc(C#Cc3cccc(Cl)c3)n12] | 3-[(3-chlorophenyl)ethynyl]-5-methoxy-7-phenylimidazo[1,2-a]pyridine | Calc'd 359.1, found 359.0 |

TABLE 12-continued

| Compound | Structure | Name | [M + H]+ |
|---|---|---|---|
| 12-22 | 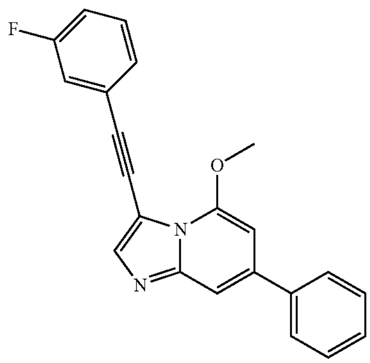 [SMILES: COc1cc(-c2ccccc2)cc2ncc(C#Cc3cccc(F)c3)n12] | 3-[(3-fluorophenyl)ethynyl]-5-methoxy-7-phenylimidazo[1,2-a]pyridine | Calc'd 343.1, found 343.0 |
| 12-23 | 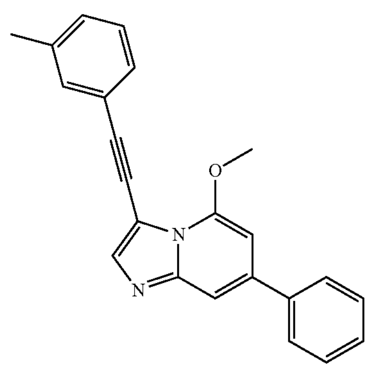 [SMILES: COc1cc(-c2ccccc2)cc2ncc(C#Cc3cccc(C)c3)n12] | 5-methoxy-3-[(3-methylphenyl)ethynyl]-7-phenylimidazo[1,2-a]pyridine | Calc'd 339.1, found 339.1 |
| 12-24 | 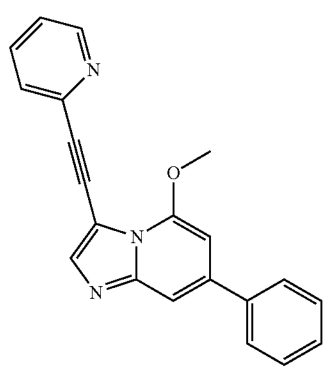 [SMILES: COc1cc(-c2ccccc2)cc2ncc(C#Cc3ccccn3)n12] | 5-methoxy-7-phenyl-3-(pyridin-2-ylethynyl)imidazo[1,2-a]pyridine | Calc'd 326.1, found 326.0 |
| 12-25 | 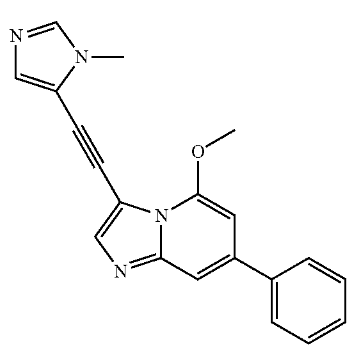 [SMILES: COc1cc(-c2ccccc2)cc2ncc(C#Cc3cncn3C)n12] | 5-methoxy-3-[(1-methyl-1H-imidazol-5-yl)ethynyl]-7-phenylimidazo[1,2-a]pyridine | Calc'd 329.1, found 329.0 |

TABLE 12-continued

| Compound | Structure | Name | [M + H]+ |
|---|---|---|---|
| 12-26 | 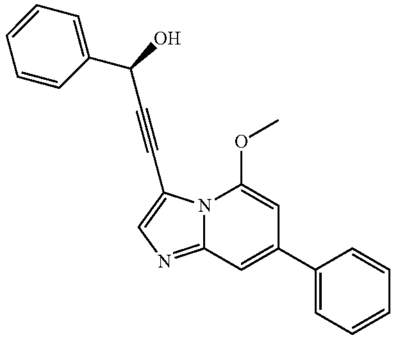 [SMILES: COc1cc(-c2ccccc2)cc2ncc(C#C[C@H](O)c3ccccc3)n12] | (1R)-3-(5-methoxy-7-phenylimidazo[1,2-a]pyridin-3-yl)-1-phenylprop-2-yn-1-ol | Calc'd 355.1, found 355.0 |
| 12-27 | 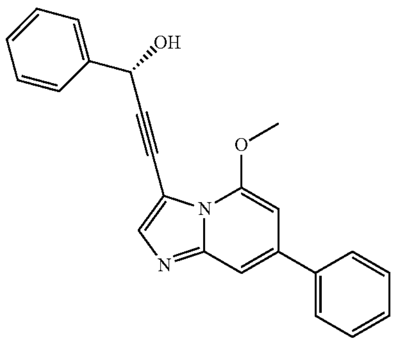 [SMILES: COc1cc(-c2ccccc2)cc2ncc(C#C[C@@H](O)c3ccccc3)n12] | (1S)-3-(5-methoxy-7-phenylimidazo[1,2-a]pyridin-3-yl)-1-phenylprop-2-yn-1-ol | Calc'd 355.1, found 355.0 |
| 12-28 | 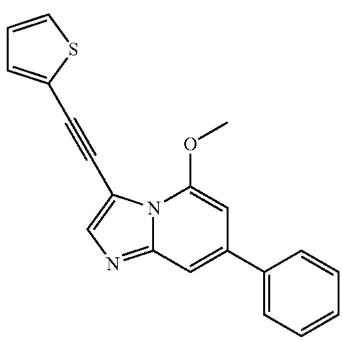 [SMILES: COc1cc(-c2ccccc2)cc2ncc(C#Cc3cccs3)n12] | 5-methoxy-7-phenyl-3-(2-thienylethynyl)imidazo[1,2-a]pyridine | Calc'd 331.1, found 331.0 |
| 12-29 | 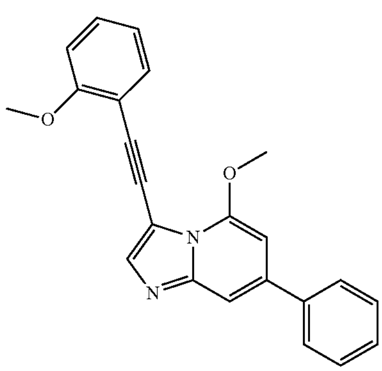 [SMILES: COc1ccccc1C#Cc1cnc2cc(-c3ccccc3)cc(OC)n12] | 5-methoxy-3-[(2-methoxyphenyl)ethynyl]-7-phenylimidazo[1,2-a]pyridine | Calc'd 355.1, found 355.0 |

TABLE 12-continued

| Compound | Structure | Name | [M + H]+ |
| --- | --- | --- | --- |
| 12-30 | 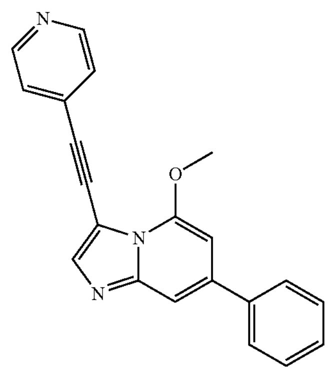 [SMILES: COc1cc(-c2ccccc2)cc2ncc(C#Cc3ccncc3)n12] | 5-methoxy-7-phenyl-3-(pyridin-4-ylethynyl)imidazo[1,2-a]pyridine | Calc'd 326.1, found 326.0 |
| 12-31 | 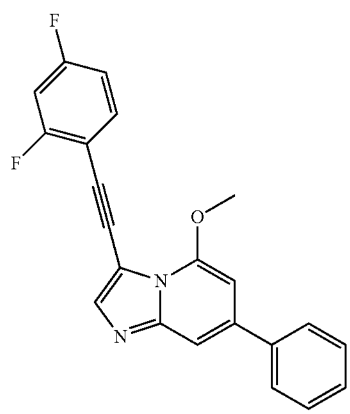 [SMILES: COc1cc(-c2ccccc2)cc2ncc(C#Cc3ccc(F)cc3F)n12] | 3-[(2,4-difluorophenyl)ethynyl]-5-methoxy-7-phenylimidazo[1,2-a]pyridine | Calc'd 361.1, found 361.0 |
| 12-32 | 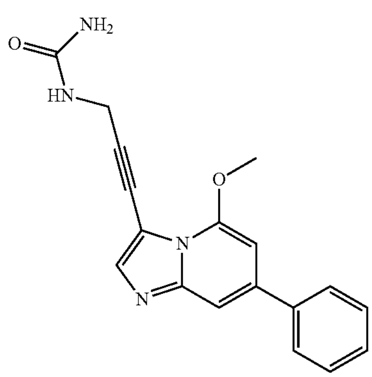 [SMILES: COc1cc(-c2ccccc2)cc2ncc(C#CCNC(N)=O)n12] | 1-[3-(5-methoxy-7-phenylimidazo[1,2-a]pyridin-3-yl)prop-2-yn-1-yl]urea | Calc'd 321.1, found 321.0 |
| 12-33 | 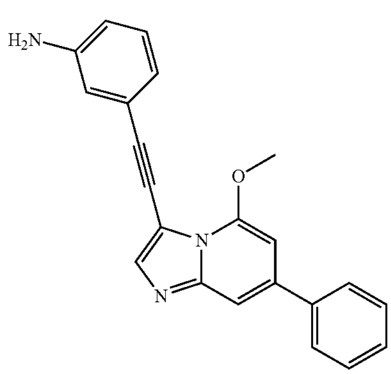 [SMILES: COc1cc(-c2ccccc2)cc2ncc(C#Cc3cccc(N)c3)n12] | 3-[(5-methoxy-7-phenylimidazo[1,2-a]pyridin-3-yl)ethynyl]aniline | Calc'd 340.1, found 340.0 |

TABLE 12-continued

| Compound | Structure | Name | [M + H]+ |
|---|---|---|---|
| 12-34 | 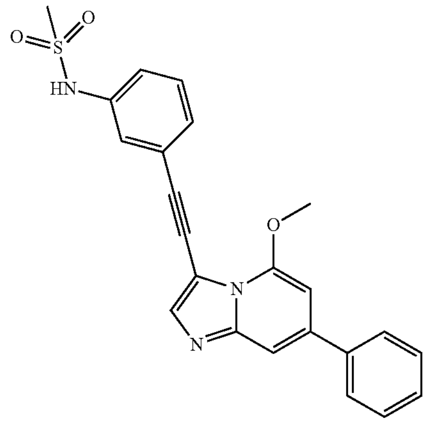 [SMILES: COc1cc(-c2ccccc2)cc2ncc(C#Cc3cccc(NS(C)(=O)=O)c3)n12] | N-{3-[(5-methoxy-7-phenylimidazo[1,2-a]pyridin-3-yl)ethynyl]phenyl}methane sulfonamide | Calc'd 418.1, found 418.0 |

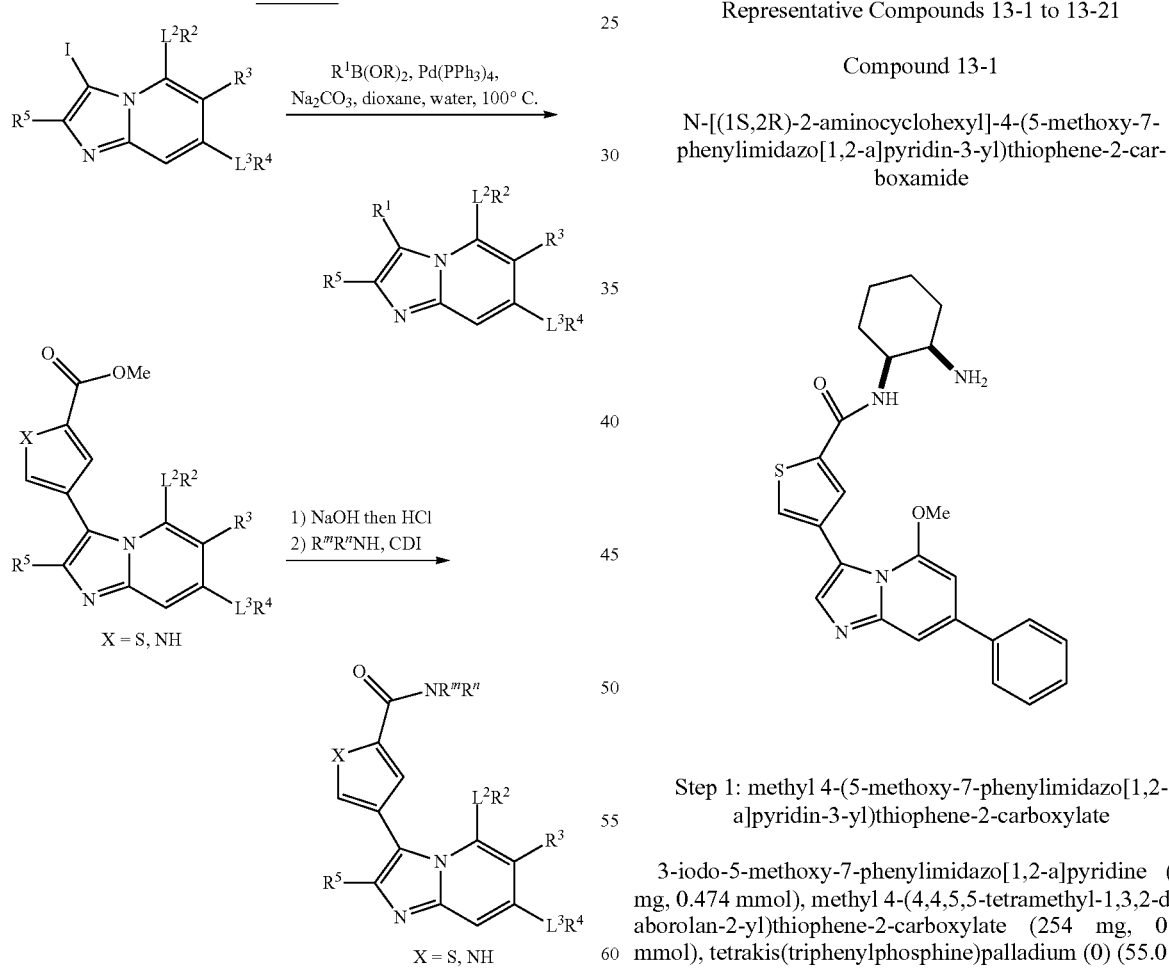

Wherein NR'''R'' is an amine group defined in L⁴R$^d$

B(OR)$_2$ is a boron ester such as tetramethyldioxaborolanyl.

EXAMPLES 13

Representative Compounds 13-1 to 13-21

Compound 13-1

N-[(1S,2R)-2-aminocyclohexyl]-4-(5-methoxy-7-phenylimidazo[1,2-a]pyridin-3-yl)thiophene-2-carboxamide Step 1: methyl 4-(5-methoxy-7-phenylimidazo[1,2-a]pyridin-3-yl)thiophene-2-carboxylate 3-iodo-5-methoxy-7-phenylimidazo[1,2-a]pyridine (166 mg, 0.474 mmol), methyl 4-(4,4,5,5-tetramethyl-1,3,2-dioxaborolan-2-yl)thiophene-2-carboxylate (254 mg, 0.948 mmol), tetrakis(triphenylphosphine)palladium (0) (55.0 mg, 0.047 mmol), and sodium bicarbonate (150 mg, 1.42 mmol) were added to a dry flask. Dioxane (5 ml) and water (0.5 ml) were added and the reaction mixture was sparged with argon for 3 minutes. The reaction mixture was heated to 90° C. After 6 h the reaction mixture was cooled to ambient temperature, diluted with ethyl acetate, washed with water, then dried over magnesium sulfate, filtered, and concentrated. The residue was purified by column chromatography on silica gel (ethyl acetate/dichloromethane gradient) to give methyl 4-(5-methoxy-7-phenylimidazo[1,2-a]pyridin-3-yl)thiophene-2-carboxylate. LRMS (ESI) calculated for $C_{20}H_{17}N_2O_3S$ [M+H]$^+$, 365.1 found 365.0.

Step 2: 4-(5-methoxy-7-phenylimidazo[1,2-a]pyridin-3-yl)thiophene-2-carboxylic acid To a solution of methyl 4-(5-methoxy-7-phenylimidazo[1,2-a]pyridin-3-yl)thiophene-2-carboxylate (94 mg, 0.26 mmol) in methanol (10 ml) and water (0.5 ml) was added a 5M aqueous solution of sodium hydroxide (0.50 ml, 2.5 mmol). The reaction mixture was heated to 70° C. After 1 h the reaction mixture was cooled and quenched with a 1N solution of hydrochloric acid (2.5 ml, 2.5 mmol), and then partially concentrated to precipitate yellow solids. The solids were washed with water and dried under vacuum to give 4-(5-methoxy-7-phenylimidazo[1,2-a]pyridin-3-yl) thiophene-2-carboxylic acid. LRMS (ESI) calculated for $C_{19}H_{15}N_2O_3S$ [M+H]$^+$, 351.1 found 351.0.

Step 3: N-[(1S,2R)-2-aminocyclohexyl]-4-(5-methoxy-7-phenylimidazo[1,2-a]pyridin-3-yl)thiophene-2-carboxamide To a solution of 4-(5-methoxy-7-phenylimidazo[1,2-a]pyridin-3-yl)thiophene-2-carboxylic acid (10.0 mg, 0.029 mmol) in N,N-dimethylformamide (1 ml) was added 1,1'-carbonyldiimidazole (7.0 mg, 0.043 mmol). After 20 minutes cis-1,2-cyclohexanediamine (0.034 ml, 0.29 mmol) was added. After 10 minutes the reaction mixture was purified directly by preparative HPLC Reverse phase (C-18), eluting with acetonitrile/water+0.05% TFA to give N-[(1S,2R)-2-aminocyclohexyl]-4-(5-methoxy-7-phenylimidazo[1,2-a] pyridin-3-yl)thiophene-2-carboxamide. $^1$H NMR (600 MHz, DMSO-d$_6$) δ 8.13 (s, 1H); 7.85 (d, 2H); 7.74 (d, 1H); 7.59 (s, 1H); 7.54 (d, 1H); 7.47-7.49 (m, 2H); 7.38-7.41 (m, 1H); 6.66 (d, 1H); 3.99 (s, 3H); 1.50-1.72 (m, 7H); 1.29-1.36 (m, 3H). LRMS (ESI) calculated for $C_{25}H_{27}N_4O_2S$ [M+H]$^+$, 447.2 found 447.1.

The compounds in the following table were prepared according to the procedure described in scheme 13 and for compound 13-1. The compounds were prepared as free bases.

TABLE 13

| Compound | Structure | Name | [M + H]+ |
|---|---|---|---|
| 13-2 | 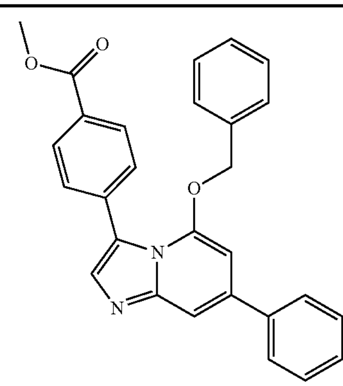 | methyl 4-[5-(benzyloxy)-7-phenylimidazo[1,2-a]pyridin-3-yl]benzoate | Calc'd 435.2, found 435.0 |
| 13-3 | 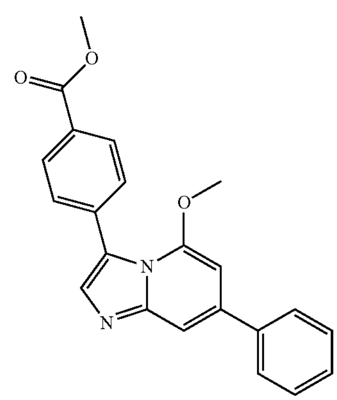 [SMILES: COC(=O)c1ccc(-c2cnc3cc(-c4ccccc4)cc(OC)n23)cc1] | methyl 4-(5-methoxy-7-phenylimidazo[1,2-a]pyridin-3-yl)benzoate | Calc'd 359.1, found 359.0 |
| 13-4 | 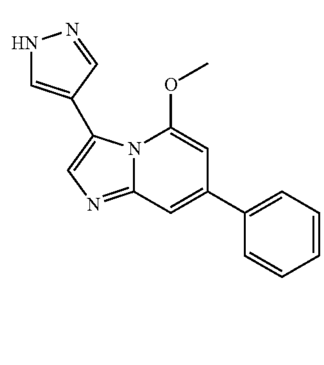 [SMILES: COc1cc(-c2ccccc2)cc2ncc(-c3cn[nH]c3)n12] | 5-methoxy-7-phenyl-3-(1H-pyrazol-4-yl)imidazo[1,2-a]pyridine | Calc'd 291.1, found 291.0 |

TABLE 13-continued

| Compound | Structure | Name | [M + H]+ |
|---|---|---|---|
| 13-5 | 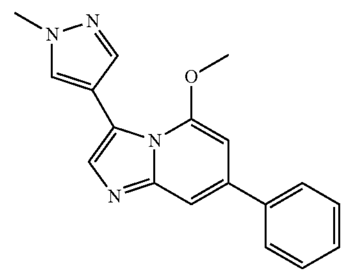 [SMILES: COc1cc(-c2ccccc2)cc2ncc(-c3cnn(C)c3)n12] | 5-methoxy-3-(1-methyl-1H-pyrazol-4-yl)-7-phenylimidazo[1,2-a]pyridine | Calc'd 305.1, found 305.0 |
| 13-6 | 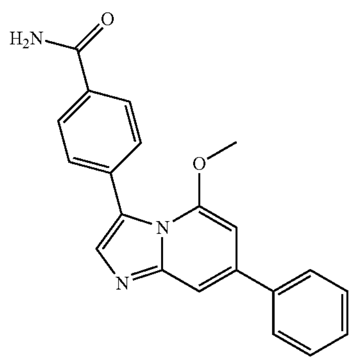 [SMILES: COc1cc(-c2ccccc2)cc2ncc(-c3ccc(C(N)=O)cc3)n12] | 4-(5-methoxy-7-phenylimidazo[1,2-a]pyridin-3-yl)benzamide | Calc'd 344.1, found 344.0 |
| 13-7 | 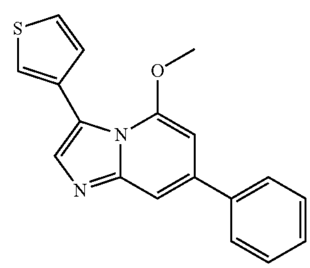 [SMILES: COc1cc(-c2ccccc2)cc2ncc(-c3ccsc3)n12] | 5-methoxy-7-phenyl-3-(3-thienyl)imidazo[1,2-a]pyridine | Calc'd 307.1, found 307.0 |
| 13-8 | 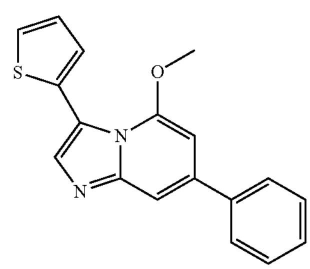 [SMILES: COc1cc(-c2ccccc2)cc2ncc(-c3cccs3)n12] | 5-methoxy-7-phenyl-3-(2-thienyl)imidazo[1,2-a]pyridine | Calc'd 307.1, found 307.0 |
| 13-9 | 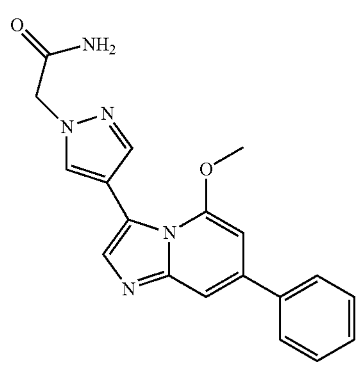 [SMILES: COc1cc(-c2ccccc2)cc2ncc(-c3cnn(CC(N)=O)c3)n12] | 2-[4-(5-methoxy-7-phenylimidazo[1,2-a]pyridin-3-yl)-1H-pyrazol-1-yl]acetamide | Calc'd 348.1, found 348.1 |

TABLE 13-continued

| Compound | Structure | Name | [M + H]+ |
|---|---|---|---|
| 13-10 | 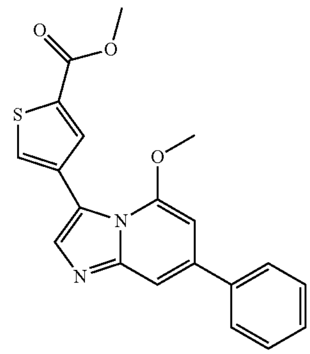 [SMILES: COC(=O)c1cc(-c2cnc3cc(-c4ccccc4)cc(OC)n23)cs1] | methyl 4-(5-methoxy-7-phenylimidazo[1,2-a]pyridin-3-yl)thiophene-2-carboxylate | Calc'd 365.1, found 365.0 |
| 13-11 | 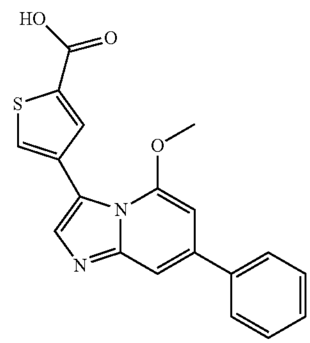 [SMILES: COc1cc(-c2ccccc2)cc2ncc(-c3csc(C(=O)O)c3)n12] | 4-(5-methoxy-7-phenylimidazo[1,2-a]pyridin-3-yl)thiophene-2-carboxylic acid | Calc'd 351.1, found 351.0 |
| 13-12 | 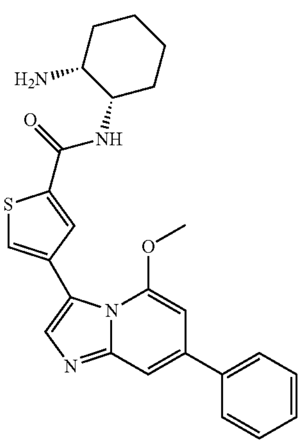 [SMILES: COc1cc(-c2ccccc2)cc2ncc(-c3csc(C(=O)N[C@H]4CCCC[C@H]4N)c3)n12] | N-[(1S,2R)-2-aminocyclohexyl]-4-(5-methoxy-7-phenylimidazo[1,2-a]pyridin-3-yl)thiophene-2-carboxamide | Calc'd 447.2, found 447.1 |
| 13-13 | 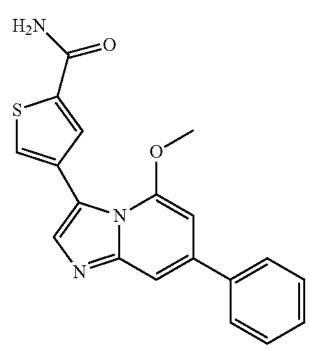 | 4-(5-methoxy-7-phenylimidazo[1,2-a]pyridin-3-yl)thiophene-2-carboxamide | Calc'd 350.1, found 350.0 |

TABLE 13-continued

| Compound | Structure | Name | [M + H]+ |
| --- | --- | --- | --- |
| 13-14 | 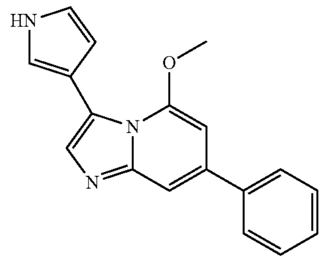 [SMILES: COc1cc(-c2ccccc2)cc2ncc(-c3cc[nH]c3)n12] | 5-methoxy-7-phenyl-3-(1H-pyrrol-3-yl)-imidazo[1,2-a]pyridine | Calc'd 290.1, found 290.0 |
| 13-15 | 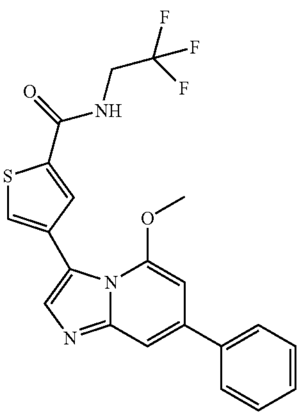 [SMILES: COc1cc(-c2ccccc2)cc2ncc(-c3csc(C(=O)NCC(F)(F)F)c3)n12] | 4-(5-methoxy-7-phenylimidazo[1,2-a]pyridin-3-yl)-N-(2,2,2-trifluoroethyl)thiophene-2-carboxamide | Calc'd 432.1, found 432.0 |
| 13-16 | 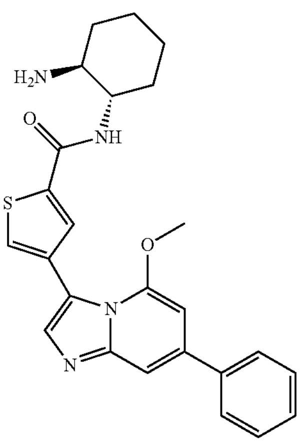 [SMILES: COc1cc(-c2ccccc2)cc2ncc(-c3csc(C(=O)N[C@H]4CCCC[C@@H]4N)c3)n12] | N-[(1S,2S)-2-aminocyclohexyl]-4-(5-methoxy-7-phenylimidazo[1,2-a]pyridin-3-yl)thiophene-2-carboxamide | Calc'd 447.2, found 447.0 |
| 13-17 | 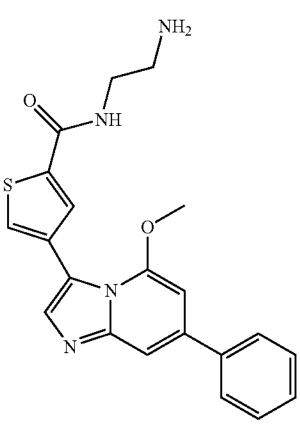 [SMILES: COc1cc(-c2ccccc2)cc2ncc(-c3csc(C(=O)NCCN)c3)n12] | N-(2-aminoethyl)-4-(5-methoxy-7-phenylimidazo[1,2-a]pyridin-3-yl)thiophene-2-carboxamide | Calc'd 393.1, found 393.0 |

TABLE 13-continued

| Compound | Structure | Name | [M + H]+ |
|---|---|---|---|
| 13-18 | 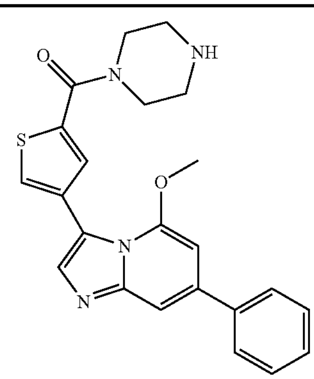 | 5-methoxy-7-phenyl-3-[5-(piperazin-1-ylcarbonyl)-3-thienyl]imidazo[1,2-a]pyridine | Calc'd 419.2, found 419.0 |
| 13-19 | 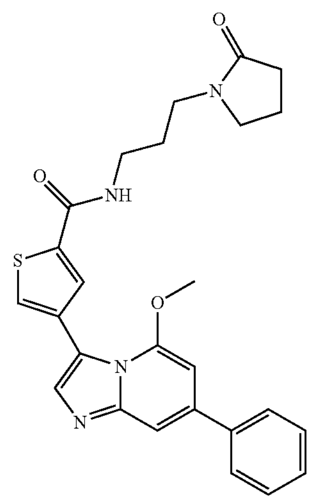 [SMILES: COc1cc(-c2ccccc2)cc2ncc(-c3csc(C(=O)NCCCN4CCCC4=O)c3)n12] | 4-(5-methoxy-7-phenylimidazo[1,2-a]pyridin-3-yl)-N-[3-(2-oxopyrrolidin-1-yl)propyl]thiophene-2-carboxamide | Calc'd 475.2, found 475.0 |
| 13-20 | 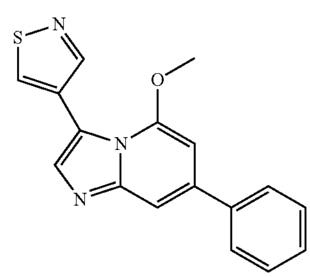 [SMILES: COc1cc(-c2ccccc2)cc2ncc(-c3cnsc3)n12] | 3-isothiazol-4-yl-5-methoxy-7-phenylimidazo[1,2-a]pyridine | Calc'd 308.1, found 308.0 |
| 13-21 | 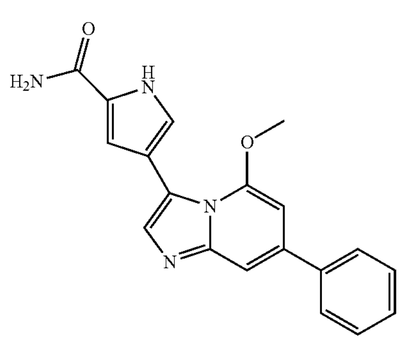 [SMILES: COc1cc(-c2ccccc2)cc2ncc(-c3c[nH]c(C(N)=O)c3)n12] | 4-(5-methoxy-7-phenylimidazo[1,2-a]pyridin-3-yl)-1H-pyrrole-2-carboxamide | Calc'd 333.1, found 333.0 |

What is claimed is:

1. A compound of formula I:

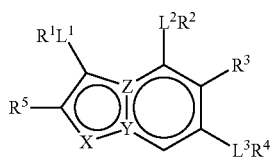

wherein:
either X and Y are both N and Z is C, or X and Z are both N and Y is C;
$L^1$ is selected from —(C≡C)(C=O)NH—, —(C≡C)(CH$_2$)$_2$NH—, —(C≡C)$_2$—, —(C≡C)—, —(C≡C)(CHOH)—, —(C≡C)(CH$_2$)NH(C=O)—, or —(C≡C)(CH$_2$)NH(C=O)—;
a is 1 or 2;
b is 0 or 1;
c is 0 or 1;
d is 0, 1, 2, 3, 4, 5 or 6;
$L^2$ is —O(CR$^a$R$^b$)$_d$— or —(NR$^c$)(C=O)$_b$—;
$L^3$ is a direct bond, —C≡C— or —(HC=CH)$_e$(CR$^a$R$^b$)$_d$(NR$^c$)$_c$—;
e is 0 or 1;
$R^1$ is hydrogen, hydroxy, cyano, halogen, $C_{1-6}$alkyl, $C_{2-10}$alkenyl, haloC$_{1-6}$alkyl, hydroxyC$_{1-6}$alkyl, $C_{1-6}$alkylcarbonyl, $C_{1-6}$alkoxy, haloC$_{1-6}$alkoxy, $C_{1-6}$alkoxycarbonyl, carboxy, nitro, N(R$^x$)$_2$, SO$_2$R$^x$, Si(R$^x$)$_3$ or a ring which is: $C_{6-10}$aryl, $C_{3-10}$cycloalkyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O, and S, not more than one heteroatom of which is O or S, a 6 membered heteroaromatic ring containing 1, 2 or 3 N atoms or a 7-15 membered unsaturated, partially saturated or saturated heterocyclic ring containing 1, 2, 3 or 4 heteroatoms independently selected from N, O and S; optionally substituted by one, two or three groups independently selected from $L^4$-R$^d$;
$R^2$ is selected from hydroxy, cyano, halogen, $C_{1-6}$alkyl, $C_{2-10}$alkenyl, haloC$_{1-6}$alkyl, hydroxyC$_{1-6}$alkyl, $C_{1-6}$alkylcarbonyl, $C_{1-6}$alkoxy, haloC$_{1-6}$alkoxy, $C_{1-6}$alkoxycarbonyl, carboxy, nitro, N(R$^x$)$_2$ or a ring which is: $C_{6-10}$aryl, $C_{3-10}$cycloalkyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 nitrogen atoms or a 7-15 membered unsaturated, partially saturated or saturated heterocyclic ring containing 1, 2, 3 or 4 heteroatoms independently selected from N, O and S; any of which rings being optionally substituted by one, two or three groups independently selected from R$^e$;
$R^3$ is selected from hydrogen, hydroxy, cyano, halogen, $C_{1-6}$alkyl, $C_{2-10}$alkenyl, haloC$_{1-6}$alkyl, hydroxy $C_{1-6}$alkyl, $C_{1-6}$alkylcarbonyl, $C_{1-6}$alkoxy, haloC$_{1-6}$alkoxy, $C_{1-6}$alkoxycarbonyl, carboxy, nitro, N(R$^x$)$_2$ or a ring which is: $C_{6-10}$aryl, $C_{6-10}$arylC$_{1-6}$alkyl, $C_{3-10}$cycloalkyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 nitrogen atoms or a 7-15 membered unsaturated, partially saturated or saturated heterocyclic ring containing 1, 2, 3 or 4 heteroatoms independently selected from N, O and S; any of which rings being optionally substituted by one, two or three groups independently selected hydroxy, cyano, halogen, $C_{1-6}$alkyl, $C_{2-10}$alkenyl, haloC$_{1-6}$alkyl and hydroxyC$_{1-6}$alkyl;
$R^4$ is selected from hydrogen, hydroxy, cyano, halogen, $C_{1-6}$alkyl, $C_{2-10}$alkenyl, haloC$_{1-6}$alkyl, hydroxy $C_{1-6}$alkyl, $C_{1-6}$alkylcarbonyl, $C_{1-6}$alkoxy, haloC$_{1-6}$alkoxy, $C_{1-6}$alkoxycarbonyl, carboxy, nitro, N(R$^x$)$_2$ or a ring which is: $C_{6-10}$aryl, $C_{6-10}$arylC$_{1-6}$alkyl, $C_{3-10}$cycloalkyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 nitrogen atoms or a 7-15 membered unsaturated, partially saturated or saturated heterocyclic ring containing 1, 2, 3 or 4 heteroatoms independently selected from N, O and S; any of which rings being optionally substituted by one, two or three groups independently selected from $L^5$-R$^f$;
$R^5$ is hydrogen, hydroxy, cyano, halogen, $C_{1-6}$alkyl, $C_{2-10}$alkenyl, haloC$_{1-6}$alkyl, hydroxyC$_{1-6}$alkyl, $C_{1-6}$alkylcarbonyl, $C_{1-6}$alkoxy, haloC$_{1-6}$alkoxy, $C_{1-6}$alkoxycarbonyl, carboxy, nitro or N(R$^x$)$_2$;
$L^4$ is a direct bond, —(CR$^a$R$^b$)$_d$(C=O)$_b$(NR$^c$)$_c$(C=O)$_b$(O)$_g$(CR$^a$R$^b$)$_d$(NR$^c$)$_c$— or —(NR$^c$)$_c$(SO$_2$)$_f$(NR$^c$)$_c$(CR$^a$R$^b$)$_d$;
$L^5$ is a direct bond or —(C=O)$_b$(NR$^c$)$_c$(C=O)$_b$(CR$^a$R$^b$)$_d$—;
f is 0 or 1;
g is 0 or 1;
each of R$^a$ and R$^b$ is independently hydrogen, hydroxy, halogen, $C_{1-6}$alkyl, $C_{2-10}$alkenyl, haloC$_{1-6}$alkyl, hydroxyC$_{1-6}$alkyl, $C_{1-6}$alkoxy or haloC$_{1-6}$alkoxy;
R$^c$ is hydrogen or $C_{1-6}$alkyl;
R$^d$ is hydroxy, oxo, cyano, halogen, $C_{1-6}$alkyl, $C_{2-10}$alkenyl, haloC$_{1-6}$alkyl, hydroxyC$_{1-6}$alkyl, $C_{1-6}$alkylcarbonyl, $C_{1-6}$alkoxy, haloC$_{1-6}$alkoxy, amino, (C$_{1-6}$alkyl)amino, di(C$_{1-6}$alkyl)amino or a ring which is: $C_{6-10}$aryl, $C_{3-10}$cycloalkyl, azetidinyl, a 5, 6 or 7 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O, and S, not more than one heteroatom of which is O or S or a 6 membered heteroaromatic ring containing 1, 2 or 3 N atoms; any of which rings being optionally substituted by one, two or three groups independently selected from hydroxy, oxo, cyano, halogen, $C_{1-6}$alkyl, $C_{2-10}$alkenyl, haloC$_{1-6}$alkyl, hydroxyC$_{1-6}$alkyl, $C_{1-6}$alkylcarbonyl, $C_{1-6}$alkoxy, haloC$_{1-6}$alkoxy, $C_{1-6}$alkoxycarbonyl, carboxy, nitro, amino, (C$_{1-6}$alkyl)amino and di(C$_{1-6}$alkyl)amino;

R$^e$ is hydroxy, cyano, halogen, C$_{1-6}$alkyl, C$_{2-10}$alkenyl, haloC$_{1-6}$alkyl, hydroxyC$_{1-6}$alkyl, C$_{1-6}$alkylcarbonyl, C$_{1-6}$alkoxy, haloC$_{1-6}$alkoxy, C$_{1-6}$alkoxycarbonyl, carboxy, or SO$_2$R$^x$;

R$^f$ is hydroxy, oxo, cyano, halogen, C$_{1-6}$alkyl, C$_{2-10}$alkenyl, haloC$_{1-6}$alkyl, hydroxyC$_{1-6}$alkyl, C$_{1-6}$alkylcarbonyl, C$_{1-6}$alkoxy, haloC$_{1-6}$alkoxy or a ring which is: C$_{6-10}$aryl, C$_{3-10}$cycloalkyl, azetidinyl, a 5, 6 or 7 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O, and S, not more than one heteroatom of which is O or S or a 6 membered heteroaromatic ring containing 1, 2 or 3 N atoms; any of which rings being optionally substituted by one, two or three groups independently selected from hydroxy, oxo, cyano, halogen, C$_{1-6}$alkyl, C$_{2-10}$alkenyl, haloC$_{1-6}$alkyl, hydroxyC$_{1-6}$alkyl, C$_{1-6}$alkylcarbonyl, C$_{1-6}$alkoxy, haloC$_{1-6}$alkoxy, C$_{1-6}$alkoxycarbonyl, carboxy, nitro, amino, (C$_{1-6}$alkyl)amino and di(C$_{1-6}$alkyl)amino;

each of R$^x$ and R$^y$ is independently hydrogen or C$_{1-6}$alkyl; or a pharmaceutically acceptable salt, stereoisomer or tautomer thereof.

2. A pharmaceutical composition comprising a compound of claim 1, or a pharmaceutically acceptable salt, stereoisomer or tautomer thereof in association with a pharmaceutically acceptable carrier.

3. A compound of claim 1, or a pharmaceutically acceptable salt, stereoisomer, tautomer thereof and an anti-cancer agent for simultaneous, separate or sequential administration.

4. A compound of claim 1, or a pharmaceutically acceptable salt, stereoisomer or tautomer thereof, for use in therapy.

5. A compound of claim 1, or a pharmaceutically acceptable salt, stereoisomer or tautomer thereof, for use in the treatment of one or more conditions ameliorated by inhibition of one or more of the kinases selected from PDK1, FGFR3, NTRK3, RP-S6K, WEE1 and MARK.

6. A method of treating one or more conditions ameliorated by inhibition of one or more of the kinases selected from PDK1, FGFR3, NTRK3, RP-S6K, WEE1 and MARK, which method comprises administration to a patient in need thereof of an effective amount of a compound of claim 1 or a composition comprising a compound of claim 1.

7. A compound which is selected from:
6-bromo-4-methoxypyrazolo[1,5-a]pyridine;
2-amino-6-bromo-4-methoxypyrazolo[1,5-a]pyridine-3-carbonitrile;
methyl 6-bromo-4-methoxy-2-methylpyrazolo[1,5-a]pyridine-3-carboxylate;
3-iodo-4-methoxy-6-(1-methyl-1H-pyrazol-4-yl)pyrazolo[1,5-a]pyridine;
3-Chloro-4-methoxy-6-(4-methyl-3-thienyl)pyrazolo[1,5-a]pyridine;
3-Chloro-4-methoxy-N-4-pyridinylpyrazolo[1,5-a]pyridin-6-amine;
4-methoxy-6-(1-methyl-1H-pyrazol-4-yl)pyrazolo[1,5-a]pyridine-3-carbonitrile;
4-methoxy-6-phenylpyrazolo[1,5-a]pyridine-3-carbonitrile;
6-bromo-3-iodo-4-methoxypyrazolo[1,5-a]pyridine;
tert-Butyl ((2E)-3-(3-chloro-4-methoxypyrazolo[1,5-a]pyridine-6-yl)-2-propen-1-yl)carbamate;
(2E)-3-(3-Chloro-4-methoxypyrazolo[1,5-a]pyridine-6-yl)-2-propen-1-amine;
3-Chloro-6-ethyl-4-methoxypyrazolo[1,5-a]pyridine;

4-methoxy-6-(1-methyl-1H-pyrazol-4-yl)pyrazolo[1,5-a]pyridine;
6-bromo-4-methoxypyrazolo[1,5-a]pyridine-3-carbonitrile;
3-bromo-4-methoxy-6-(1-methyl-1H-pyrazol-4-yl)pyrazolo[1,5-a]pyridine;
3-chloro-4-methoxy-6-(1-methyl-1H-pyrazol-4-yl)pyrazolo[1,5-a]pyridine;
4-(3-chloro-4-methoxypyrazolo[1,5-a]pyridin-6-yl)-N-(2-furylmethyl)benzamide;
3-chloro-4-methoxy-6-[4-(morpholin-4-ylcarbonyl)phenyl]pyrazolo[1,5-a]pyridine;
3-chloro-4-methoxy-6-(6-morpholin-4-ylpyridin-3-yl)pyrazolo[1,5-a]pyridine;
3-chloro-4-methoxy-6-[2-(4-methylpiperazin-1-yl)pyridin-4-yl]pyrazolo[1,5-a]pyridine;
5-(3-chloro-4-methoxypyrazolo[1,5-a]pyridin-6-yl)-N,N-dimethylpyridin-2-amine;
3-chloro-6-(3-furyl)-4-methoxypyrazolo[1,5-a]pyridine;
N-[4-(3-chloro-4-methoxypyrazolo[1,5-a]pyridin-6-yl)phenyl]morpholine-4-carboxamide;
3-chloro-4-methoxy-6-[4-(2-oxa-5-azabicyclo[2.2.1]hept-5-ylcarbonyl)phenyl]pyrazolo[1,5-a]pyridine;
3-chloro-4-methoxy-6-{4-[(4-methoxypiperidin-1-yl)carbonyl]phenyl}pyrazolo[1,5-a]pyridine;
3-chloro-4-methoxy-6-(4-pyridin-4-ylphenyl)pyrazolo[1,5-a]pyridine;
4-(3-chloro-4-methoxypyrazolo[1,5-a]pyridin-6-yl)-N-phenylbenzamide;
4-(3-chloro-4-methoxypyrazolo[1,5-a]pyridin-6-yl)-N-(2-methoxyethyl)benzamide;
5-(3-chloro-4-methoxypyrazolo[1,5-a]pyridin-6-yl)pyridin-2-amine;
5-(3-chloro-4-methoxypyrazolo[1,5-a]pyridin-6-yl)pyridin-2-ol;
3-iodo-4-methoxy-2-methyl-6-(1-methyl-1H-pyrazol-4-yl)pyrazolo[1,5-a]pyridine;
3-chloro-4-methoxy-1-phenylpyrazolo[1,5-a]pyridin-6-amine;
3-chloro-4-methoxy-6-(4-morpholinyl)pyrazolo[1,5-a]pyridine;
3-chloro-6-((E)-2-cyclopropylvinyl)-4-methoxypyrazolo[1,5-a]pyridine;
3-chloro-4-methoxy-6-((1E)-3-methoxyvinyl)-4-methoxypyrazolo[1,5-a]pyridine;
3-chloro-6-(4-fluorobenzyl)-4-methoxypyrazolo[1,5-a]pyridine;
5-(2-(3-chloro-4-methoxypyrazolo[1,5-a]pyridin-6-yl)ethyl)-2,2-dimethyl-1,3-dioxan-5-ol;
5-(3-chloro-4-methoxypyrazolo[1,5-a]pyridin-6-yl)pyrimidin-2-amine;
3-chloro-4-methoxy-6-(4-methyl-3-thienyl)pyrazolo[1,5-a]pyridine;
4-methoxy-6-(1-methyl-1H-pyrazol-4-yl)-3-(pyridin-3-ylethynyl)pyrazolo[1,5-a]pyridine;
3-(cyclopropylethynyl)-4-methoxy-6-(1-methyl-1H-pyrazol-4-yl)pyrazolo[1,5-a]pyridine;
3-{4-[3-(cyclopropylethynyl)-4-methoxypyrazolo[1,5-a]pyridin-6-yl]-1H-pyrazol-1-yl}-2-fluoropropan-1-ol;
4-methoxy-3-[(5-methyl-1-phenyl-1H-pyrazol-4-yl)ethynyl]-6-(1-methyl-1H-pyrazol-4-yl)pyrazolo[1,5-a]pyridine;
4-methoxy-6-(1-methyl-1H-pyrazol-4-yl)-3-[(5-methyl-1-pyridin-2-yl-1H-pyrazol-4-yl)ethynyl]pyrazolo[1,5-a]pyridine;

4-methoxy-6-(1-methyl-1H-pyrazol-4-yl)-3-[(3-methyl-1-pyridin-2-yl-1H-pyrazol-4-yl)ethynyl]pyrazolo[1,5-a]pyridine;

3-[(3,5-dimethyl-1-phenyl-1H-pyrazol-4-yl)ethynyl]-4-methoxy-6-(1-methyl-1H-pyrazol-4-yl)pyrazolo[1,5-a]pyridine;

3-[(5-ethyl-1-phenyl-1H-pyrazol-4-yl)ethynyl]-4-methoxy-6-(1-methyl-1H-pyrazol-4-yl)pyrazolo[1,5-a]pyridine;

3-[(5-cyclopropyl-1-phenyl-1H-pyrazol-4-yl)ethynyl]-4-methoxy-6-(1-methyl-1H-pyrazol-4-yl)pyrazolo[1,5-a]pyridine;

4-methoxy-6-(1-methyl-1H-pyrazol-4-yl)-3-{[5-methyl-1-(2-thienyl)-1H-pyrazol-4-yl]ethynyl}pyrazolo[1,5-a]pyridine;

4-methoxy-6-(1-methyl-1H-pyrazol-4-yl)-3-{[1-methyl-2-(2-thienyl)-1H-imidazol-5-yl]ethynyl}pyrazolo[1,5-a]pyridine;

3-methoxy-N-(4-{[4-methoxy-6-(1-methyl-1H-pyrazol-4-yl)pyrazolo[1,5-a]pyridin-3-yl]ethynyl}pyridin-2-yl)benzenesulfonamide;

N-(4-{[4-methoxy-6-(1-methyl-1H-pyrazol-4-yl)pyrazolo[1,5-a]pyridin-3-yl]ethynyl}pyridin-2-yl)-N'-phenylurea;

pyridin-3-ylmethyl 3-{[4-methoxy-6-(1-methyl-1H-pyrazol-4-yl)pyrazolo[1,5-a]pyridin-3-yl]ethynyl}azetidine-1-carboxylate;

6-bromo-3-(cyclopropylethynyl)-4-methoxypyrazolo[1,5-a]pyridine;

4-methoxy-6-(1-methyl-1H-pyrazol-4-yl)-3-[(trimethylsilyl)ethynyl]pyrazolo[1,5-a]pyridine;

3-ethynyl-4-methoxy-6-(1-methyl-1H-pyrazol-4-yl)pyrazolo[1,5-a]pyridine;

4-methoxy-3-[(4-methoxyphenyl)ethynyl]-6-(1-methyl-1H-pyrazol-4-yl)pyrazolo[1,5-a]pyridine;

3,6-bis(cyclopropylethynyl)-4-methoxypyrazolo[1,5-a]pyridine;

3-(cyclopropylethynyl)-4-methoxy-6-phenylpyrazolo[1,5-a]pyridine;

3-(cyclopropylethynyl)-4-methoxy-6-(1H-pyrazol-5-yl)pyrazolo[1,5-a]pyridine;

3-(4-methoxy-6-phenylpyrazolo[1,5-a]pyridine-3-yl)prop-2-yn-1-ol;

3-(4-methoxy-6-phenylpyrazolo[1,5-a]pyridine-3-yl)prop-2-ynamide;

4-methoxy-3-[(4-methoxyphenyl)ethynyl]-6-phenylpyrazolo[1,5-a]pyridine;

4-methoxy-6-phenyl-3-(pyridine-3-ylethynyl)pyrazolo[1,5-a]pyridine;

3-(cyclopropylethynyl)-4-methoxy-6-pyridin-4-ylpyrazolo[1,5-a]pyridine;

4-methoxy-3-[(1-methyl-1H-imidazol-5-yl)ethynyl]-6-(1-methyl-1H-pyrazol-4-yl)pyrazolo[1,5-a]pyridine;

N-(3-{[4-methoxy-6-(1-methyl-1H-pyrazol-4-yl)pyrazolo[1,5-a]pyridine-3-yl]ethynyl}phenyl)acetamide;

3-(cyclopropylethynyl)-4-methoxy-6-pyridin-3-ylpyrazolo[1,5-a]pyridine;

3-(cyclopropylethynyl)-4-methoxy-6-pyrimidin-5-ylpyrazolo[1,5-a]pyridine;

N-{4-[4-methoxy-6-(1-methyl-1H-pyrazol-4-yl)pyrazolo[1,5-a]pyridine-3-yl]but-3-yn-1-yl}methanesulfonamide;

tert-butyl 3-{3-[4-methoxy-6-(1-methyl-1H-pyrazol-4-yl)pyrazolo[1,5-a]pyridine-3-yl]prop-2-yn-1-yl}pyrrolidine-1-carboxylate;

tert-butyl 2-{3-[4-methoxy-6-(1-methyl-1H-pyrazol-4-yl)pyrazolo[1,5-a]pyridine-3-yl]prop-2-yn-1-yl}pyrrolidine-1-carboxylate;

4-methoxy-6-(1-methyl-1H-pyrazol-4-yl)-3-(pyridine-4-ylethynyl)pyrazolo[1,5-a]pyridine;

5-{[4-methoxy-6-(1-methyl-1H-pyrazol-4-yl)pyrazolo[1,5-a]pyridine-3-yl]ethynyl}pyridine-2-amine;

4-{[4-methoxy-6-(1-methyl-1H-pyrazol-4-yl)pyrazolo[1,5-a]pyridine-3-yl]ethynyl}pyridine-2-amine;

tert-butyl 3-{[4-methoxy-6-(1-methyl-1H-pyrazol-4-yl)pyrazolo[1,5-a]pyridine-3-yl]ethynyl}azetidine-1-carboxylate;

tert-butyl 3-{[4-methoxy-6-(1-methyl-1H-pyrazol-4-yl)pyrazolo[1,5-a]pyridine-3-yl]ethynyl}pyrrolidine-1-carboxylate;

tert-butyl 4-{[4-methoxy-6-(1-methyl-1H-pyrazol-4-yl)pyrazolo[1,5-a]pyridine-3-yl]ethynyl}piperidine-1-carboxylate;

4-methoxy-6-(1-methyl-1H-pyrazol-4-yl)-3-[(6-pyrrolidin-1-ylpyridin-3-yl)ethynyl]pyrazolo[1,5-a]pyridine;

1-(3-{[4-methoxy-6-(1-methyl-1H-pyrazol-4-yl)pyrazolo[1,5-a]pyridine-3-yl]ethynyl}phenyl)ethanone;

3-{[4-methoxy-6-(1-methyl-1H-pyrazol-4-yl)pyrazolo[1,5-a]pyridine-3-yl]ethynyl}phenol;

3-[(3,5-dimethyl-1H-pyrazol-4-yl)ethynyl]-4-methoxy-6-(1-methyl-1H-pyrazol-4-yl)pyrazolo[1,5-a]pyridine;

3-[(3,5-dimethylisoxazol-4-yl)ethynyl]-4-methoxy-6-(1-methyl-1H-pyrazol-4-yl)pyrazolo[1,5-a]pyridine;

4-{[4-methoxy-6-(1-methyl-1H-pyrazol-4-yl)pyrazolo[1,5-a]pyridine-3-yl]ethynyl}-N,N-dimethyl-1H-imidazole-1-sulfonamide;

4-methoxy-6-(1-methyl-1H-pyrazol-4-yl)-3-[(1-methyl-1H-pyrazol-4-yl)ethynyl]pyrazolo[1,5-a]pyridine;

4-{[4-methoxy-6-(1-methyl-1H-pyrazol-4-yl)pyrazolo[1,5-a]pyridine-3-yl]ethynyl}pyridine-2-carboxamide;

4-methoxy-3-[(6-methoxypyridin-3-yl)ethynyl]-6-(1-methyl-1H-pyrazol-4-yl)pyrazolo[1,5-a]pyridine;

5-{[4-methoxy-6-(1-methyl-1H-pyrazol-4-yl)pyrazolo[1,5-a]pyridine-3-yl]ethynyl}pyridine-2-ol;

3-[(2-chloropyridin-4-yl)ethynyl]-4-methoxy-6-(1-methyl-1H-pyrazol-4-yl)pyrazolo[1,5-a]pyridine;

4-methoxy-3-[(1-methyl-1H-imidazol-4-yl)ethynyl]-6-(1-methyl-1H-pyrazol-4-yl)pyrazolo[1,5-a]pyridine;

3-[(6-fluoropyridin-3-yl)ethynyl]-4-methoxy-6-(1-methyl-1H-pyrazol-4-yl)pyrazolo[1,5-a]pyridine;

5-{[4-methoxy-6-(1-methyl-1H-pyrazol-4-yl)pyrazolo[1,5-a]pyridine-3-yl]ethynyl}-1,3-thiazol-2-amine;

N-(4-{[4-methoxy-6-(1-methyl-1H-pyrazol-4-yl)pyrazolo[1,5-a]pyridin-3-yl]ethynyl}pyridin-2-yl)acetamide;

4-methoxy-6-(1-methyl-1H-pyrazol-4-yl)-3-(1,3-thiazol-2-ylethynyl)pyrazolo[1,5-a]pyridine;

4-methoxy-3-[(5-methylisoxazol-4-yl)ethynyl]-6-(1-methyl-1H-pyrazol-4-yl)pyrazolo[1,5-a]pyridine;

3-(1H-imidazol-4-ylethynyl)-4-methoxy-6-(1-methyl-1H-pyrazol-4-yl)pyrazolo[1,5-a]pyridine;

4-methoxy-6-(1-methyl-1H-pyrazol-4-yl)-3-[(1,3,5-trimethyl-1H-pyrazol-4-yl)ethynyl]pyrazolo[1,5-a]pyridine;

tert-butyl 4-{[4-methoxy-6-(1-methyl-1H-pyrazol-4-yl)pyrazolo[1,5-a]pyridin-3-yl]ethynyl}-1H-pyrazole-1-carboxylate;

4-methoxy-6-(1-methyl-1H-pyrazol-4-yl)-3-(1H-pyrazol-4-ylethynyl)pyrazolo[1,5-a]pyridine;

3-[(1-benzyl-1H-pyrazol-4-yl)ethynyl]-4-methoxy-6-(1-methyl-1H-pyrazol-4-yl)pyrazolo[1,5-a]pyridine;

3-(azetidin-3-ylethynyl)-4-methoxy-6-(1-methyl-1H-pyrazol-4-yl)pyrazolo[1,5-a]pyridine;

4-methoxy-3-[(2-methyl-1H-imidazol-4-yl)ethynyl]-6-(1-methyl-1H-pyrazol-4-yl)pyrazolo[1,5-a]pyridine;

4-methoxy-6-(1-methyl-1H-pyrazol-4-yl)-3-(pyrrolidin-3-ylethynyl)pyrazolo[1,5-a]pyridine;

methyl 4-{[4-methoxy-6-(1-methyl-1H-pyrazol-4-yl)pyrazolo[1,5-a]pyridin-3-yl]ethynyl}-1H-pyrrole-2-carboxylate;

3-{[4-methoxy-6-(1-methyl-1H-pyrazol-4-yl)pyrazolo[1,5-a]pyridin-3-yl]ethynyl}imidazo[1,2-a]pyridine;

3,3'-buta-1,3-diyne-1,4-diylbis[4-methoxy-6-(1-methyl-1H-pyrazol-4-yl)pyrazolo[1,5-a]pyridine];

4-{[4-methoxy-6-(1-methyl-1H-pyrazol-4-yl)pyrazolo[1,5-a]pyridin-3-yl]ethynyl}-1-methyl-1H-pyrazol-3-amine;

3-{[4-methoxy-6-(1-methyl-1H-pyrazol-4-yl)pyrazolo[1,5-a]pyridin-3-yl]ethynyl}imidazo[1,2-a]pyrazine;

3-[(5-tert-butyl-1,3,4-thiadiazol-2-yl)ethynyl]-4-methoxy-6-(1-methyl-1H-pyrazol-4-yl)pyrazolo[1,5-a]pyridine;

4-methoxy-6-(1-methyl-1H-pyrazol-4-yl)-3-[(5-methyl-1,3,4-thiadiazol-2-yl)ethynyl]pyrazolo[1,5-a]pyridine;

3-[(5-cyclopropyl-1,3,4-thiadiazol-2-yl)ethynyl]-4-methoxy-6-(1-methyl-1H-pyrazol-4-yl)pyrazolo[1,5-a]pyridine;

3-{[4-methoxy-6-(1-methyl-1H-pyrazol-4-yl)pyrazolo[1,5-a]pyridin-3-yl]ethynyl}-5,6,7,8-tetrahydroimidazo[1,2-a]pyridine;

3-[(5-ethyl-1,3,4-thiadiazol-2-yl)ethynyl]-4-methoxy-6-(1-methyl-1H-pyrazol-4-yl)pyrazolo[1,5-a]pyridine;

tert-butyl 3-{[4-methoxy-6-(1-methyl-1H-pyrazol-4-yl)pyrazolo[1,5-a]pyridin-3-yl]ethynyl}-5,6-dihydro[1,2,4]triazolo[4,3-a]pyrazine-7(8H)-carboxylate;

N-(5-{[4-methoxy-6-(1-methyl-1H-pyrazol-4-yl)pyrazolo[1,5-a]pyridin-3-yl]ethynyl}-1,3-thiazol-2-yl)acetamide;

3-{[4-methoxy-6-(1-methyl-1H-pyrazol-4-yl)pyrazolo[1,5-a]pyridin-3-yl]ethynyl}-6-methylimidazo[1,2-a]pyridine;

4-methoxy-3-[(1-methyl-2-phenyl-1H-imidazol-5-yl)ethynyl]-6-(1-methyl-1H-pyrazol-4-yl)pyrazolo[1,5-a]pyridine;

3-{[1-(2-fluorophenyl)-5-methyl-1H-pyrazol-4-yl]ethynyl}-4-methoxy-6-(1-methyl-1H-pyrazol-4-yl)pyrazolo[1,5-a]pyridine;

3-{[1-(4-chlorophenyl)-5-methyl-1H-pyrazol-4-yl]ethynyl}-4-methoxy-6-(1-methyl-1H-pyrazol-4-yl)pyrazolo[1,5-a]pyridine;

3-{[4-methoxy-6-(1-methyl-1H-pyrazol-4-yl)pyrazolo[1,5-a]pyridin-3-yl]ethynyl}-7-methylimidazo[1,2-a]pyridine;

3-{[1-(4-tert-butylphenyl)-5-methyl-1H-pyrazol-4-yl]ethynyl}-4-methoxy-6-(1-methyl-1H-pyrazol-4-yl)pyrazolo[1,5-a]pyridine;

3-{[1-(4-fluorophenyl)-5-methyl-1H-pyrazol-4-yl]ethynyl}-4-methoxy-6-(1-methyl-1H-pyrazol-4-yl)pyrazolo[1,5-a]pyridine;

3-{[1-(2-chlorophenyl)-5-methyl-1H-pyrazol-4-yl]ethynyl}-4-methoxy-6-(1-methyl-1H-pyrazol-4-yl)pyrazolo[1,5-a]pyridine;

3-{[4-methoxy-6-(1-methyl-1H-pyrazol-4-yl)pyrazolo[1,5-a]pyridin-3-yl]ethynyl}-8-methylimidazo[1,2-a]pyridine;

3-[(1,2-dimethyl-1H-imidazol-5-yl)ethynyl]-4-methoxy-6-(1-methyl-1H-pyrazol-4-yl)pyrazolo[1,5-a]pyridine;

4-methoxy-6-(1-methyl-1H-pyrazol-4-yl)-3-[(1-phenyl-1H-pyrazol-4-yl)ethynyl]pyrazolo[1,5-a]pyridine;

3-[(1,5-dimethyl-1H-pyrazol-4-yl)ethynyl]-4-methoxy-6-(1-methyl-1H-pyrazol-4-yl)pyrazolo[1,5-a]pyridine;

4-methoxy-3-{[5-methyl-1-(3-methylphenyl)-1H-pyrazol-4-yl]ethynyl}-6-(1-methyl-1H-pyrazol-4-yl)pyrazolo[1,5-a]pyridine;

4-methoxy-3-{[1-(3-methoxyphenyl)-5-methyl-1H-pyrazol-4-yl]ethynyl}-6-(1-methyl-1H-pyrazol-4-yl)pyrazolo[1,5-a]pyridine;

4-methoxy-6-(1-methyl-1H-pyrazol-4-yl)-3-[(5-methyl-1-pyridin-3-yl-1H-pyrazol-4-yl)ethynyl]pyrazolo[1,5-a]pyridine;

3-{[1-(3-chlorophenyl)-5-methyl-1H-pyrazol-4-yl]ethynyl}-4-methoxy-6-(1-methyl-1H-pyrazol-4-yl)pyrazolo[1,5-a]pyridine;

3-{[1-(3-fluorophenyl)-5-methyl-1H-pyrazol-4-yl]ethynyl}-4-methoxy-6-(1-methyl-1H-pyrazol-4-yl)pyrazolo[1,5-a]pyridine;

4-methoxy-3-{[1-(2-methoxyphenyl)-5-methyl-1H-pyrazol-4-yl]ethynyl}-6-(1-methyl-1H-pyrazol-4-yl)pyrazolo[1,5-a]pyridine;

3-{[1-(4,5-dimethyl-1,3-thiazol-2-yl)-5-methyl-1H-pyrazol-4-yl]ethynyl}-4-methoxy-6-(1-methyl-1H-pyrazol-4-yl)pyrazolo[1,5-a]pyridine;

3-{[1-(2,6-dimethylphenyl)-5-methyl-1H-pyrazol-4-yl]ethynyl}-4-methoxy-6-(1-methyl-1H-pyrazol-4-yl)pyrazolo[1,5-a]pyridine;

3-{[1-(2-fluorophenyl)-3-methyl-1H-pyrazol-4-yl]ethynyl}-4-methoxy-6-(1-methyl-1H-pyrazol-4-yl)pyrazolo[1,5-a]pyridine;

3-{[1-(4-fluorophenyl)-3-methyl-1H-pyrazol-4-yl]ethynyl}-4-methoxy-6-(1-methyl-1H-pyrazol-4-yl)pyrazolo[1,5-a]pyridine;

4-methoxy-3-[(3-methyl-1-phenyl-1H-pyrazol-4-yl)ethynyl]-6-(1-methyl-1H-pyrazol-4-yl)pyrazolo[1,5-a]pyridine;

3-[(5-tert-butyl-1-phenyl-1H-pyrazol-4-yl)ethynyl]-4-methoxy-6-(1-methyl-1H-pyrazol-4-yl)pyrazolo[1,5-a]pyridine;

3-[(5-isopropyl-1-phenyl-1H-pyrazol-4-yl)ethynyl]-4-methoxy-6-(1-methyl-1H-pyrazol-4-yl)pyrazolo[1,5-a]pyridine;

3-[(5-cyclobutyl-1-phenyl-1H-pyrazol-4-yl)ethynyl]-4-methoxy-6-(1-methyl-1H-pyrazol-4-yl)pyrazolo[1,5-a]pyridine;

4-methoxy-6-(1-methyl-1H-pyrazol-4-yl)-3-{[5-methyl-1-(3-thienyl)-1H-pyrazol-4-yl]ethynyl}pyrazolo[1,5-a]pyridine;

4-{[4-methoxy-6-(1-methyl-1H-pyrazol-4-yl)pyrazolo[1,5-a]pyridin-3-yl]ethynyl}-1',5-dimethyl-1'H-1,4'-bipyrazole;

4-methoxy-6-(1-methyl-1H-pyrazol-4-yl)-3-(3-pyrrolidin-3-ylprop-1-yn-1-yl)pyrazolo[1,5-a]pyridine;

4-methoxy-6-(1-methyl-1H-pyrazol-4-yl)-3-[(5-pyridin-3-yl-1,3,4-thiadiazol-2-yl)ethynyl]pyrazolo[1,5-a]pyridine;

4-methoxy-6-(1-methyl-1H-pyrazol-4-yl)-3-{[1-methyl-2-(3-thienyl)-1H-imidazol-5-yl]ethynyl}pyrazolo[1,5-a]pyridine;

4-methoxy-3-{[2-(2-methoxyethyl)-1-methyl-1H-imidazol-5-yl]ethynyl}-6-(1-methyl-1H-pyrazol-4-yl)pyrazolo[1,5-a]pyridine;

3-[(2-isopropyl-1-methyl-1H-imidazol-5-yl)ethynyl]-4-methoxy-6-(1-methyl-1H-pyrazol-4-yl)pyrazolo[1,5-a]pyridine;

3-[(2-cyclobutyl-1-methyl-1H-imidazol-5-yl)ethynyl]-4-methoxy-6-(1-methyl-1H-pyrazol-4-yl)pyrazolo[1,5-a]pyridine;
4-methoxy-6-(1-methyl-1H-pyrazol-4-yl)-3-{[1-methyl-2-(tetrahydrofuran-3-yl)-1H-imidazol-5-yl]ethynyl}pyrazolo[1,5-a]pyridine;
3-{[2-(3-furyl)-1-methyl-1H-imidazol-5-yl]ethynyl}-4-methoxy-6-(1-methyl-1H-pyrazol-4-yl)pyrazolo[1,5-a]pyridine;
3-[(2-cyclopentyl-1-methyl-1H-imidazol-5-yl)ethynyl]-4-methoxy-6-(1-methyl-1H-pyrazol-4-yl)pyrazolo[1,5-a]pyridine;
3-{[2-(fluoromethyl)-1-methyl-1H-imidazol-5-yl]ethynyl}-4-methoxy-6-(1-methyl-1H-pyrazol-4-yl)pyrazolo[1,5-a]pyridine;
4-methoxy-3-{[1-methyl-2-(5-methylisoxazol-3-yl)-1H-imidazol-5-yl]ethynyl}-6-(1-methyl-1H-pyrazol-4-yl)pyrazolo[1,5-a]pyridine;
3-{[2-(2-furyl)-1-methyl-1H-imidazol-5-yl]ethynyl}-4-methoxy-6-(1-methyl-1H-pyrazol-4-yl)pyrazolo[1,5-a]pyridine;
4-methoxy-6-(1-methyl-1H-pyrazol-4-yl)-3-[(1-methyl-2-pyridin-2-yl-1H-imidazol-5-yl)ethynyl]pyrazolo[1,5-a]pyridine;
4-methoxy-3-{[1-methyl-2-(4-methyl-1,3-thiazol-2-yl)-1H-imidazol-5-yl]ethynyl}-6-(1-methyl-1H-pyrazol-4-yl)pyrazolo[1,5-a]pyridine;
4-methoxy-3-{[1-methyl-2-(2-methyl-1,3-thiazol-4-yl)-1H-imidazol-5-yl]ethynyl}-6-(1-methyl-1H-pyrazol-4-yl)pyrazolo[1,5-a]pyridine;
methyl 3-{[4-methoxy-6-(1-methyl-1H-pyrazol-4-yl)pyrazolo[1,5-a]pyridin-3-yl]ethynyl}azetidine-1-carboxylate;
benzyl 3-{[4-methoxy-6-(1-methyl-1H-pyrazol-4-yl)pyrazolo[1,5-a]pyridin-3-yl]ethynyl}azetidine-1-carboxylate;
pyridin-2-ylmethyl 3-{[4-methoxy-6-(1-methyl-1H-pyrazol-4-yl)pyrazolo[1,5-a]pyridin-3-yl]ethynyl}azetidine-1-carboxylate;
4-{[4-methoxy-6-(1-methyl-1H-pyrazol-4-yl)pyrazolo[1,5-a]pyridin-3-yl]ethynyl}-1,5-naphthyridine;
4-{[4-methoxy-6-(1-methyl-1H-pyrazol-4-yl)pyrazolo[1,5-a]pyridin-3-yl]ethynyl}-1,8-naphthyridine;
4-{[4-methoxy-6-(1-methyl-1H-pyrazol-4-yl)pyrazolo[1,5-a]pyridin-3-yl]ethynyl}quinazoline;
N-(4-{[4-methoxy-6-(1-methyl-1H-pyrazol-4-yl)pyrazolo[1,5-a]pyridin-3-yl]ethynyl}pyridin-2-yl)-2-methylbenzenesulfonamide;
N-(4-{[4-methoxy-6-(1-methyl-1H-pyrazol-4-yl)pyrazolo[1,5-a]pyridin-3-yl]ethynyl}pyridin-2-yl)benzenesulfonamide;
3-(2,7-diazaspiro[3.5]non-2-ylmethyl)-4-methoxy-6-(1-methyl-1H-pyrazol-4-yl)pyrazolo[1,5-a]pyridine;
N-{[4-methoxy-6-(1-methyl-1H-pyrazol-4-yl)pyrazolo[1,5-a]pyridin-3-yl]methyl}pyridin-3-amine;
3-(2,6-diazaspiro[3.3]hept-2-ylmethyl)-4-methoxy-6-(1-methyl-1H-pyrazol-4-yl)pyrazolo[1,5-a]pyridine;
N-{[4-methoxy-6-(1-methyl-1H-pyrazol-4-yl)pyrazolo[1,5-a]pyridin-3-yl]methyl}-2-pyrrolidin-1-ylethanamine;
2-(1H-imidazol-4-yl)-N-{[4-methoxy-6-(1-methyl-1H-pyrazol-4-yl)pyrazolo[1,5-a]pyridin-3-yl]methyl}ethanamine;
1-cyclopropyl-N-{[4-methoxy-6-(1-methyl-1H-pyrazol-4-yl)pyrazolo[1,5-a]pyridin-3-yl]methyl}methanamine;
N-{[4-methoxy-6-(1-methyl-1H-pyrazol-4-yl)pyrazolo[1,5-a]pyridin-3-yl]methyl}-2-(1,3-thiazol-2-yl)ethanamine;
2-({[4-methoxy-6-(1-methyl-1H-pyrazol-4-yl)pyrazolo[1,5-a]pyridin-3-yl]methyl}amino)-6-methylbenzoic acid;
N-{[4-methoxy-6-(1-methyl-1H-pyrazol-4-yl)pyrazolo[1,5-a]pyridin-3-yl]methyl}-3-(trifluoromethyl)pyridin-4-amine;
3-bromo-N-{[4-methoxy-6-(1-methyl-1H-pyrazol-4-yl)pyrazolo[1,5-a]pyridin-3-yl]methyl}pyridin-4-amine;
5-({[4-methoxy-6-(1-methyl-1H-pyrazol-4-yl)pyrazolo[1,5-a]pyridin-3-yl]methyl}amino)pyridine-2-carbonitrile;
N-{[4-methoxy-6-(1-methyl-1H-pyrazol-4-yl)pyrazolo[1,5-a]pyridin-3-yl]methyl}-1,3,5-trimethyl-1H-pyrazol-4-amine;
2-chloro-N-{[4-methoxy-6-(1-methyl-1H-pyrazol-4-yl)pyrazolo[1,5-a]pyridin-3-yl]methyl}pyridin-4-amine;
N-{[4-methoxy-6-(1-methyl-1H-pyrazol-4-yl)pyrazolo[1,5-a]pyridin-3-yl]methyl}imidazo[1,2-a]pyridin-3-amine;
N-[3-({[4-methoxy-6-(1-methyl-1H-pyrazol-4-yl)pyrazolo[1,5-a]pyridin-3-yl]methyl}amino)phenyl]acetamide;
5-({[4-methoxy-6-(1-methyl-1H-pyrazol-4-yl)pyrazolo[1,5-a]pyridin-3-yl]methyl}amino)pyridin-2-ol;
6-methoxy-N-{[4-methoxy-6-(1-methyl-1H-pyrazol-4-yl)pyrazolo yl]methyl}pyridin-3-amine;
N-{[4-methoxy-6-(1-methyl-1H-pyrazol-4-yl)pyrazolo[1,5-a]pyridin-3-yl]methyl}pyrazin-2-amine;
N-{[4-methoxy-6-(1-methyl-1H-pyrazol-4-yl)pyrazolo[1,5-a]pyridin-3-yl]methyl}pyridazin-3-amine;
3-({[4-methoxy-6-(1-methyl-1H-pyrazol-4-yl)pyrazolo[1,5-a]pyridin-3-yl]methyl}amino)pyridin-2-ol;
N-{[4-methoxy-6-(1-methyl-1H-pyrazol-4-yl)pyrazolo[1,5-a]pyridin-3-yl]methyl}benzene-1,4-diamine;
N-{[4-methoxy-6-(1-methyl-1H-pyrazol-4-yl)pyrazolo[1,5-a]pyridin-3-yl]methyl}-1H-indazol-5-amine;
N-{[4-methoxy-6-(1-methyl-1H-pyrazol-4-yl)pyrazolo[1,5-a]pyridin-3-yl]methyl}-1H-benzimidazol-5-amine;
5-({[4-methoxy-6-(1-methyl-1H-pyrazol-4-yl)pyrazolo[1,5-a]pyridin-3-yl]methyl}amino)-1,3-dihydro-2H-benzimidazol-2-one;
N-{[4-methoxy-6-(1-methyl-1H-pyrazol-4-yl)pyrazolo[1,5-a]pyridin-3-yl]methyl}-1H-indol-6-amine;
N-{[4-methoxy-6-(1-methyl-1H-pyrazol-4-yl)pyrazolo[1,5-a]pyridin-3-yl]methyl}-4-methylpyridin-3-amine;
N-{[4-methoxy-6-(1-methyl-1H-pyrazol-4-yl)pyrazolo[1,5-a]pyridin-3-yl]methyl}-2-methylpyridin-3-amine;
N-{[4-methoxy-6-(1-methyl-1H-pyrazol-4-yl)pyrazolo[1,5-a]pyridin-3-yl]methyl}pyrimidin-5-amine;
N-{[4-methoxy-6-(1-methyl-1H-pyrazol-4-yl)pyrazolo[1,5-a]pyridin-3-yl]methyl}-6-methylpyridin-3-amine;
N-{[4-methoxy-6-(1-methyl-1H-pyrazol-4-yl)pyrazolo[1,5-a]pyridin-3-yl]methyl}-1,2,3-thiadiazol-5-amine;
N-benzyl-4-methoxy-6-(1-methyl-1H-pyrazol-4-yl)pyrazolo[1,5-a]pyridin-3-amine;
4-methoxy-6-(1-methyl-1H-pyrazol-4-yl)-3-morpholin-4-ylpyrazolo[1,5-a]pyridine;
3-(2,7-diazaspiro[3.5]non-2-yl)-4-methoxy-6-(1-methyl-1H-pyrazol-4-yl)pyrazolo[1,5-a]pyridine;
3-(2,6-diazaspiro[3.5]non-2-yl)-4-methoxy-6-(1-methyl-1H-pyrazol-4-yl)pyrazolo[1,5-a]pyridine;
4-methoxy-6-(1-methyl-1H-pyrazol-4-yl)-N-(2-pyridin-2-ylethyl)pyrazolo[1,5-a]pyridin-3-amine;

4-methoxy-6-(1-methyl-1H-pyrazol-4-yl)-N-(2-pyridin-3-ylethyl)pyrazolo[1,5-a]pyridin-3-amine;
4-methoxy-6-(1-methyl-1H-pyrazol-4-yl)-N-(2-pyridin-4-ylethyl)pyrazolo[1,5-a]pyridin-3-amine;
4-methoxy-6-(1-methyl-1H-pyrazol-4-yl)-N-(pyridin-3-ylmethyl)pyrazolo[1,5-a]pyridin-3-amine;
4-methoxy-6-(1-methyl-1H-pyrazol-4-yl)-N-(pyridin-4-ylmethyl)pyrazolo[1,5-a]pyridin-3-amine;
4-methoxy-6-(1-methyl-1H-pyrazol-4-yl)-N-(pyridin-2-ylmethyl)pyrazolo[1,5-a]pyridin-3-amine;
4-methoxy-6-(1-methyl-1H-pyrazol-4-yl)-N-pyridin-3-ylpyrazolo[1,5-a]pyridin-3-amine;
4-methoxy-6-(1-methyl-1H-pyrazol-4-yl)-N-[(1-methyl-1H-pyrazol-4-yl)methyl]pyrazolo[1,5-a]pyridin-3-amine;
4-methoxy-6-(1-methyl-1H-pyrazol-4-yl)-N-pyridin-4-ylpyrazolo[1,5-a]pyridin-3-amine;
N'-[4-methoxy-6-(1-methyl-1H-pyrazol-4-yl)pyrazolo[1,5-a]pyridin-3-yl]-N,N-dimethylpropane-1,3-diamine;
3-(5-bromo-1-benzothien-2-yl)-4-methoxy-6-(1-methyl-1H-pyrazol-4-yl)pyrazolo[1,5-a]pyridine;
3-{1-[2-(3,5-dimethyl-1H-pyrazol-4-yl)ethyl]-1H-1,2,3-triazol-4-yl}-4-methoxy-6-(1-methyl-1H-pyrazol-4-yl)pyrazolo[1,5-a]pyridine;
4-Methoxy-6-(1-methyl-1H-pyrazol-4-yl)-3-(1H-pyrazol-4-yl)-pyrazolo[1,5-a]pyridine;
4-Methoxy-6-(1-methyl-1H-pyrazol-4-yl)-3-(1-pyridin-2-ylmethyl-1H-pyrazol-4-yl)-pyrazolo[1,5-a]pyridine;
4-methoxy-6-(1-methyl-1H-pyrazol-4-yl)-3-[1-(2-morpholin-4-ylethyl)-1H-1,2,3-triazol-4-yl]pyrazolo[1,5-a]pyridine;
3-{1-[2-(3,5-dimethylisoxazol-4-yl)ethyl]-1H-1,2,3-triazol-4-yl}-4-methoxy-6-(1-methyl-1H-pyrazol-4-yl)pyrazolo[1,5-a]pyridine;
3-[1-(2-fluoropyridin-3-yl)-1H-1,2,3-triazol-4-yl]-4-methoxy-6-(1-methyl-1H-pyrazol-4-yl)pyrazolo[1,5-a]pyridine;
4-[4-methoxy-6-(1-methyl-1H-pyrazol-4-yl)pyrazolo[1,5-a]pyridin-3-yl]benzonitrile;
4-methoxy-6-(1-methyl-1H-pyrazol-4-yl)-3-(4-pyridin-4-ylphenyl)pyrazolo[1,5-a]pyridine;
5-[4-methoxy-6-(1-methyl-1H-pyrazol-4-yl)pyrazolo[1,5-a]pyridin-3-yl]-1H-indazole;
N-{4-[4-methoxy-6-(1-methyl-1H-pyrazol-4-yl)pyrazolo[1,5-a]pyridin-3-yl]benzyl}acetamide;
N-benzyl-4-[4-methoxy-6-(1-methyl-1H-pyrazol-4-yl)pyrazolo[1,5-a]pyridin-3-yl]benzamide;
4-[4-methoxy-6-(1-methyl-1H-pyrazol-4-yl)pyrazolo[1,5-a]pyridin-3-yl]benzamide;
4-methoxy-6-(1-methyl-1H-pyrazol-4-yl)-3-(4-pyridin-2-ylphenyl)pyrazolo[1,5-a]pyridine;
N-(2-furylmethyl)-4-[4-methoxy-6-(1-methyl-1H-pyrazol-4-yl)pyrazolo[1,5-a]pyridin-3-yl]benzamide;
1-ethyl-3-{2-methoxy-4-[4-methoxy-6-(1-methyl-1H-pyrazol-4-yl)pyrazolo[1,5-a]pyridin-3-yl]phenyl}urea;
2-fluoro-4-[4-methoxy-6-(1-methyl-1H-pyrazol-4-yl)pyrazolo[1,5-a]pyridin-3-yl]-N-phenylbenzamide;
N-benzyl-2-methoxy-5-[4-methoxy-6-(1-methyl-1H-pyrazol-4-yl)pyrazolo[1,5-a]pyridin-3-yl]benzenesulfonamide;
4-methoxy-6-(1-methyl-1H-pyrazol-4-yl)-3-(4-pyridin-3-ylphenyl)pyrazolo[1,5-a]pyridine;
4-methoxy-6-(1-methyl-1H-pyrazol-4-yl)-N-pyridin-4-yl)pyrazolo[1,5-a]pyridine-3-carboxamide;
N-(2,3-dimethylpyridin-4-yl)-4-methoxy-6-(1-methyl-1H-pyrazol-4-yl)pyrazolo[1,5-a]pyridine-3-carboxamide;
N-[4-(acetylamino)phenyl]-4-methoxy-6-(1-methyl-1H-pyrazol-4-yl)pyrazolo[1,5-a]pyridine-3-carboxamide;
4-methoxy-6-(1-methyl-1H-pyrazol-4-yl)pyrazolo[1,5-a]pyridine-3-carboxamide;
4-methoxy-6-(1-methyl-1H-pyrazol-4-yl)pyrazolo[1,5-a]pyridine-3-carboxylic acid;
4-methoxy-6-(1-methyl-1H-pyrazol-4-yl)-N-[2-(1,3-thiazol-2-yl)ethyl]pyrazolo[1,5-a]pyridine-3-carboxamide;
4-methoxy-N-methyl-6-(1-methyl-1H-pyrazol-4-yl)pyrazolo[1,5-a]pyridine-3-carboxamide;
N-(cyclopropylmethyl)-4-methoxy-6-(1-methyl-1H-pyrazol-4-yl)pyrazolo[1,5-a]pyridine-3-carboxamide;
N-[3-(dimethylamino)propyl]-4-methoxy-6-(1-methyl-1H-pyrazol-4-yl)pyrazolo[1,5-a]pyridine-3-carboxamide;
4-methoxy-6-(1-methyl-1H-pyrazol-4-yl)-N-(pyridin-2-ylmethyl)pyrazolo[1,5-a]pyridine-3-carboxamide;
4-methoxy-6-(1-methyl-1H-pyrazol-4-yl)-N-(pyridin-3-ylmethyl)pyrazolo[1,5-a]pyridine-3-carboxamide;
4-methoxy-6-(1-methyl-1H-pyrazol-4-yl)-N-(pyridin-4-ylmethyl)pyrazolo[1,5-a]pyridine-3-carboxamide;
4-methoxy-6-(1-methyl-1H-pyrazol-4-yl)-N-(2-pyridin-2-ylethyl)pyrazolo[1,5-a]pyridine-3-carboxamide;
4-methoxy-6-(1-methyl-1H-pyrazol-4-yl)-N-(2-pyridin-4-ylethyl)pyrazolo[1,5-a]pyridine-3-carboxamide;
4-methoxy-6-(1-methyl-1H-pyrazol-4-yl)-N-pyridin-3-ylpyrazolo[1,5-a]pyridine-3-carboxamide;
4-methoxy-6-(1-methyl-1H-pyrazol-4-yl)-N-[3-(trifluoromethyl)pyridin-4-yl]pyrazolo[1,5-a]pyridine-3-carboxamide;
N-(1-benzylpyrrolidin-3-yl)-4-methoxy-6-(1-methyl-1H-pyrazol-4-yl)pyrazolo[1,5-a]pyridine-3-carboxamide;
N-[1-(hydroxymethyl)cyclopentyl]-4-methoxy-6-(1-methyl-1H-pyrazol-4-yl)pyrazolo[1,5-a]pyridine-3-carboxamide;
N-[5-(ethylsulfonyl)-2-hydroxyphenyl]-4-methoxy-6-(1-methyl-1H-pyrazol-4-yl)pyrazolo[1,5-a]pyridine-3-carboxamide;
N-(4-aminopyridin-2-yl)-4-methoxy-6-(1-methyl-1H-pyrazol-4-yl)pyrazolo[1,5-a]pyridine-3-carboxamide;
4-methoxy-N-(6-methoxyquinolin-4-yl)-6-(1-methyl-1H-pyrazol-4-yl)pyrazolo[1,5-a]pyridine-3-carboxamide;
4-methoxy-N,6-bis(1-methyl-1H-pyrazol-4-yl)pyrazolo[1,5-a]pyridine-3-carboxamide;
N-(3-cyclopropyl-1-methyl-1H-pyrazol-5-yl)-4-methoxy-6-(1-methyl-1H-pyrazol-4-yl)pyrazolo[1,5-a]pyridine-3-carboxamide;
N-imidazo[1,2-a]pyridin-3-yl-4-methoxy-6-(1-methyl-1H-pyrazol-4-yl)pyrazolo[1,5-a]pyridine-3-carboxamide;
N-[5-(aminocarbonyl)-1-ethyl-1H-pyrazol-4-yl]-4-methoxy-6-(1-methyl-1H-pyrazol-4-yl)pyrazolo[1,5-a]pyridine-3-carboxamide;
4-(benzyloxy)-3-bromo-6-(1-methyl-1H-pyrazol-4-yl)pyrazolo[1,5-a]pyridine;
3-bromo-6-(1-methyl-1H-pyrazol-4-yl)-4-(piperidin-3-ylmethoxy)pyrazolo[1,5-a]pyridine;
3-(cyclopropylethynyl)-6-(1-methyl-1H-pyrazol-4-yl)-4-(pyridin-3-ylmethoxy)pyrazolo[1,5-a]pyridine;
3-(cyclopropylethynyl)-6-(1-methyl-1H-pyrazol-4-yl)-4-(pyridin-2-ylmethoxy)pyrazolo[1,5-a]pyridine;
tert-butyl 3-({[3-bromo-6-(1-methyl-1H-pyrazol-4-yl)pyrazolo[1,5-a]pyridin-4-yl]oxy}methyl)piperidine-1-carboxylate;
6-(1-methyl-1H-pyrazol-4-yl)-4-(pyridin-2-ylmethoxy)pyrazolo[1,5-a]pyridine;

4-(benzyloxy)-3-(cyclopropylethynyl)-6-(1-methyl-1H-pyrazol-4-yl)pyrazolo[1,5-a]pyridine;
6-(1-methyl-1H-pyrazol-4-yl)-4-(pyridin-4-ylmethoxy)pyrazolo[1,5-a]pyridine;
3-(cyclopropylethynyl)-6-(1-methyl-1H-pyrazol-4-yl)-4-(pyridin-4-ylmethoxy)pyrazolo[1,5-a]pyridine;
tert-butyl 3-({[6-(1-methyl-1H-pyrazol-4-yl)pyrazolo[1,5-a]pyridin-4-yl]oxy}methyl)piperidine-1-carboxylate;
3-bromo-6-(1-methyl-1H-pyrazol-4-yl)-4-{[1-(methylsulfonyl)piperidin-3-yl]methoxy}pyrazolo[1,5-a]pyridine;
3-[(1-methyl-1H-imidazol-5-yl)ethynyl]-6-(1-methyl-1H-pyrazol-4-yl)-4-(pyridin-3-ylmethoxy)pyrazolo[1,5-a]pyridine;
tert-butyl [6-(1-methyl-1H-pyrazol-4-yl)pyrazolo[1,5-a]pyridin-4-yl]carbamate;
4-{2-[4-methoxy-6-(1-methyl-1H-pyrazol-4-yl)pyrazolo[1,5-a]pyridin-3-yl]ethyl}pyridin-2-amine;
1-[4-methoxy-6-(1-methyl-1H-pyrazol-4-yl)pyrazolo[1,5-a]pyridin-3-yl]-2-[1-(trifluoroacetyl)azetidin-3-yl]ethanone;
3-ethyl-4-methoxy-6-(1-methyl-1H-pyrazol-4-yl)pyrazolo[1,5-a]pyridine;
5-(benzyloxy)-7-phenylimidazo[1,2-a]pyridine;
5-(benzyloxy)-3-iodo-7-phenylimidazo[1,2-a]pyridine;
3-iodo-5-methoxy-7-phenylimidazo[1,2-a]pyridine;
5-methoxy-7-phenyl-3-(pyridin-3-ylethynyl)imidazo[1,2-a]pyridine;
3-(5-methoxy-7-phenylimidazo[1,2-a]pyridin-3-yl)prop-2-ynamide;
3-(cyclopropylethynyl)-5-methoxy-7-phenylimidazo[1,2-a]pyridine;
3-(5-methoxy-7-phenylimidazo[1,2-a]pyridin-3-yl)prop-2-yn-1-amine;
3-(5-methoxy-7-phenylimidazo[1,2-a]pyridin-3-yl)prop-2-yn-1-ol;
5-(benzyloxy)-3-(cyclopropylethynyl)-7-phenylimidazo[1,2-a]pyridine;
3-(cyclopropylethynyl)-5-methoxy-7-(1-methyl-1H-pyrazol-4-yl)imidazo[1,2-a]pyridine;
3-(3-cyclopentylprop-1-yn-1-yl)-5-methoxy-7-phenylimidazo[1,2-a]pyridine;
(2S)-4-(5-methoxy-7-phenylimidazo[1,2-a]pyridin-3-yl)but-3-yn-2-ol;
(2R)-4-(5-methoxy-7-phenylimidazo[1,2-a]pyridin-3-yl)but-3-yn-2-ol;
5-methoxy-3-[(4-methoxyphenyl)ethynyl]-7-phenylimidazo[1,2-a]pyridine;
5-methoxy-7-phenyl-3-{[4-(trifluoromethyl)phenyl]ethynyl}imidazo[1,2-a]pyridine;
3-[(4-chlorophenyl)ethynyl]-5-methoxy-7-phenylimidazo[1,2-a]pyridine;
5-methoxy-7-phenyl-3-(3-thienylethynyl)imidazo[1,2-a]pyridine;
4-[(5-methoxy-7-phenylimidazo[1,2-a]pyridin-3-yl)ethynyl]benzonitrile;
3-[(4-fluorophenyl)ethynyl]-5-methoxy-7-phenylimidazo[1,2-a]pyridine;
5-methoxy-7-phenyl-3-(phenylethynyl)imidazo[1,2-a]pyridine;
5-methoxy-3-[(2-methylphenyl)ethynyl]-7-phenylimidazo[1,2-a]pyridine;
3-[(2-chlorophenyl)ethynyl]-5-methoxy-7-phenylimidazo[1,2-a]pyridine;
3-[(2-fluorophenyl)ethynyl]-5-methoxy-7-phenylimidazo[1,2-a]pyridine;
3-[(3-chlorophenyl)ethynyl]-5-methoxy-7-phenylimidazo[1,2-a]pyridine;
3-[(3-fluorophenyl)ethynyl]-5-methoxy-7-phenylimidazo[1,2-a]pyridine;
5-methoxy-3-[(3-methylphenyl)ethynyl]-7-phenylimidazo[1,2-a]pyridine;
5-methoxy-7-phenyl-3-(pyridin-2-ylethynyl)imidazo[1,2-a]pyridine;
5-methoxy-3-[(1-methyl-1H-imidazol-5-yl)ethynyl]-7-phenylimidazo[1,2-a]pyridine;
(1R)-3-(5-methoxy-7-phenylimidazo[1,2-a]pyridin-3-yl)-1-phenylprop-2-yn-1-ol;
(1S)-3-(5-methoxy-7-phenylimidazo[1,2-a]pyridin-3-yl)-1-phenylprop-2-yn-1-ol;
5-methoxy-7-phenyl-3-(2-thienylethynyl)imidazo[1,2-a]pyridine;
5-methoxy-3-[(2-methoxyphenyl)ethynyl]-7-phenylimidazo[1,2-a]pyridine;
5-methoxy-7-phenyl-3-(pyridin-4-ylethynyl)imidazo[1,2-a]pyridine;
3-[(2,4-difluorophenyl)ethynyl]-5-methoxy-7-phenylimidazo[1,2-a]pyridine;
1-[3-(5-methoxy-7-phenylimidazo[1,2-a]pyridin-3-yl)prop-2-yn-1-yl]urea;
3-[(5-methoxy-7-phenylimidazo[1,2-a]pyridin-3-yl)ethynyl]aniline;
N-{3-[(5-methoxy-7-phenylimidazo[1,2-a]pyridin-3-yl)ethynyl]phenyl}methanesulfonamide;
N-[(1S,2R)-2-aminocyclohexyl]-4-(5-methoxy-7-phenylimidazo[1,2-a]pyridin-3-yl)thiophene-2-carboxamide;
methyl 4-[5-(benzyloxy)-7-phenylimidazo[1,2-a]pyridin-3-yl]benzoate;
methyl 4-(5-methoxy-7-phenylimidazo[1,2-a]pyridin-3-yl)benzoate;
5-methoxy-7-phenyl-3-(1H-pyrazol-4-yl)imidazo[1,2-a]pyridine;
5-methoxy-3-(1-methyl-1H-pyrazol-4-yl)-7-phenylimidazo[1,2-a]pyridine;
4-(5-methoxy-7-phenylimidazo[1,2-a]pyridin-3-yl)benzamide;
5-methoxy-7-phenyl-3-(3-thienyl)imidazo[1,2-a]pyridine;
5-methoxy-7-phenyl-3-(2-thienyl)imidazo[1,2-a]pyridine;
2-[4-(5-methoxy-7-phenylimidazo[1,2-a]pyridin-3-yl)-1H-pyrazol-1-yl]acetamide;
methyl 4-(5-methoxy-7-phenylimidazo[1,2-a]pyridin-3-yl)thiophene-2-carboxylate;
4-(5-methoxy-7-phenylimidazo[1,2-a]pyridin-3-yl)thiophene-2-carboxylic acid;
N-[(1S,2R)-2-aminocyclohexyl]-4-(5-methoxy-7-phenylimidazo[1,2-a]pyridin-3-yl)thiophene-2-carboxamide;
4-(5-methoxy-7-phenylimidazo[1,2-a]pyridin-3-yl)thiophene-2-carboxamide;
5-methoxy-7-phenyl-3-(1H-pyrrol-3-yl)imidazo[1,2-a]pyridine;
4-(5-methoxy-7-phenylimidazo[1,2-a]pyridin-3-yl)-N-(2,2,2-trifluoroethyl)thiophene-2-carboxamide;
N-[(1S,2S)-2-aminocyclohexyl]-4-(5-methoxy-7-phenylimidazo[1,2-a]pyridin-3-yl)thiophene-2-carboxamide;
N-(2-aminoethyl)-4-(5-methoxy-7-phenylimidazo[1,2-a]pyridin-3-yl)thiophene-2-carboxamide;
5-methoxy-7-phenyl-3-[5-(piperazin-1-ylcarbonyl)-3-thienyl]imidazo[1,2-a]pyridine;

4-(5-methoxy-7-phenylimidazo[1,2-a]pyridin-3-yl)-N-[3-(2-oxopyrrolidin-1-yl)propyl]thiophene-2-carboxamide;
3-isothiazol-4-yl-5-methoxy-7-phenylimidazo[1,2-a]pyridine; or
4-(5-methoxy-7-phenylimidazo[1,2-a]pyridin-3-yl)-1H-pyrrole-2-carboxamide;
and pharmaceutically acceptable salts, stereoisomers and tautomers thereof.

* * * * *